(12) United States Patent
Pitts et al.

(10) Patent No.: US 7,176,214 B2
(45) Date of Patent: Feb. 13, 2007

(54) IMIDAZO-FUSED OXAZOLO[4,5-β]PYRIDINE AND IMIDAZO-FUSED THIAZOLO[4,5-β]PYRIDINE BASED TRICYCLIC COMPOUNDS AND PHARMACEUTICAL COMPOSITIONS COMPRISING SAME

(75) Inventors: William J. Pitts, Newtown, PA (US); Makonen Belema, North Haven, CT (US); Patrice Gill, Chateauguay (CA); James Kempson, Princeton, NJ (US); Yuping Qiu, Glastonbury, CT (US); Claude A. Quesnelle, Brossard (CA); Steven H. Spergel, Warrington, PA (US); Fred Christopher Zusi, Hamden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 159 days.

(21) Appl. No.: 10/848,412

(22) Filed: May 18, 2004

(65) Prior Publication Data

US 2005/0101626 A1    May 12, 2005

Related U.S. Application Data

(60) Provisional application No. 60/472,246, filed on May 21, 2003.

(51) Int. Cl.
*A61K 31/4353* (2006.01)
*C07D 498/12* (2006.01)

(52) U.S. Cl. .......................... 514/293; 546/83; 544/60; 544/126; 544/361; 540/575; 540/599; 514/218; 514/228.5; 514/212; 514/232.8; 514/253; 514/254

(58) Field of Classification Search ................ 514/293, 514/218, 228.5, 212, 232.8, 253, 254; 546/83; 544/60, 126, 361; 540/599, 575
See application file for complete search history.

(56) References Cited

U.S. PATENT DOCUMENTS

2003/0078277 A1    4/2003  Hibi et al.

FOREIGN PATENT DOCUMENTS

| EP | 251536 | 1/1988 |
|---|---|---|
| EP | 556008 | 8/1993 |
| WO | WO 99/29693 | 6/1999 |
| WO | WO 00/34248 | 6/2000 |
| WO | WO 02/102377 | 12/2002 |
| WO | WO 03/080112 | 10/2003 |
| WO | WO 03/080114 | 10/2003 |
| WO | WO 01/00587 | 1/2004 |

OTHER PUBLICATIONS

Thomas et al., Halogeno-1,2,5-thiadiazolopyridines and 1,2,5-selenadiazolopyridines. Heterocycles, vol. 20, No. 6, pp. 1043-1048, 1983.

Burke et al., "BMS-345541 is a highly selective inhibitor of IkB kinase that binds at an allosteric site of the enzyme and blocks NF-kB-dependent transcription in mice," J. Biol. Chem., Jan. 17, 2003, vol. 278, No. 3, pp. 1450-1456.

*Primary Examiner*—Charanjit S. Aulakh
(74) *Attorney, Agent, or Firm*—Mary K. VanAtten

(57) ABSTRACT

The present invention provides for pyrazolopurine-based tricyclic compounds having the formula (I),

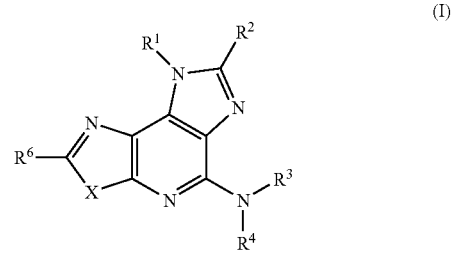

wherein $R^1$, $R^2$, $R^3$, $R^4$, $R^5$ and $R^6$ are as described herein. The present invention further provides pharmaceutical compositions comprising such compounds, as well as the use of such compounds for treating inflammatory and immune diseases.

20 Claims, No Drawings

IMIDAZO-FUSED OXAZOLO[4,5-β]PYRIDINE AND IMIDAZO-FUSED THIAZOLO[4,5-β]PYRIDINE BASED TRICYCLIC COMPOUNDS AND PHARMACEUTICAL COMPOSITIONS COMPRISING SAME

CROSS REFERENCE TO RELATED APPLICATIONS

The present application claims the priority benefits of U.S. Provisional Application No. 60/472,246, filed May 21, 2003, which is expressly incorporated fully herein by reference.

FIELD OF THE INVENTION

The present invention relates to imidazo-fused oxazolo [4,5-b]pyridine and imidazo-fused thiazolo[4,5-b]pyridine based tricyclic compounds, to methods of using the compounds in treating inflammatory and immune diseases, and cancer and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Additionally, certain neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury,*" Neuroscience and Biobehavioral Reviews, Vol. 20, No. 3 (1996), at pp. 445–452. More recently agents which inhibit the action of TNF-α have demonstrated clinical utility in a variety of diseases such as rheumatoid arthritis, psoriasis, and inflammatory bowel disease. See, e.g. Keating, et al. "*Infliximab: An Updated Review of its use in Crohn's Disease and Rheumatoid Arthritis*" BioDrugs Vol 16, (2002) pp. 111–148, and Hanns-Martin, et al. "*Perspectives for TNF-alpha-targeting Therapies.*" Arthritis Res. Vol 4. Supp 3 (2002) pp. S17–24.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs or P-38 inhibitors). These drugs are useful in treating a variety of diseases. See Dinarello, "*Role of Pro- and Anti-Inflammatory Cytokines During Inflammation: Experimental and Clinical Findings, Review*, Vol. 0393-974X (1997), at pp. 91–103.

Recently, attention has focussed on the role of Nuclear factor κB (NF-κB) in the activation pathway that leads to production of TNF-α and other inflammatory cytokines and gene products. Besides TNF-α, NF-κB is involved in the regulation of a variety of genes involved in immune function and inflammation. These include the cytokines IL-1, IL-2, IL-6, IL-2Rα, and GM-GSF, the chemokines IL-8, MCP-1 (CCR2), and RANTES, the adhesion molecules, intercellular adhesion molecule-1 (ICAM-1), vascular cellular adhesion molecule-1 (VCAM-1) and E-selectin, the proteases matrix metalloproteinase-1 (MMP-1), MMP-9 and MMP-13, and the pro-inflammatory enzymes cyclooxygenase-2 (COX-2), iNOS, and cPLA$_2$. Thus, inhibition of NF-κB and/or its activation pathway provides a means for treating various diseases including autoimmune diseases, inflammatory diseases, Alzheimer's disease, atherosclerosis, oncogenesis, and so forth by a variety of modes of action (i.e. cytokine reduction, chemokine reduction, reduction of adhesion molecule expression, decreased expression of certain proteases implicated in inflammatory and immune disease processes, and decreased production of enzymes which produce pro-inflammatory mediators) which have been implicated in a variety of disease progression. See, e.g., Baldwin, "*The NF-κB and IκB Proteins: New Discoveries and Insights,*" Annual Rev. Immunol., Vol. 14 (1996), at pp. 649–81; see also Christman et al., "*Impact of Basic Research on Tomorrow's Medicine, The Role of Nuclear Factor-κB in Pulmonary Diseases,*" Chest, Vol. 117 (2000), at pp. 1482–87, and Roshak, et al., "*Small-molecule Inhibitors of NF-κB for the Treatment of Inflammatory Joint Disease.*" Current Opinion in Pharmacol. Vol. 2 (2002) pp. 316–321.

Additionally attention has focussed on inhibition of NF-κB and/or its activation pathway to provide a means for treating cancer. Genes which mediate either tumorigenesis or tumor metastasis are regulated by NF-κB. In addition NF-κB is know to be activated by carcinogens and tumor promotors. See e.g., Karin et al.; "*NF-κB in Cancer: From Innocent Bystander to Major Culprit,*" Nature Rev. Cancer., Vol. 2 (2002) at pp. 301–310; see also Bharti et al.; "*Nuclear factor-kappa B and cancer: its role in prevention and therapy*" in Biochem. Pharmacol. at pp. 883–888.

IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Thus inhibitors of IKK-1 and/or IKK-2 would prevent translocation of NF-κB to the nucleus and prevent transcription of the pro-inflammatory gene products described above. For example see Burke, et al. "*BMS-345541 is a Highly Selective Inhibitor of IκB Kinase that Binds at an Allosteric Site of the Enzyme and Blocks NF-κB dependent Transcription in Mice.*" J. Biol. Chem. Vol. 278, (2003) pp. 1450–1456.

The therapeutic effects of glucocorticoids are mediated in part by their ability to inhibit NF-κB activity by two mechanisms, i.e., up-regulating IκB protein levels and inhibiting NF-κB subunits. The deleterious side effects of glucocorticoids (such as osteoporosis, hyperglycemia, fat redistribution, etc.) have been postulated to result from the interaction of glucocorticoids with the glucocorticoid receptor (GR) or the glucocorticoid response element (GRE). For example see Schacke, et al. "*Mechanisms Involved in the Side Effects of Glucocorticoids*" Pharmacol. and Therapeutics Vol 96 (2002) pp. 23–43. Thus inhibitors of IKK-1 and/or IKK-2 inhibitors should provide much of the therapeutic benefit of glucocorticoids with a greatly improved side effect profile.

As may be appreciated, those in the field of pharmaceutical research continue to seek to develop new compounds and compositions having increased effectiveness, bioavailability, and solubility, having fewer side effects, and/or providing the physician and patient with a choice of treatment options. Particularly in the area of immune response, individuals respond differently depending upon the type of treatment and chemical agent used. Mechanisms of action continue to be studied to aid in understanding the immune response and in developing compounds effective for treating inflammatory and immune-related disorders.

The present invention provides for novel tricyclic compounds useful as inhibitors of IKK.

SUMMARY OF THE INVENTION

Accordingly, the present invention provides novel inhibitors of IKK enzyme activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides for a novel process and intermediates for the preparation of the heterocyclic systems described within this document.

The present invention provides a method for treating disorders selected from rheumatoid arthritis, asthma, inflammaotry bowel disease, chronic obstructive pulmonary disease, psoriasis, and cancer, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel compounds for use in therapy.

The present invention provides the use of novel compounds for the manufacture of a medicament for the treatment of inflammatory diseases and cancer.

These and other features of the invention, which will become apparent during the following detailed description, have been achieved by the inventors' discovery that compounds of formula (I):

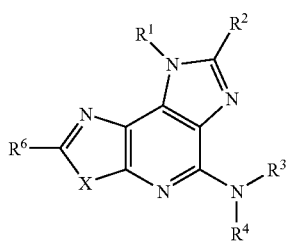

(I)

or stereoisomers or pharmaceutically acceptable salts thereof, wherein $R^1$, $R^2$, $R^3$, $R^4$, $R^6$, and X are defined below, are effective modulators of chemokine activity.

DETAILED DESCRIPTION OF EMBODIMENTS OF THE INVENTION

The invention is directed to compounds of formula (I), useful in treating inflammatory or immune conditions or cancer:

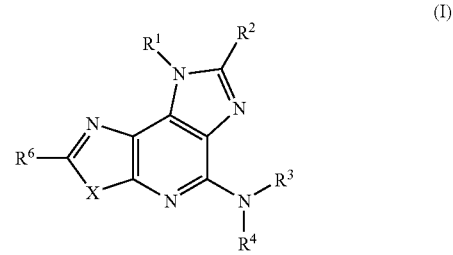

(I)

enantiomers, diastereomers, salts, and solvates thereof wherein

X is selected from O or S;

$R^1$ is selected from hydrogen, $C_{1-3}$ alkyl, $C_{2-3}$ alkenyl, and $C_{2-3}$ alkynyl;

$R^2$ is hydrogen, halo, cyano,
  (b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^a}$, $Z^{2^a}$ and $Z^{3^a}$; or
  (c) $-OR^{10^a}$, $-SR^{10^a}$, or $-SO_2R^{10^a}$;

$R^3$ and $R^4$ are independently selected from
  (a) hydrogen,
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^b}$, $Z^{2^b}$ and $Z^{3^b}$;
  (c) $-OR^{11}$, $-NR^{12}R^{13}$, $-N(R^{12})C(O)R^{14}$, $-N(R^{12})C(O)OR^{14}$, $-N(R^{12})SO_2R^{14}$, $-N(R^{12})C(O)NR^{12^a}R^{13}$, or $-N(R^{12})SO_2NR^{12^a}R^{13}$ or $-C(O)OR^{14}$, $-C(O)R^{11}$, $-C(O)NR^{12}R^{13}$, $-SO_2R^{14}$, $-SO_2NR^{12}R^{13}$;
  (d) $R^3$ and $R^4$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$;

$R^6$ is
  (a) hydrogen, hydroxy, halo, or cyano,
  (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
  (c) $-OR^{7^a}$, $-SR^{7^a}$, $-NR^{8^a}R^{9^a}$, $-N(R^{8^a})SO_2R^{10}$, $-N(R^{8^a})SO_2NR^{8^b}R^{9^b}$, $-N(R^{8^a})SO_2R^{10}$, $-N(R^{8^a})C(O)R^{7^a}$, $-N(R^{8^a})N(R^{8^a})C(O)R^{7^a}$, $-N(R^{8^a})C(O)NR^{8^a}R^{9^b}$, $-N(R^{8^a})C(O)OR^{7^a}$, $-SO_2R^{10}$, $-SO_2NR^{8^b}R^{9^b}$, $-C(O)R^{7^a}$, $-C(O)OR^{7^a}$, $-OC(O)R^{7^a}$, $-C(O)NR^{8^a}R^{9^a}$, or $-OC(O)NR^{8^a}R^{9^a}$;

$R^{7^a}$ and $R^{7^b}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or $R^{10}$, $R^{10a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo) alkyl, heteroaryl, or (heteroaryl)alkyl;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—N$Y^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—N$Y^2Y^3$,
(14) —$U^1$—N($Y^4$)—C(S)—N$Y^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—N$Y^2Y^3$,
(18) —$U^1$—C(O)—N$Y^2Y^3$,
(19) —$U^1$—OC(O)—N$Y^2Y^3$
(20) —$U^1$—S(O)$_2$—N($Y^4$)—$Y^1$,
(21) —$U^1$—N($Y^4$)—C(=N$V^{1a}$)—N$Y^2Y^3$,
(22) —$U^1$—N($Y^4$)—C(=N$V^{1a}$)—$Y^1$,
(23) —$U^1$—C(=N$V^{1a}$)—N$Y^2Y^3$,
(24) oxo;
(25) —$U^1$—$Y^5$;

$V^{1a}$ is independently hydrogen, alkyl, —CN, —C(O)$Y^1$, —S(O)$_2Y^5$, S(O)$_2$N$Y^2Y^3$;

$Y^1$, $Y^2$, $Y^3$, $Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group —N=C$Y^6Y^7$ where $Y^6$ and $Y^7$ are each independently H or alkyl; and $Z^4$, $Z^5$, and $Z^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo) alkyl, heteroaryl, or (heteroaryl)alkyl;
(3) —$U^1$—O—$Y^{5a}$,
(4) —$U^1$—S—$Y^{5a}$,
(5) —$U^1$—C(O)$_t$—H, —$U^1$—C(O)$_t$—$Y^{5a}$ where t is 1 or 2,
(6) —$U^1$—SO$_3$—H, or —$U^1$—S(O)$_t$$Y^{5a}$,
(7) —$U^1$-halo,
(8) —$U^1$-cyano,
(9) —$U^1$-nitro,
(10) —$U^1$—N$Y^{2a}Y^{3a}$,
(11) —$U^1$—N($Y^{4a}$)—C(O)—$Y^{1a}$,
(12) —$U^1$—N($Y^{4a}$)—C(S)—$Y^{1a}$,
(13) —$U^1$—N($Y^{4a}$)—C(O)—N$Y^{2a}Y^{3a}$,
(14) —$U^1$—N($Y^{4a}$)—C(S)—N$Y^{2a}Y^{3a}$,
(15) —$U^1$—N($Y^{4a}$)—C(O)O—$Y^{5a}$,
(16) —$U^1$—N($Y^{4a}$)—S(O)$_2$—$Y^{1a}$,
(17) —$U^1$—N($Y^{4a}$)—S(O)$_2$—N$Y^{2a}Y^{3a}$,
(18) —$U^1$—C(O)—N$Y^{2a}Y^{3a}$,
(19) —$U^1$—OC(O)—N$Y^{2a}Y^{3a}$,
(20) —$U^1$—S(O)$_2$—N($Y^{4a}$)—$Y^{1a}$,
(21) —$U^1$—N($Y^{4a}$)—C(=N$V^{1a}$)—N$Y^{2a}Y^{3a}$,
(22) —$U^1$—N($Y^{4a}$)—C(=N$V^{1a}$)—$Y^{1a}$,
(23) —$U^1$—C(=N$V^{1a}$)—N$Y^{2a}Y^{3a}$,
(24) oxo;
(25) —$U^1$—$Y^{5a}$;

$Y^{1a}$, $Y^{2a}$, $Y^{3a}$, $Y^{4a}$ and $Y^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

$U^1$ is independently
(1) a single bond,
(2) alkylene,
(3) alkenylene, or
(4) alkynylene.

In another embodiment, the present invention is directed to compounds of formula (I), wherein $R^3$ and $R^4$ are independently
(a) hydrogen,
(b) alkyl, haloalkyl, (hydroxy)alkyl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1^b}$, $Z^{2^b}$ and $Z^{3^b}$;

(c) —$NR^{12}R^{13}$; or (d) $R^3$ and $R^4$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$.

In another embodiment, the present invention is directed to compounds of formula (I), wherein $R^6$ is (a) hydrogen, alkyl, alkenyl, alkynyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1^d}$, $Z^{2^d}$ and $Z^{3^d}$; or (b) —$OR^{7^a}$, —$SR^{7^a}$, $NR^{8^a}R^{9^a}$, $N(R^{8^a})SO_2R^{10}$, —$N(R^{8^a})SO_2NR^{8^a}R^{9^b}$, —$N(R^{8^a})SO_2R^{10}$, —$N(R^{8^a})C(O)R^{7^a}$, —$N(R^{8^a})N(R^{8^a})C(O)R^{7^a}$, $N(R^{8^a})C(O)NR^{8^a}R^{9^a}$, —$N(R^{8^a})C(O)OR^{7^a}$, —$SO_2R^{10}$, —$SO_2NR^{8^a}R^{9^a}$, —$C(O)R^{7^a}$, —$C(O)OR^{7^a}$, —$OC(O)R^{7^a}$, —$C(O)NR^{8^a}R^{9^a}$, or —$OC(O)NR^{8^a}R^{9^a}$.

In another embodiment, the present invention is directed to compounds of formula (I), wherein $R^{7^a}$ is independently selected from (a) hydrogen, or (b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^c}$, $Z^{2^c}$ and $Z^{3^c}$.

In another embodiment, the present invention is directed to compounds of formula (I), wherein $R^3$ and $R^4$ are independently hydrogen, alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$; —$NR^{12}R^{13}$; or alternatively, $R^3$ and $R^4$ together with the nitrogen atom to which they are attached combine to form a 3 to 6 membered heterocyclic ring selected from piperidinyl, morpholinyl, pyrrolidinyl, piperazinyl, and azetidinyl; optionally independently substituted as valence allows with one or more $Z^{1^b}$, $Z^{2^b}$ and $Z^{3^b}$;

$R^6$ is (a) hydrogen, alkyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1^d}$, $Z^{2^d}$ and $Z^{3^d}$; or (b) —$OR^{7^a}$, —$SR^{7^a}$, —$NR^{8^a}R^{9^a}$, —$N(R^{8^a})SO_2R^{10}$, —$N(R^{8^a})SO_2R^{10}$, —$N(R^{8^a})C(O)R^{7^a}$, —$N(R^{8^a})N(R^{8^a})C(O)R^{7^a}$, —$N(R^{8^a})C(O)NR^{8^a}R^{9^a}$, —$SO_2R^{10}$, —$C(O)R^{7^a}$, or —$C(O)NR^{8^a}R^{9^a}$.

In another embodiment, the present invention is directed to compounds of formula (I), wherein $R^1$ is hydrogen, methyl, ethyl, propyl, i-propyl, prop-2-enyl, prop-1-enyl; and $R^2$ is hydrogen, methyl, trifluoromethyl, and phenyl.

The invention is directed to compounds of formula (I), useful in treating inflammatory or immune conditions or cancer:

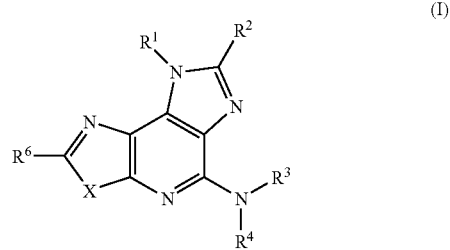

(I)

enantiomers, diastereomers, salts, and solvates thereof wherein

X is selected from O or S;

$R^1$ is selected from hydrogen and $C_{1-3}$ alkyl;

$R^2$ is (a) hydrogen, halo, cyano, (b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^a}$, $Z^{2^a}$ and $Z^{3^a}$; or (c) —$OR^{10^a}$, —$SR^{10^a}$, or —$SO_2R^{10^a}$;

$R^3$ and $R^4$ are independently selected from (a) hydrogen, (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^b}$, $Z^{2^b}$ and $Z^{3^b}$;

(c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12^a}R^{13}$, or —$N(R^{12})SO_2NR^{12^a}R^{13}$ or —$C(O)OR^{14}$, —$C(O)R^{11}$, —$C(O)NR^{12}R^{13}$, —$SO_2R^{14}$, —$SO_2NR^{12}R^{13}$,;

(d) $R^3$ and $R^4$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$;

$R^6$ is (a) hydrogen, hydroxy, halo, or cyano, (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or (c) —$OR^{7^a}$, —$SR^{7^a}$, —$NR^{8^a}R^{9^a}$, —$N(R^{8^a})SO_2R^{10}$, —$N(R^{8^a})SO_2NR^{8^a}R^{9^b}$, $N(R^{8^a})SO_2R^{10}$, —$N(R^{8^a})C(O)R^{7^a}$, —$N(R^{8^a})C(O)NR^{8^a}R^{9^b}$, —$N(R^{8^a})C(O)OR^{7^a}$, —$SO_2R^{10}$, —$SO_2NR^{8^a}R^{9^b}$, —$C(O)R^{7^a}$, —$C(O)OR^{7^a}$, —$OC(O)R^{7^a}$, —$C(O)NR^{8^a}R^{9^a}$, or —$OC(O)NR^{8^a}R^{9^a}$;

$R^{7^a}$ and $R^{7^b}$ are independently (a) hydrogen, or (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^c}$, $Z^{2^c}$ and $Z^{3^c}$;

$R^{8^a}$, $R^{8^b}$, $R^{9^a}$ and $R^{9^b}$ are independently (a) hydrogen, (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$; or $R^{10}$, $R^{10a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^d}$, $Z^{2^d}$ and $Z^{3^d}$;

$R^{11}$, $R^{12}$, $R^{12a}$ and $R^{13}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$;

$Z^{1^{b-1^e}}$, $Z^{2^{b-2^e}}$, and $Z^{3^{b-3^e}}$ are optional substituents at each occurance independently to selected from —$W^1$—$V^1$; —$W^2$—$V^2$; —$W^3$—$V^3$; —$W^4$—$V^4$; —$W^5$—$V^5$;

where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—C(O)$_t$H, —$U^1$—C(O)$_t$—$Y^5$ where t is 1 or 2,
  (6) —$U^1$—SO$_3$—H, or —$U^1$—S(O)$_t Y^5$,
  (7) —$U^1$-halo,
  (8) —$U^1$-cyano,
  (9) —$U^1$-nitro,
  (10) —$U^1$—N$Y^2 Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—N$Y^2 Y^3$,
  (14) —$U^1$—N($Y^4$)—C(S)—N$Y^2 Y^3$,
  (15) —$U^1$—N($Y^4$)—C(O)O—$Y^5$,
  (16) —$U^1$—N($Y^4$)—S(O)$_2$—$Y^1$,
  (17) —$U^1$—N($Y^4$)—S(O)$_2$—N$Y^2 Y^3$,
  (18) —$U^1$—C(O)—N$Y^2 Y^3$,
  (19) —$U^1$—OC(O)—N$Y^2 Y^3$,
  (20) —$U^1$—S(O)$_2$—N($Y^4$)—$Y^1$,
  (21) —$U^1$—N($Y^4$)—C(=N$V^{1a}$)—N$Y^2 Y^3$,
  (22) —$U^1$—N($Y^4$)—C(=N$V^{1a}$)—$Y^1$,
  (23) —$U^1$—C(=N$V^{1a}$)—N$Y^2 Y^3$,
  (24) oxo;
  (25) —$U^1$—$Y^5$;

$V^{1a}$ is independently hydrogen, alkyl, —CN, —C(O)$Y^1$, —S(O)$_2 Y^5$, S(O)$_2$N$Y^2 Y^3$;

$Y^1$, $Y^2$, $Y^3$, $Y^4$ and $Y^5$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl; or
  (2) $Y^2$ and $Y^3$ may together be alkylene or alkenylene, completing a 3- to 8-membered saturated or unsaturated ring together with the atoms to which they are attached, or
  (4) $Y^2$ and $Y^3$ together with the nitrogen atom to which they are attached may combine to form a group —N=C$Y^6 Y^7$ where $Y^6$ and $Y^7$ are each independently H or alkyl; and $U^1$ is independently
  (1) a single bond,
  (2) alkylene,
  (3) alkenylene, or
  (4) alkynylene.

In another embodiment, the present invention is directed to compounds of formula (I) wherein
$R^3$ and $R^4$ are independently
  (a) hydrogen,
  (b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1^b}$, $Z^{2^b}$ and $Z^{3^b}$;
  (c) —NR$^{12}$R$^{13}$; or
  (d) $R^3$ and $R^4$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$.

In another embodiment, the present invention is directed to compounds of formula (I) wherein
$R^6$ is
  (a) alkyl, alkenyl, alkynyl, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
  (b) —OR$^{7a}$, —SR$^{7a}$, —NR$^{8a}$R$^{9a}$, N(R$^{8a}$)SO$_2$R$^{10}$, —N(R$^{8a}$)SO$_2$NR$^{8b}$R$^{9b}$, —N(R$^{8a}$)SO$_2$R$^{10}$, —N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$.

In another embodiment, the present invention is directed to compounds of formula (I) wherein
$R^{7a}$ is independently selected from
  (a) hydrogen, or
  (b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^e}$, $Z^{2^e}$ and $Z^{3^e}$.

In another embodiment, the present invention is directed to compounds of formula (I) wherein
$Z^{1^b}$, $Z^{2^b}$ and $Z^{3^b}$ are optional substituents independently selected from alkyl, heteroaryl, —OH, —O—$Y^5$, —$U^1$—N$Y^2 Y^3$, —C(O)$_t$H, —C(O)$_t Y^5$;

$Z^{1^c}$ is
  (a) —OH, —OY$^5$ or
  (b) aryl optionally substituted with —OH or —OY$^5$;

$Z^{1^d}$, $Z^{2^d}$ and $Z^{3^d}$ are optional substituents independently selected from
  (a) cyano, halo, —OH, —OY$^5$, —U$^1$—NY$^2$Y$^3$, —C(O)$_t$H, —C(O)$_t$Y, —S(O)$_t$Y$^5$;
  (b) alkyl or alkoxy optionally substituted with one or more cyano, halo, —OH, —OY, —U$^1$—NY$^2$Y$^3$, —C(O)$_t$H, —C(O)$_t$Y, —S(O)$_t$Y, —U$^1$-heteroaryl.

In another embodiment, the present invention is directed to compounds of formula (I) wherein
$R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$;

alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1^b}$, $Z^{2^b}$ and $Z^{3^b}$;

$R^6$ is
- (a) alkynyl optionally substituted with $Z^{1^d}$ where $Z^{1^d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$;
- (b) aryl optionally independently substituted as valence allows with one or more $Z^{1^d}$, $Z^{2^d}$ and $Z^{3^d}$; or
- (c) —$OR^{7^a}$, —$SR^{7^a}$, —$SO_2R^{10}$, —$SO_2NR^{8^a}R^{9^b}$, —$OC(O)R^{7^a}$, or —$OC(O)NR^{8^a}R^{9^a}$; $Z^{1^b}$, $Z^{2^b}$ and $Z^{3^b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$, where $U^1$ is a bond or alkylene;

$Z^{1^c}$ is
- (a) —OY where Y is aryl, or
- (b) aryl optionally substituted with —OH or —OY where Y is alkyl;

$Z^{1^d}$, $Z^{2^d}$ and $Z^{3^d}$ are optional substituents independently selected from
- (a) cyano, halo, —OH, —OY, —$C(O)_tH$, —$C(O)_tY$, —$S(O)_tY$, or
- (b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—$C(O)$—$Y^1$, —$U^1$—$N(Y^4)$—$C(O)$—$Y^1$, or —$U^1$—$N(Y^4)$—$S(O)_2$—$Y^1$,
  where $U^1$ is a bond or alkylene.

In another embodiment, the present invention is directed to compounds of formula (I) wherein
$R^1$ is alkyl; and
$R^2$ is hydrogen In another embodiment, the present invention is directed to compounds of formula (I) wherein the compounds are selected from the compounds of Table A2, A3 and of the Examples.

The invention also relates to pharmaceutical compositions containing at least one compound of formula (I) and a pharmaceutically-acceptable carrier or diluent, for use in treating inflammatory and immune diseases or cancer. Also included within the invention are methods of treating such diseases comprising administering to a mammal in need of such treatment an effective amount of at least one compound of formula (I).

In another embodiment, $R^6$ is phenyl substituted with 0–3 $Z^{1^d}$, $Z^{2^d}$ and $Z^{3^d}$.

In another embodiment, $R^6$ is —$OR^{7^a}$, —$SR^{7^a}$, —$NR^{8^a}R^{9^a}$, —$N(R^{8^a})SO_2R^{10}$, —$N(R^{8^a})SO_2NR^{8^a}R^{9^b}$, —$N(R^{9^a})SO_2R^{10}$, —$N(R^{8^a})C(O)R^{7^a}$, —$N(R^{8^a})C(O)NR^{8^a}R^{9^b}$, —$N(R^{8^a})C(O)OR^{7^a}$, —$SO_2R^{10}$, —$SO_2NR^{8^a}R^{9^b}$, —$C(O)R^{7^a}$, —$C(O)OR^{7^a}$, —$OC(O)R^{7^a}$, —$C(O)NR^{8^a}R^{9^a}$, or —$OC(O)NR^{8^a}R^{9^a}$.

In another embodiment, $R^1$ is hydrogen, methyl, or ethyl.
In another embodiment, $R^2$ is hydrogen.
In another embodiment, $R^1$ is selected from hydrogen, $C_{1-3}$ alkyl, and $C_{2-3}$ alkenyl; and $R^2$ is hydrogen, alkyl, haloalkyl, or aryl.

In another embodiment, $R^3$ and $R^4$ are independently selected from
- (a) hydrogen,
- (b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1^b}$, $Z^{2^b}$ and $Z^{3^b}$;
- (c) —$NR^{12}R^{13}$; or
- (d) $R^3$ and $R^4$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$.

In another embodiment, $R^3$ and $R^4$ are independently selected from
- (a) alkyl which may be optionally independently substituted as valence allows with one or more $Z^{1^b}$, $Z^{2^b}$ and $Z^{3^b}$; or
- (b) —$C(O)OR^{14}$, —$C(O)R^{11}$, —$C(O)NR^{12}R^{13}$, —$SO_2R^{14}$, —$SO_2NR^{12}R^{13}$.

In another embodiment, $R^3$ and $R^4$ are independently selected from
- (a) alkyl which may be optionally independently substituted as valence allows with one or more $Z^{1^b}$, $Z^{2^b}$ and $Z^{3^b}$; or
  wherein $Z^{1^b}$, $Z^{2^b}$ and $Z^{3^b}$ is H, heterocyclo, heteroaryl, any of which may be optionally independently substituted as valence allows with one or more $Z^4$, $Z^5$ and $Z^6$; or —$U^1$—$NY^2Y^3$,
- (b) —$C(O)OR^{14}$, —$C(O)R^{11}$, —$C(O)NR^{12}R^{13}$, —$SO_2R^{14}$, —$SO_2NR^{12}R^{13}$.

In another embodiment, $R^3$ and $R^4$ are independently selected from hydrogen, alkyl, (hydroxy)alkyl, or (heteroaryl)alkyl any of which may be optionally independently substituted as valence allows with 1–2 $Z^{1^b}$, $Z^{2^b}$ and $Z^{3^b}$; —$NR^{12}R^{13}$; or $R^3$ and $R^4$ together with the nitrogen atom to which they are attached combine to form a 3 to 8 membered heterocyclic ring optionally independently substituted as valence allows with one or more $Z^{1^b}$, $Z^{2^b}$ and $Z^{3^b}$;

$Z^{1^b}$, $Z^{2^b}$ and $Z^{3^b}$ are selected from hydrogen, alkyl, —$U^1$—O—$Y^5$, —$U^1$, —$NY^2Y^3$, and $U^1$ is a single bond or alkylene, In another embodiment, $Y^5$ is H or alkyl, wherein the alkyl is selected from methyl, ethyl, propyl, i-propyl, butyl, i-butyl, t-butyl, pentyl, and hexyl;

$Y^2$ and $Y^3$ are independently selected from alkyl wherein the alkyl is selected from methyl, ethyl, propyl, i-propyl, butyl, i-butyl, t-butyl, pentyl, and hexyl.

In another embodiment, $R^3$ and $R^4$ are independently selected from hydrogen, alkyl, wherein the alkyl is selected from methyl, ethyl, propyl, i-propyl, butyl, i-butyl, t-butyl, pentyl, and hexyl; (hydroxy)alkyl, or (heteroaryl)alkyl, wherein (heteroaryl)alkyl is (tetrazolyl)methyl; any of which may be optionally independently substituted with 1 $Z^{1^b}$; —$NR^{12}R^{13}$; or $R^3$ and $R^4$ together with the nitrogen atom to which they are attached combine to form a 3 to 8 membered heterocyclic ring, wherein the ring is selected from piperidinyl, and morpholinyl, optionally independently substituted with 1 $Z^{1^b}$.

In another embodiment, $R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1^b}$, $Z^{2^b}$ and $Z^{3^b}$;
alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1^b}$, $Z^{2^b}$ and $Z^{3^b}$.

In another embodiment, $R^6$ is
(a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
(b) —$OR^{7^a}$, —$SR^{7^a}$, —$NR^{8^a}R^{9^a}$, —$N(R^{8^a})C(O)R^{7^a}$, —$N(R^{8^a})N(R^{8^a})C(O)R^{7^a}$, —$N(R^{8^a})C(O)NR^{8^b}R^{9^b}$, —$N(R^{8^a})C(O)OR^{7^a}$, —$SO_2R^{10}$, —$SO_2NR^{8^a}R^{9^a}$, —$C(O)R^{7^a}$, —$C(O)OR^{7^a}$, —$OC(O)R^{7^a}$, —$C(O)NR^{8^a}R^{9^a}$, or —$OC(O)NR^{8^a}R^{9^a}$.

In another embodiment, $R^6$ is
(a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1^d}$, $Z^{2^d}$ and $Z^{3^d}$; or
(b) —$OR^{7^a}$, —$SR^{7^a}$, —$NR^{8^a}R^{9^a}$, —$N(R^{8^a})C(O)R^{7^a}$, —$N(R^{8^a})N(R^{8^a})C(O)R^{7^a}$, $N(R^{8^a})C(O)NR^{8^b}R^{9^b}$, —$N(R^{8^a})C(O)OR^{7^a}$, —$SO_2R^{10}$, —$SO_2NR^{8^a}R^{9^a}$, —$C(O)R^{7^a}$, —$C(O)OR^{7^a}$, —$OC(O)R^{7^a}$, —$C(O)NR^{8^a}R^{9^a}$, or —$OC(O)NR^{8^a}R^{9^a}$;
wherein $Z^{1^d}$, $Z^{2^d}$ and $Z^{3^d}$ is —$W^4$—$V^4$; where $W^4$ is
(1) a bond
(2) alkyl, (hydroxy)alkyl, alkenyl, haloalkyl, heteroaryl, or (heteroaryl)alkyl; and
where $V^4$ is
(1) H
(2) aryl, (aryl)alkyl, heterocyclo, (heterocyclo)alkyl, heteroaryl, or (heteroaryl)alkyl;
(3) —$U^1$—O—$Y^5$,
(4) —$U^1$—$C(O)_t$—H, —$U^1$—$C(O)_t$—$Y^5$ where t is 1 or 2,
(5) —$U_1$—$SO_3$—H, or —$U^1$—$S(O)_tY^5$,
(6) —$U^1$-halo,
(7) —$U^1$—$NY^2Y^3$,
(8) —$U^1$—$N(Y^4)$—C(O)—$Y^1$,
(8) —$U^1$—$N(Y^4)$—C(O)—$NY^2Y^3$,
(10) —$U^1$—$N(Y^4)$—C(O)O—$Y^5$,
(11) —$U^1$—$N(Y^4)$—$S(O)_2$—$Y^1$,
(12) —$U^1$—$N(Y^4)$—$S(O)_2$—$NY^2Y^3$,
(13) —$U^1$—C(O)—$NY^2Y^3$,
(14) —$U^1$—OC(O)—$NY^2Y^3$
(15) —$U^1$—$S(O)_2$—$N(Y^4)$—$Y^1$; and
$U^1$ is a bond.

In another embodiment, $R^6$ is
(a) alkynyl optionally substituted with $Z^{1^d}$ where $Z^{1^d}$ is aryl which may be further optionally independently substituted with one or more cyano, halo, —OH, —OY, —$U^1$-$NY^2Y^3$, —$C(O)_tH$, —$C(O)_tY$, or, —$S(O)_tY$;
(b) aryl optionally independently substituted as valence allows with one or more $Z^{1^d}$, $Z^{2^d}$ and $Z^{3^d}$; or
(c) —$OR^{7^a}$, —$SR^{7^a}$, —$SO_2R^{10}$, —$SO_2NR^{8^a}R^{9^b}$, —$OC(O)R^{7^a}$, or —$OC(O)NR^{8^a}R^{9^a}$;
$Z^{1^b}$, $Z^{2^b}$ and $Z^{3^b}$ are optional substituents independently selected from —OH, —OY, —$U^1$—$NY^2Y^3$, —$C(O)_tH$, —$C(O)_tY$, —$U^1$—$N(Y^4)$—C(O)—$Y^1$, or —$U^1$—$N(Y^4)$—C(O)O—$Y^5$.

In another embodiment
$R^6$ is
(a) alkynyl optionally substituted with $Z^{1^d}$ where $Z^{1^d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$;

(b) aryl optionally independently substituted as valence allows with one or more $Z^{1^d}$, $Z^{2^d}$ and $Z^{3^d}$; or
(c) —$R^{7^a}$, —$SR^{7^a}$, —$SO_2R^{10}$, —$SO_2NR^{8^b}R^{9^b}$, —$OC(O)R^{7^a}$, or —$OC(O)NR^{8^a}R^{9^a}$;
$Z^{1^b}$, $Z^{2^b}$ and $Z^{3^b}$ are optional substituents independently selected from —OH, —OY, —$U^1$—$NY^2Y^3$, —$C(O)_tH$, —$C(O)_tY$, —$U^1$—$N(Y^4)$—C(O)—$Y^1$, or —$U^1$—$N(Y^4)$—C(O)O—$Y^5$,
where
$U^1$ is a bond or alkylene;
$Z^{1^c}$ is
(a) —OY where Y is aryl, or
(b) aryl optionally substituted with —OH or —OY where Y is alkyl;
$Z^{1^d}$, $Z^{2^d}$ and $Z^{3^d}$ are optional substituents independently selected from
(a) cyano, halo, —OH, —OY, —$C(O)_tH$, —$C(O)_tY$, —$S(O)_tY$, or
(b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—C(O)—$Y^1$, —$U^1$—$N(Y^4)$—C(O)—$Y^1$, or —$U^1$—$N(Y^4)$—$S(O)_2$—$Y^1$,
where
$U^1$ is a bond or alkylene.

In another embodiment
$R^6$ is
(a) alkynyl optionally substituted with $Z^{1^d}$ where $Z^{1^d}$ is phenyl which may be further optionally independently substituted with 0–1 cyano, halo, —OH, —OY, —$U^1$—$NY^2Y^3$, —$C(O)_tH$, —$C(O)_tY$, or, —$S(O)_tY$;
(b) phenyl optionally independently substituted as valence allows with one or more $Z^{1^d}$, $Z^{2^d}$ and $Z^{3^d}$; or
(c) —$OR^{7^a}$, —$SR^{7^a}$;
$Z^{1^b}$, $Z^{2^b}$ and $Z^{3^b}$ are optional substituents independently selected from —OH, —OY, —$U^1$—$NY^2Y^3$, —$C(O)_tH$, —$C(O)_tY$, —$U^1$—$N(Y^4)$—C(O)—$Y^1$, or —$U^1$—$N(Y^4)$—C(O)O—$Y^5$,
where
$U^1$ is a bond or alkylene, wherein alkylene is selected from methylene, ethylene, propylene, and butylene;
$Z^{1^c}$ is
(a) —OY where Y is phenyl, or
(b) phenyl optionally substituted with 0–1 —OH or —OY where Y is alkyl selected from methyl, ethyl, propyl, i-propyl, butyl, i-butyl, t-butyl, pentyl, hexyl;
$Z^{1^d}$, $Z^{2^d}$ and $Z^{3^d}$ are optional substituents independently selected from
(a) cyano, halo, —OH, —OY, —$C(O)_tH$, —$C(O)_tY$, —$S(O)_tY$, or
(b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—C(O)—$Y^1$, —$U^1$—$N(Y^4)$—C(O)—$Y^1$, or —$U^1$—$N(Y^4)$—$S(O)_2$—$Y^1$,
where
$U^1$ is a bond or alkylene, wherein alkylene is selected from methylene, ethylene, propylene, and butylene.

In another embodiment, $Y^1$, $Y^2$, $Y^3$, and $Y^4$ are indepndtly selected from hydrogen, alkyl, wherein alkyl is selected from alkyl is selected from methyl, ethyl, propyl, i-propyl, butyl, i-butyl, t-butyl, pentyl, and hexyl; aryl wherein aryl is phenyl, (aryl)alkyl.

In another embodiment, the present invention is directed to a compound of Formula (I), wherein the compound is selected from the compounds of the Examples or of Tables.

In another embodiment, the present invention is directed to a pharmaceutical composition, comprising a pharmaceutically acceptable carrier and a therapeutically effective amount of a compound of Formula (I).

In another embodiment, the present invention is directed to a method of treating an inflammatory or immune disease or disorder comprising administering to a mammal in need thereof a therapuetically-effective amount of at least one compound of formula (I).

In another embodiment, the present invention is directed to a method of treating cancer comprising administering to a mammal in need thereof a therapuetically-effective amount of at least one compound of formula (I)

In another embodiment, the present invention is directed to a method of treating an inflammatory or immune disease or disorder selected from, rheumatoid arthritis, asthma, inflammatory bowel disease, chronic obstructive pulmonary disease, and psoriasis.

In another embodiment, the present invention is directed the use of a compound of Formula (I) in the preparation of a medicament for the treatment of an inflammatory or immune disease.

In another embodiment, the present invention is directed the use of a compound of Formula (I) in the preparation of a medicament for the treatment of cancer.

In another embodiment, the present invention is directed to the use of a compound of Formula (I) in the preparation of a medicament for the treatment of an inflammatory or immune disease.

In another embodiment, the present invention is directed to the use of a compound of Formula (I) in the preparation of a medicament for the treatment of cancer.

In another embodiment, the present invention is directed to the use of a compound of Formula (I) in the preparation of a medicament for the treatment of an inflammatory or immune disease, wherein the disease is selected from, rheumatoid arthritis, asthma, inflammatory bowel disease, chronic obstructive pulmonary disease, and psoriasis.

In another embodiment, the present invention is directed to the use of a compound of Formula (I) for use in therapy.

In another embodiment, the present invention is directed to. A compound of formula (II),

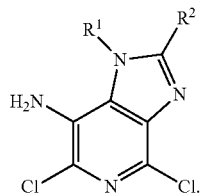
(II)

In another embodiment, the present invention is directed to a process of preparing the compound of Formula (II), comprising the steps of

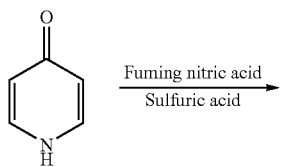

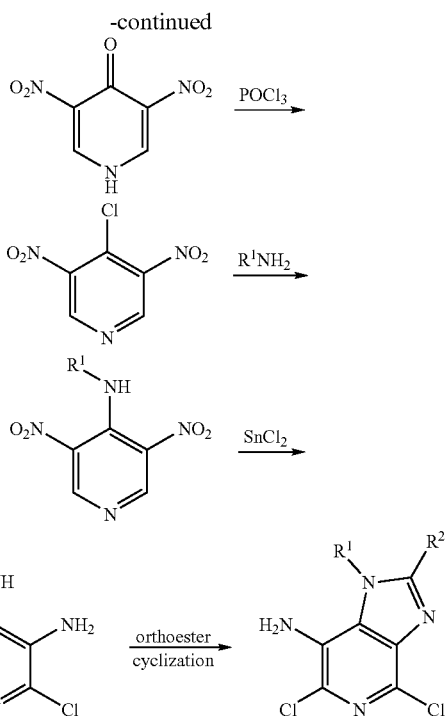

wherein $R^1$ and $R^2$ are as defined above.

In another embodiment, the present invention is directed to compounds of formula (II) which are useful as intermediates in the preparation of compounds of Formula (I)

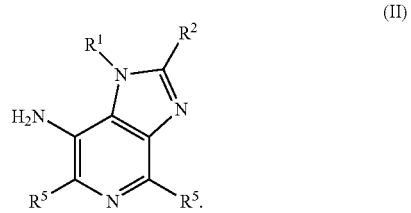
(II)

enantiomers, diastereomers, salts, and solvates thereof wherein $R^1$ is selected from hydrogen, $C_{1-3}$ alkyl, $C_{2-3}$ alkenyl, and $C_{2-3}$ alkynyl;

$R^2$ is hydrogen, halo, cyano,
  (b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^a}$, $Z^{2^a}$ and $Z^{3^a}$; or
  (c) —$OR^{10^a}$, —$SR^{10^a}$, or —$SO_2R^{10^a}$;

$R^5$, at each occurrence, is independently selected from F, Cl, Br, and I;

$R^{10^a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1^a}$, $Z^{2^a}$ and $Z^{3^a}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^5$,
(4) —$U^1$—S—$Y^5$,
(5) —$U^1$—C(O),H, —$U^1$—C(O)$_t$$Y^5$ where t is 1 or 2,
(6) —$U_1$—$SO_3$—H, or —$U^1$—S(O)$_t$$Y^5$,
(7) —$U^1$—halo,
(8) —$U^1$-cyano,
(9) —$U^1$—nitro,
(10) —$U^1$—$NY^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—$NY^2Y^3$,
(14) —$U^1$—N($Y^4$)—C(S)—$NY^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—$NY^2Y^3$,
(18) —$U^1$—C(O)—$NY^2Y^3$,
(19) —$U^1$—OC(O)—$NY^2Y^3$
(20) —$U^1$—S(O)$_2$—N($Y^4$)—$Y^1$,
(21) —$U^1$—N($Y^4$)—C(=N$V^{1a}$)—$NY^2Y^3$,
(22) —$U^1$—N($Y^4$)—C(=N$V^{1a}$)—$Y^1$,
(23) —$U^1$—C(=N$V^{1a}$)—$NY^2Y^3$,
(24) oxo;
(25) —$U^1$—$Y^5$;

$V^{1a}$ is independently hydrogen, alkyl, —CN, —C(O)$Y^1$, —S(O)$_2Y^5$, S(O)$_2NY^2Y^3$;

$Y^1$, $Y^2$, $Y^3$, $Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more $Z^4$, $Z^5$ and $Z^6$; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group —N=C$Y^6Y^7$ where $Y^6$ and $Y^7$ are each independently H or alkyl; and $Z^4$, $Z^5$, and $Z^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O$Y^{5a}$,
(4) —$U^1$—S—$Y^{5a}$,
(5) —$U^1$—C(O)$_t$—H, —$U^1$—C(O)$_t$—$Y^{5a}$ where t is 1 or 2,
(6) —$U^1$—$SO_3$—H, or —$U^1$—S(O)$_t$$Y^{5a}$,
(7) —$U^1$—halo,
(8) —$U^1$—cyano,
(9) —$U^1$—nitro,
(10) —$U^1$—$NY^{2a}Y^{3a}$,
(11) —$U^1$—N($Y^{4a}$)—C(O)—$Y^{1a}$,
(12) —$U^1$—N($Y^{4a}$)—C(S)—$Y^{1a}$,
(13) —$U^1$—N($Y^{4a}$)—C(O)—$NY^{2a}Y^{3a}$,
(14) —$U^1$—N($Y^{4a}$)—C(S)—$NY^{2a}Y^{3a}$,
(15) —$U^1$—N($Y^{4a}$)—C(O)O—$Y^{5a}$,
(16) —$U^1$—N($Y^{4a}$)—S(O)$_2$—$Y^{1a}$,
(17) —$U^1$—N($Y^{4a}$)—S(O)$_2$—$NY^{2a}Y^{3a}$,
(18) —$U^1$—C(O)—$NY^{2a}Y^{3a}$,
(19) —$U^1$—OC(O)—$NY^{2a}Y^{3a}$
(20) —$U^1$—S(O)$_2$—N($Y^{4a}$)—$Y^{1a}$,
(21) —$U^1$—N($Y^{4a}$)—C(=N$V^{1a}$)—$NY^{2a}Y^{3a}$,
(22) —$U^1$—N($Y^{4a}$)—C(=N$V^{1a}$)—$Y^{1a}$,
(23) —$U^1$—C(=N$V^{1a}$)—$NY^{2a}Y^{3a}$,
(24) oxo;
(25) —$U^1$—$Y^{5a}$;

$Y^{1a}$, $Y^{2a}$, $Y^{3a}$, $Y^{4a}$ and $Y^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

$U^1$ is independently
(1) a single bond,
(2) alkylene,
(3) alkenylene, or
(4) alkynylene.

In another embodiment, the present invention is directed to compounds of formula (III) which are useful as intermediates in the preparation of compounds of Formula (I)

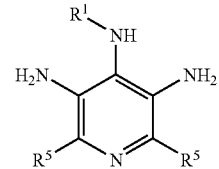

(III)

enantiomers, diastereomers, salts, and solvates thereof wherein $R^1$ is selected from hydrogen, $C_{1-3}$ alkyl, $C_{2-3}$ alkenyl, and $C_{2-3}$ alkynyl; and $R^5$, at each occurrence, is independently selected from F, Cl, Br, and I.

In another embodiment, the present invention is directed to compounds of formulas (II) and (III) which are useful as intermediates in the preparation of compounds of Formula (I) wherein $R^1$ is selected from hydrogen, $C_{1-3}$ alkyl, and $C_{2-3}$ alkenyl;

$R^2$ is hydrogen, alkyl, haloalkyl, or aryl; and $R^5$ is selected from Cl and Br.

In another embodiment, the present invention is directed to the use of a compound of Forumla (II) as an intermediate for the production of a compound of Formula (I).

In another embodiment, the present invention is directed to a process for preparing a compound of Formula (I) from the compound of Formula (II) comprising the steps described in Schemes II and III.

In another embodiment, the present invention is directed to a process for preparing a compound of Formula (II) from a compound of Formula (III)

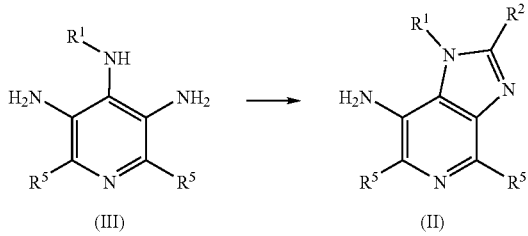

comprising reacting the compound of Formula (III) with an orthoester of formula $R^2$—$C(OR)_3$, wherein R is alkyl to obtain the compound of Formula (II).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention.

Furthermore, any elements of an embodiment are meant to be combined with any and all other elements from any of the embodiments to describe additional embodiments.

Definitions

The following are definitions of terms used in this specification. The initial definition provided for a group or term herein applies to that group or term throughout the present specification, individually or as part of another group, unless otherwise indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced. The term "optionally independently substituted as valence allows", as used herein, means that the any one or more hydrogens on the designated variable is independently replaced with a selection from the indicated group, provided that the designated variable's normal valency is not exceeded, and that the substitution results in a stable compound.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "alkyl" as used herein by itself or as part of another group refers to straight and branched chain hydrocarbons, containing 1 to 20 carbons, alternatively, 1 to 10 carbons, or 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 4 carbon atoms, are an alternative embodiment.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The term "alkenyl" as used herein by itself or as part of another group refers to straight or branched chain radicals of 2 to 20 carbons, alternatively, 2 to 12 carbons, or 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, alternatively, 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

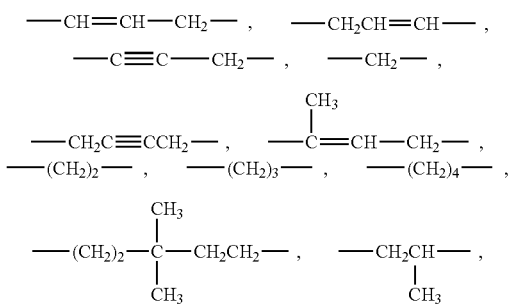

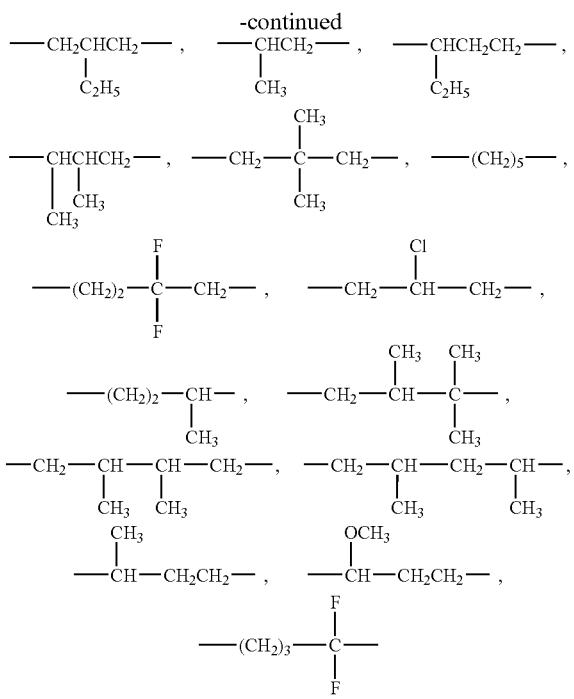

and the like. Alkylene groups may be optionally independently substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, alternatively, 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

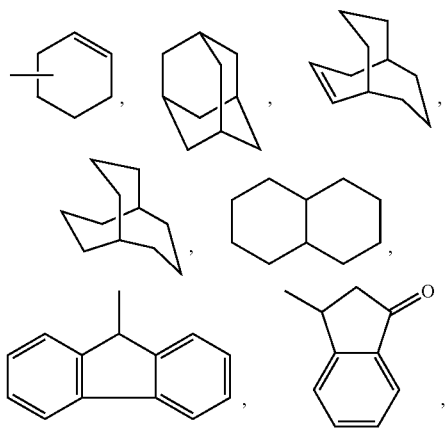

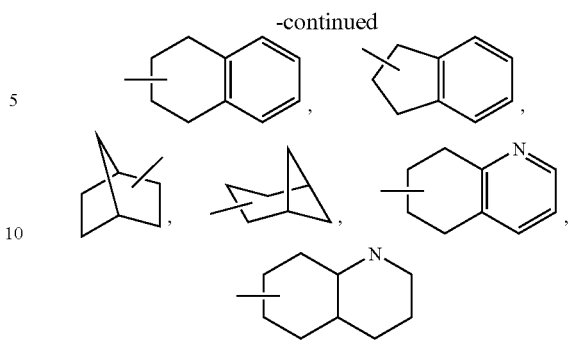

and the like.

The term "cycloalkylene" as employed herein refers to a "cycloalkyl" group which includes free bonds and thus is a linking group such as

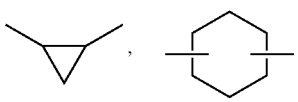

and the like.

One skilled in the field will understand that, when the designation "$CO_2$" is used herein, this is intended to refer to the group

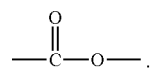

The term "alkoxy" refers to an alkyl or substituted alkyl group as defined above bonded through an oxygen atom (—O—), i.e., the groups —$OR_d$, wherein $R_d$ is alkyl or substituted alkyl.

The term "alkylthio" refers to an alkyl or substituted alkyl group as defined above bonded through a sulfur atom (—S—), i.e., the groups —$SR_d$, wherein $R_d$ is alkyl or substituted alkyl.

The term "acyl" refers to a carbonyl group linked to an organic radical, more particularly, the group $C(=O)R_g$, wherein $R_g$ can be selected from alkyl, alkenyl, substituted alkyl, or substituted alkenyl, as defined herein.

The term "alkoxycarbonyl" refers to a carboxy group

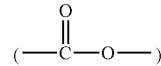

linked to an organic radical ($CO_2R_g$), wherein $R_g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

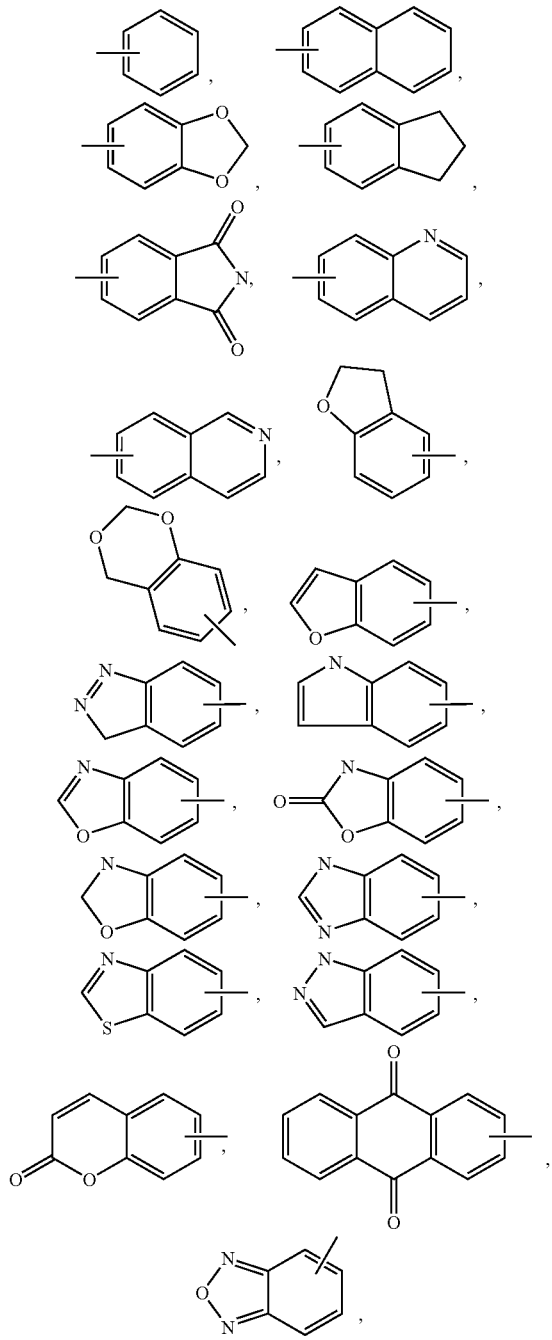

and the like.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

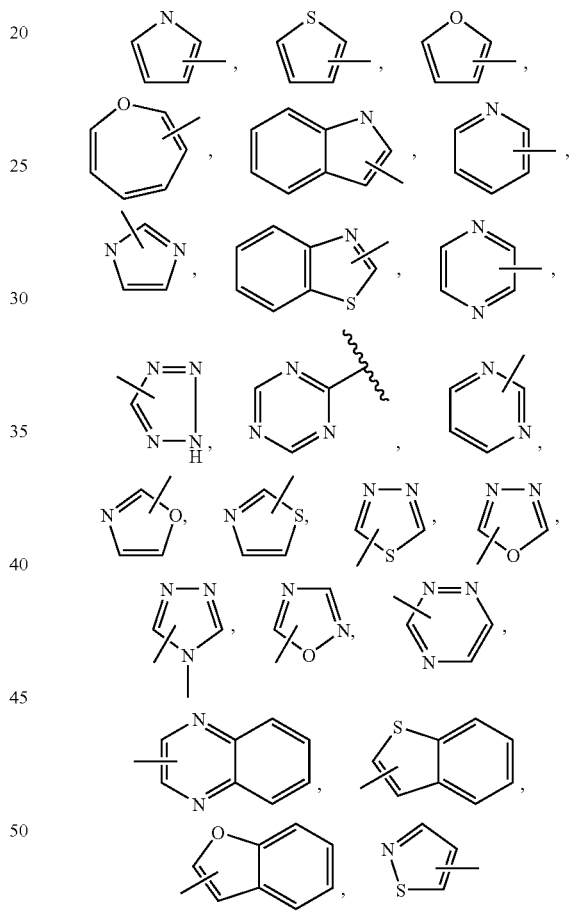

and the like.

In compounds of formula (I), heteroaryl groups include

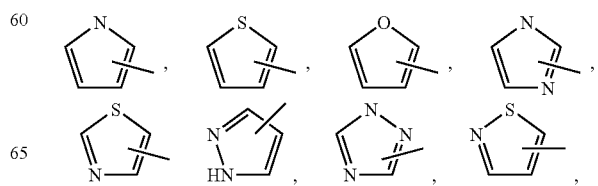

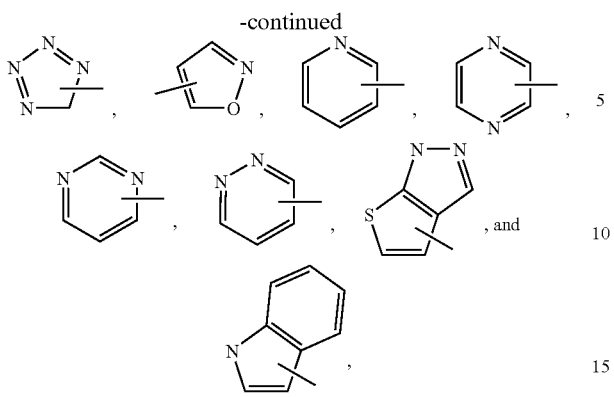

and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, alternatively, containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

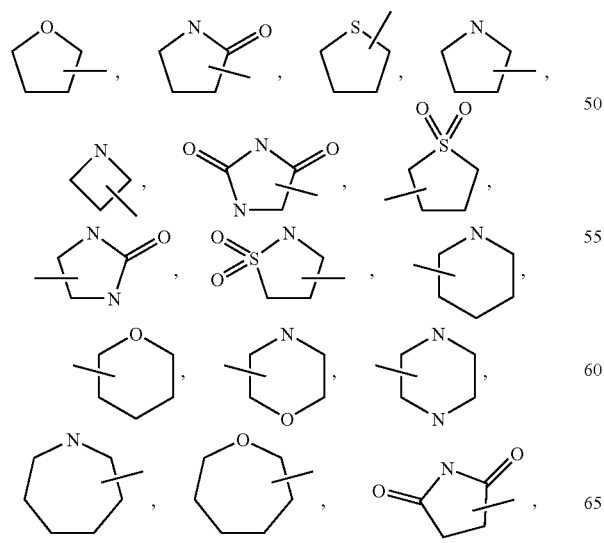

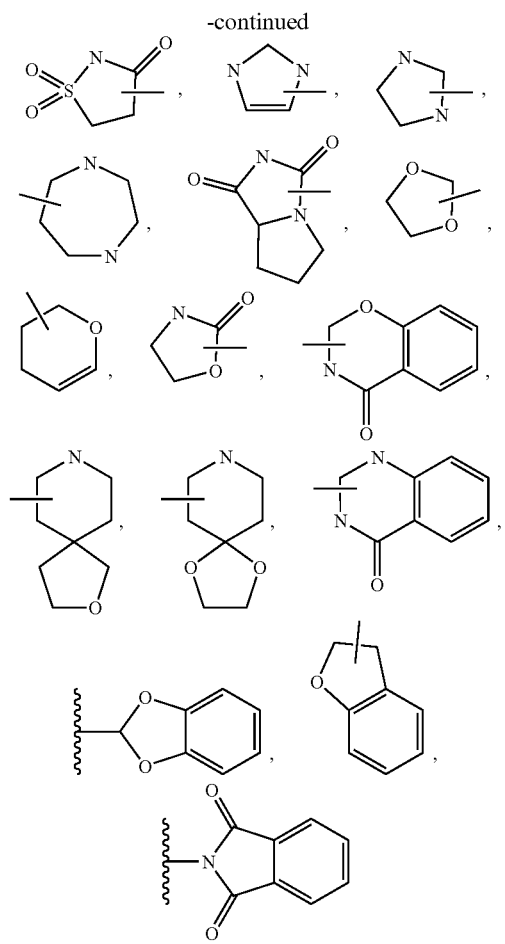

and the like.

Heterocyclo groups in compounds of formula (I) include

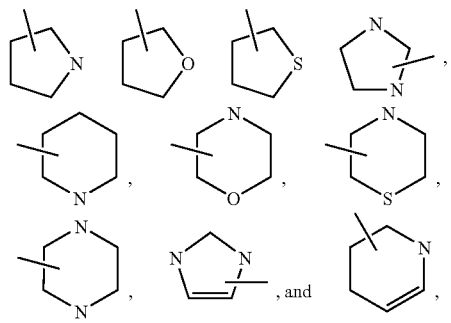

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, alternativley, 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309–396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113–191 (1991);

c) H. Bundgaard, *Advanced Drug Delivery Reviews*, Vol. 8, p. 1–38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit IKK or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Methods of Preparation

Compounds of Formula I may be prepared by reference to the methods illustrated in the following Schemes I through III. As shown therein the end product is a compound having the same structural formula as Formula I. It will be understood that any compound of Formula I may be produced by Scheme I–III by the suitable selection of reagents with appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

The sequence described in Scheme I entails the nitration of 4-hydroxy pyridine, I-1 to provide the known compound I-2. followed by conversion to the corresponding known chloro-pyridine I-3. Subsequent addition of an amine such as methylamine provides the previously un-described compound I-4. Reduction of both nitro groups and simultaneous chlorination of the intermediate triaminopyridine occurs on treatment of I-4 with tin(II) chloride to produce I-5. This important intermediate can be reacted with triethyl orthoformate to provide fused imidazole I-6. Acylation either by reaction with an acid choride or other suitable carboxylic acid activation procedure would provide I-7, which upon heating closes to produce the tricyclic system I-8. Reaction with an amine produces the desired product I-9.

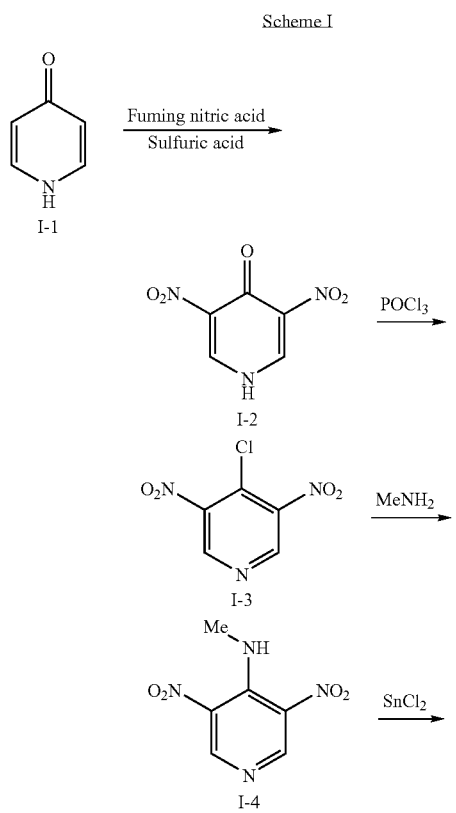

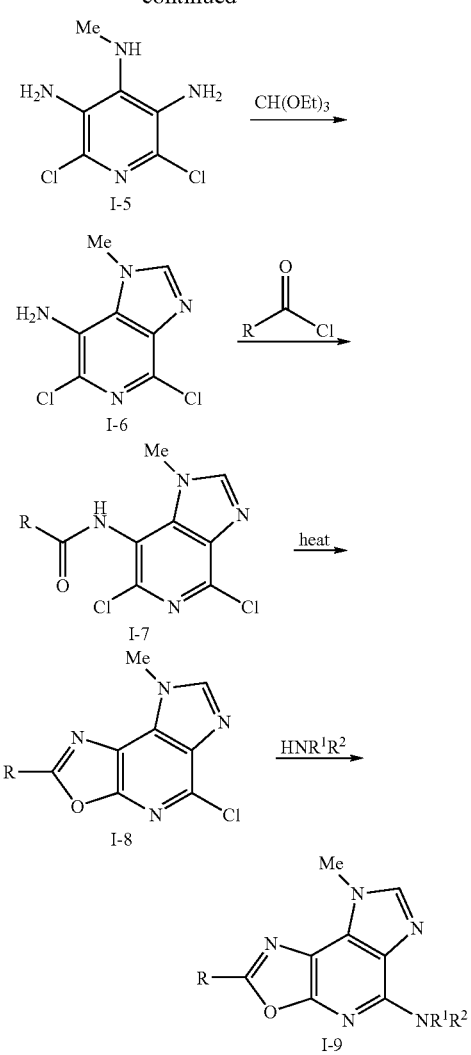

Reaction of I-7 to produce a fused thiazole system is outlined in Scheme II. Reaction of the intermediate amide I-7 with Lawesson's reagent at elevated temperature produces the thioamide which closes to produce II-1. Reaction with an amine produces the desired tricyclic compound II-2.

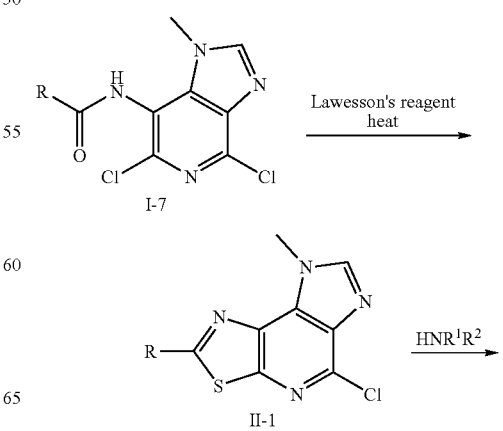

-continued

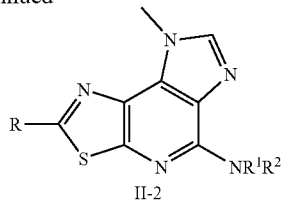
II-2

Fused thiazoles with substituents not readily incorporated by the procedure of Scheme II can be produced as depicted in Scheme III. Intermediate I-6 is reacted with potassium ethylthioxanthate to produce intermediate III-1. This potassium salt may be directly trapped with an alkyl halide or a alkyl halide containing synthetic resin to produce III-2. Reaction of III-2 with an amine produces the desired compound III-3. This route has the advantage of manipulating functionality at the other end of the molecule. Thus product III-3 can be oxidized to the sulfone III-4, which in addition to being a compound of Formula I, is also a useful intermediate. Displacement of the sulfone group by an amine at elevated temperature produces compound III-5, which is also a compound of Formula I. Alternatively hydrolysis of the sulfone group with aqueous sodium hydroxide followed by treatment with phosphorous oxychloride produces intermediate III-6 which upon reaction with either a boronic acid or organotin reagent with a palladium catalyst will produce compounds III-7 which are also a compound of Formula I.

Scheme III

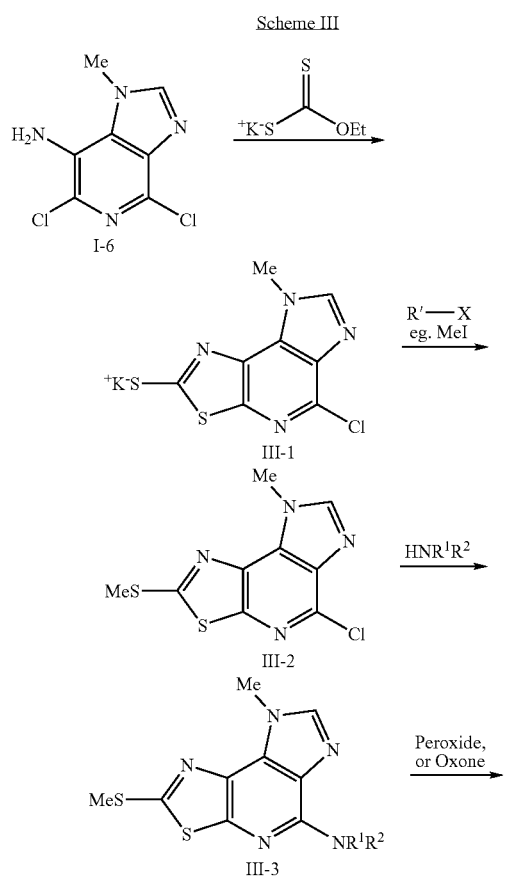

-continued

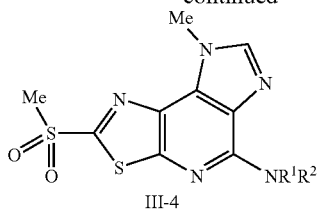

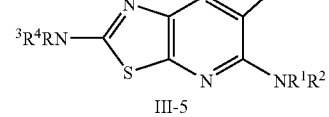

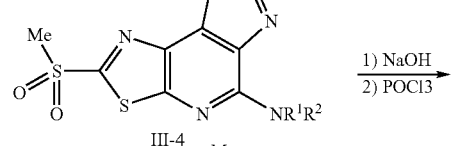

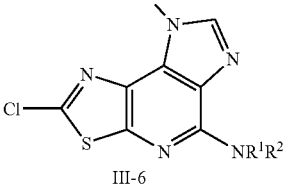

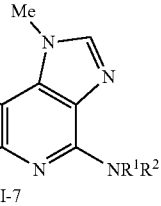

An additional useful method of preparing compounds of Formula I are described in scheme IV. Reaction of III-4 with hydrazine produces IV-1. Reaction with copper (II) bromide produces IV-2 which can be reacted in an analogous manner to III-6 to produce compounds III-7. Alternatively IV-1 can be condensed with ketoesters or diketones to produce compounds IV-3 which are also compounds of Formula 1.

Scheme IV

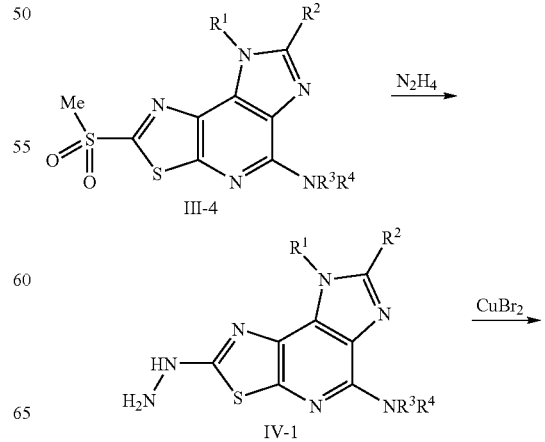

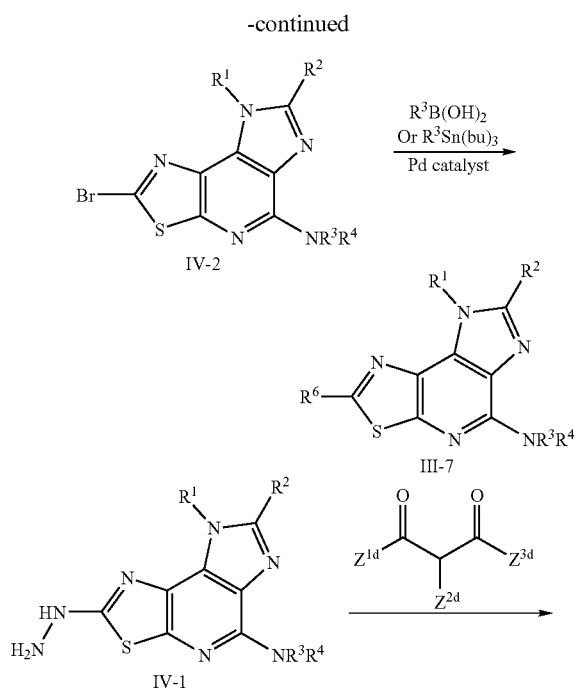
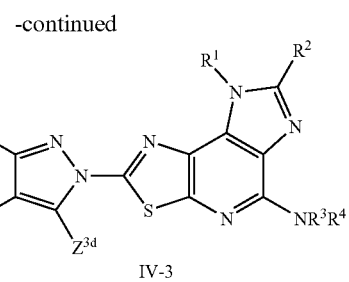

Additional useful methods for the preparation of compounds of Formula I are described in Scheme V. Reaction of thiophosgene with I-6 produces the isothiocyanate V-1. Reaction with either a substituted amine of ammonia provides the useful intermediate V-2. Treatment of V-2 with an appropriate base such as sodium methoxide at elevated temperatures provides intermediate V-3. Reaction of V-3 with an amine will produce compounds of structure III-5. In the case where V-1 was reacted with ammonia, further reaction by diazotization and treatment with copper (II) bromide will provide intermediate V-4. Reaction of V-4 with either a boronic acid or organotin reagent with a palladium catalyst will produce compounds V-5 which after reaction with an amine will produce compounds of structure III-7.

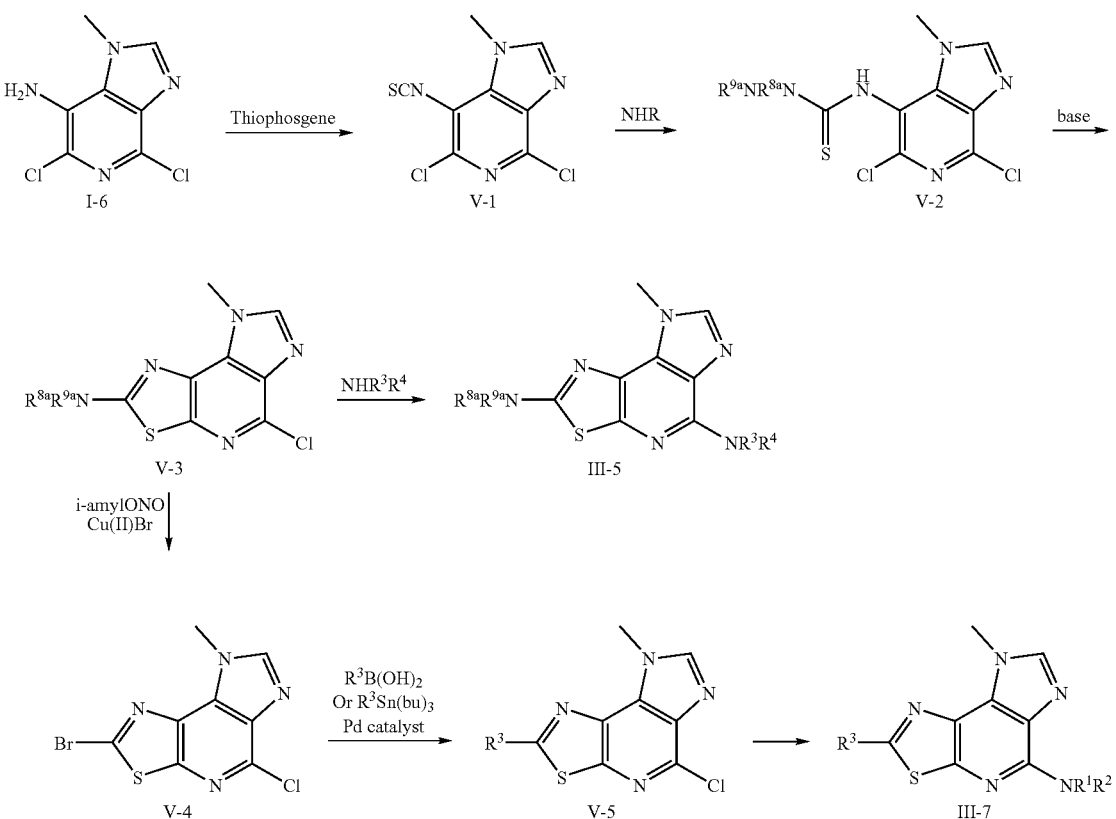

Alternatively compounds of Formula I can be produced by the method outlined in Scheme VI. Displacement of either a sulfoxide or a halide intermediate with the salt of an alcohol provides compounds V-1 which are also a compound of Formula I.

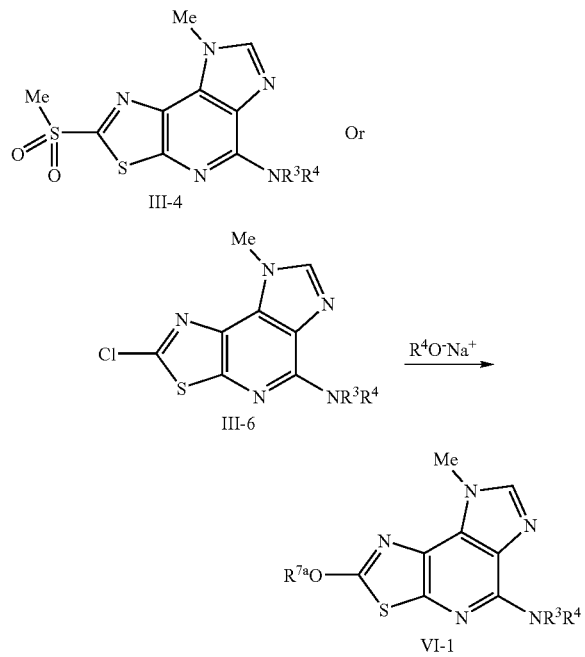

Alternatively compounds of Formula I can be produced by the method outlined in Scheme VII. Intermediate V-4 can be selectively carbonylated in the presence of a palladium catalyst, to produce carboxylic acid ester VII-1. Hydrolysis of the ester with aqueous sodium hydroxide produces carboxylic acid VII-2. Reaction with an amine produces compound VII-3 which is a compound of Formula I. Coupling of carboxylic acid VII-3 with amines produces amides VII-4 which are also compounds of Formula I.

In another embodiment, the present invention is directed to a process for preparing a compound of Formula (II) from a compound of Formula (III)

comprising reacting the compound of Formula (III) with an orthoester of formula $R^2$—$C(OR)_3$, wherein R is alkyl to obtain the compound of Formula (II), wherein $R^1$, $R^2$, and $R^5$ are as described elsewhere. The reaction may be performed in an inert solvent. The reaction is typically run at temperatures from above room temperature, such as about 40° C., to the boiling point of the solvent.

Suitable inert solvents include, but are not intended to be limited to, ether solvents such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether. Other solvents include, but are not intended to be limited to DMF, NMP, acetonitrile, alcoholic solvents such as methanol, ethanol, propanol, i-propanol, and butanol, and hydrocarbon solvents such as benzene, cyclohexane, pentane, hexane, hexanes, toluene, cycloheptane, methylcyclohexane, heptane, ethylbenzene, m-, o-, or p-xylene, mesitylene, octane, indane, nonane, or naphthalene.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| Abbreviations | |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc | tert-butoxycarbonyl |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | normal |
| Pd/C | Palladium on carbon |
| Ph | Phenyl |
| Pr | Propyl |
| PSI | Pounds per square inch |
| Ret Time | Retention time |
| rt or RT | Room temperature |
| sat. | Saturated |
| S-Tol-BINAP | (S)-(-)-2,2'-Bis(di-p-tolylphosphino)-1,1'-binapthyl |
| t | tert |
| TFA | Trifluoroacetic acid |
| THF | Tetrahydrofuran |
| YMC | YMC Inc, Wilmington, NC 28403 |

Example A1

8-Methyl-5-methylamino-2-phenyl-8H-imidazo[4,5-d]oxazolo[5,4-b]pyridine

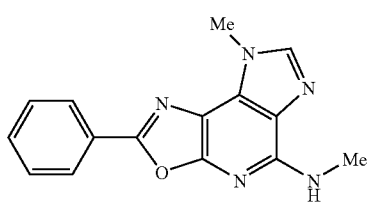

A1

A1.1

3,5-Dinitro-1H-pyridin-4-one

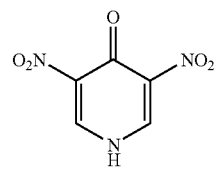

A1.1

4-Hydroxypyridine (40.0 g, 0.42 mol) was added portionwise to fuming nitric acid (140 ml) and sulfuric acid (500 ml). The resulting mixture was heated to 140° C. for 12 hours. The reaction mixture was cooled in an ice-bath and cautiously poured onto ice (500 ml). The yellow solid which precipitated was collected by filtration and dried under vacuum to yield A1.1 (70.0 g, 90%). $^1$H-NMR (DMSO-$d_6$) δ: 4.06 (2H, s). HPLC: 98.9%, ret. time=0.173 min., LC/MS $(M-H)^+$=184.

Scale-up:

250 g of 4-hydroxy pyridine was mixed with 3.2 L of concentrated sulfuric acid at 0–5° C. and 900 ml fuming nitric acid was added dropwise to it maintaining the temperature in the same range. The reaction mass was refluxed over night. The mass was cooled down and poured over crushed ice. It was then filtered and washed with 2 L of water, to provide A1.1 in 52% yield as a pale yellow solid.

A1.2

(3,5-Dinitro-pyridin-4-yl)methylamine

A1.2

A1.1 (10.0 g, 0.051 mol) was added portionwise to a mixture of phosphorus oxychloride (25 ml) and PCl$_5$ (17.0 g, 0.082 mol). The reaction mixture was heated to reflux under a nitrogen atmosphere for 12 hours. The reaction mixture was allowed to cool to room temperature and the phosphorus oxychloride removed in vacuo. The residue was suspended in dry THF (50 ml) and cooled to 0° C. Methylamine (32 ml, 2.0M in THF, 0.064 mol) was added dropwise over 20 minutes under a nitrogen atmosphere and the resulting solution was allowed to warm to room temperature over 1 hour. The reaction mixture was evaporated in vacuo and the residue suspended in ethyl acetate (200 ml) which was then filtered and the filtrate evaporated in vacuo to leave the crude product. The crude product was recrystallised from methanol (100 ml) to give A1.2 as a tan solid (7.2 g, 71% for two steps). HPLC: 98%, ret. time=1.58 min., LC/MS $(M+H)^+$=199.

Scale-up:

500 ml of POCl$_3$ was added to 150 g of A1.1. 250 g of PCl$_5$ was added to it and refluxed until it became clear solution. Then about half the quantity of POCl$_3$ was removed under vacuum. Then 3×100 ml xylene was added slowly to the reaction mass and stripped off. The residue was dissolved in 400 ml of xylene and 2 L of 2M solution of CH$_3$NH$_2$ was added to it slowly at 0–20° C. It was stirred at RT over night and the solvent was removed. The residue was recrystalized from methanol to provide A1.2 in 58% yield as a yellow to brown solid.

A1.3

2,6-Dichloro-N'-methyl-pyridine-3,4,5-triamine

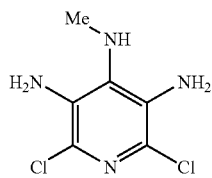

A1.3

A solution of A1.2 (60.0 g, 0.30 mol) in concentrated hydrochloric acid (300 ml) was heated to 90° C. Tin (II) chloride (85.0 g, 0.45 mol) was added portionwise over 1 hour with vigorous effervesence noted for the first equivalent of tin chloride added. The reaction mixture was heated for a further hour before the addition of more tin chloride (28.0 g, 0.15 mol) and continued heating for 2 more hours. The reaction mixture was cooled to 0° C. and cautiously basified with concentrated ammonium hydroxide (200 ml). The precipitated solid was filtered off and the filtrate extracted with ethyl acetate (5×200 ml). The combined organics were dried (MgSO4) and evaporated in vacuo to leave A1.3 as a brown solid (28.0 g, 46%). HPLC: 98%, ret. time=1.58 min., LC/MS (M+H)$^+$=208.

Scale-up:

100 g of A1.2 was dissolved in 600 ml con. HCl and cooled to 0° C. 170 g of SnCl$_2$.2H$_2$O was added portion wise. The reaction mixture was then heated to 90° C. in an oil bath for 2–3 hours. TLC indicated the complete consumption of the starting material and conversion to mono reduced product. A further portion of 170 g of SnCl$_2$.H$_2$O was added after raising the temperature to 100° C. The conversion of mono reduced product to final compound was ensured by TLC. Then the reaction mass was cooled down to 0° C. and cautiously basified with 1 L aqueous ammonia. The solid was filtered off and the filtrate was extracted with 6×500 ml of ethyl acetate. The paste like mass was again dissolved in 4×500 ml of ethyl acetate and the combined extracts were concentrated to afford 45 g of the crude. The crude on purification by filtration column gave 28 g (27%) of A1.3 as a yellow solid

A1.4

7-Amino-4,6-dichloro-1-methyl-1H-imidazo[4,5-c]pyridine

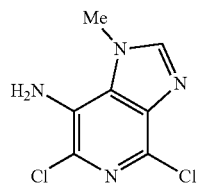

A1.4

Triethylorthoformate (25.0 ml, 0.15 mol) was added in one portion to a suspension of A1.3 (28 g, 0.14 mol) in dry acetonitrile (400 ml). The reaction mixture was heated to reflux for 4 hours and then cooled to room temperature. The reaction mixture was evaporated in vacuo to leave A1.4 as a brown powder. $^1$H-NMR (DMSO-d$_6$) δ: 8.20 (1H, s), 5.49 (2H, br. s), 4.07 (3H, s). HPLC: 98%, ret. time=0.78 min., LC/MS (M+H)$^+$=218.

A1.5

N-(4,6-Dichloro-1-methyl-1H-imidazole[4,5-c]pyridin-7-yl)benzamide

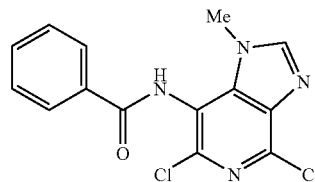

A1.5

Benzoyl chloride (1.2 g, 10.1 mmol) in dry acetonitrile (100 ml) was added in one portion to a suspension of the amine A1.4 (2.0 g, 9.2 mmol) and the resulting mixture was heated to 70° C. for six hours. The reaction mixture was concentrated in vacuo to leave the crude product which was precipitaed with methanol and filtered to give pure A1.5 (1.3 g, 44%). $^1$H-NMR (DMSO-d$_6$) δ: 8.30 (1H, s), 8.20 (2H, app. d, J=1 Hz), 7.87 (2H, app. t, J=6 Hz), 7.70 (2H, app. t, J=8 Hz), 5.55 (1H, s), 4.15 (3H, s). HPLC: 98%, ret. time=1.20 min., LC/MS (M+H)$^+$=320.

A1.6

5-Chloro-8-methyl-2-phenyl-8H-imidazo[4,5-d]oxazolo[5,4-b]pyridine

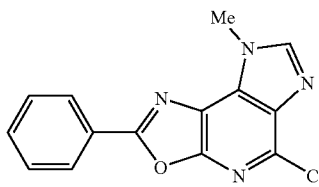

A1.6

Sodium carbonate (0.35 g, 3.3 mmol) was added in one portion to a solution of A1.5 (0.96 g, 3.0 mmol) in N,N-dimethylformamide (30 ml) and the reaction mixture was heated to 160° C. for 24 hours. The reaction mixture was cooled to room temperature and evaporated in vacuo. The residue was partioned between dichloromethane (50 ml) and water (50 ml). The separated organic layer was dried (MgSO$_4$) and evaporated in vacuo to leave the oxazole A1.6 (0.42 g, 49%). $^1$H-NMR (DMSO-d$_6$) δ: 8.34 (1H, s), 8.05 (2H, dd, J=6 Hz, 1 Hz), 7.50–7.45 (3H, m), 4.02 (3H, s). HPLC: 98%, ret. time=1.74 min., LC/MS (M+H)$^+$=285.

A1.7

8-Methyl-5-methylamino-2-phenyl-8H-imidazo[4,5-d]oxazolo[5,4-b]pyridine

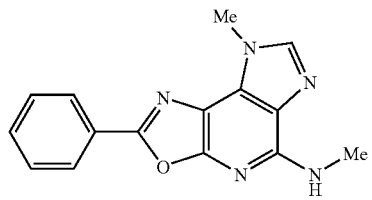

A1

Methylamine hydrochloride (104 mg, 1.54 mmol) and diisopropylethylamine (0.54 ml, 3.08 mmol) were each added in one portion to a suspension of A1.6 (200 mg, 0.7 mmol) in n-butanol (1 ml). The reaction mixture was heated in the microwave at 180° C. for 4 hours. The reaction mixture was evaporated in vacuo and the residue suspended between ethyl acetate (5 ml) and water (5 ml). The separated organic layer was dried (MgSO$_4$) and evaporated in vacuo to leave the crude product which was purified by prep. HPLC (reverse phase) to yield A1(38 mg, 19%). $^1$H-NMR (DMSO-d$_6$) δ: 8.20 (1H, s), 8.07–7.98 (2H, m), 7.49–7.38 (3H, m), 4.83 (3H, s), 4.08 (3H, s). HPLC: 98%, ret. time=1.64 min., LC/MS (M+H)$^+$=280.

A1 was crystallized from dilute aqueous hydrochloric acid to produce tan crystals suitable for x-ray diffraction. The x-ray experimental data is summarized in Table A1, and the graphic depiction of A1 is shown below.

TABLE A1

| Example A1 - HCl, H$_2$O | Crystal Form: H-1 | Comments: |
|---|---|---|
| Chemical formula: C$_{15}$H$_{14}$N$_5$O$^+$Cl$^-$ H$_2$O | | Crystallization solvent: aq. HCL Crystal description: thin tan elongated plates |
| a: 31.574(2) Å | α: 90° | Melting point: 136–45(t), 234–41(m) ° C. |
| b: 12.1289(9) Å | β: 104.367(4) ° | Measured indices: ±h, ±k, ±l |
| c: 8.7005(4) Å | γ: 90° | Temperature(° C.): +22 |
| V: 3227.7(3) Å$^3$ | Z: 8 | (2θ)max. °: 100(kccd) |
| Space group: C2/c | V/Z: 403 Å$^3$ | No. of independent reflections: 1544 |
| D$_{calc}$(g-cm$^{-3}$): 1.374 | | No. of observed reflections (I ≧ 3σ): 1097 |
| Absorption coefficient, cm$^{-1}$: 22.6 | | No. refined variables: 208 |
| Molecular volume (V$_m$): 275 | | R: 0.093 |
| Molecular Surface Area: 439 | | Rw: 0.136 |
| Packing coefficient (Z · V$_m$/V$_c$): 0.68 | | Avg. errors (C, N, O): .015 Å 1° Solvent: 1 H2O site Occupancy: 0.5 |

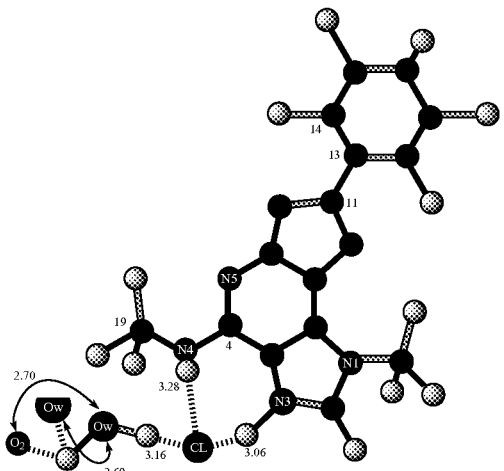

Solid state conformation and H-bonding in a monohydrate of Example A1, HCl salt. Ow20B is a neighboring water related by a 2-fold axis, while neighboring water Owi is related by an inversion center. The solvent site is 50% occupied.

Examples A2–A19

Examples A2–A19 was prepared in a similar manner to that used for Example A1. Intermediate A1.4 was reacted with the appropriate acid chloride to produce R$^1$ was substituted for benzoyl chloride in step A1.5. The appropriate amine (either free base or hydrochloride salt) to produce R$^2$ was substituted for methylamine hydrochloride in step A1.7. Example A15 and A16 were prepared from Example A3 by the method of Halberg, et. al. J. Org. Chem. (2000) 7984–7989. Example A19 was isolated as a side product during the preparation of example A17. Example A18 was obtained by reacting A19 with thionyl chloride in toluene to generate the acid chloride followed by methylamine addition.

TABLE A2

| Ex. | R$^1$ | R$^2$ | Name | HPLC Retention (min) | MS Reported |
|---|---|---|---|---|---|
| A2 | 4-fluorophenyl | —NHMe | 8-Methyl-5-methylamino-2-[4-fluorophenyl]-8H-imidazo[4,5-d]oxazolo[5,4-b]pyridine | 1.86$^1$ | 298.14 |
| A3 | 3-bromophenyl | —NHMe | 8-Methyl-5-methylamino-2-[3-bromophenyl]-8H-imidazo[4,5-d]oxazolo[5,4-b]pyridine | 1.94$^1$ | 358.05 |

TABLE A2-continued

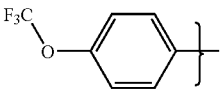

| Ex. | R¹ | R² | Name | HPLC Retention (min) | MS Reported |
|---|---|---|---|---|---|
| A4 | 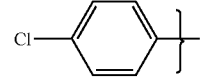 | —NHMe | 8-Methyl-5-methylamino-2-[4-trifluoromethoxyphenyl]8H-imidazo[4,5-d]oxazolo[5,4-b]pyridine | 3.87 | 364.12 |
| A5 | 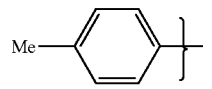 | —NHMe | 8-Methyl-5-methylamino-2-[4-chlorophenyl]-8H-imidazo[4,5-d]oxazolo[5,4-b]pyridine | 3.75 | 314.16 |
| A6 | 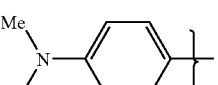 | —NHMe | 8-Methyl-5-methylamino-2-[4-methylphenyl]-8H-imidazo[4,5-d]oxazolo[5,4-b]pyridine | 3.56 | 294.16 |
| A7 | 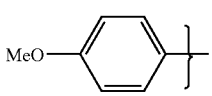 | —NHMe | 8-Methyl-5-methylamino-2-[4-(dimethylamino)phenyl]-8H-imidazo[4,5-d]oxazolo[5,4-b]pyridine | 3.26 | 323.23 |
| A8 | 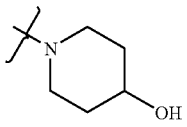 | —NHMe | 8-Methyl-5-methylamino-2-[4-methoxyphenyl]-8H-imidazo[4,5-d]oxazolo[5,4-b]pyridine | 3.29 | 310.17 |
| A9 | Ph- | 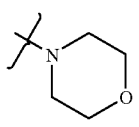 | 8-Methyl-5-[4-hydroxypiperidin-1-yl]-2-phenyl-8H-imidazo[4,5-d]oxazolo[5,4-b]pyridine | 1.720[1] | 350.64 |
| A10 | Ph- | 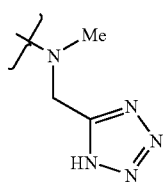 | 8-Methyl-5-[morpholin-1-yl]-2-phenyl-8H-imidazo[4,5-d]oxazolo[5,4-b]pyridine | 1.847[1] | 336.21 |
| A11 | Ph- |  | 8-Methyl-5-[(tetrazol-5-ylmethyl)methylamino]-2-phenyl-8H-imidazo[4,5-d]oxazolo[5,4-b]pyridine | 1.613[1] | 362.13 |

TABLE A2-continued

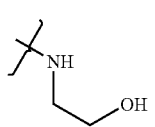

| Ex. | R[1] | R[2] | Name | HPLC Retention (min) | MS Reported |
|---|---|---|---|---|---|
| A12 | Ph- | 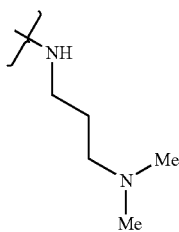 | 8-Methyl-5-[2-hydroxyethylamino]-2-phenyl-8H-imidazo[4,5-d]oxazolo[5,4-b]pyridine | 1.640[1] | 280.12 |
| A13 | Ph- | 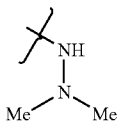 | 8-Methyl-5-[3-(dimethylamino)propylamino]-2-phenyl-8H-imidazo[4,5-d]oxazolo[5,4-b]pyridine | 1.363[1] | 351.28 |
| A14 | Ph- | 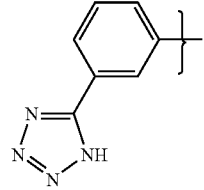 | 8-Methyl-5-[N'N'-dimethylhydrazino]-2-phenyl-8H-imidazo[4,5-d]oxazolo[5,4-b]pyridine | 1.280[1] | 309.37 |
| A15 | 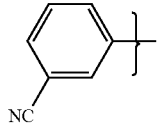 | —NHMe | 8-Methyl-5-methylamino-2-[3-(tetrazol-5-yl)phenyl]-8H-imidazo[4,5-d]oxazolo[5,4-b]pyridine | 1.483[1] | 348.19 |
| A16 | 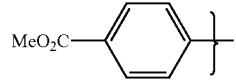 | —NHMe | 8-Methyl-5-methylamino-2-[3-cyanophenyl]-8H-imidazo[4,5-d]oxazolo[5,4-b]pyridine | 1.563[1] | 306.131 |
| A17 | 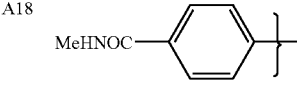 | —NHMe | 8-Methyl-5-methylamino-2-[4-(methoxycarbonyl)phenyl]-8H-imidazo[4,5-d]oxazolo[5,4-b]pyridine | 3.487 | 338.16 |
| A18 |  | —NHMe | 8-Methyl-5-methylamino-2-[4-(methylaminocarbonyl)phenyl]-8H-imidazo[4,5-d]oxazolo[5,4-b]pyridine | 2.697 | 337.35 |

TABLE A2-continued

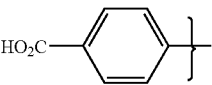

| Ex. | R¹ | R² | Name | HPLC Retention (min) | MS Reported |
|---|---|---|---|---|---|
| A19 | HO₂C—⟨phenyl⟩— | —NHMe | 8-Methyl-5-methylamino-2-[4-(carboxy)phenyl]-8H-imidazo[4,5-d]oxazolo[5,4-b]pyridine | 3.077 | 324.14 |

[1] LC-MS Conditions: Column YMC ODS-A S7 C28 3.0 × 50 mm; 2 min gradient from 9:1 water/MeOH with 0.1% TFA; flow rate 5 mL/min; injection volume 10 μL.

Example A20

8-Methyl-5-methylamino-2-[3-[2-(tetrazol-5yl)(E)-ethenyl]phenyl]-8H-imidazo[4,5-d]oxazolo[5,4-b]pyridine

Example A21 & A22

8-Methyl-5-methylamino-2-[3-[2-(tetrazol-5-yl)ethyl]phenyl]-8H-imidazo[4,5-d]oxazolo[5,4-b]pyridine and 8-methyl-5-dimethylamino-2-[3-[2-(tetrazol-5-yl)ethyl]phenyl]-8H-imidazo[4,5-d]oxazolo[5,4-b]pyridine

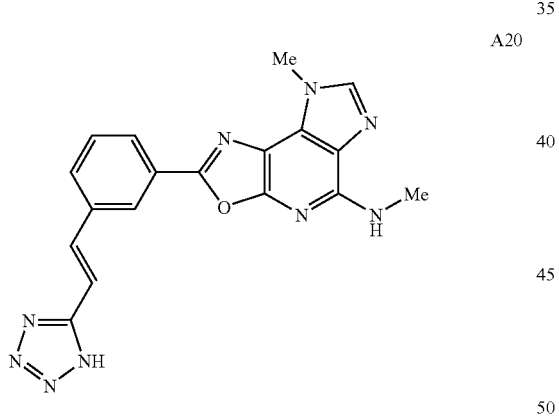

A20

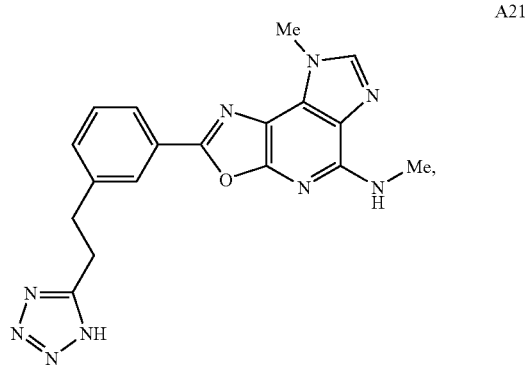

A21

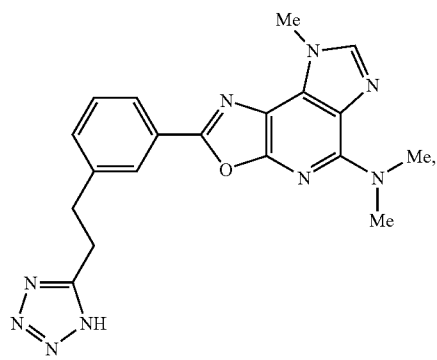

A22

Vinyl tetrazole (21 mg, 0.21 mmol) was added in one portion to a solution of bromide A3 (51 mg, 0.14 mmol) in dry DMF (1 ml). Palladium acetate (1 mg, 1.4×10⁻⁵ mol), phosphorus acid tris(4-methylphenyl)ester (1 mg, 2.8×10⁻⁵ mol) and triethylamine (0.02 ml, 0.14 mmol) were each added in one portion and the resulting mixture heated in the microwave at 120° C. for 900 s. The DMF was removed in vacuo and the residue acidified with 1N hydrochloric acid (2 ml). The aqueous phase was extracted with ethyl acetate (3×20 ml), the combined organics dried (MgSO₄) and evaporated in vacuo to leave a crude residue which was purified by preparative hplc to give A20 (38 mg, 42%) as a white solid. HPLC: 98%, ret. time=1.57 min., LC/MS (M+H)⁺=374.17.

10% Palladium on carbon (200 mg) was added in one portion to a solution of A20 (190 mg, 0.51 mmol) in dry methanol (25 ml) under a nitrogen atmosphere. The reaction vessel was repeatedly (4×) evacuated and purged with hydrogen and allowed to stir at room temperature for 12 hours. The reaction mixture was filtered through a pad of celite and washed with copious amounts of methanol. Evaporation of the solvent in vacuo afforded the crude product which was purified by preparative HPLC to give A21 as a tan brown solid (128 mg, 67%). HPLC: 98%, ret. time=1.41 min., LC/MS (M+H)$^+$=376.15.

A22 was prepared in a similar manner to A21 starting from the dimethylamine-olefin precursor: (36 mg, 45%). HPLC: 98%, ret. time=1.58 min., LC/MS (M+H)$^+$=390.14.

Examples A23–A27

Examples A24 to A27 are listed in Table A3. These examples were prepared from the starting Example listed, using the method described for Examples A20 and A21.

TABLE A3

| Ex. | R$^1$ | Starting Example/ Methods | Name | HPLC Retention (min) | MS Reported |
|---|---|---|---|---|---|
| A23 | NC-CH=CH- | A31/A20 | 8-Methyl-5-methylamino-2-[3-(2-cyano-(E)-ethenyl)phenyl]-8H-imidazo[4,5-d]oxazolo[5,4-b]pyridine | 1.633 | 331.172 |
| A24 | HO$_2$C-CH$_2$CH$_2$- | A3/A20, A21 | 8-Methyl-5-methylamino-2-[3-(2-carboxyethyl) phenyl]-8H-imidazo[4,5-d]oxazolo[5,4-b]pyridine | 1.560 | 352.17 |
| A25 | EtO$_2$C-C(Me)=CH- | A3/A20 | 8-Methyl-5-methylamino-2-[3-(2-ethoxycarbonyl-(E)-prop-2-enyl)phenyl]-8H-imidazo[4,5-d]oxazolo[5,4-b]pyridine | 2.007 | 392.17 |
| A26 | HO$_2$C-CH(Me)-CH$_2$- | A24/A21 | 8-Methyl-5-methylamino-2-[3-(2-carboxy-(E)-prop-2-enyl)phenyl]-8H-imidazo[4,5-d]oxazolo[5,4-b]pyridine | 1.670 | 366.21 |

Examples A27–A28 were prepared in a similar manner to that used for Example A1. Intermediate A1.4 was reacted with the appropriate acid chloride to produce $R^1$ in step A1.5. The appropriate amine (either free base or hydrochloride salt) to produce $R^2$ was substituted for methylamine hydrochloride in step A1.7.

TABLE A4

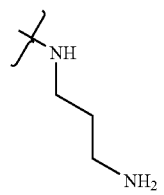

| Ex. | $R^1$ | $R^2$ | Name | HPLC Retention (min) | MS Reported |
|---|---|---|---|---|---|
| A27 | Ph- | ⟨NH-CH2CH2CH2-NH2⟩ | 4-Methyl-7-[3-aminopropylamino]-2-phenyl-4H-imidazo[4,5-d]oxazolo[4,5-b]pyridine | 1.340 | 323.41 |
| A28 | Ph- | ⟨NH-CH2CH2CH2-NHMe⟩ | 4-Methyl-7-[3-methylaminopropylamino]-2-phenyl-4H-imidazo[4,5-d]oxazolo[4,5-b]pyridine | 1.317 | 337.46 |

Examples A29–A57

Examples A29–A57 were prepared in a similar manner to that used for Example A1. Intermediate A1.4 was reacted with the appropriate acid chloride to produce $R^1$ substituted for benzoyl chloride in step A1.5. The appropriate amine (either free base or hydrochloride salt) to produce $R^2$ was substituted for methylamine hydrochloride in step A1.7.

TABLE A5

| Ex. | $R^1$ | $R^2$ | Name | HPLC Retention (min) | MS Reported |
|---|---|---|---|---|---|
| A29 | iPr (Me2CH-) | —NHMe | 8-Methyl-5-methylamino-2-(2-methylethyl)-8H-imidazo[4,5-d]oxazolo[5,4-b]pyridine | 1.28[1] | 246.31 |
| A30 | iPr (Me2CH-) | —NMe2 | 8-Methyl-5-dimethylamino-2-(2-methylethyl)-8H-imidazo[4,5-d]oxazolo[5,4-b]pyridine | 1.52[1] | 260.32. |

TABLE A5-continued

| Ex. | R¹ | R² | Name | HPLC Retention (min) | MS Reported |
|---|---|---|---|---|---|
| A31 | Me-C(Me)(Me)-CH₂- (neopentyl) | NHMe | 8-Methyl-5-methylamino-2-(2,2-dimethylpropyl)-8H-imidazo[4,5-d]oxazolo[5,4-b]pyridine | 1.53[2] | 274.38 |
| A32 | cyclopentylmethyl | NHMe | 8-Methyl-5-methylamino-2-(cyclopentylmethyl)-8H-imidazo[4,5-d]oxazolo[5,4-b]pyridine | 1.66[1] | 286.37 |
| A33 | 2-furyl | —NHMe | 8-Methyl-5-methylamino-2-(2-furyl)-8H-imidazo[4,5-d]oxazolo[5,4-b]pyridine | 1.31[1] | 270.33 |
| A34 | 2,4-dimethylphenyl | —NHMe | 8-Methyl-5-methylamino-2-(2,4-dimethylphenyl)-8H-imidazo[4,5-d]oxazolo[5,4-b]pyridine | 3.77[3] | 308.41 |
| A35 | 3,4-dimethylphenyl | —NHMe | 8-Methyl-5-methylamino-2-(3,4-dimethylphenyl)-8H-imidazo[4,5-d]oxazolo[5,4-b]pyridine | 3.74[3] | 308.41 |
| A36 | 3-methylphenyl | —NHMe | 8-Methyl-5-methylamino-2-(3-methylphenyl)-8H-imidazo[4,5-d]oxazolo[5,4-b]pyridine | 3.56[3] | 294.44 |
| A37 | 3-trifluoromethyl-4-methylphenyl | —NHMe | 8-Methyl-5-methylamino-2-(3-trifluoromethyl-4-methylphenyl)-8H-imidazo[4,5-d]oxazolo[5,4-b]pyridine | 3.99[3] | 362.40 |
| A38 | 3-trifluoromethylphenyl | —NHMe | 8-Methyl-5-methylamino-2-(3-trifluoromethylphenyl)-8H-imidazo[4,5-d]oxazolo[5,4-b]pyridine | 3.77[3] | 348.36 |

TABLE A5-continued

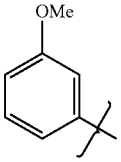

| Ex. | R¹ | R² | Name | HPLC Retention (min) | MS Reported |
|---|---|---|---|---|---|
| A39 | 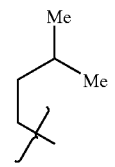 OMe | —NHMe | 8-Methyl-5-methylamino-2-(3-methoxyphenyl)-8H-imidazo[4,5-d]oxazolo[5,4-b]pyridine | 3.37³ | 310.41 |
| A40 | 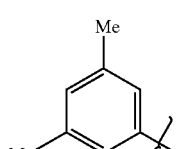 Me, Me | —NHMe | 8-Methyl-5-methylamino-2-(2-methylbutyl)-8H-imidazo[4,5-d]oxazolo[5,4-b]pyridine | 3.26³ | 274.45 |
| A41 | 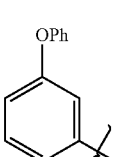 Me, Me | —NHMe | 8-Methyl-5-methylamino-2-(3,5-dimethylphenyl)-8H-imidazo[4,5-d]oxazolo[5,4-b]pyridine | 3.83³ | 308.40 |
| A42 | 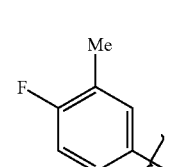 OPh | —NHMe | 8-Methyl-5-methylamino-2-(3-phenyloxyphenyl)-8H-imidazo[4,5-d]oxazolo[5,4-b]pyridine | 4.04³ | 372.42 |
| A43 | 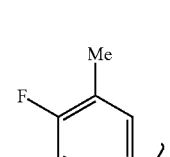 Me, F | —NHMe | 8-Methyl-5-methylamino-2-(3-methyl-4-fluorophenyl)-8H-imidazo[4,5-d]oxazolo[5,4-b]pyridine | 3.70³ | 372.42 |
| A44 | Me, F | —NHEt | 8-Methyl-5-ethylamino-2-(3-methyl-4-fluorophenyl)-8H-imidazo[4,5-d]oxazolo[5,4-b]pyridine | 3.89³ | 326.39 |
| A45 | 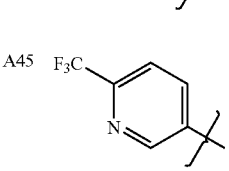 F₃C, N | —NHMe | 8-Methyl-5-methylamino-2-(2-trifluoromethylpyridin-5-yl)-8H-imidazo[4,5-d]oxazolo[5,4-b]pyridine | 3.37³ | 349.40 |

TABLE A5-continued

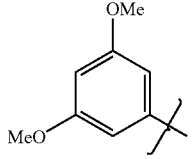

| Ex. | R¹ | R² | Name | HPLC Retention (min) | MS Reported |
|---|---|---|---|---|---|
| A46 |  | —NHMe | 8-Methyl-5-methylamino-2-(3,5-dimethoxyphenyl)-8H-imidazo[4,5-d]oxazolo[5,4-b]pyridine | 3.53² | 340.43 |
| A47 | 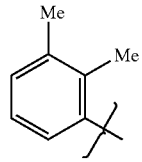 | —NHMe | 8-Methyl-5-methylamino-2-(trans-2-phenyl cyclopropyl)-8H-imidazo[4,5-d]oxazolo[5,4-b]pyridine | 3.39² | 320.43 |
| A48 | 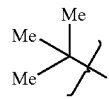 | —NHMe | 8-Methyl-5-methylamino-2-(2,3-dimethylphenyl)-8H-imidazo[4,5-d]oxazolo[5,4-b]pyridine | 3.61⁴ | 308.47 |
| A49 | 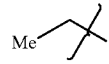 | —NHMe | 8-Methyl-5-methylamino-2-(2,2-dimethylethyl)-8H-imidazo[4,5-d]oxazolo[5,4-b]pyridine | 2.60⁵ | 260.1 |
| A50 | 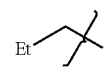 | —NHMe | 8-Methyl-5-methylamino-2-ethyl-8H-imidazo[4,5-d]oxazolo[5,4-b]pyridine | 1.87⁵ | 232.5 |
| A51 | 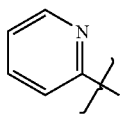 | —NHMe | 8-Methyl-5-methylamino-2-propyl-8H-imidazo[4,5-d]oxazolo[5,4-b]pyridine | 2.25⁵ | 246.5 |
| A52 | Ph- | —NHCH₂Ph | 8-Methyl-5-(Phenylmethylamino)-2-phenyl-8H-imidazo[4,5-d]oxazolo[5,4-b]pyridine | 3.73⁵ | 3.56.1 |
| A53 | 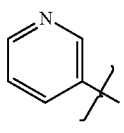 | —NHMe | 8-Methyl-5-methylamino-2-(pyridine-2-yl)-8H-imidazo[4,5-d]oxazolo[5,4-b]pyridine | 2.08⁵ | 281.1 |
| A54 | 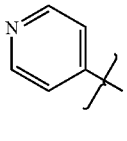 | —NHMe | 8-Methyl-5-methylamino-2-(pyridine-3-yl)-8H-imidazo[4,5-d]oxazolo[5,4-b]pyridine | 1.75⁵ | 281.1 |
| A55 |  | —NHMe | 8-Methyl-5-methylamino-2-(pyridine-4-yl)-8H-imidazo[4,5-d]oxazolo[5,4-b]pyridine | 1.44⁵ | 281.1 |
| A56 | Ph- | —NHiPr | 8-Methyl-5-(2-methylethylamino)-2-phenyl-8H-imidazo[4,5-d]oxazolo[5,4-b]pyridine | 3.77² | 308.24 |

TABLE A5-continued

| Ex. | R¹ | R² | Name | HPLC Retention (min) | MS Reported |
|-----|-----|-----|------|----------------------|-------------|
| A57 | Me- | —NHMe | 8-Methyl-5-methylamino-2-methyl-8H-imidazo[4,5-d]oxazolo[5,4-b]pyridine | 1.46[5] | 218.4 |

HPLC column conditions-
[1]Column: Phenomenex 25 ® Solvent A: 10% MeOH/water 0.1% TFA, Solvent B: 90% MeOH/water, 0.1% TFA.
[2]Column: YMC ODSA S7 3.0 mm × 50 mm (2 min grad) Solvent A: 10% MeOH/water 0.1% TFA, Solvent B: 90% MeOH/water, 0.1% TFA.
[3]Column: Shimadzu VP-ODS ®, 4.6 × 50 mm, 4 min grad, Solvent A: 10% MeOH/water 0.1% TFA, Solvent B: 90% MeOH/water, 0.1% TFA.
[4]Column: Phenomenex Prime ® 4.6 × 50 mm (4 min grad) A: 10% MeOH/water 0.1% TFA, Solvent B: 90% MeOH/water, 0.1% TFA.
[5]Column: Chromolith SpeedROD ® 4.6 × 50 mm (4 min grad) Solvent A: 10% MeOH-90% H₂O 0.2% phosphoric acid Solvent B: 90% MeOH-10% H₂O-0.2% phosphoric acid.

Example A58

8-Methyl-5-(2-aminoethylamino)-2-phenyl-8H-imidazo[4,5-d]oxazolo[5,4-b]pyridine

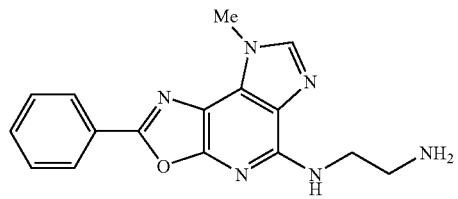

A58

Ethylenediamine (270 mg, 4.5 mmol) was added in one portion to a suspension of A1.6 (50 mg, 0.18 mmol) in ethanol (1 ml). The reaction mixture was heated in an oilbath set at 85° C. for 3 days. The reaction mixture was evaporated in vacuo and the residue suspended between ethyl acetate (5 ml) and water (5 ml). The separated organic layer was dried (MgSO₄) and evaporated in vacuo to leave the crude product which was purified by flash column chromatography to yield A58 (36 mg, 64%). ¹H-NMR (D₃COD) δ: 8.17–8.15 (2H, m), 8.02 (1H, s), 7.55–7.51 (3H, m), 4.20 (2H, s), 3.70 (2H, J=6.32, t). 3.01 (2H, J=6.05 m t). HPLC: 98%, ret. time=2.11 min., Column: Chromolith SpeedROD® 4.6×50 mm (4 min gradient) Solvent A: 10% MeOH, 90% H₂O, 0.2% phosphoric acid; Solvent B: 90% MeOH, 10% H₂O, 0.2% phosphoric acid; LC/MS (M+H)⁺=309.6

Examples A59–A72 were prepared in a similar manner to that used for Example A1 step A1.7. Intermediate A1.6 was reacted with the appropriate amine (either free base or hydrochloride salt) to produce R².

TABLE A6

| Ex. | R² | Name |
|-----|-----|------|
| A59 | ⤳NH–CH₂CH₂CH₂–NMe₂ | 8-Methyl-5-[3-dimethylaminopropylamino]-2-phenyl-8H-imidazo[4,5-d]oxazolo[5,4-b]pyridine |

TABLE A6-continued

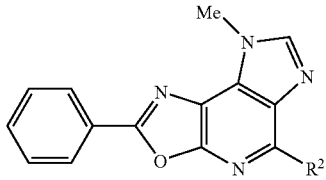

| Ex. | R² | Name |
|---|---|---|
| A60 | —NHEt | 8-Methyl-5-[ethylamino]-2-phenyl-8H-imidazo[4,5-d]oxazolo[5,4-b]pyridine |
| A61 |  | 8-Methyl-5-[(2-hydroxypropyl)amino]-2-phenyl-8H-imidazo[4,5-d]oxazolo[5,4-b]pyridine |
| A62 | 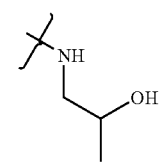 | 8-Methyl-5-[cyclopentylamino]-2-phenyl-8H-imidazo[4,5-d]oxazolo[5,4-b]pyridine |
| A63 | 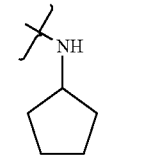 | 8-Methyl-5-[2-dimethylaminoethylamino]-2-phenyl-8H-imidazo[4,5-d]oxazolo[5,4-b]pyridine |
| A64 | 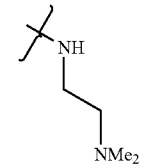 | 8-Methyl-5-[((tetrahydrofuran-2-yl)methyl)amino]-2-phenyl-8H-imidazo [4,5-d]oxazolo[5,4-b]pyridine |
| A65 | 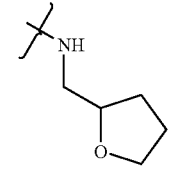 | 8-Methyl-5-[2-(acetylamino)ethylamino]-2-phenyl-8H-imidazo[4,5-d]oxazolo[5,4-b]pyridine |
| A66 | 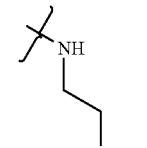 | 8-Methyl-5-[(5-hydroxy-3-oxypentyl)amino]-2-phenyl-8H-imidazo[4,5-d]oxazolo[5,4-b]pyridine |
| A67 | 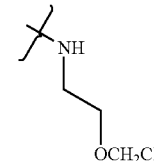 | 8-Methyl-5-[2-(1-pyrrolidinyl)ethylamino]-2-phenyl-8H-imidazo[4,5-d]oxazolo[5,4-b]pyridine |

TABLE A6-continued

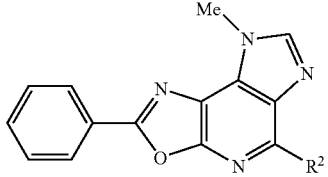

| Ex. | R² | Name |
|---|---|---|
| A68 | 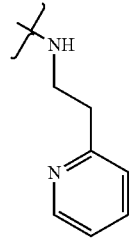 | 8-Methyl-5-[2-(pyridin-2-yl))ethylamino]-2-phenyl-8H-imidazo[4,5-d]oxazolo[5,4-b]pyridine |
| A69 | 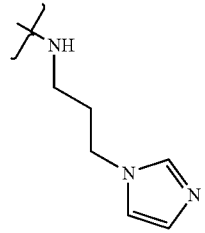 | 8-Methyl-5-[3-(imidazol-1-yl)propylamino]-2-phenyl-8H-imidazo[4,5-d]oxazolo[5,4-b]pyridine |
| A70 | 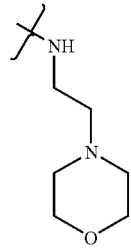 | 8-Methyl-5-[2-(morpholin-4-yl)ethylamino]-2-phenyl-8H-imidazo[4,5-d]oxazolo[5,4-b]pyridine |
| A71 | 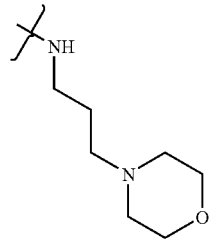 | 8-Methyl-5-[3-(morphylin-4-yl)propylamino]-2-phenyl-8H-imidazo[4,5-d]oxazolo[5,4-b]pyridine |
| A72 | 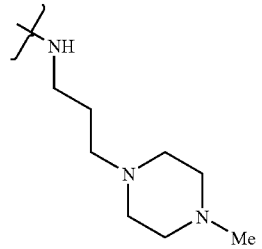 | 8-Methyl-5-[3-(1-methyl-4-piperazinyl)propylamino]-2-phenyl-8H-imidazo[4,5-d]oxazolo[5,4-b]pyridine |

Example A73

8-Methyl-5-methylamino-2-(3-aminomethyl)phenyl-8H-imidazo[4,5-d]oxazolo[5,4-b]pyridine

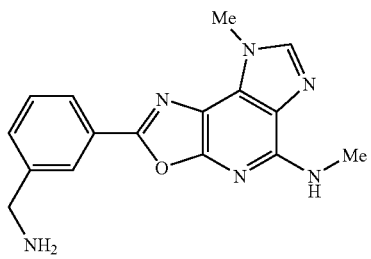

A73

A16 (2.10 g, 7.0 mmol) was suspended in THF (70 mL) and stirred at room temperature. Lithium aluminum hydride 1.0 molar solution in THF (7 mL, 7.0 mmol) was added dropwise. The reaction mixture was observed to be exothermic, and allowed to stir at room temperature overnight. HPLC/LC MS showed complete conversion to product. The reaction mixture was carefully quenched by the sequential addition of 7 mL of water, followed by 7 mL of 15% aqueous sodium hydroxide, followed by 21 mL of water followed by stirring for 1 h. The reaction mixture was filtered though a pad of Celite® and the solvent removed under vacuum. The crude product was triturated with hexane, filtered and air dried to yield 1.91 g of crude product. A second trituration with methanol/THF yielded 1.8 g (85%) of A73. $^1$H NMR (CD$_3$OD) δ 8.28 (1H, s), 8.20 (1H, d), 8.14 (1H, s), 7.76–7.60 (3H, m), 4.21 (2H, s) 3.13 (3H, s). LC-MS Ret. Time=1.05 min. Column: Phenomenex® S5. 4.6×30 mm(2 min gradient/5 mL/min flow rate) Solvent A: 10% MeOH, 90% H$_2$O, 0.1% TFA, Solvent B: 90% MeOH, 10% H$_2$O, ), 1% TFA. M$^+$H=309.24.

Example A74

8-Methyl-5-methylamino-2-[(3-acetylaminomethyl)phenyl]-8H-imidazo[4,5-d]oxazolo[5,4-b]pyridine

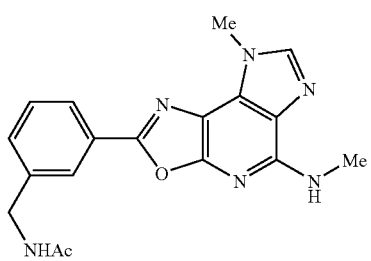

A74

A73 (30 mg, 0.097 mmol), acetic anhydride (0.5 mL, 5.3 mmol), and pyridine (0.5 mL, 6.1 mmol) were added sequentially to THF (5 mL) and stirred at room temperature overnight. HPLC/MS confirmed the reaction had consumed all starting material. The reaction mixture was concentrated under vacuum, and purified by reverse phase HPLC to provide 20.3 mg (60%) of A74. $^1$H NMR (CD$_3$OD) δ: 8.20 (s, 1H), 7.90–7.80 (m, 2H), 7.54–7.20 (m, 2H), 4.34 (s, 2H), 4.04 (s, 3H), 1.96 (s, 3H). LCMS: Ret. Time=1.27 min. Column: Phenomenex® S5. 4.6×30 mm(2 min gradient/5 mL/min flow rate) Solvent A: 10% MeOH, 90% H$_2$O, 0.1% TFA, Solvent B: 90% MeOH, 10% H$_2$O, ), 1% TFA. M$^+$H=351.28.

Examples A75–A160

Examples A75–A160 described in Table A7 were prepared by a solution phase library methodology. To an individual well of a 48-position MiniBlock® reactor was added 112 μL of a 0.50 M solution of the appropriate carboxylic acid in dimethylacetamide (DMA) (0.056 mmol, 1.7 equiv); 60 μL of a 0.93 M solution of 1-hydroxybenzotriazole in DMA (0.056 mmol, 1.7 equiv); 46 mg of polystyrene-supported N,N'-diisopropylcarbodiimide (PS-DIC) (1.21 mmol/g, 1.7 equiv); and 330 μL of 1,2-dichloroethane (DCE). The reactor was agitated via orbital shaker for 10 min. Finally, 300 μL of a 0.11 M solution of A73 in DMA (0.033 mmol, 1.0 equiv) was added to the reactor well, and the reactor was agitated for 14 h at rt. The crude product was filtered, rinsed with additional DMA, then purified by standard preparative HPLC-MS (H$_2$O/MeOH/0.1% TFA, gradient 35–90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS H$_2$O/MeOH/0.1% TFA, gradient 10–90% MeOH over 4 min, 4 mL/min, 4.6×50 mm 5 um Phenomenex® Primesphere column Retention time and observed mass are reported.

For those compounds which were derived from amino acid (Example 143–Example 156) acid labile protecting groups were utilized. These examples were coupled as described above and the protecting group(s) were removed by being taken up in 1 mL of 2:1/DCE:TFA for 1 hour, then concentrated again. Purification was performed by standard preparative HPLC-MS as described above.

TABLE A7

| Ex. | R¹ | Name | HPLC Retention (min) | MS Reported |
|---|---|---|---|---|
| A75 | (2,2-dimethyl substituent)–C(O)–phenyl | 8-Methyl-5-methylamino-2-[3-(phenylcarbonylaminomethyl)phenyl]-8H-imidazo[4,5-d]oxazolo[5,4-b]pyridine | 3.01 | 413.04 |
| A76 | –C(O)–Et | 8-Methyl-5-methylamino-2-[3-(ethylcarbonylaminomethyl)-phenyl]-8H-imidazo[4,5-d]oxazolo[5,4-b]pyridine | 2.71 | 365.06 |
| A77 | –C(O)–pyrazin-2-yl | 8-Methyl-5-methylamino-2-[3-(pyrazin-2-ylcarbonylaminomethyl)phenyl]-8H-imidazo[4,5-d]oxazolo[5,4-b]pyridine | 2.78 | 415.04 |
| A78 | –C(O)–(1-cyanocyclopropyl) | 8-Methyl-5-methylamino-2-[3-(1-cyanocyclopropylcarbonylaminomethyl)-phenyl]-8H-imidazo[4,5-d]oxazolo[5,4-b]pyridine | 2.86 | 402.03 |
| A79 | –C(O)–(1-phenylcyclopropyl) | 8-Methyl-5-methylamino-2-[3-(1-phenylcyclopropylcarbonylaminomethyl)-phenyl]-8H-imidazo[4,5-d]oxazolo[5,4-b]pyridine | 3.46 | 453.00 |
| A80 | –C(O)–(trans-2-phenylcyclopropyl) | 8-Methyl-5-methylamino-2-[3-((trans-2-phenylcyclopropyl)carbonylaminomethyl)-phenyl]-8H-imidazo[4,5-d]oxazolo[5,4-b]pyridine | 3.35 | 453.09 |
| A81 | –C(O)–cyclobutyl | 8-Methyl-5-methylamino-2-[3-(cyclobutylcarbonylaminomethyl)phenyl]-8H-imidazo[4,5-d]oxazolo[5,4-b]pyridine | 3.03 | 391.16 |
| A82 | –C(O)–cyclopentyl | 8-Methyl-5-methylamino-2-[3-(cyclopentylcarbonylaminomethyl)phenyl]-8H-imidazo[4,5-d]oxazolo[5,4-b]pyridine | 3.05 | 405.05 |
| A83 | –C(O)–(1-phenylcyclopentyl) | 8-Methyl-5-methylamino-2-[3-(1-phenylcyclopentylcarbonylaminomethyl)-phenyl]-8H-imidazo[4,5-d]oxazolo[5,4-b]pyridine | 3.57 | 481.07 |

TABLE A7-continued

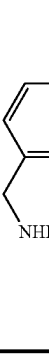

| Ex. | R¹ | Name | HPLC Retention (min) | MS Reported |
|---|---|---|---|---|
| A84 | 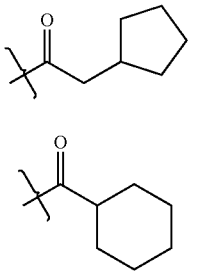 | 8-Methyl-5-methylamino-2-[3-(cyclopentylmethylcarbonylaminomethyl)-phenyl]-8H-imidazo[4,5-d]oxazolo[5,4-b]pyridine | 3.23 | 419.07 |
| A85 | 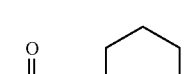 | 8-Methyl-5-methylamino-2-[3-(cyclohexylcarbonylaminomethyl)phenyl]-8H-imidazo[4,5-d]oxazolo[5,4-b]pyridine | 3.23 | 419.05 |
| A86 | 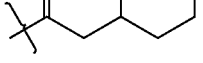 | 8-Methyl-5-methylamino-2-[3-(cyclohexylmethylcarbonylaminomethyl)-phenyl]-8H-imidazo[4,5-d]oxazolo[5,4-b]pyridine | 3.40 | 433.07 |
| A87 | 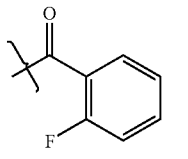 | 8-Methyl-5-methylamino-2-[3-((2-fluorophenyl)carbonylaminomethyl)-phenyl]-8H-imidazo[4,5-d]oxazolo[5,4-b]pyridine | 3.04 | 431.00 |
| A88 | 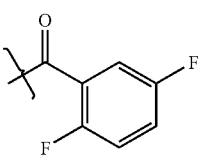 | 5-Methyl-8-methylamino-2-[3-((2,5-difluorophenyl)carbonylaminomethyl)-phenyl]-8H-imidazo[4,5-d]oxazolo[5,4-b]pyridine | 3.13 | 448.98 |
| A89 | 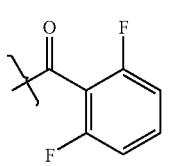 | 8-Methyl-5-methylamino-2-[3-((2,6-difluorophenyl)carbonylaminomethyl)-phenyl]-8H-imidazo[4,5-d]oxazolo[5,4-b]pyridine | 2.86 | 449.02 |
| A90 | 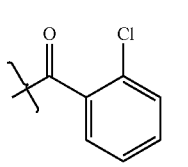 | 8-Methyl-5-methylamino-2-[3-((2-chlorophenyl)carbonylaminomethyl)-phenyl]-8H-imidazo[4,5-d]oxazolo[5,4-b]pyridine | 2.99 | 446.99 |
| A91 | 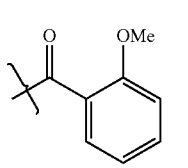 | 8-Methyl-5-methylamino-2-[3-((2-methoxyphenyl)carbonylaminomethyl)-phenyl]-8H-imidazo[4,5-d]oxazolo[5,4-b]pyridine | 3.17 | 443.01 |

TABLE A7-continued

| Ex. | R¹ | Name | HPLC Retention (min) | MS Reported |
|---|---|---|---|---|
| A92 | 2-trifluoromethylphenyl C(=O)– | 8-Methyl-5-methylamino-2-[3-((2-trifluoromethylphenyl)-carbonylaminomethyl)phenyl]-8H-imidazo[4,5-d]oxazolo[5,4-b]pyridine | 3.08 | 481.02 |
| A93 | 3-fluorophenyl C(=O)– | 8-Methyl-5-methylamino-2-[3-((3-fluorophenyl)carbonylaminomethyl)-phenyl]-8H-imidazo[4,5-d]oxazolo[5,4-b]pyridine | 3.14 | 431.00 |
| A94 | 3-dimethylaminophenyl C(=O)– | 8-Methyl-5-methylamino-2-[3-((3-dimethylaminophenyl)-carbonylaminomethyl)phenyl]-8H-imidazo[4,5-d]oxazolo[5,4-b]pyridine | 2.65 | 456.18 |
| A95 | 3-methoxyphenyl C(=O)– | 8-Methyl-5-methylamino-2-[3-((3-methoxyphenyl)aminophenyl)carbonylaminomethyl)phenyl]-8H-imidazo[4,5-d]oxazolo[5,4-b]pyridine | 3.10 | 443.01 |
| A96 | 3-methylphenyl C(=O)– | 8-Methyl-5-methylamino-2-[3-((3-methylphenyl)aminophenyl)-carbonylaminomethyl)phenyl]-8H-imidazo[4,5-d]oxazolo[5,4-b]pyridine | 3.22 | 427.01 |
| A97 | 4-(dimethylamino)phenyl C(=O)– | 8-Methyl-5-methylamino-2-[3-(4-(dimethylamino)phenyl-carbonylaminomethyl)phenyl]-8H-imidazo[4,5-d]oxazolo[5,4-b]pyridine | 3.05 | 456.16 |
| A98 | (CH₃)₂CH–C(=O)– | 8-Methyl-5-methylamino-2-[3-((2-methylethyl)carbonylaminomethyl)-phenyl]-8H-imidazo[4,5-d]oxazolo[5,4-b]pyridine | 2.75 | 379.10 |
| A99 | (CH₃)₂CHCH₂–C(=O)– | 8-Methyl-5-methylamino-2-[3-((2-methylpropyl)carbonylaminomethyl)-phenyl]-8H-imidazo[4,5-d]oxazolo[5,4-b]pyridine | 2.91 | 393.07 |

TABLE A7-continued

| Ex. | R¹ | Name | HPLC Retention (min) | MS Reported |
|---|---|---|---|---|
| A100 | C(=O)C(Me)(Me)CH₂-... (neopentyl carbonyl; -C(O)CH₂C(Me)₃) | 8-Methyl-5-methylamino-2-[3-((2,2-dimethylpropyl)carbonylaminomethyl)-phenyl]-8H-imidazo[4,5-d]oxazolo[5,4-b]pyridine | 3.16 | 407.09 |
| A101 | -C(O)CH₂CH(Me)Me | 8-Methyl-5-methylamino-2-[3-((2-methylpropyl)carbonylaminomethyl)-phenyl]-8H-imidazo[4,5-d]oxazolol[5,4-b]pyridine | 2.96 | 393.07 |
| A102 | -C(O)CH₂CH₂OPh | 8-Methyl-5-methylamino-2-[3-((2-phenyloxyethyl)carbonylaminomethyl)-phenyl]-8H-imidazo[4,5-d]oxazolo[5,4-b]pyridine | 3.10 | 457.01 |
| A103 | -C(O)CH₂CH₂Ph | 8-Methyl-5-methylamino-2-[3-(phenylethylcarbonylaminomethyl)-phenyl]-8H-imidazo[4,5-d]oxazolo[5,4-b]pyridine | 3.18 | 440.99 |
| A104 | -C(O)CH₂CH₂Me | 8-Methyl-5-methylamino-2-[3-(propylcarbonylaminomethyl)phenyl]-8H-imidazo[4,5-d]oxazolo[5,4-b]pyridine | 2.93 | 379.16 |
| A105 | -C(O)-(2-furyl) | 8-Methyl-5-methylamino-2-[3-((2-furyl)carbonylaminomethyl)phenyl]-8H-imidazo[4,5-d]oxazolo[5,4-b]pyridine | 2.74 | 403.05 |
| A106 | -C(O)-cycloheptyl | 8-Methyl-5-methylamino-2-[3-(cycloheptylcarbonylaminomethyl)-phenyl]-8H-imidazo[4,5-d]oxazolo[5,4-b]pyridine | 3.37 | 433.09 |
| A107 | -C(O)C(Me)(Me)Me (t-Bu carbonyl) | 8-Methyl-5-methylamino-2-[3-((2,2-dimethylethyl)carbonylaminomethl)-phenyl]-8H-imidazo[4,5-d]oxazolo[5,4-b]pyridine | 2.94 | 393.06 |
| A108 | -C(O)CHF₂ | 8-Methyl-5-methylamino-2-[3-((difluoromethyl)carbonylaminomethyl)-phenyl]-8H-imidazo[4,5-d]oxazolo[5,4-b]pyridine | 2.63 | 387.01 |
| A109 | -C(O)CH₂Ph | 8-Methyl-5-methylamino-2-[3-((difluoromethyl)carbonylaminomethyl)-phenyl]-8H-imidazo[4,5-d]oxazolo[5,4-b]pyridine | 3.03 | 427.01 |

TABLE A7-continued

| Ex. | R¹ | Name | HPLC Retention (min) | MS Reported |
|---|---|---|---|---|
| A110 | (2-trifluoromethyl)phenyl-CH₂-C(O)- | 8-Methyl-5-methylamino-2-[3-((2-(trifluoromethyl)phenyl)-carbonylaminomethyl)phenyl]-8H-imidazo[4,5-d]oxazolo[5,4-b]pyridine | 3.26 | 494.99 |
| A111 | trans-PhCH=CH-C(O)- | 8-Methyl-5-methylamino-2-[3-(3-(trans-phenylethenyl)carbonylaminomethyl)-phenyl]-8H-imidazo[4,5-d]oxazolo[5,4-b]pyridine | 3.26 | 439.03 |
| A112 | Ph-(CH₂)₃-C(O)- | 8-Methyl-5-methylamino-2-[3-(3-(3-phenylpropyl)carbonylaminomethyl)-phenyl]-8H-imidazo[4,5-d]oxazolo[5,4-b]pyridine | 3.35 | 455.04 |
| A113 | Me-(CH₂)₃-C(O)- | 8-Methyl-5-methylamino-2-[3-(butylcarbonylaminomethyl)phenyl]-8H-imidazo[4,5-d]oxazolo[5,4-b]pyridine | 3.00 | 393.06 |
| A114 | Me-(CH₂)₄-C(O)- | 8-Methyl-5-methylamino-2-[3-(pentylcarbonylaminomethyl)phenyl]-8H-imidazo[4,5-d]oxazolo[5,4-b]pyridine | 3.21 | 407.10 |
| A115 | thiophen-2-yl-CH₂-C(O)- | 8-Methyl-5-methylamino-2-[3-(thiophen-2-ylmethylcarbonylaminomethyl)phenyl]-8H-imidazo[4,5-d]oxazolo[5,4-b]pyridine | 3.08 | 433.11 |
| A116 | thiophen-3-yl-C(O)- | 8-Methyl-5-methylamino-2-[3-(thiophen-3-ylcarbonylaminomethyl)phenyl]-8H-imidazo[4,5-d]oxazolo[5,4-b]pyridine | 2.91 | 418.99 |
| A117 | indol-3-yl-CH₂-C(O)- | 8-Methyl-5-methylamino-2-[3-(indol-3-ylmethylcarbonylaminomethyl)phenyl]-8H-imidazo[4,5-d]oxazolo[5,4-b]pyridine | 2.99 | 466.04 |
| A118 | furan-2-yl-C(O)- (benzofuran-2-yl) | 8-Methyl-5-methylamino-2-[3-(furan-2-ylcarbonylaminomethyl)phenyl]-8H-imidazo[4,5-d]oxazolo[5,4-b]pyridine | 3.35 | 453.00 |

TABLE A7-continued

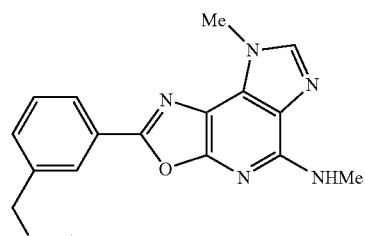

| Ex. | R[1] | Name | HPLC Retention (min) | MS Reported |
|---|---|---|---|---|
| A119 | 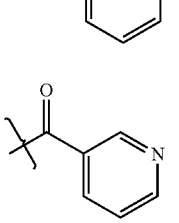 | 8-Methyl-5-methylamino-2-[3-(pyridin-2-ylcarbonylaminomethyl)phenyl]-8H-imidazo[4,5-d]oxazolo[5,4-b]pyridine | 2.98 | 414.05 |
| A120 | 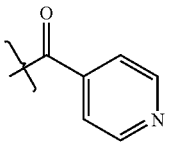 | 8-Methyl-5-methylamino-2-[3-(pyridin-3-ylcarbonylaminomethyl)phenyl]-8H-imidazo[4,5-d]oxazolo[5,4-b]pyridine | 2.53 | 414.12 |
| A121 | 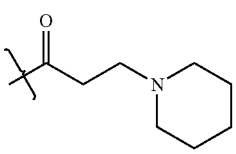 | 8-Methyl-5-methylamino-2-[3-(pyridin-4-ylcarbonylaminomethyl)phenyl]-8H-imidazo[4,5-d]oxazolo[5,4-b]pyridine | 2.49 | 414.12 |
| A122 | 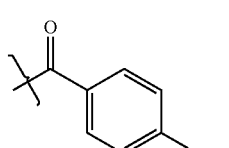 | 8-Methyl-5-methylamino-2-[3-(2-piperidin-1-ylethylcarbonylaminomethyl)-phenyl]-8H-imidazo[4,5-d]oxazolo[5,4-b]pyridine | 2.40 | 448.12 |
| A123 | 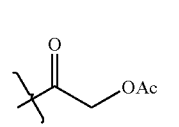 | 8-Methyl-5-methylamino-2-[3-(4-nitrophenylcarbonylaminomethyl)phenyl]-8H-imidazo[4,5-d]oxazolo[5,4-b]pyridine | 3.16 | 457.98 |
| A124 | 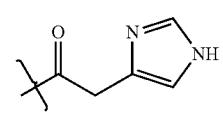 | 8-Methyl-5-methylamino-2-[3-(acyloxyethylcarbonylaminomethyl)-phenyl]-8H-imidazo[4,5-d]oxazolo[5,4-b]pyridine | 2.52 | 409.04 |
| A125 | 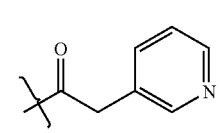 | 8-Methyl-5-methylamino-2-[3-(imidazol-2-ylmethylcarbonylaminomethyl)phenyl]-8H-imidazo[4,5-d]oxazolo[5,4-b]pyridine | 2.27 | 417.14 |
| A126 | | 8-Methyl-5-methylamino-2-[3-(pyridin-3-ylmethylcarbonylaminomethyl)phenyl]-8H-imidazo[4,5-d]oxazolo[5,4-b]pyridine | 2.30 | 428.06 |

TABLE A7-continued

| Ex. | R¹ | Name | HPLC Retention (min) | MS Reported |
|---|---|---|---|---|
| A127 | (2-methyl-2-phenylpropanoyl) | 8-Methyl-5-methylamino-2-[3-((1-methyl-1-phenylethyl)carbonylaminomethyl)-phenyl]-8H-imidazo[4,5-d]oxazolo[5,4-b]pyridine | 3.34 | 455.04 |
| A128 | (3-methoxycarbonylbenzoyl) | 8-Methyl-5-methylamino-2-[3-(3-methylcarboxyphenylcarbonyl aminomethyl)phenyl]-8H-imidazo[4,5-d]oxazolo[5,4-b]pyridine | 3.17 | 471.03 |
| A129 | (cyclopropylacetyl) | 8-Methyl-5-methylamino-2-[3-(cyclopropylethylcarbonylaminomethyl)-phenyl]-8H-imidazo[4,5-d]oxazolo[5,4-b]pyridine | 2.97 | 391.16 |
| A130 | (methoxyacetyl) | 8-Methyl-5-methylamino-2-[3-(methoxymethylcarbonylaminomethyl)-phenyl]-8H-imidazo[4,5-d]oxazolo[5,4-b]pyridine | 2.54 | 395.08 |
| A131 | (thiadiazol-4-ylcarbonyl) | 8-Methyl-5-methylamino-2-[3-(thiadiazol-4-ylcarbonylaminomethyl)phenyl]-8H-imidazo[4,5-d]oxazolo[5,4-b]pyridine | 2.77 | 421.01 |
| A132 | (2-(pyridin-3-yl)thiazol-4-ylcarbonyl) | 8-Methyl-5-methylamino-2-[3-(2-(pyridine-3-yl)thiazol-4-yl)-carbonylaminomethyl)phenyl]-8H-imidazo[4,5-d]oxazolo[5,4-b]pyridine | 2.97 | 497.07 |
| A133 | (4-dimethylaminophenylacetyl) | 8-Methyl-5-methylamino-2-[3-(4-dimethyaminophenylmethylcarbonyl-aminomethyl)phenyl]-8H-imidazol[4,5-d]oxazolo[5,4-b]pyridine | 2.40 | 470.18 |
| A134 | (3,3,3-trifluoropropanoyl) | 8-Methyl-5-methylamino-2-[3-(2,2,2-trifluoroethylcarbonylaminomethyl)-phenyl]-8H-imidazo[4,5-d]oxazolo[5,4-b]pyridine | 2.78 | 419.03 |

TABLE A7-continued

| Ex. | R¹ | Name | HPLC Retention (min) | MS Reported |
|---|---|---|---|---|
| A135 | | 8-Methyl-5-methylamino-2-[3-((1-ethyl-3-methylpyrazol-5-yl)carbonylaminomethyl)-phenyl]-8H-imidazo[4,5-d]oxazolo[5,4-b]pyridine | 3.08 | 445.04 |
| A136 | | 8-Methyl-5-methylamino-2-[3-((4-bromo-1-ethyl-3-methylpyrazol-5-yl)-carbonylaminomethyl)phenyl]-8H-imidazo[4,5-d]oxazolo[5,4-b]pyridine | 3.35 | 522.99 |
| A137 | | 8-Methyl-5-methylamino-2-[3-(2-methylsulfonylphenylcarbonyl aminomethyl)phenyl]-8H-imidazo[4,5-d]oxazolo[5,4-b]pyridine | 2.70 | 490.99 |
| A138 | | 8-Methyl-5-methylamino-2-[3-(dihydrobenzoxazol-7-ylcarbonylaminomethyl)phenyl]-8H-imidazo[4,5-d]oxazolo[5,4-b]pyridine | 3.29 | 455.03 |
| A139 | | 8-Methyl-5-methylamino-2-[3-((5-methylisoxazol-4-yl)carbonylaminomethyl)phenyl]-8H-imidazo[4,5-d]oxazolo[5,4-b]pyridine | 2.90 | 418.00 |
| A140 | | 8-Methyl-5-methylamino-2-[3-(cycloheptylmethylcarbonylaminomethyl)-phenyl]-8H-imidazo[4,5-d]oxazolo[5,4-b]pyridine | 3.54 | 447.12 |
| A141 | | 8-Methyl-5-methylamino-2-[3-(dimethylaminomethylcarbonyl-aminomethyl)phenyl]-8H-imidazo[4,5-d]oxazolo[5,4-b]pyridine | 2.23 | 394.11 |

TABLE A7-continued

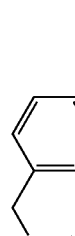

| Ex. | R[1] | Name | HPLC Retention (min) | MS Reported |
|---|---|---|---|---|
| A142 | 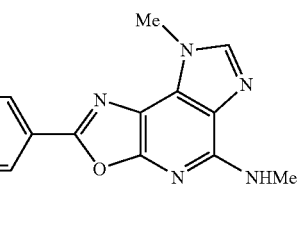 | 8-Methyl-5-methylamino-2-[3-((3-methylphenyl)carbonylaminomethyl)-phenyl]-8H-imidazo[4,5-d]oxazolo[5,4-b]pyridine | 3.07 | 427.01 |
| A143 | 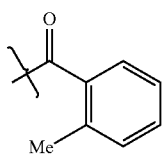 | 8-Methyl-5-methylamino-2-[3-(aminomethylcarbonylaminomethyl)-phenyl]-8H-imidazo[4,5-d]oxazolo[5,4-b]pyridine | 2.19 | 366.04 |
| A144 | 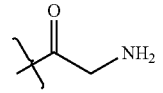 | 8-Methyl-5-methylamino-2-[3(S-aminoethylcarbonylaminomethyl)phenyl]-8H-imidazo[4,5-d]oxazolo[5,4-b]pyridine | 2.24 | 380.06 |
| A145 | 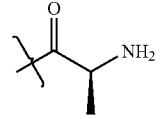 | 8-Methyl-5-methylamino-2-[3-((R-2-amino-3-methylpropyl)-carbonylaminomethyl)phenyl]-8H-imidazo[4,5-d]oxazolo[5,4-b]pyridine | 2.45 | 408.08 |
| A146 | 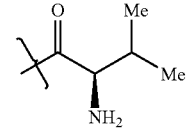 | 8-Methyl-5-methylamino-2-[3-((R-2-amino-4-methylbutyl)-carbonylaminomethyl)phenyl]-8H-imidazo[4,5-d]oxazolo[5,4-b]pyridine | 2.64 | 422.05 |
| A147 | 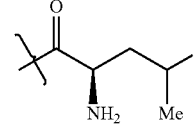 | 8-Methyl-5-methylamino-2-[3-(R-aminophenylmethylcarbonylaminomethyl)-phenyl]-8H-imidazo[4,5-d]oxazolo[5,4-b]pyridine | 2.54 | 442.03 |
| A148 | 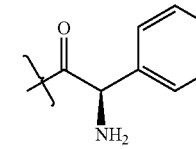 | 8-Methyl-5-methylamino-2-[3-(R-amino-2-(phenyl)ethylcarbonylaminomethyl)-phenyl]-8H-imidazo[4,5-d]oxazolo[5,4-b]pyridine | 2.74 | 456.07 |
| A149 | 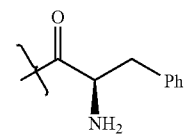 | 8-Methyl-5-methylamino-2-[3-(R-aminoethylcarbonylaminomethyl)phenyl]-8H-imidazo[4,5-d]oxazolo[5,4-b]pyridine | 2.22 | 380.08 |

TABLE A7-continued

| Ex. | R¹ | Name | HPLC Retention (min) | MS Reported |
|---|---|---|---|---|
| A150 | | 8-Methyl-5-methylamino-2-[3-(R-2-(aminocarbonyl)-1-aminoethylcarbonylaminomethyl)phenyl]-8H-imidazo[4,5-d]oxazolo[5,4-b]pyridine | 2.12 | 423.03 |
| A151 | | 8-Methyl-5-methylamino-2-[3-(S-1-amino-2-imidazol-4-yl-ethylcarbonylaminomethyl)phenyl]-8H-imidazo[4,5-d]oxazolo[5,4-b]pyridine | 2.04 | 446.03 |
| A152 | | 8-Methyl-5-methylamino-2-[3-(R-1-amino-R-2-methylbutylcarbonylaminomethyl)phenyl]-8H-imidazo[4,5-d]oxazolo[5,4-b]pyridine | 2.61 | 422.11 |
| A153 | | 8-Methyl-5-methylamino-2-[3-(R-1-amino-4-aminobutylcarbonylaminomethyl)-phenyl]-8H-imidazo[4,5-d]oxazolo[5,4-b]pyridine | 2.03 | 423.07 |
| A154 | | 8-Methyl-5-methylamino-2-[3-(S-1-amino-4-guanidinylbutylcarbonylaminomethyl)-phenyl]-8H-imidazo[4,5-d]oxazolo[5,4-b]pyridine | 2.07 | 465.09 |
| A155 | | 8-Methyl-5-methylamino-2-[3-(R-1-amino-S-2-hydroxypropylcarbonylaminomethyl)-phenyl]-8H-imidazo[4,5-d]oxazolo[5,4-b]pyridine | 2.25 | 410.04 |
| A156 | | 8-Methyl-5-methylamino-2-[3-(R-1-amino-2-carboxyethylcarbonylaminomethyl)-phenyl]-8H-imidazo[4,5-d]oxazolo[5,4-b]pyridine | 2.21 | 424.01 |
| A157 | | 8-Methyl-5-methylamino-2-[benzothiazol-6-ylcarboxyphenylcarbonylaminomethyl)-phenyl]-8H-imidazo[4,5-d]oxazolo[5,4-b]pyridine | 2.96 | 470.03 |

TABLE A7-continued

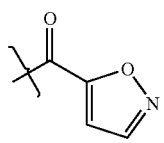

| Ex. | R[1] | Name | HPLC Retention (min) | MS Reported |
|---|---|---|---|---|
| A158 | 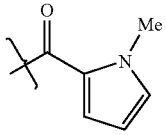 | 8-Methyl-5-methylamino-2-[isoxazol-5-ylcarboxyphenylcarbonylaminomethyl)-phenyl]-8H-imidazo[4,5-d]oxazolo[5,4-b]pyridine | 2.66 | 404.03 |
| A159 | | 8-Methyl-5-methylamino-2-[1-methylpyrrol-2-ylcarboxyphenylcarbonylaminomethyl)-phenyl]-8H-imidazo[4,5-d]oxazolo[5,4-b]pyridine | 2.93 | 416.10 |
| A160 | 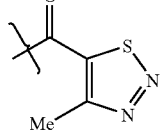 | 8-Methyl-5-methylamino-2-[1-methylpyrrol-2-ylcarboxyphenylcarbonylaminomethyl)-phenyl]-8H-imidazo[4,5-d]oxazolo[5,4-b]pyridine | 2.89 | 435.04 |

Examples A161–A169

Examples A161–A169 described in Table A8 were prepared by a solution phase library methodology. To an individual well of a 48-position MiniBlock® reactor was added 35 mg of sodium carbonate (0.33 mmol, 10 equiv); 180 μL of a 0.50 M solution of the appropriate chloroformate in tetrahydrofuran (THF) (0.090 mmol, 2.7 equiv); and 220 μL of a 0.15 M solution of A73 in THF (0.033 mmol, 1.0 equiv). The reactor was agitated via orbital shaker overnight at rt. The crude product was filtered, rinsed with additional THF, and dried via centrifugal evaporation; the dried sample was reconstituted in 2 mL of 1:1/DMSO:MeOH, then purified by standard preparative HPLC-MS (H₂O/MeOH/0.1% TFA, gradient 35–90% MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H₂O/MeOH/0.1% TFA).

TABLE A8

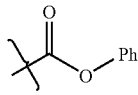

| Ex. | R[1] | Name | HPLC Retention (min) | MS Reported |
|---|---|---|---|---|
| A161 | | 8-Methyl-5-methylamino-2-[3-(phenyloxycarbonylaminomethyl)phenyl]-8H-imidazo[4,5-d]oxazolo[5,4-b]pyridine | 3.31 | 429.12 |

TABLE A8-continued

| Ex. | R¹ | Name | HPLC Retention (min) | MS Reported |
|---|---|---|---|---|
| A162 | -C(O)-O-Et | 8-Methyl-5-methylamino-2-[3-(ethyloxycarbonylaminomethyl)phenyl]-8H-imidazo[4,5-d]oxazolo[5,4-b]pyridine | 3.05 | 381.15 |
| A163 | -C(O)-O-CH₂CH₂-OMe | 8-Methyl-5-methylamino-2-[3-(2-methoxyethyloxycarbonylaminomethyl)-phenyl]-8H-imidazo[4,5-d]oxazolo[5,4-b]pyridine | 2.87 | 411.15 |
| A164 | -C(O)-O-CH₂-C≡CH | 8-Methyl-5-methylamino-2-[3-(2-propynyloxycarbonylaminomethyl)-phenyl]-8H-imidazo[4,5-d]oxazolo[5,4-b]pyridine | 2.94 | 391.14 |
| A165 | -C(O)-O-(4-F-C₆H₄) | 8-Methyl-5-methylamino-2-[3-(4-fluorophenyloxycarbonylaminomethyl)-phenyl]-8H-imidazo[4,5-d]oxazolo[5,4-b]pyridine | 3.25 | 447.01 |
| A166 | -C(O)-O-(4-MeO-C₆H₄) | 8-Methyl-5-methylamino-2-[3-(4-methoxyphenyloxycarbonylaminomethyl)-phenyl]-8H-imidazo[4,5-d]oxazolo[5,4-b]pyridine | 3.21 | 459.02 |
| A167 | -C(O)-O-(2-naphthyl) | 8-Methyl-5-methylamino-2-[3-(2-napthyloxycarbonylaminomethyl)phenyl]-8H-imidazo[4,5-d]oxazolo[5,4-b]pyridine | 3.55 | 479.01 |
| A168 | -C(O)-O-CH(Me)₂ | 8-Methyl-5-methylamino-2-[3-(isopropyloxycarbonylaminomethyl)-phenyl]-8H-imidazo[4,5-d]oxazolo[5,4-b]pyridine | 3.12 | 395.08 |
| A169 | -C(O)-O-CH₂CH₂-C≡CH | 8-Methyl-5-methylamino-2-[3-(3-butynyloxycarbonylaminomethyl)phenyl]-8H-imidazo[4,5-d]oxazolo[5,4-b]pyridine | 2.94 | 405.01 |

Examples A170–A180

Examples A170–A180 described in Table A9 were prepared by a solution phase library methodology. To an individual well of a 48-position MiniBlock® reactor was added 264 µL of a 0.25 M solution of the sulfonyl chloride in 1,2-dichloroethane (DCE) (0.066 mmol, 2.0 equiv); 13 mg of polyvinylpyridine resin (PVP) (10 mmol/g, 0.13 mmol, 4.0 equiv); and 250 µL of a 0.13 M solution of A73 in DCE (0.033 mmol, 1.0 equiv). The reactor was agitated via orbital shaker overnight at rt. The crude product was filtered, rinsed with additional DCE, diluted to a volume of 2 mL with MeOH, then purified by standard preparative HPLC-MS (H₂O/MeOH/0.1% TFA, gradient 35–90%

MeOH over 15 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H₂O/MeOH/0.1% TFA).

TABLE A9

| Ex. | R¹ | Name | HPLC Retention (min) | MS Reported |
|---|---|---|---|---|
| A170 | | 8-Methyl-5-methylamino-2-[3-(2-nitrophenylsulfonyloaminomethyl)phenyl]-8H-imidazo[4,5-d]oxazolo[5,4-b]pyridine | 2.95 | 493.97 |
| A171 | | 8-Methyl-5-methylamino-2-[3-(propylsulfonyloaminomethyl)phenyl]-8H-imidazo[4,5-d]oxazolo[5,4-b]pyridine | 2.87 | 415.03 |
| A172 | | 8-Methyl-5-methylamino-2-[3-(2-nitrophenylsulfonyloaminomethyl)phenyl]-8H-imidazo[4,5-d]oxazolo[5,4-b]pyridine | 3.17 | 466.98 |
| A173 | | 8-Methyl-5-methylamino-2-[3-((2-acetamido-4-methylthiazol-5-yl)-sulfonyloaminomethyl)phenyl]-8H-imidazo[4,5-d]oxazolo[5,4-b]pyridine | 2.75 | 527.01 |
| A174 | | 8-Methyl-5-methylamino-2-[3-(4-fluorophenylsulfonyloaminomethyl)-phenyl]-8H-imidazo[4,5-d]oxazolo[5,4-b]pyridine | 3.14 | 466.99 |
| A175 | | 8-Methyl-5-methylamino-2-[3-(2-trifluoromethoxyphenylsulfonyl-oaminomethyl)phenyl]-8H-imidazo[4,5-d]oxazolo[5,4-b]pyridine | 3.26 | 533.03 |
| A176 | | 8-Methyl-5-methylamino-2-[3-(3,5-dimethylisoxazol-4-ylsulfonyloaminomethyl)phenyl]-8H-imidazo[4,5-d]oxazolo[5,4-b]pyridine | 2.95 | 468.01 |

TABLE A9-continued

| Ex. | R¹ | Name | HPLC Retention (min) | MS Reported |
|---|---|---|---|---|
| A177 | | 8-Methyl-5-methylamino-2-[3-(2,5-difluorophenylsulfonyloaminomethyl)-phenyl]-8H-imidazo[4,5-d]oxazolo[5,4-b]pyridine | 3.14 | 484.99 |
| A178 | | 8-Methyl-5-methylamino-2-[3-(4-acetylphenylsulfonyloaminomethyl)-phenyl]-8H-imidazo[4,5-d]oxazolo[5,4-b]pyridine | 2.91 | 491.02 |
| A179 | | 8-Methyl-5-methylamino-2-[3-(5-methylisoxazol-4-ylsulfonyloaminomethyl)phenyl]-8H-imidazo[4,5-d]oxazolo[5,4-b]pyridine | 2.86 | 453.99 |
| A180 | | 8-Methyl-5-methylamino-2-[3-(thiophen-3-ylsulfonyloaminomethyl)phenyl]-8H-imidazo[4,5-d]oxazolo[5,4-b]pyridine | 2.96 | 454.98 |

Example A181

2-[3-(1-amino-1-methylethyl)phenyl]-N,8-dimethyl-8H-imidazo[4,5-d]oxazolo[5,4-b]pyridine

Example A182

2-[3-(1-acetamido-1-methylethyl)phenyl]-N,8-dimethyl-8H-imidazo[4,5-d]oxazolo[5,4-b]pyridine

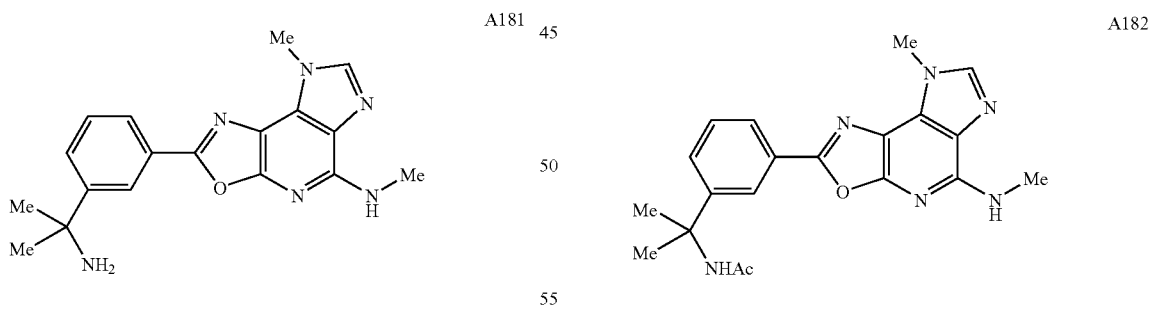

Cerium chloride (482 mg, 2.0 mmol) was dissolved in THF and cooled to −78° C. Methyl lithium (2 mL of a 1.6 M solution in ether) was added dropwise and the mixture stirred for 1 h. A suspension of A16 (200 mg, 0.66 mmol) was added and the reaction mixture was allowed to warm to room temperature and stirred overnight. The reaction mixture was quenched by the addition of 1 mL of water and 50% NH4OH solution. The reaction mixture was filtered and the filtrate concentrated in vacuo. The residue was purified by preparatory HPLC to provide 28 mg or A181 as a yellow solid. LCMS M+H=337.

A181 (23 mg, 0.06 mmol), 0.5 mL of acetic anhydride, and 0.5 mL of pyridine were dissolved in 5 mL of anhydrous THF and stirred at room temperature overnight. The reaction mixture was concentrated and the residue purified by reverse phase preparatory HPLC to yield 15 mg of A182 as an off white solid. LCMS (Phenomenex S5® 4.6×30 mm) 2 min gradient 10% Solvent A 10% MeOH, 90% H$_2$O, 0.1% TFA, Solvent B 90% MeOH, 10% H$_2$O, 0.1% TFA, Retention time=1.41 min, M+H=379.26. $^1$H NMR CD$_3$OD: δ 8.20 s, 1H, 8.05, s, 1H, 7.90 d, 1H, 7.60–7.40, m, 2H, 4.1, s, 3H, 3.1, s, 3H, 2.05, s, 3H, 1.80, s, 6H.

Example A183

2-[3-(1-amino-1-methylethyl)phenyl]-N,8-dimethyl-8H-imidazo[4,5-d]oxazolo[5,4-b]pyridine

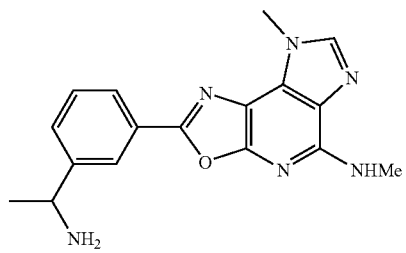

A183

A16 (304 mg, 1.0 mmol) was suspended in 20 mL of THF. Methyl magnesium bromide (3 mL of a 3M solution in diethylether) was added during which the reaction mixture became exothermic and the solution became homogenious. The reaction mixture was allowed to stir overnight at room temperature. Lithium aluminum hydride (2 mL of a 1 M solution in THF) was added and the reaction mixture stirred for an additional 2 hours. The reaction was stirred and quenched by the sequential addition of 4 mL of water followed by 2 mL of 15% aqueous NaOH, followed by the addition of 12 mL of water. The supernatant (top layer) was decanted from the reaction mixture and concentrated to yield 300 mg of a redish brown solid, which was purified by reverse phase HPLC to yield 245 mg of A183 as a tan solid. (Phenomenex S5® 4.6×50 mm) 2 min gradient 10% Solvent A 10% MeOH, 90% H$_2$O, 0.1% TFA, Solvent B 90% MeOH, 10% H$_2$O, 0.1% TFA, Retention time=1.12 min, M+H=323.26. $^1$H NMR CD$_3$OD: δ 8.30–8.10, m, 3H, 7.65, s, 2H, 4.60, m, 1H, 4.20, s, 3H, 3.05, S, 3h, 1.74, D, 3H.

Example A184

N-[1-[5-[8-methyl-5-(methylamino)-8H-imidazo[4,5-d]oxazolo[5,4-b]pyridin-2-yl]phenyl]ethyl]acetamide

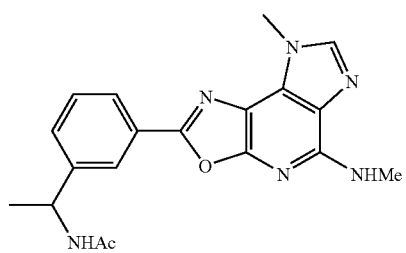

A184

A183 (20 mg, 0.055 mmol) was dissolved in 5 mL of anhydrous THF. 0.2 mL of acetic anhydride and 0.5 mL of pyridine were added and the reaction mixture stirred at room temperature overnight. The reaction mixture was quenched by the addition of 20% aqueous HCl, and concentrated in vacuo. The residue was dissolved in 2 mL of methanol, filtered and the filtrate was purified by reverse phase preparatory HPLC to provide 7 mg of A184 as a white solid. $^1$H NMR CD$_3$OD: δ 8.23, s, 1H, 8.11, s, 1H, 8.02–8.00, m, 1H-7.52, m, 2H, 5.15, m, 1H, 4.21, s, 3H, 3.32, s, 3H 2.17, 2, 3H, 1.60, d, 3H. (Phenomenex S5® 4.6×50 mm) 2 min gradient 10% Solvent A 10% MeOH, 90% H2O, 0.1% TFA, Solvent B 90% MeOH, 10% H$_2$O, 0.1% TFA, Retention time=1.34 min, M+H=365.30.

Chiral Separation of A184

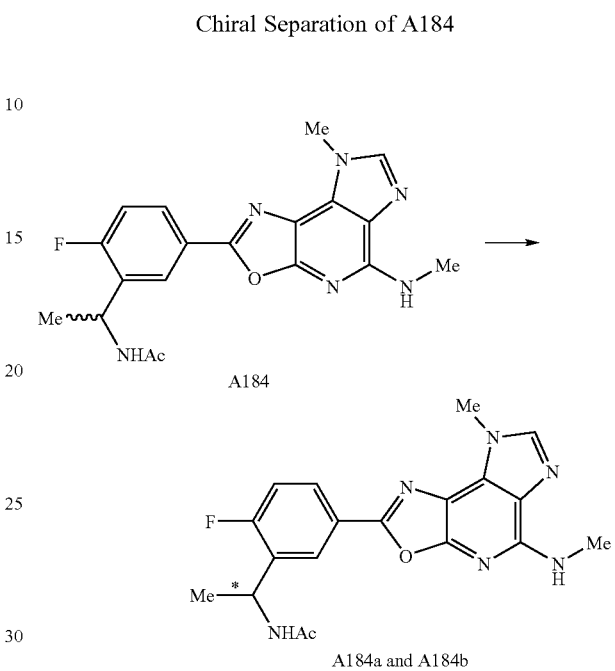

A184

A184a and A184b

A184 (~30 mg) was dissolved in approximately 20 mL of a solution of 60% EtOH, 40% Heptane, 0.1% diisopropyl-ethylamine and purified using a Chiralpak AS® 500 mm×20 mm 10 micron HPLC column (Evaporation of the mobile phase provided the separated enantiomers.

A184a Fast Eluting Enantiomer: 13.4 mg white solid (+) by CD detection (254 nM) A184b Slow Eluting Enantiomer: 11.1 mg white solid (−) by CD detection (254 nM).

Example A185

N-[1-[5-[8-methyl-5-(methylamino)-8H-imidazo[4,5-d]oxazolo[5,4-b]pyridin-2-yl]phenyl]ethyl]N-methylurea

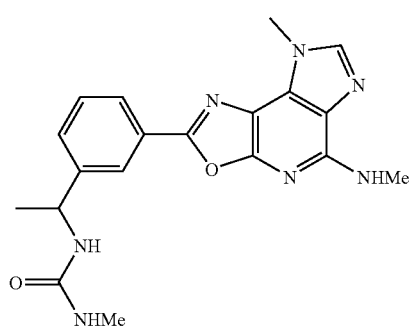

A185

A183 (20 mg, 0.055 mmol) was dissolved in 5 mL of anhydrous THF. 0.2 mL of methyl isocyanate, and 0.5 mL of pyridine were added and the reaction mixture was stirred overnight at room temperature. The reaction mixture was concentrated in vacuo, and the residue taken up in 3 mL of MeOH and filtered. The solid was dried to yield 8 mg of A185 as a white solid. The filtrate was purified by reverse phase preparatory HPLC to yield 4 mg of A185 as a white solid. (Phenomenex S5® 4.6×50 mm) 2 min gradient 10% Solvent A 10% MeOH, 90% H$_2$O, 0.1% TFA, Solvent B 90% MeOH, 10% H2O, 0.1% TFA, Retention time=1.31 min, M+H=380.30. $^1$H NMR d6DMSO: δ 8.19, s, 1H, 8.09, s, 1H, 8.02–8.00, m, 1H, 7.58–7,49, m, 2H, 7.40, br s, 1H, 6.36, br s, 1H, 4.89, m, 1H, 4.18, s, 3H, 3.04, s, 3H, 2.27, s, 3H, 2, 3H, 1.44, d, 3H.

Example B1

N,8-dimethyl-2-phenyl-8H-imidazo[4,5-d]thiazolo[5,4-b]pyridin-5-amine

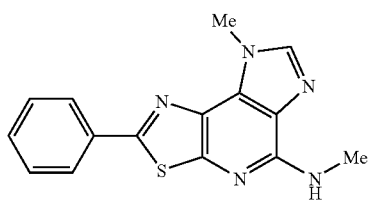

B1

B1.1

N,8-dimethyl-2-phenyl-5-chloro-8H-imidazo[4,5-d]thiazolo[5,4-b]pyridine

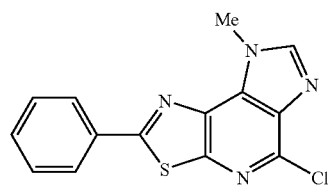

B1.1

A mixture of A1.5 (43 mg; 0.13 mmol) and Lawesson's reagent (80 mg; 0.2 mmol) in 2 ml of toluene was heated to 110° C. for 5 hrs. After cooling to room temperature, 1,8-diazabicyclo[5.4.0]undec-7-ene (0.06 mL; 0.4 mmol) was added and the reaction mixture was allowed to stir for 60 hrs. The volatiles were removed in vacuo and the residue was dissolved in 2 ml of N,N-dimethylacetamide. After adding potassium carbonate (50 mg; 0.36 mmol), the reaction mixture was heated to 160° C. for 1 hr. The reaction mixture was cooled to room temperature and partitioned between ethyl acetate (20 mL) and water (20 mL). After washing with water (2×20 mL) and brine (20 mL), the organic layer was dried (MgSO$_4$). Filtration and concentration afforded a crude residue that was purified by preparative thin layer chromatography (20×20 cm; 1 mm thick silica gel plate) using ethyl acetate as the eluent. Extraction of the pure band with ethyl acetate, filtration and concentration afforded 21 mg (75%) of B1.1 as an off-white solid. HPLC: 95.1% at 1.89 min (retention time) (Phenominex S5 ODS column 4.6×50 mm eluting with 10–90% aqueous methanol over 2 minutes containing 0.1% TFA, 4 ml/min, monitoring at 254 nm); MS (ES): m/z 301.05 [M+H]$^+$

B1.2

N,8-dimethyl-2-phenyl-8H-imidazo[4,5-d]thiazolo[5,4-b]pyridin-5-amine

A mixture of B1.1 (19 mg; 0.063 mmol), methylamine hydrochloride (22 mg; 0.32 mmol) and diisopropylethylamine (0.092 mL; 0.5 mmol) in 0.5 ml of n-butanol was heated to 180° C. for 4.5 hrs in a sealed tube, using a microwave apparatus. After cooling to room temperature, the reaction mixture was partitioned between ethyl acetate (20 mL) and saturated sodium bicarbonate solution (20 mL). The aqueous layer was extracted with ethyl acetate (20 mL) and the combined organic layers were dried (MgSO$_4$). Filtration and concentration afforded a residue that was triturated with ethyl ether and dried to afford 6 mg (33%) of B1 as a yellow powder. HPLC: 99% at 1.53 min (retention time) (Phenominex S5 ODS column 4.6×50 mm eluting with 10–90% aqueous methanol over 2 minutes containing 0.1% TFA, 4 mL/min, monitoring at 254 nm); MS (ES): m/z 296.15 [M+H]$^+$.

Example B2

N,8-dimethyl-2-(methylthio)-8H-imidazo[4,5-d]thiazolo[5,4-b]pyridin-5-amine

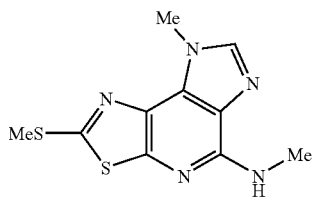

B2

B2.1

N,8-dimethyl-2-(methylthio)-5-chloro-8H-imidazo[4,5-d]thiazolo[5,4-b]pyridine

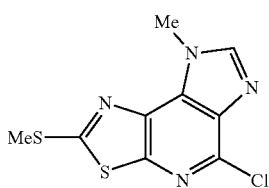

B2.1

A1.4 (2.17 g, 10 mmol) and potassium thioxanthate (3.05 g, 20 mmol) were added to 20 mL of DMF and heated for 2.5 h at 145° C. The reaction mixture was cooled to room temperature then placed in an ice bath and cooled to ~0° C. Methyl iodide (1.24 ml, 20 mmol) was added and the reaction mixture stirred for 1 hour in the ice bath. Volatile liquids were removed at ~45° C. under high vacuum. The residue was partitioned between chloroform (150 mL) and sat. sodium bicarbonate (100 mL). The aqueous layer was washed with additional chloroform (2×75 mL). The combined organic layers were dried over magnesium sulfate, filtered, and evaporated to provide a cream colored solid. The crude product was triturated with hot ethyl acetate (~75 mL) which was allowed to cool to room temperature, and the product collected by filtration. 1.49 g (55%) of B2.1 was isolated as a cream colored solid, which was >95% pure by LCMS ((M+H)$^+$=271.16, 273.17).

B2.2

N,8-dimethyl-2-(methylthio)-8H-imidazo[4,5-d]thiazolo[5,4-b]pyridin-5-amine

B2.1 (540 mg, 2 mmol) and 1.5 mL of methylamine in ethyl alcohol (12 mmol) was added to n-butanol (5 mL) and heated to 180° C. in a sealed tube for 4 h, and cooled to room temperature. HPLC indicated that the reaction had not proceeded to completion. Additional methylamine in ethyl alcohol (12 mmol) was added and the reaction vessel sealed and heated for an additional 4 h. The reaction mixture was cooled to room temperature and the volatile solvent removed under vacuum. The residue was triturated with water and the residue dried under high vacuum to provide 428 mg (91%) of B2 as a white powder. (M+H)$^+$=266.25. (HPLC>95%).

B2 was crystallized from ethyl acetate to produce crystals suitable for x-ray diffraction. The x-ray experimental data is summarized in Table B1, and the graphic depiction of B2 is shown below.

TABLE B1

| Crystal Form: N-1 | | |
|---|---|---|
| Example B3 | | |
| | | Crystallization solvent: EtOAc |
| Chemical formula: | | Crystal description: prisms |
| C$_{10}$H$_{11}$N$_5$S$_2$ | | |
| a: 7.8459(5)Å | α: 66.154(7)° | Melting point: 185–192° C. |
| b: 8.3787(7)Å | β: 87.604(6)° | Measured indices: h, ±k, ±l |
| c: 10.1136(8)Å | γ: 88.513(6)° | Temperature (° C.): 25 |
| V: 607.54(8)Å$^3$ | Z: 2 | (2θ)max.: 140° |
| Space group: P-1 | V/Z: 304Å$^3$ | No. of independent reflections: 2157 |
| D$_{calc}$ (g-cm$^{-3}$): 1.450 | D$_{obs}$: | No. of observed reflections (I ≧ 3σ): 1632 |
| Absorption coefficient: 37.966 cm$^{-1}$ | | No. refined variables: 154 |
| Molecular volume (V$_m$): 212 | | R: 0.048 |
| Molecular Surface Area: 320 | | Rw: 0.064 |
| Packing coefficient (Z · V$_m$/V$_c$): 0.72 | | Avg. errors (C,N,O): 0.004Å 0.25° |
| Comments: | | Solvent: none Occupancy: none |

TABLE B1-continued

| Crystal Form: N-1 |
|---|
| Example B3 |

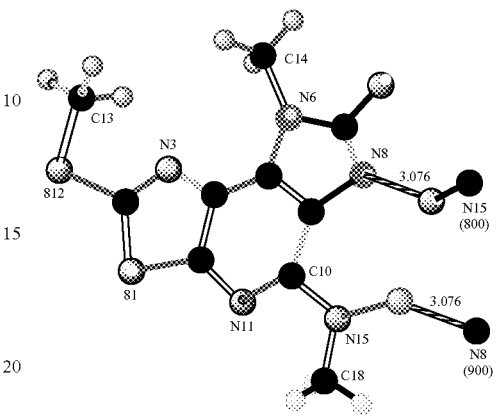

Solid state conformation and H-bonding in a free base of Example B2.

Example B3

N-(3-methoxylropyl)-8-methyl-2-(methylthio)-8H-imidazo[4,5-d]thiazolo[5,4-b]pyridin-5-amine

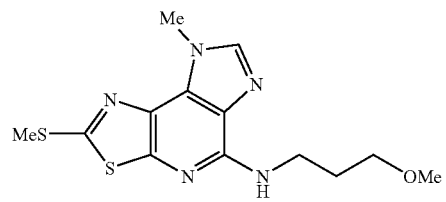

B2.1 (40 mg, 0.14 mmol) and 3-methoxypropylamine (102 μL, 0.14 mmol) were reacted in a manner similar to that described for step B2.2 to provide 17 mg of B3 as an off-white powder. (M+H)$^+$=323.25. (HPLC>95%).

Example B4

N,8-dimethyl-2-[(1-methylethyl)thiol-8H-imidazo[4,5-d]thiazolo[5,4-b]pyridin-5-amine

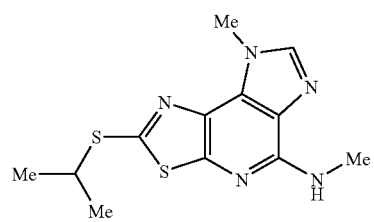

Example B4 was prepared in a similar manner to example B2 with methyl iodide being substituted with 2-iodopropane

Example B5

N,8-dimethyl-2-(methylsulfonyl)-8H-imidazo[4,5-d]thiazolo[5,4-b]pyridin-5-amine

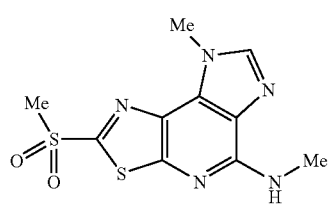

B5

B2 (150 mg, 0.57 mmol) was dissolved in methylene chloride (6 mL). m-Chloroperbenzoic acid 65%, (376 mg, 1.42 mmol) was added and the reaction mixture stirred at room temperature for 1 h. The reaction mixture was diluted with chloroform (~30 mL) and washed with saturated aqueous sodium bicarbonate (30 mL) followed by 5% aqueous sodium bisulfite (30 mL) and again with saturated aqueous sodium bicarbonate (30 mL). The organic layer was decolorized with activated charcoal, filtered through Celite,® and concentrated to a yellow solid. The solid was triturated with hot ethyl acetate which was allowed to cool and collected by filtration to provide 88 mg (54%) of B5 as a yellow powder. A second crop of B5, 21 mg (12%) was obtained after the mother liquor was allowed to stand for one day. $(M+H)^+ = 297.00$ (HPLC>98%).

Example B6

N,8-dimethyl-2-(1-piperidinyl)-8H-imidazo[4,5-d]thiazolo[5,4-b]pyridin-5-amine

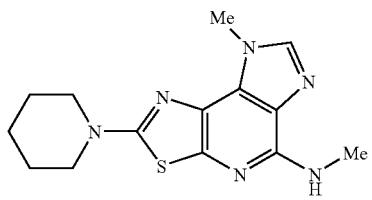

B6

B5 (26 mg, 0.087 mmol), potassium carbonate (14 mg, 0.10 mmol) and piperidine (0.4 ml, 344 mg, 4.0 mmol) were dissolved in DMA (0.2 mL), and heated to 200° C. for 1 h. in a microwave oven. The volatile components were removed under high vacuum, and the residue was partitioned between ethyl acetate (30 mL) and brine (30 mL). The organic layer was separated, dried over magnesium sulfate, filtered and concentrated to provide the crude product. The crude product was purified by preparatory HPLC to provide 17 mg (45%) of B6 as a gray powder. $(M+H)^+ = 303.31$ (HPLC>98%).

Example B7

2-(hexahydro-1H-azepin-1-yl)-N,8-dimethyl-8H-imidazo[4,5-d]thiazolo[5,4-b]pyridin-5-amine

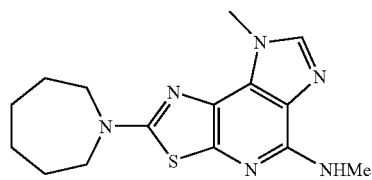

B7

B7.1

N,8-dimethyl-2-(methylsulfonyl)-8H-imidazo[4,5-d]thiazolo[5,4-b]pyridin-5-acetamide

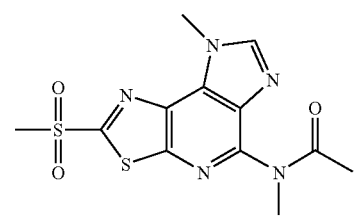

B7.1

A suspension of B5 (900 mg, 3.03 mmol) in AcOH (10 mL) and Ac₂O (10 mL) was heated to 125° C. in a sealed tube, which became homogeneous after 5 min, with stirring overnight. The reaction was cooled to room temperature, concentrated and the residue triturated with EtOAc to provide 890 mg (87%) of B7.1 as a tan solid: MS (ES): m/z 340 $[M+H]^+$ (HPLC 99%).

B7.2

2-(hexahydro-1H-azepin-1-yl)-N,8-dimethyl-8H-imidazo[4,5-d]thiazolo[5,4-b]pyridin-5-amine A solution of B7.1 (0.5 mL of a 0.088 M solution in NMP) and azepane (homopiperazine) (1 mL of a 1M solution in NMP) was heated in a Personal Chemistry microwave at 200° C. for 30 min. NaOH (2N, 0.25 mL) was added and reheated in the microwave at 150° C. for 10 min. AcOH (0.5 mL) was added and purified directly by preparative HPLC to afford 2.2 mg (16%) B7 as a film: MS (ES): m/z 317 $[M+H]^+$ (HPLC 98%).

Examples B8–B28

Examples B8–B28 described in Table B1 were prepared in a similar manner to that used for Example B7 step B7.2 with the appropriate amine substituted for azepane (homopiperazine).

TABLE B1

| Example Number | Structure | Name | Retention Time (min) | Observed Mass |
|---|---|---|---|---|
| B8 | 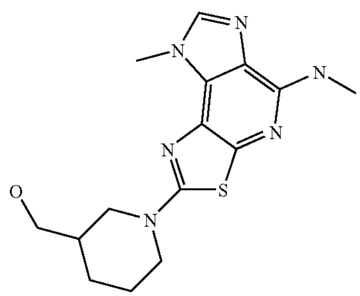 | 3-piperidinemethanol, 1-[8-methyl-5-(methylamino)-8H-imidazo[4,5-d]thiazolo[5,4-b]pyridin-2-yl]- | 1.08 | 333.06 |
| B9 | 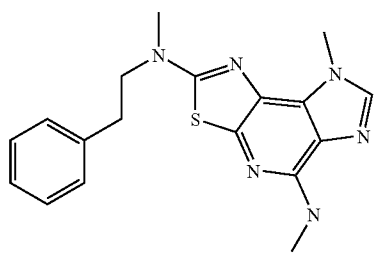 | 8H-imidazo[4,5-d]thiazolo[5,4-b]pyridine-2,5-diamine, $N^2,N^5,8$-trimethyl-$N^2$-(2-phenylethyl)- | 1.49 | 353.06 |
| B10 | 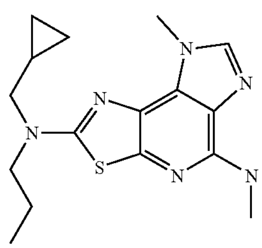 | 8H-imidazo[4,5-d]thiazolo[5,4-b]pyridine-2,5-diamine, $N^2$-(cyclopropylmethyl)-$N^5$,8-dimethyl-$N^2$-propyl- | 1.54 | 331.07 |
| B11 | 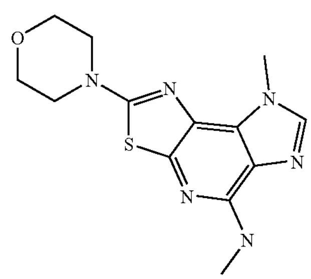 | 8H-imidazo[4,5-d]thiazolo[5,4-b]pyridin-5-amine, N,8-dimethyl-2-(4-morpholinyl)- | 1.07 | 305.03 |
| B12 | 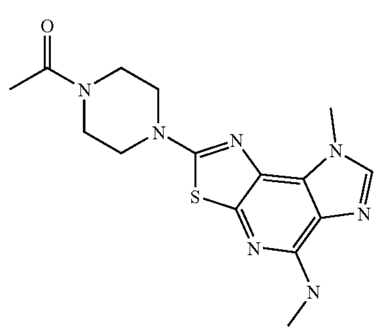 | piperazine, 1-acetyl-4-[8-methyl-5-(methylamino)-8H-imidazo[4,5-d]thiazolo[5,4-b]pyridin-2-yl]- | 1.00 | 346.05 |

TABLE B1-continued

| Example Number | Structure | Name | Retention Time (min) | Observed Mass |
|---|---|---|---|---|
| B13 | 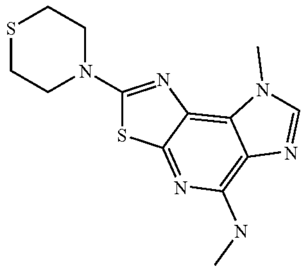 | 8H-imidazo[4,5-d]thiazolo[5,4-b]pyridin-5-amine, N,8-dimethyl-2-(4-thiomorpholinyl)- | 1.24 | 321.03 |
| B14 | 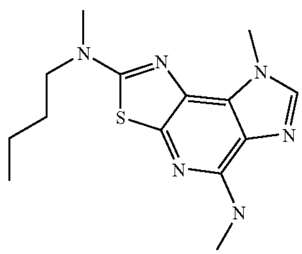 | 8H-imidazo[4,5-d]thiazolo[5,4-b]pyridine-2,5-diamine, $N^2$-butyl-$N^2$,$N^5$,8-trimethyl- | 1.41 | 305.10 |
| B15 | 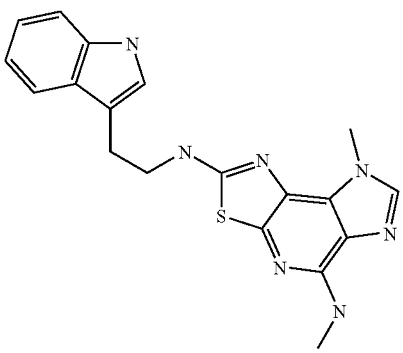 | 8H-imidazo[4,5-d]thiazolo[5,4-b]pyridine-2,5-diamine, $N^2$-[2-(1H-indol-3-yl)ethyl]-$N^5$,8-dimethyl- | 1.40 | 378.04 |
| B16 | 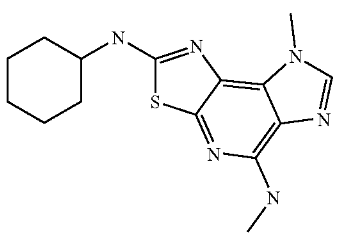 | 8H-imidazo[4,5-d]thiazolo[5,4-b]pyridine-2,5-diamine, $N^2$-cyclohexyl-$N^5$,8-dimethyl- | 1.42 | 317.06 |
| B17 | 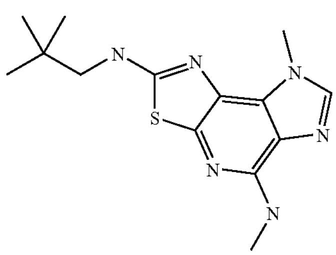 | 8H-imidazo[4,5-d]thiazolo[5,4-b]pyridine-2,5-diamine, $N^2$-(2,2-dimethylpropyl)-$N^5$,8-dimethyl- | 1.38 | 305.10 |

TABLE B1-continued

| Example Number | Name | Retention Time (min) | Observed Mass |
|---|---|---|---|
| B18 | 8H-imidazo[4,5-d]thiazolo[5,4-b]pyridine-2,5-diamine, $N^2$-cyclopentyl-$N^5$,8-dimethyl- | 1.31 | 303.06 |
| B19 | 8H-imidazo[4,5-d]thiazolo[5,4-b]pyridine-2,5-diamine, $N^5$,8-dimethyl-$N^2$-(phenylmethyl)- | 1.32 | 325.06 |
| B20 | 8H-imidazo[4,5-d]thiazolo[5,4-b]pyridine-2,5-diamine, $N^5$,8-dimethyl-$N^2$-pentyl | 1.43 | 305.1 |
| B21 | 8H-imidazo[4,5-d]thiazolo[5,4-b]pyridine-2,5-diamine, $N^2$-(3-methoxypropyl)-$N^5$,8-dimethyl- | 1.08 | 307.08 |
| B22 | 8H-imidazo[4,5-d]thiazolo[5,4-b]pyridine-2,5-diamine, $N^5$,8-dimethyl-$N^2$-(2-methylpropyl)- | 1.29 | 291.08 |

TABLE B1-continued

| Example Number | Structure | Name | Retention Time (min) | Observed Mass |
|---|---|---|---|---|
| B23 | 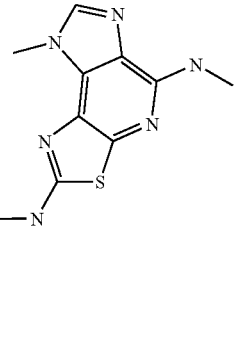 | 8H-imidazo[4,5-d]thiazolo[5,4-b]pyridine-2,5-diamine, $N^2$-[(4-methoxyphenyl)-methyl]-$N^5$,8-dimethyl- | 1.33 | 355.00 |
| B24 | 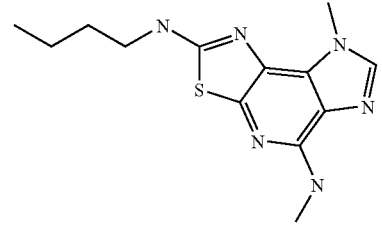 | 8H-imidazo[4,5-d]thiazolo[5,4-b]pyridine-2,5-diamine, $N^2$-butyl-$N^5$,8-dimethyl- | 1.31 | 291.08 |
| B25 | 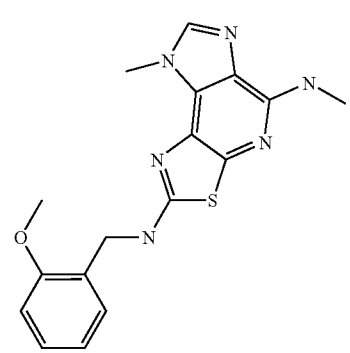 | 8H-imidazo[4,5-d]thiazolo[5,4-b]pyridine-2,5-diamine, $N^2$-[(2-methoxyphenyl)-methyl]-$N^5$,8-dimethyl- | 1.38 | 355.00 |
| B26 | 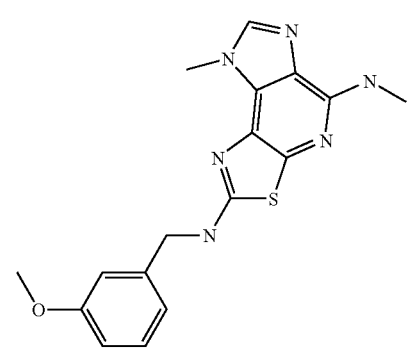 | 8H-imidazo[4,5-d]thiazolo[5,4-b]pyridine-2,5-diamine, $N^2$-[(3-methoxyphenyl)-methyl]-$N^5$,8-dimethyl- | 1.34 | 355.02 |
| B27 | 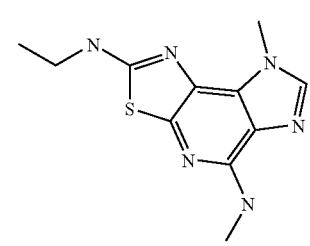 | 8H-imidazo[4,5-d]thiazolo[5,4-b]pyridine-2,5-diamine, $N^2$-ethyl-$N^5$,8-dimethyl- | 1.08 | 263.06 |

TABLE B1-continued

| Example Number | Structure | Name | Retention Time (min) | Observed Mass |
|---|---|---|---|---|
| B28 | 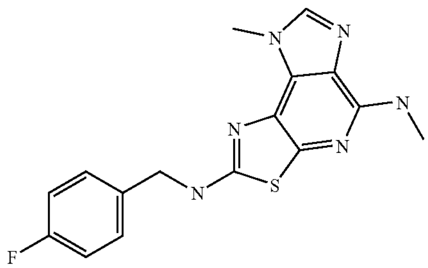 | 8H-imidazo[4,5-d]thiazolo[5,4-b]pyridine-2,5-diamine, N²-[(4-fluorophenyl)methyl]-N⁵,8-dimethyl- | 1.36 | 343.04 |

HPLC conditions: Column: Phenomenex Primesphere C18-HC 4.6 × 30 mm; Solvent A: 10% CH3CN/water 0.05% TFA, Solvent B: 90% CH3CN/water, 0.05% TFA.

Example B29

$N^2$-(2-ethoxyethyl)-$N^5$,8-dimethyl-8H-imidazo[4,5-d]thiazolo[5,4-b]pyridine-2,5-diamine,

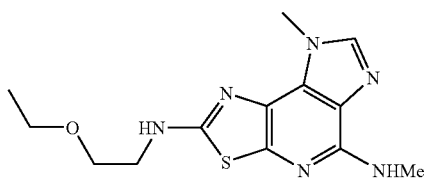

B29.1

$N^5$,8-dimethyl-2-hydroxy-8H-imidazo[4,5-d]thiazolo[5,4-b]pyridine-2,5-diamine

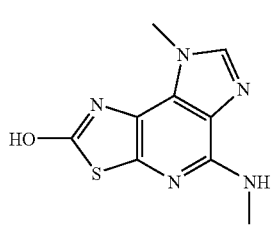

B29.1

To a stirred mixture of B2 (5.22 g, 19.6 mmol) in MeOH (80 mL) was added a suspension of Oxone (35 g) in H₂O (80 mL). After 3 h, the reaction was partially concentrated, diluted with H₂O, neutralized with NaHCO3 then the solid collected by filtration. To the sulfone intermediate (3.22 g) as a suspension in H₂O (25 mL) was added 5N NaOH and heated to 120° C. for 3 h. The reaction was acidified with 20 mL AcOH and the solid collected by filtration to afford 2.22 g (48%) B29.1 as a tan solid: MS (ES): m/z 236 [M+H]⁺ (HPLC 95%).

Alternative Synthesis of B29.1

Potassium hydroxide (840 mg, 15 mmol) in 10 ml of hot ethanol and hydroxylamine hydrochloride (695 mg, 10 mmol) in 10 ml of hot ethanol were mixed and allowed to cool to room temperature. The resulting suspension was filtered and the filtrate was added to B5 (297 mg; 1 mmol). After refluxing for 3 hrs, the reaction mixture was allowed to cool to room temperature and stand 3 days. After filtering, the filter cake was washed with ethanol and ethyl ether to give a 240 mg of a violet powder. A 35 mg portion of this powder was purified by preparatory HPLC to provide 13 mg (38%*) of B29.1 as a yellow powder. (M+H)⁺=236.11 (HPLC>99%).

*based on 35 mg sample.

B29.2

$N^5$,8-dimethyl-2-chloro-8H-imidazo[4,5-d]thiazolo[5,4-b]pyridine-2,5-diamine

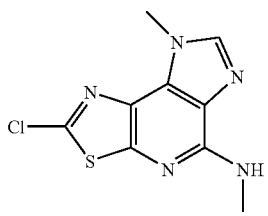

A mixture of B29.1 (1.00 g, 4.25 mmol), pyridine (0.35 mL) in POCl3 (20 mL) was heated to 140° C. with stirring for 48 h. The reaction was cooled to rt, concentrated, the residue partitioned between 1% H2SO4 and CHCl₃, the aqueous phase separated and extracted with THF (2×). The combined organic phases were dried (MgSO₄), filtered and concentrated to dryness. The residue was triturated with CHCl₃/EtOAc 1:10 to provide 975 mg (90%) S2 as a beige solid: MS (ES): m/z 254 [³⁵Cl M+H]⁺ (HPLC 98%).

B29.3

N²-(2-ethoxyethyl)-N⁵,8-dimethyl-8H-imidazo[4,5-d]thiazolo[5,4-b]pyridine-2,5-diamine To a solution of B29.2 (10 mg, 0.039 mmol) in NMP (0.5 mL) was added a solution of ethoxyethylamine (1 mL of a 0.5M solution in NMP) and K2CO3 (10 mg) and then heated to 140° C. overnight. The reaction was cooled to room temperature, AcOH (0.50 mL) was added, filtered and purified directly by preparative HPLC to afford 3.3 mg (28%) B29 as a film: MS (ES): m/z 307 [M+H]⁺ (HPLC 100%).

Examples B30–B50

Examples B30–B50 described in Table B2 were prepared in a similar manner to that used for Example B29 by reacting B29.2 with the appropriate amine substituted for ethoxyethylamine.

TABLE B2

| Example Number | Structure | Name | Retention Time (min) | Observed Mass |
|---|---|---|---|---|
| B30 | 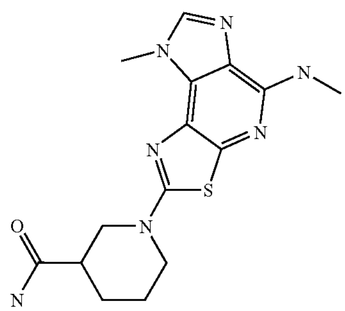 | 3-piperidinecarboxamide, 1-[8-methyl-5-(methylamino)-8H-imidazo[4,5-d]thiazolo[5,4-b]pyridin-2-yl]- | 0.97 | 346.05 |
| B31 | 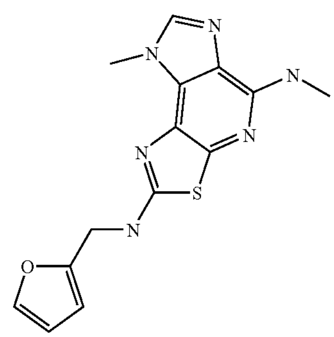 | 8H-imidazo[4,5-d]thiazolo[5,4-b]pyridine-2,5-diamine, N²-(2-furanylmethyl)-N⁵,8-dimethyl- | 1.20 | 315.01 |
| B32 | 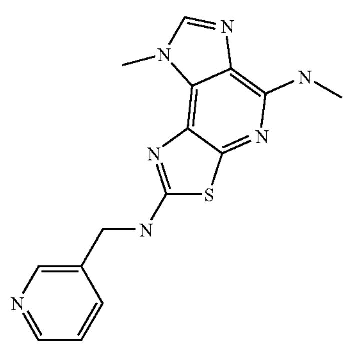 | 8H-imidazo[4,5-d]thiazolo[5,4-b]pyridine-2,5-diamine, N⁵,8-dimethyl-N²-(3-pyridinylmethyl)- | 0.57 | 326.02 |
| B33 | 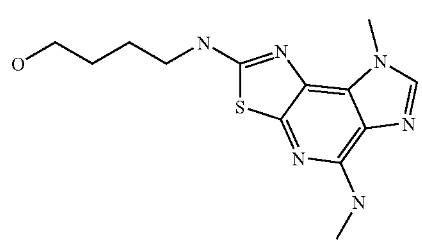 | 1-butanol, 4-[[8-methyl-5-(methylamino)-8H-imidazo[4,5-d]thiazolo[5,4-b]pyridin-2-yl]amino]- | 0.94 | 307.02 |

TABLE B2-continued

| Example Number | Structure | Name | Retention Time (min) | Observed Mass |
|---|---|---|---|---|
| B34 | 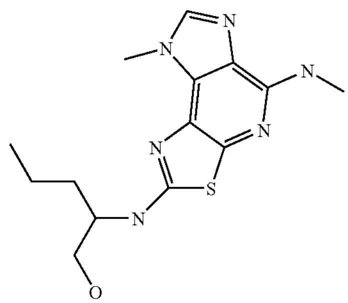 | 1-pentanol, 2-[[8-methyl-5-(methylamino)-8H-imidazo[4,5-d]thiazolo[5,4-b]pyridin-2-yl]amino]- | 1.11 | 321.03 |
| B35 | 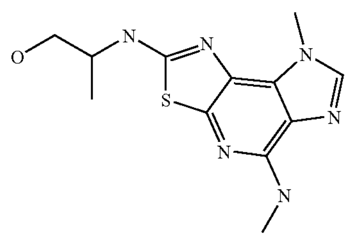 | 1-propanol, 2-[[8-methyl-5-(methylamino)-8H-imidazo[4,5-d]thiazolo[5,4-b]pyridin-2-yl]amino]- | 0.92 | 293.00 |
| B36 | 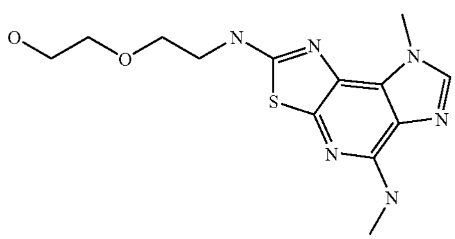 | ethanol, 2-[2-[[8-methyl-5-(methylamino)-8H-imidazo[4,5-d]thiazolo[5,4-b]pyridin-2-yl]amino]ethoxy]- | 0.90 | 323.01 |
| B37 | 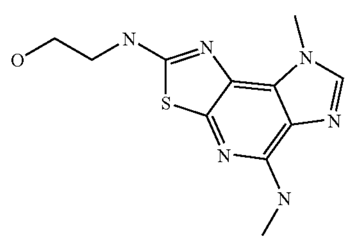 | ethanol, 2-[[8-methyl-5-(methylamino)-8H-imidazo[4,5-d]thiazolo[5,4-b]pyridin-2-yl]amino]- | 0.76 | 279.05 |
| B38 | 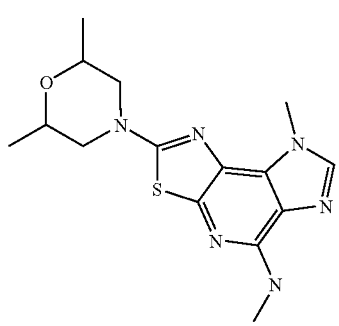 | 8H-imidazo[4,5-d]thiazolo[5,4-b]pyridin-5-amine, 2-(2,6-dimethyl-4-morpholinyl)-N,8-dimethyl- | 1.22 | 333.06 |

TABLE B2-continued

| Example Number | Structure | Name | Retention Time (min) | Observed Mass |
|---|---|---|---|---|
| B39 | 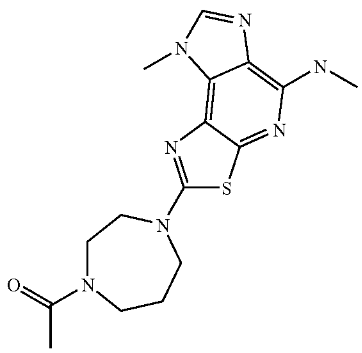 | 1H-1,4-diazepine, 1-acetylhexahydro-4-[8-methyl-5-(methylamino)-8H-imidazo[4,5-d]thiazolo[5,4-b]pyridin-2-yl]- | 0.97 | 360.00 |
| B40 | 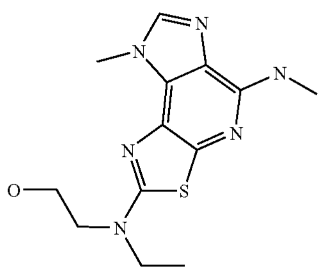 | ethanol, 2-[ethyl[8-methyl-5-(methylamino)-8H-imidazo[4,5-d]thiazolo[5,4-b]pyridin-2-yl]amino]- | 1.03 | 307.02 |
| B41 | 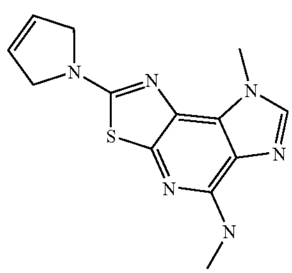 | 8H-imidazo[4,5-d]thiazolo[5,4-b]pyridin-5-amine, 2-(2,5-dihydro-1H-pyrrol-1-yl)-N,8-dimethyl- | 1.16 | 287.04 |
| B42 | 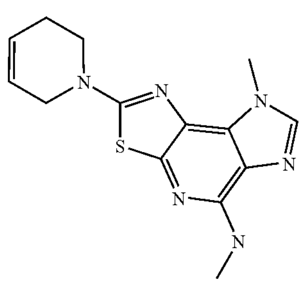 | 8H-imidazo[4,5-d]thiazolo[5,4-b]pyridin-5-amine, 2-(3,6-dihydro-1(2H)-pyridinyl)-N,8-dimethyl- | 1.27 | 301.00 |
| B43 | 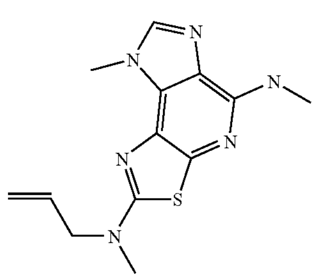 | 8H-imidazo[4,5-d]thiazolo[5,4-b]pyridine-2,5-diamine, $N^2,N^5,8$-trimethyl-$N^2$-2-propenyl- | 1.23 | 289.04 |

TABLE B2-continued

| Example Number | Structure | Name | Retention Time (min) | Observed Mass |
|---|---|---|---|---|
| B44 | 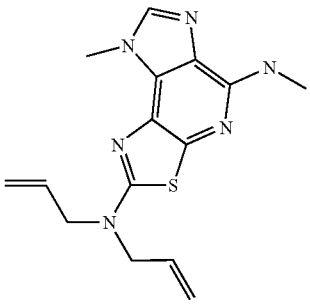 | 8H-imidazo[4,5-d]thiazolo[5,4-b]pyridine-2,5-diamine, $N^5$,8-dimethyl-$N^2$,$N^2$-di-2-propenyl- | 1.42 | 315.01 |
| B45 | 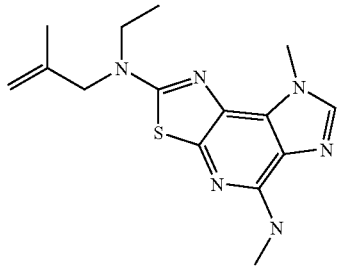 | 8H-imidazo[4,5-d]thiazolo[5,4-b]pyridine-2,5-diamine, $N^2$-ethyl-$N^5$,8-dimethyl-$N^2$-(2-methyl-2-propenyl)- | 1.46 | 317.06 |
| B46 | 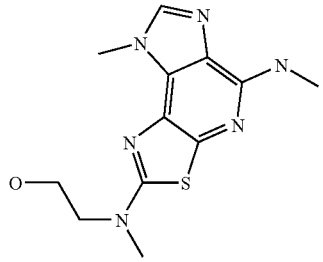 | ethanol, 2-[methyl[8-methyl-5-(methylamino)-8H-imidazo[4,5-d]thiazolo[5,4-b]pyridin-2-yl]amino]- | 0.92 | 293.00 |
| B47 | 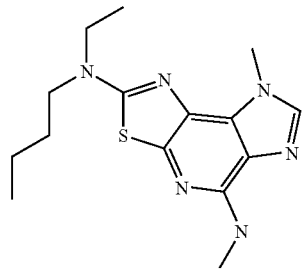 | 8H-imidazo[4,5-d]thiazolo[5,4-b]pyridine-2,5-diamine, $N^2$-butyl-$N^2$-ethyl-$N^5$,8-dimethyl- | 1.53 | 319.04 |
| B48 | 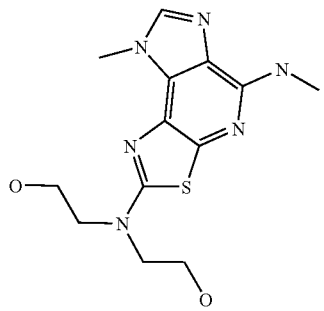 | ethanol, 2,2'-[[8-methyl-5-(methylamino)-8H-imidazo[4,5-d]thiazolo[5,4-b]pyridin-2-yl]imino]bis- | 0.78 | 323.01 |

TABLE B2-continued

| Example Number | Structure | Name | Retention Time (min) | Observed Mass |
|---|---|---|---|---|
| B49 | 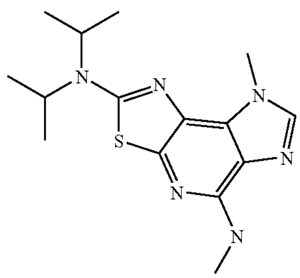 | 8H-imidazo[4,5-d]thiazolo[5,4-b]pyridine-2,5-diamine, $N^5$,8-dimethyl-$N^2$,$N^2$-bis(1-methylethyl)- | 1.53 | 319.04 |
| B50 | 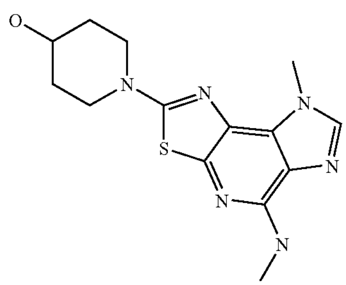 | 4-piperidinol, 1-[8-methyl-5-(methylamino)-8H-imidazo[4,5-d]thiazolo[5,4-b]pyridin-2-yl]- | 0.97 | 320.04 |

HPLC conditions: Column: Phenomenex Primesphere C18-HC 4.6 × 30 mm; Solvent A: 10% CH3CN/water 0.05% TFA, Solvent B: 90% CH3CN/water, 0.05% TFA.

Example B51

2-fluoro-N-[8-methyl-5-(methylamino)-8H-imidazo[4,5-d]thiazolo[5,4-b]pyridin-2-yl]-benzamide

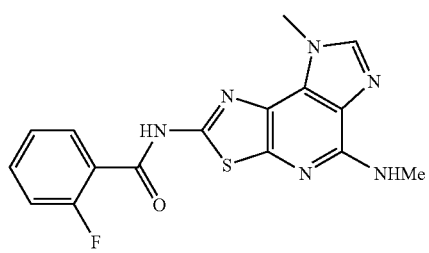

B51

B51.1

N-Methyl-4-methoxybenzylamine

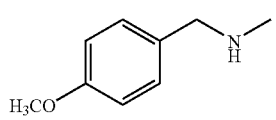

B51.1

A mixture of p-methoxybenzaldehyde (25 ml; 200 mmol) and 8M methylamine in ethanol (100 ml; 800 mmol) in 100 ml of ethanol was stirred at rt for 18 hours. After removing the volatiles in vacuo, the residue was dissolved in 300 ml of fresh ethanol and sodium borohydride (8.5 g; 225 mmol) was added portionwise over 1.5 hr. Following the addition, the reaction mixture was concentrated to ~⅓ volume and water (50 ml) was added. After cooling in an ice bath, the stirred mixture was carefully acidified to pH ~2 with 5% aqueous $H_2SO_4$. After stirring 15 minutes, the mixture was basified to pH 14 with 6N NaOH and extracted with ethyl ether (400 ml). The ether layer was washed with water (200 ml), brine (100 ml) and dried over $MgSO_4$. Concentration afforded 28.04 g (93%) of B51.1 as a colorless liquid. $(M+H)^+$=152.13 (HPLC>94%).

B51.2

N,8-dimethyl-N-[(4-methoxyphenyl)methyl]-2-(methylthio)-8H-imidazo[4,5-d]thiazolo[5,4-b]pyridin-5-amine

B51.2

A mixture of B2.1 (279 mg; 1 mmol) and B51.1 (0.5 ml; 3 mmol) in 1.5 ml of n-BuOH was heated to 180° C. for 1 hr in a microwave apparatus. After removing the volatiles in vacuo, the residue was partitioned between EtOAc (50 ml) and water (50 ml). The organic layer was washed with brine (25 ml), dried (MgSO$_4$) and concentrated to afford a light yellow gum. Ethyl ether (5 ml) was added, followed by hexane (10 ml). The mixture was concentrated by a ⅓ and the resulting semi-solid was stirred under hexane for 18 hr. Filtration and drying afforded 345 mg (90%) of B51.2 as a light yellow powder. (M+H)$^+$=386.23 (HPLC>99%).

B51.3

8-Methyl-2-(methylsulfonyl)-N-methyl-N-(4-methoxyphenyl)methyl-8H-imidazo[4,5-d]thiazolo[5,4-b]pyridin-5-amine

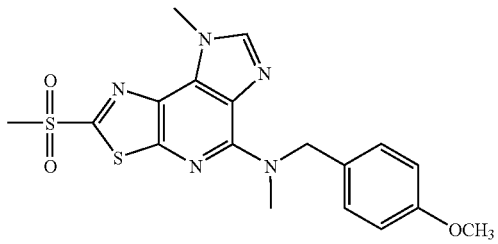

B51.3

Hydrogen peroxide, 30% (11 ml) was added to a suspension of B51.2 (3.72 g; 9.66 mmol) and sodium tungstate dehydrate (330 mg; 0.97 mmol) in 50 ml of MeOH at 0° C. After stirring 24 hr at rt, additional hydrogen peroxide, 30% (11 ml) and tungstate dehydrate (80 mg; 0.23 mmol) were added and the reaction mixture was heated to 55° C. for 6 hr. After adding 50 ml of 10% sodium sulfite solution, the MeOH was removed in vacuo and the suspension was filtered. The filter cake was rinsed with water and dried to afford 3.50 g (87%) of B51.3 as an off white powder. (M+H)$^+$=418.22 (HPLC>90%).

B51.4

8-Methyl-2-hydrazino-N-methyl-N-(4-methoxyphenyl)methyl-8H-imidazo[4,5-d]thiazolo[5,4-b]pyridin-5-amine

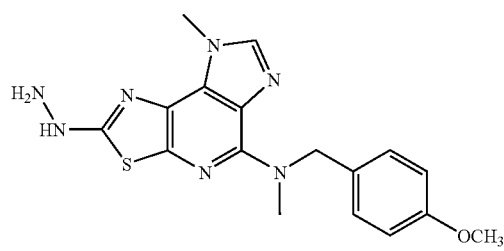

B51.4

A mixture of B51.3 (3.5 g; 8.4 mmol), hydrazine hydrate (15 ml) and ethanol (15 ml) was heated to 120° C. for 3 hrs. After cooling to room temperature, 15 ml of ethanol was added and the suspension was filtered. The filter cake was rinsed with ethanol and dried to afford 2.7 g (88%) of B51.4 as an off white solid. (M+H)$^+$=370.29 (HPLC>81%).

B51.5

8-Methyl-2-azido-N-methyl-N-(4-methoxyphenyl)methyl-8H-imidazo[4,5-d]thiazolo[5,4-b]pyridin-5-amine

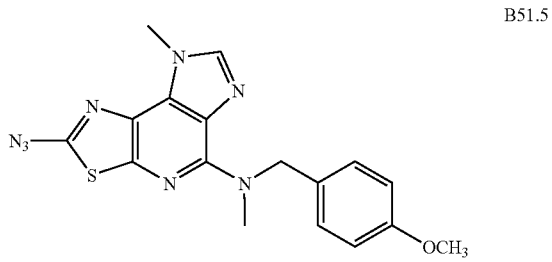

B51.5

A suspension of B51.4 (2.72 g; 7.37 mmol) in 15 ml of AcOH and 5 ml of water was stirred until complete dissolution was observed (~15 minutes). The solution was cooled to an internal temperature of −5° C. with vigorous stirring. A solution of sodium nitrite (0.51 g; 7.4 mmol) in 7 ml of water was added dropwise over ~10 minutes, while maintaining the internal temperature at −6° C. to −4° C. The reaction starts as a light orange solution that becomes darker orange early in the addition. Approximately half way through the addition a solid begins to form and by the end of the addition the reaction mixture is a very thick, dark purple suspension. Immediately after the addition was completed, the reaction mixture is partitioned between EtOAc (500 ml) and ice cold 2N NaOH (300 ml). After separating the layers, the aqueous layer was thoroughly agitated with EtOAc (250 ml) until two clear layers were observed. The combined organic layers were washed with water (300 ml) and this water layer was back extracted with CHCl$_3$ (100 ml). The combined organic layers were dried (MgSO$_4$) and concentrated to afford 2.8 g (99%) of B51.5 as a dark green solid. (M+H)$^+$=381.26 (HPLC=75%).

B51.6

8-Methyl-2-amino-N-methyl-N-(4-methoxyphenyl)methyl-8H-imidazo[4,5-d]thiazolo[5,4-b]pyridin-5-amine

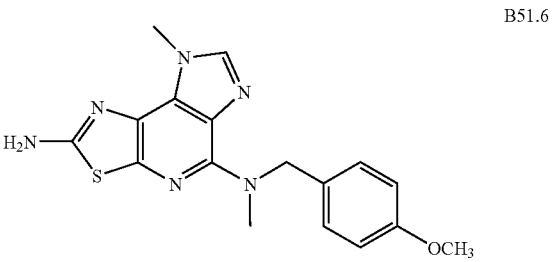

B51.6

A solution of B51.5 (2.8 g; 7.37 mmol) in 50 ml of warm THF was added dropwise over 30 minutes to a suspension of lithium aluminum hydride (0.92 g; 23 mmol) in 50 ml of ethyl ether at 0° C. After stirring 30 minutes at 0° C. and 1 hr at rt, the reaction mixture was re-cooled to 0° C. Freshly prepared saturated sodium sulfate solution was carefully added until gas evolution ceased. After stirring 15 minute, MgSO₄ was added and the suspension was filtered though Celite®. The filter cake was washed with hot THF (2×50 ml), hot EtOAc (2×50 ml) and hot CHCl₃ (2×50 ml). The dark green filtrate was concentrated and the residue was chromatographed on a 5×15 cm silica gel column using a gradient of 1 L each: 25% EtOAc/Hex, 50% EtOAc/Hex, 75% EtOAc/Hex, EtOAc and 500 ml of 5% MeOH/EtOAc. Concentration of the pure fractions afforded 1.07 g (41%) of B51.6 as an olive green powder. (M+H)⁺=355.29 (HPLC>97%).

B51.7

2-fluoro-N-[8-methyl-5-(methylamino)-8H-imidazo[4,5-d]thiazolo[5,4-b]pyridin-2-yl]-benzamide A mixture of B51.6 (9.2 mg; 1 mL of a 0.026M solution in THF), 2-fluorobenzoyl chloride (1 mL of a 0.04M solution in THF) and pyridine (50 μL) were shaken in a 1 dram vial for 72 h. HPLC analysis showed incomplete reaction, therefore more 2-fluorobenzoyl chloride (50 μL, neat material) and pyridine (500 μL) were added and the reaction shaken overnight. The reaction was concentrated on the Speedvac then treated with NH₃/MeOH solution and shaken overnight. The reaction was concentrated, diluted with DMF and purified by preparative HPLC. The purified and concentrated intermediate was subsequently treated with TFA (1 mL) and shaken for 4 h, then concentrated on the speedvac, diluted with DMF and purified by preparative HPLC to provide 5.6 mg (60%) B51 as a film: MS (ES): m/z 357 [M+H]⁺ (HPLC 100%).

Examples B52–B98

Examples B52–B98 described in Table B3 were prepared in a similar manner to that used for Example B51 by reacting B51.6 with the appropriate acid chloride

TABLE B3

| Ex. No. | Structure | Name | Retention Time (min) | Observed Mass |
|---|---|---|---|---|
| B52 | 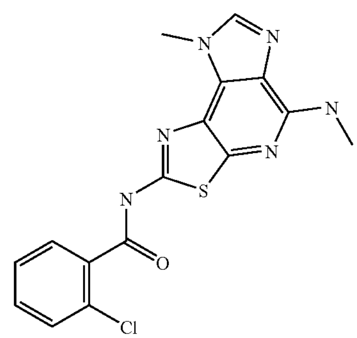 | benzamide, 2-chloro-N-[8-methyl-5-(methylamino)-8H-imidazo[4,5-d]-thiazolo[5,4-b]pyridin-2-yl]- | 1.45 | 373.14 |
| B53 | 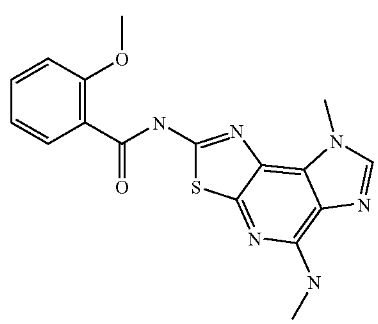 | benzamide, 2-methoxy-N-[8-methyl-5-(methylamino)-8H-imidazo[4,5-d]thiazolo[5,4-b]pyridin-2-yl]- | 1.50 | 369.17 |
| B54 | 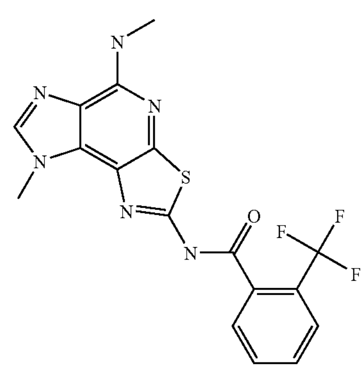 | benzamide, N-[8-methyl-5-(methylamino)-8H-imidazo[4,5-d]thiazolo[5,4-b]pyridin-2-yl]-2-(trifluoromethyl)- | 1.50 | 369.17 |

TABLE B3-continued

| Ex. No. | Structure | Name | Retention Time (min) | Observed Mass |
|---|---|---|---|---|
| B55 | 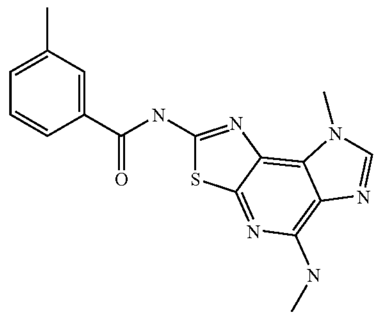 | benzamide, 3-methyl-N-[8-methyl-5-(methylamino)-8H-imidazo[4,5-d]-thiazolo[5,4-b]pyridin-2-yl]- | 1.55 | 353.18 |
| B56 | 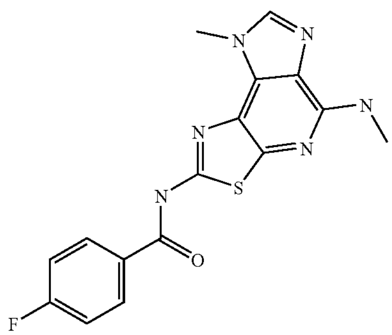 | benzamide, 4-fluoro-N-[8-methyl-5-(methylamino)-8H-imidazo[4,5-d]-thiazolo[5,4-b]pyridin-2-yl]- | 1.49 | 357.19 |
| B57 | 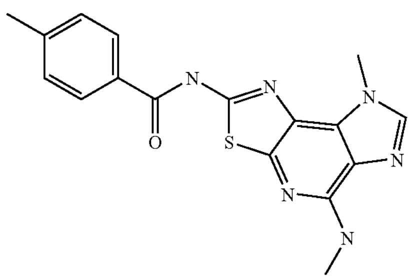 | benzamide, 4-methyl-N-[8-methyl-5-(methylamino)-8H-imidazo[4,5-d]-thiazolo[5,4-b]pyridin-2-yl]- | 1.54 | 353.25 |
| B58 | 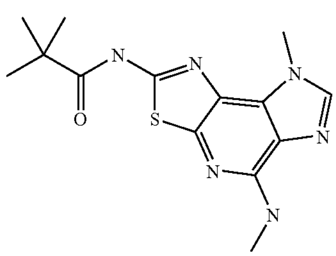 | propanamide, 2,2-dimethyl-N-[8-methyl-5-(methylamino)-8H-imidazo[4,5-d]thiazolo[5,4-b]pyridin-2-yl]- | 1.38 | 319.28 |
| B59 | 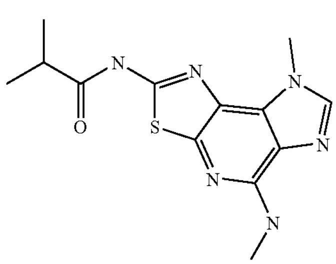 | propanamide, 2-methyl-N-[8-methyl-5-(methylamino)-8H-imidazo[4,5-d]thiazolo[5,4-b]pyridin-2-yl]- | 1.27 | 305.26 |

TABLE B3-continued

| Ex. No. | Structure | Name | Retention Time (min) | Observed Mass |
|---|---|---|---|---|
| B60 | 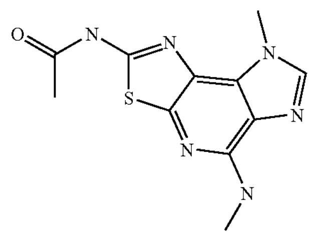 | acetamide, N-[8-methyl-5-(methylamino)-8H-imidazo[4,5-d]thiazolo[5,4-b]pyridin-2-yl]- | 1.06 | 277.24 |
| B61 | 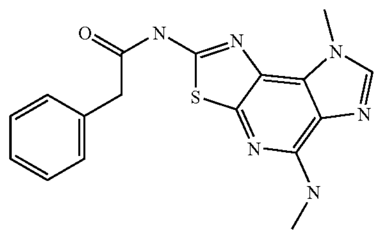 | benzeneacetamide, N-[8-methyl-5-(methylamino)-8H-imidazo[4,5-d]-thiazolo[5,4-b]pyridin-2-yl]- | 1.45 | 353.22 |
| B62 | 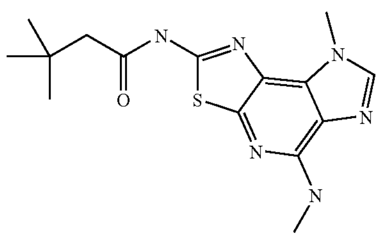 | butanamide, 3,3-dimethyl-N-[8-methyl-5-(methylamino)-8H-imidazo[4,5-d]thiazolo[5,4-b]pyridin-2-yl]- | 1.48 | 333.27 |
| B63 | 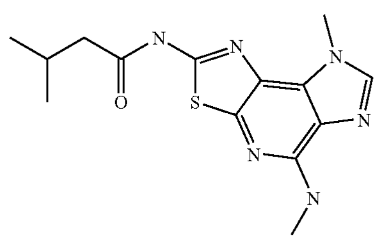 | butanamide, 3-methyl-N-[8-methyl-5-(methylamino)-8H-imidazo[4,5-d]thiazolo[5,4-b]pyridin-2-yl]- | 1.38 | 319.26 |
| B64 | 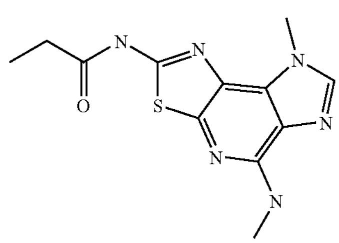 | propanamide, N-[8-methyl-5-(methylamino)-8H-imidazo[4,5-d]thiazolo[5,4-b]pyridin-2-yl]- | 1.16 | 291.26 |
| B65 | 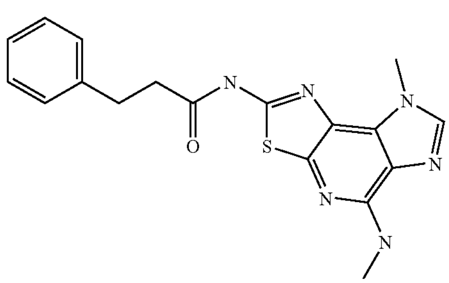 | benzenepropanamide, N-[8-methyl-5-(methylamino)-8H-imidazo[4,5-d]thiazolo[5,4-b]pyridin-2-yl]- | 1.53 | 367.22 |

TABLE B3-continued

| Ex. No. | Structure | Name | Retention Time (min) | Observed Mass |
|---|---|---|---|---|
| B66 | 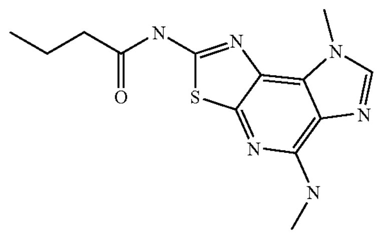 | butanamide, N-[8-methyl-5-(methylamino)-8H-imidazo[4,5-d]thiazolo[5,4-b]pyridin-2-yl]- | 1.26 | 305.22 |
| B67 | 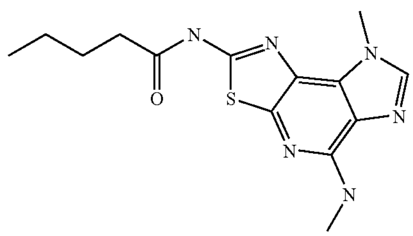 | pentanamide, N-[8-methyl-5-(methylamino)-8H-imidazo[4,5-d]thiazolo[5,4-b]pyridin-2-yl]- | 1.41 | 319.26 |
| B68 | 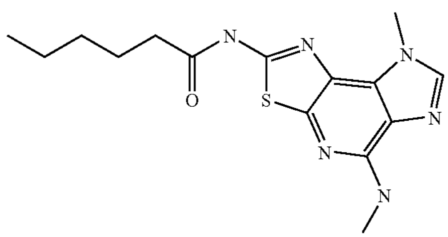 | hexanamide, N-[8-methyl-5-(methylamino)-8H-imidazo[4,5-d]thiazolo[5,4-b]pyridin-2-yl]- | 1.53 | 367.22 |
| B69 | 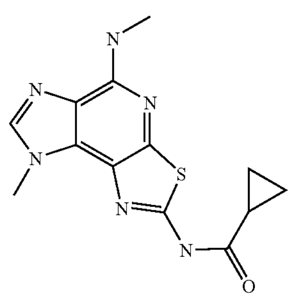 | cyclopropanecarboxamide, N-[8-methyl-5-(methylamino)-8H-imidazo[4,5-d]thiazolo[5,4-b]pyridin-2-yl]- | 1.20 | 303.23 |
| B70 | 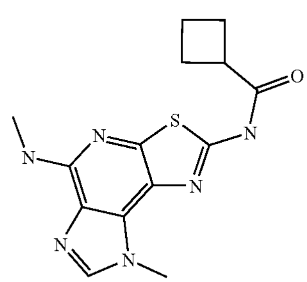 | cyclobutanecarboxamide, N-[8-methyl-5-(methylamino)-8H-imidazo[4,5-d]thiazolo[5,4-b]pyridin-2-yl]- | 1.31 | 317.22 |
| B71 | 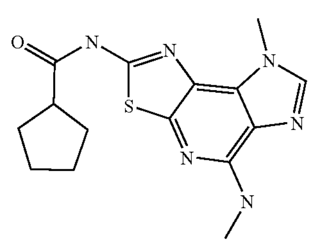 | cyclopentanecarboxamide, N-[8-methyl-5-(methylamino)-8H-imidazo[4,5-d]thiazolo[5,4-b]pyridin-2-yl]- | 1.42 | 331.24 |

TABLE B3-continued

| Ex. No. | Structure | Name | Retention Time (min) | Observed Mass |
| --- | --- | --- | --- | --- |
| B72 | 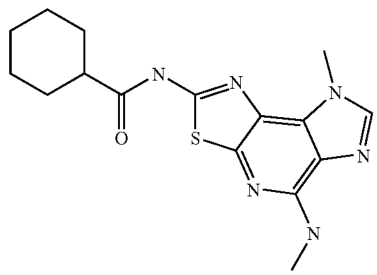 | cyclohexanecarboxamide, N-[8-methyl-5-(methylamino)-8H-imidazo[4,5-d]thiazolo[5,4-b]pyridin-2-yl]- | 1.52 | 345.25 |
| B73 | 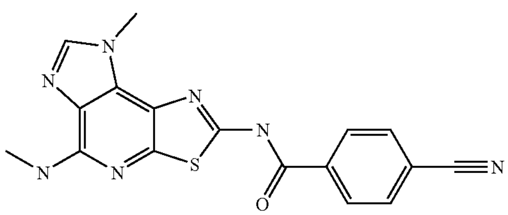 | benzamide, 4-cyano-N-[8-methyl-5-(methylamino)-8H-imidazo[4,5-d]-thiazolo[5,4-b]pyridin-2-yl]- | 1.42 | 364.18 |
| B74 | 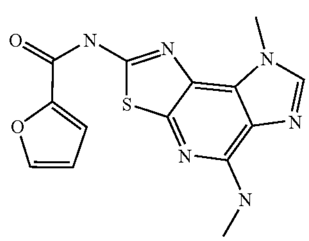 | 2-furancarboxamide, N-[8-methyl-5-(methylamino)-8H-imidazo[4,5-d]-thiazolo[5,4-b]pyridin-2-yl]- | 1.24 | 329.20 |
| B75 | 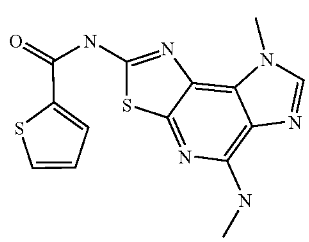 | 2-thiophenecarboxamide, N-[8-methyl-5-(methylamino)-8H-imidazo[4,5-d]thiazolo[5,4-b]pyridin-2-yl]- | 1.37 | 345.15 |
| B76 | 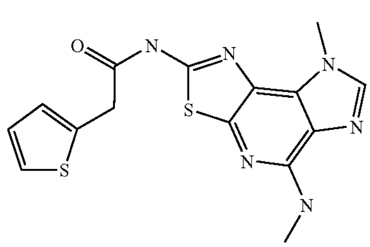 | 2-thiopheneacetamide, N-[8-methyl-5-(methylamino)-8H-imidazo[4,5-d]thiazolo[5,4-b]pyridin-2-yl]- | 1.40 | 359.16 |

TABLE B3-continued

| Ex. No. | Structure | Name | Retention Time (min) | Observed Mass |
|---|---|---|---|---|
| B77 | 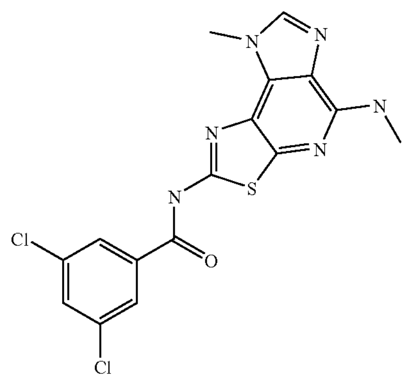 | benzamide, 3,5-dichloro-N-[8-methyl-5-(methylamino)-8H-imidazo[4,5-d]thiazolo[5,4-b]pyridin-2-yl]- | 1.83 | 407.12 |
| B78 | 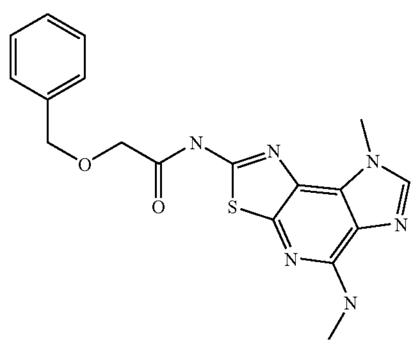 | acetamide, N-[8-methyl-5-(methylamino)-8H-imidazo[4,5-d]thiazolo[5,4-b]pyridin-2-yl]-2-(phenylmethoxy)- | 1.53 | 383.22 |
| B79 | 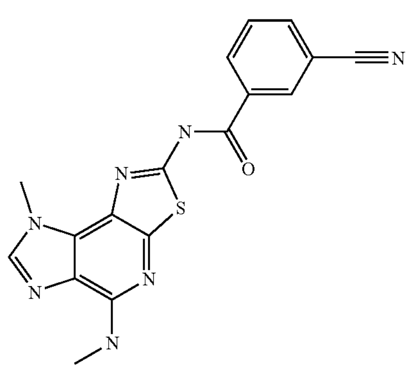 | benzamide, 3-cyano-N-[8-methyl-5-(methylamino)-8H-imidazo[4,5-d]thiazolo[5,4-b]pyridin-2-yl]- | 1.41 | 364.18 |
| B80 | 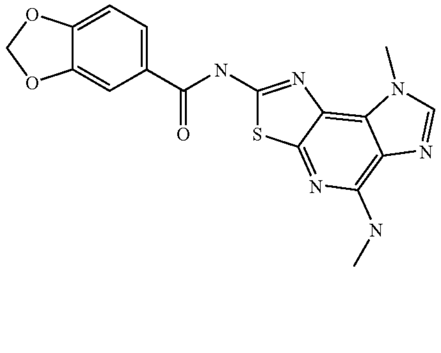 | 1,3-benzodioxole-5-carboxamide, N-[8-methyl-5-(methylamino)-8H-imidazo[4,5-d]thiazolo[5,4-b]pyridin-2-yl]- | 1.43 | 383.17 |

TABLE B3-continued

| Ex. No. | Structure | Name | Retention Time (min) | Observed Mass |
|---|---|---|---|---|
| B81 | 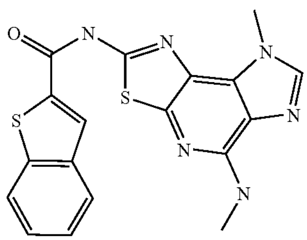 | benzo[b]thiophene-2-carboxamide, N-[8-methyl-5-(methylamino)-8H-imidazo[4,5-d]thiazolo[5,4-b]pyridin-2-yl]- | 1.70 | 395.14 |
| B82 | 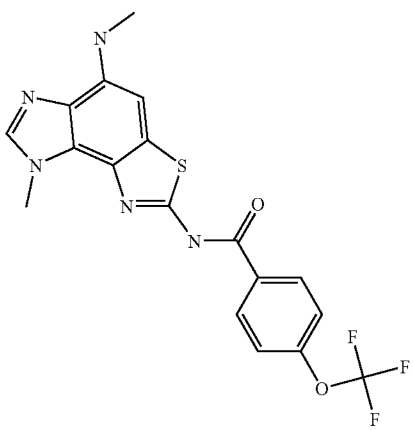 | benzamide, N-[8-methyl-5-(methylamino)-8H-imidazo[4,5-d]thiazolo[5,4-b]pyridin-2-yl]-4-(trifluoromethoxy)- | 1.73 | 423.17 |
| B83 | 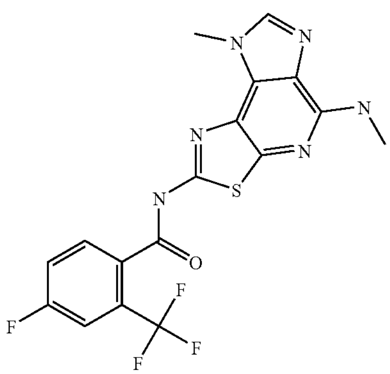 | benzamide, 4-fluoro-N-[8-methyl-5-(methylamino)-8H-imidazo[4,5-d]thiazolo[5,4-b]pyridin-2-yl]-2-(trifluoromethyl)- | 1.57 | 425.17 |
| B84 | 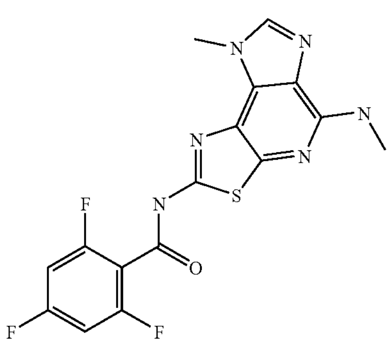 | benzamide, 2,4,6-trifluoro-N-[8-methyl-5-(methylamino)-8H-imidazo[4,5-d]thiazolo[5,4-b]pyridin-2-yl]- | 1.47 | 393.16 |

TABLE B3-continued

| Ex. No. | Structure | Name | Retention Time (min) | Observed Mass |
|---|---|---|---|---|
| B85 | 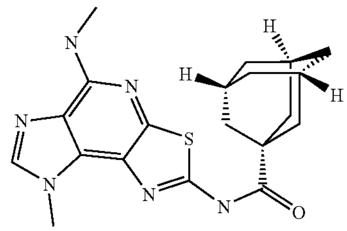 | tricyclo[3.3.1.1³,⁷]decane-1-carboxamide, N-[8-methyl-5-(methylamino)-8H-imidazo[4,5-d]-thiazolo[5,4-b]pyridin-2-yl]- | 1.81 | 397.27 |
| B86 | 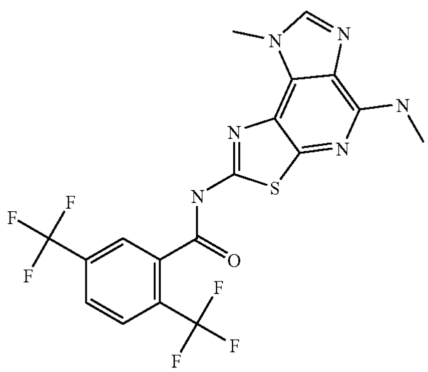 | benzamide, N-[8-methyl-5-(methylamino)-8H-imidazo[4,5-d]thiazolo[5,4-b]pyridin-2-yl]-2,5-bis(trifluoromethyl)- | 1.74 | 475.12 |
| B87 | 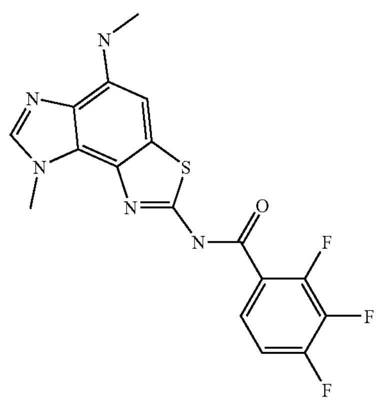 | benzamide, 2,3,4-trifluoro-N-[8-methyl-5-(methylamino)-8H-imidazo[4,5-d]thiazolo[5,4-b]pyridin-2-yl]- | 1.55 | 393.13 |
| B88 | 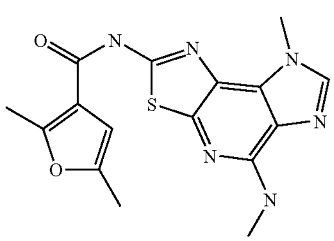 | 3-furancarboxamide, 2,5-dimethyl-N-[8-methyl-5-(methylamino)-8H-imidazo[4,5-d]thiazolo[5,4-b]pyridin-2-yl]- | 1.52 | 357.18 |
| B89 | 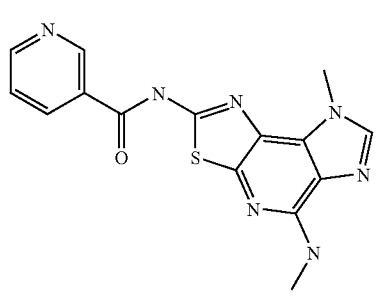 | 3-pyridinecarboxamide, N-[8-methyl-5-(methylamino)-8H-imidazo[4,5-d]thiazolo[5,4-b]pyridin-2-yl]- | 1.17 | 340.18 |

TABLE B3-continued

| Ex. No. | Structure | Name | Retention Time (min) | Observed Mass |
|---|---|---|---|---|
| B90 | 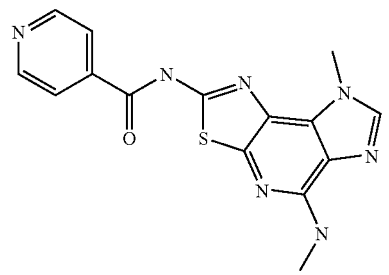 | 4-pyridinecarboxamide, N-[8-methyl-5-(methylamino)-8H-imidazo[4,5-d]thiazolo[5,4-b]pyridin-2-yl]- | 1.16 | 340.18 |
| B91 | 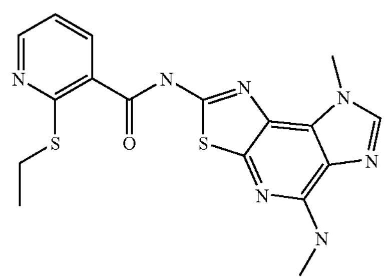 | 3-pyridinecarboxamide, 2-(ethylthio)-N-[8-methyl-5-(methylamino)-8H-imidazo[4,5-d]thiazolo[5,4-b]pyridin-2-yl]- | 1.50 | 400.16 |
| B92 | 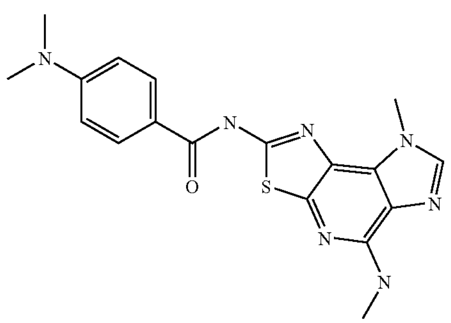 | benzamide, 4-(dimethylamino)-N-[8-methyl-5-(methylamino)-8H-imidazo[4,5-d]-thiazolo[5,4-b]pyridin-2-yl]- | 1.50 | 382.23 |
| B93 | 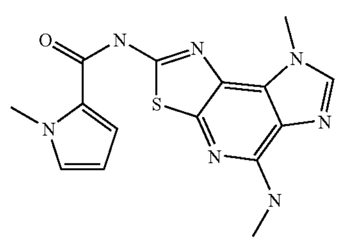 | 1H-pyrrole-2-carboxamide, 1-methyl-N-[8-methyl-5-(methylamino)-8H-imidazo[4,5-d]thiazolo[5,4-b]pyridin-2-yl]- | 1.37 | 342.19 |
| B94 | 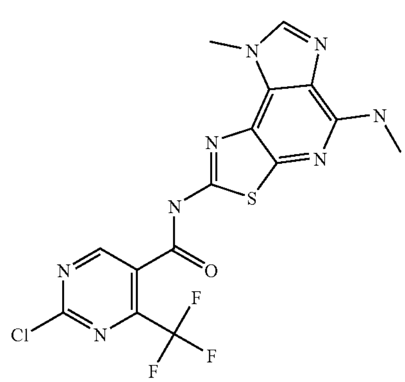 | 5-pyrimidinecarboxamide, 2-chloro-N-[8-methyl-5-(methylamino)-8H-imidazo[4,5-d]thiazolo[5,4-b]pyridin-2-yl]-4-(trifluoromethyl)- | 1.17 | 443.16 |

TABLE B3-continued

| Ex. No. | Structure | Name | Retention Time (min) | Observed Mass |
|---|---|---|---|---|
| B95 | 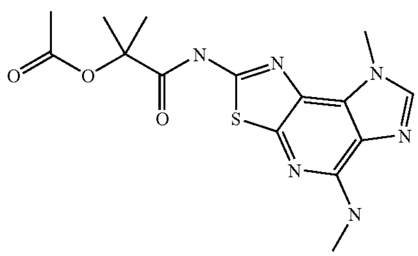 | propanamide, 2-(acetyloxy)-2-methyl-N-[8-methyl-5-(methylamino)-8H-imidazo[4,5-d]-thiazolo[5,4-b]pyridin-2-yl]- | 1.28 | 363.20 |
| B96 | 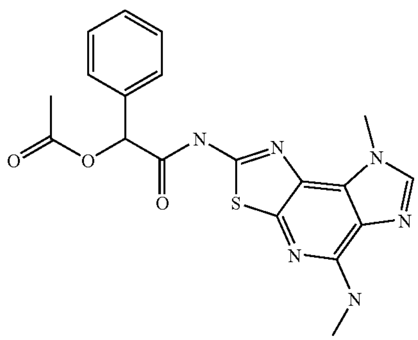 | benzeneacetamide, alpha-(acetyloxy)-N-[8-methyl-5-(methylamino)-8H-imidazo[4,5-d]thiazolo[5,4-b]pyridin-2-yl]- | 1.48 | 411.23 |
| B97 | 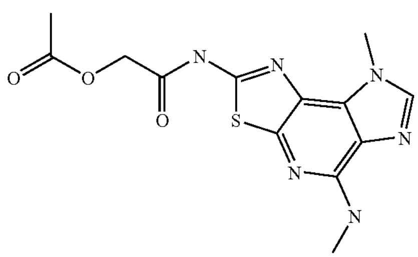 | acetamide, 2-(acetyloxy)-N-[8-methyl-5-(methylamino)-8H-imidazo[4,5-d]thiazolo[5,4-b]pyridin-2-yl]- | 1.14 | 335.2 |
| B98 | 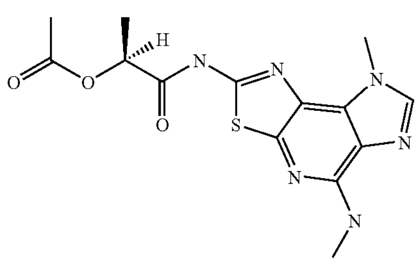 | propanamide, 2-(acetyloxy)-N-[8-methyl-5-(methylamino)-8H-imidazo[4,5-d]thiazolo[5,4-b]pyridin-2-yl]-, (2S)- | 1.22 | 349.20 |
| B90 | 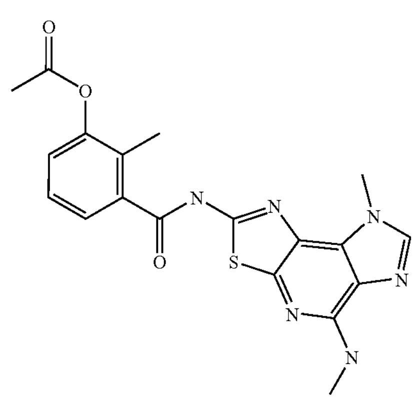 | benzamide, 3-(acetyloxy)-2-methyl-N-[8-methyl-5-(methylamino)-8H-imidazo[4,5-d]thiazolo[5,4-b]pyridin-2-yl]- | 1.44 | 411.22 |

TABLE B3-continued

| Ex. No. | Structure | Name | Retention Time (min) | Observed Mass |
|---|---|---|---|---|
| B91 | 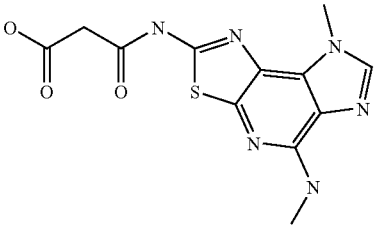 | propanoic acid, 3-[[8-methyl-5-(methylamino)-8H-imidazo[4,5-d]thiazolo[5,4-b]pyridin-2-yl]amino]-3-oxo- | 0.37 | 321.18 |
| B92 | 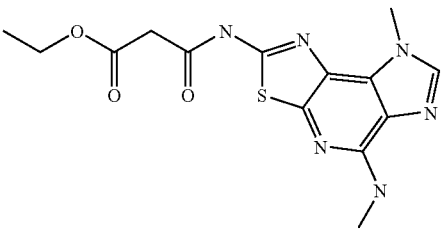 | propanoic acid, 3-[[8-methyl-5-(methylamino)-8H-imidazo[4,5-d]thiazolo[5,4-b]pyridin-2-yl]amino]-3-oxo-, ethyl ester | 1.24 | 349.19 |
| B93 | 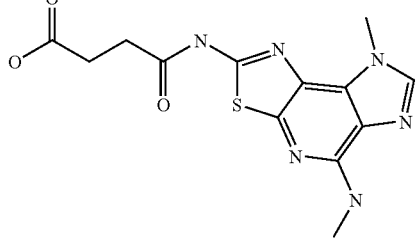 | butanoic acid, 4-[[8-methyl-5-(methylamino)-8H-imidazo[4,5-d]thiazolo[5,4-b]pyridin-2-yl]amino]-4-oxo- | 0.40 | 333.20 |
| B94 | 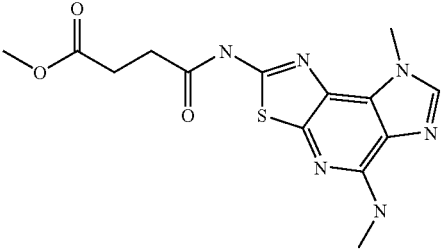 | butanoic acid, 4-[[8-methyl-5-(methylamino)-8H-imidazo[4,5-d]thiazolo[5,4-b]pyridin-2-yl]amino]-4-oxo-, methyl ester | 1.17 | 349.19 |
| B95 | 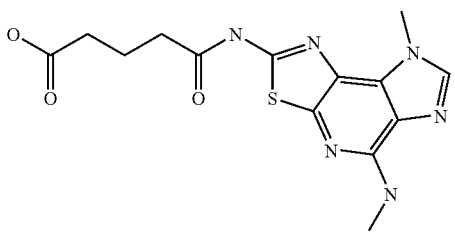 | pentanoic acid, 5-[[8-methyl-5-(methylamino)-8H-imidazo[4,5-d]thiazolo[5,4-b]pyridin-2-yl]amino]-5-oxo- | 0.50 | 347.21 |

TABLE B3-continued

| Ex. No. | Structure | Name | Retention Time (min) | Observed Mass |
|---|---|---|---|---|
| B96 | 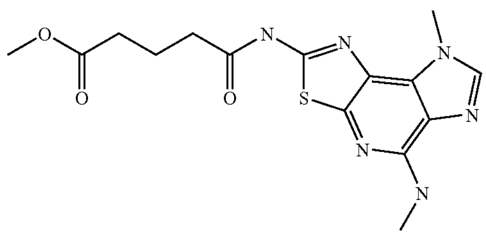 | pentanoic acid, 5-[[8-methyl-5-(methylamino)-8H-imidazo[4,5-d]thiazolo[5,4-b]pyridin-2-yl]amino]-5-oxo-, methyl ester | 1.22 | 363.22 |
| B97 | 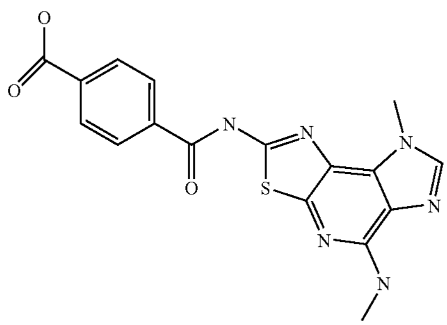 | benzoic acid, 4-[[[8-methyl-5-(methylamino)-8H-imidazo[4,5-d]thiazolo[5,4-b]pyridin-2-yl]amino]carbonyl]- | 0.97 | 381.15 |
| B98 | 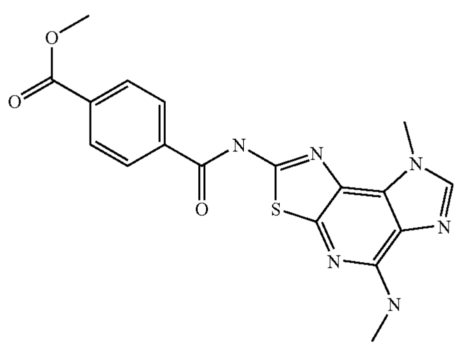 | benzoic acid, 4-[[[8-methyl-5-(methylamino)-8H-imidazo[4,5-d]thiazolo[5,4-b]pyridin-2-yl]amino]carbonyl]-, methyl ester | 1.48 | 397.19 |

HPLC Conditions: Column: Phenomenex Primesphere C18-HC 4.6 × 30 mm; Solvent A: 10% CH3CN/water 0.05% NH4OAc, Solvent B: 90% CH3CN/water, 0.05%

Example B99

1-[4-[8-methyl-5-(methylamino)-8H-imidazo[4,5-d]thiazolo[5,4-b]pyridin-2-yl]phenyl]-ethanone

B99.1

8-Methyl-2-(methylsulfonyl)-5-chloro-8H-imidazo[4,5-d]thiazolo[5,4-b]pyridine

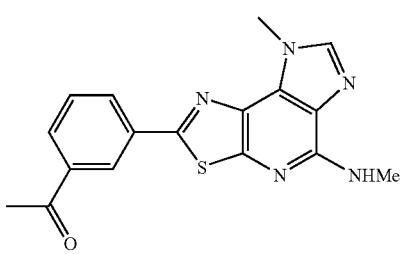

B99

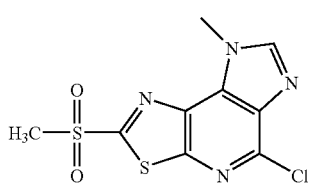

B99.1

To a mechanically stirred solution of B2.1 (12.00 g, 44.32 mmol) in MeOH (150 mL) and H₂O (150 mL) was added Oxone (160.9 g, 0.262 mol). This suspension was stirred for 48 h, at which time the stirring was stopped, the reaction was partially concentrated, diluted with H₂O, brought to pH ~7 with 5N NaOH and the resulting solid collected by filtration, washed with H₂O and dried under vacuum overnight. B99.1 was obtained (11.30 g, 84%) as a cream solid: MS (ES): m/z 303 [³⁵Cl M+H]⁺ (HPLC 99%).

B99.2

8-Methyl-2-hydrazino-5-chloro-8H-imidazo[4,5-d]thiazolo[5,4-b]pyridine

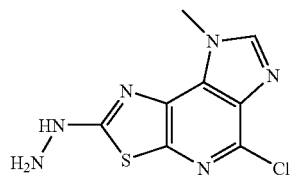

B99.2

To a stirred suspension of B99.1 (11.22 g, 37.06 mmol) in EtOH (150 mL) was added hydrazine hydrate (30 mL). This suspension was stirred overnight, at which time the stirring was stopped and the solid collected by filtration, washed with EtOH and dried under vacuum overnight to afford 9.26 g (98%) B99.2 as a cream solid: MS (ES): m/z 255 [³⁵Cl M+H]⁺ (HPLC 95%).

B99.3

8-Methyl-2-bromo-5-chloro-8H-imidazo[4,5-d]thiazolo[5,4-b]pyridine

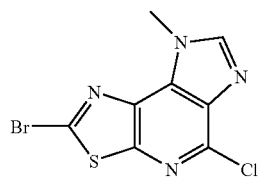

B99.3

To a stirred solution of CuBr₂ (24.50 g, 0.1097 mol) in AcOH (120 mL) and H₂O (20 mL) was added portionwise over 10 min B99.2 (9.26 g, 36.36 mmol) and stirred for 4 h. The reaction was diluted with H₂O (700 mL) and the solid collected by filtration, washed sequentially with H₂O, conc. NH₄OH (2×) until very little blue copper complex eluted and H₂O, then dried. Obtained 8.69 g (79%) B99.3 as a tan solid: MS (ES): m/z 303 [³⁵Cl ⁷⁹Br M+H]⁺ (HPLC 95%).

Alternative Synthesis of B99.3

B99.3.1

4,6-Dichloro-7-isothiocyanato-1-methyl-1H-imidazo[4,5-c]pyridine

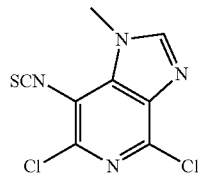

B99.3.1

Thiophosgene (0.8 ml) was added dropwise to a mixture of A1.4 (2.17 g, 0.01 moles), Hunig's base (1.24 g, 0.01 moles) in 100 ml. dioxane at room temperature. After complete addition the reaction mixture was heated at reflux for 8 hrs. On cooling the product precipitated out and was separated by filtration. B99.3.1 was obtained as a tan solid (1.77 g, 68%). ESI m/z=259.08, 261.07, 263.08 [M+H; calcd for C₈H₄Cl₂N₄S+H:259]; HPLC RT=2.883 min[4 min grad, 10% MeOH/water to 90% MeOH/water, 0.1% TFA, Xterra C18, 4.6×50 mm, 5 micron column].

B99.3.2

1-(4,6-Dichloro-1-methyl-1H-imidazo[4,5-c]pyridine-7-yl)thiourea

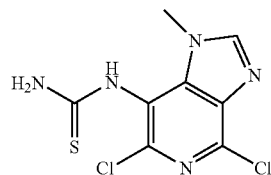

B99.3.2

Ammonia was bubbled through a mixture of B99.3.1 (0.259, 0.001 moles) in 100 ml. 33% wt. solution of ammonia in dioxane at room temperature until a white solid precipitated out. The passage of ammonia was ceased and the reaction mixture stirred an additional hour at room temperature. B99.3.2 was obtained as a white solid by filtration (0.220 g., 80%). ESI m/z=276.05, 278.05, 280.05 [M+H; calcd for C₈H₃Cl₂N₅S+H:276]; HPLC RT=0.912 min[4 min grad, 10% MeOH/water to 90% MeOH/water, 0.1% TFA, ShimadzuVP-ODS, 4.6×50 mm, 5 micron column].

B99.3.3

8-Methyl-2-amino-5-chloro-8H-imidazo[4,5-d]thiazolo[5,4-b]pyridine

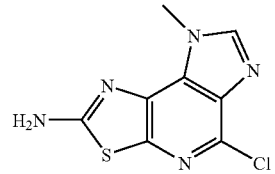

B99.3.3

A mixture of B99.3.2 (0.276, 0.001 moles), sodium methoxide powder (0.108 g, 0.001 moles) in 20 ml. N-methylpyrrolidinone(NMP) was heated at 120° C. in a sealed reaction vessel for 4 hours. at room temperature. The reaction mixture was concentrated in vacuo, and partitioned between ethyl acetate and water. The organics were combined, concentrated in vacuo and the residue chromatographed using Reverse-Phase PREP LC. B99.3.3 was obtained as a white solid. (0.112 g., 47%). ESI m/z=240.20, 242.21, [M+H; calcd for C₈H₃ClN₅S+H:239]; HPLC RT=1.743 min[4 min grad, 10% MeOH/water to 90% MeOH/water, 0.1% TFA, Xterra C18, 4.6×50 mm, 5 micron column].

B99.3.4

8-Methyl-2-bromo-5-chloro-8H-imidazo[4,5-d]thiazolo[5,4-b]pyridine

Isoamylnitrite (1 mL.) was added sequentially to a stirred mixture of B99.3.3 (0.100 g, 0.0004 moles), Cu(II)Br(0.093 g, 0.0004 moles), in 100 ml. acetonitrile at approx. 65° C. After complete addition the reaction mixture was heated at reflux for 8 hrs. The reaction mixture was cooled to room temperature then filtered through a silica gel pad. The filtrate was concentrated in vacuo and the residue purified by chromatography using Reverse-Phase PREP LC. B99.3 was obtained as a tan solid (0.075 g, 60%). ESI m/z=303.17, 305.16, 307.14[M+H; calcd for $C_8H_4BrClN_4S$+H:303]; HPLC RT=2.722 min[4 min grad, 10% MeOH/water to 90% MeOH/water, 0.1% TFA, Xterra C18, 4.6×50 mm, 5 micron column]

B99.4

1-[4-[8-methyl-5-chloro-8H-imidazo[4,5-d]thiazolo[5,4-b]pyridin-2-yl]phenyl]-ethanone

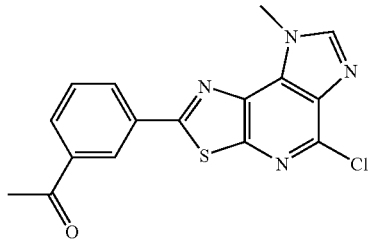

To a stirred solution of B99.3 (203 mg, 0.669 mmol), 3-acetylphenyl boronic acid (191 mg, 1.16 mmol) and $Pd(PPh_3)_4$ (34 mg, 0.0294 mmol) in DME (5 mL and EtOH (2 mL) was added $K_2CO_3$ (1 mL, 2M in $H_2O$) and then heated to reflux. After 1 h, the reaction was cooled to rt and the solid collected by filtration, washed with EtOH to afford 126.7 mg (55%) of B99.4 as a yellow solid: m/z 343 [$^{35}$Cl M+H]$^+$ (HPLC 98%).

B99.5

1-[4-[8-methyl-5-(methylamino)-8H-imidazo[4,5-d]thiazolo[5,4-b]pyridin-2-yl]phenyl]ethanone A suspension of B99.4 (905 mg, 2.64 mmol) and $MeNH_2$ (14 mL, 33 wt % in EtOH) was heated for 20 min at 150° C. in the Personal Chemistry microwave. Once cooled to rt, the reaction was diluted with EtOH (40 mL), 10% HCl (60 mL) was then added and stirred at rt. After 3 h, the reaction was diluted $H_2O$, the resulting solid was collected by filtration, washed with $H_2O$, dried to afford 694 mg (78%) B99 as a yellow solid: m/z 338 [M+H]$^+$ (HPLC 98%).

Example B100

N,8-dimethyl-2-[3-[1-[(2-phenylethyl)amino]ethyl]phenyl]-8H-imidazo[4,5-d]thiazolo[5,4-b]pyridin-5-amine

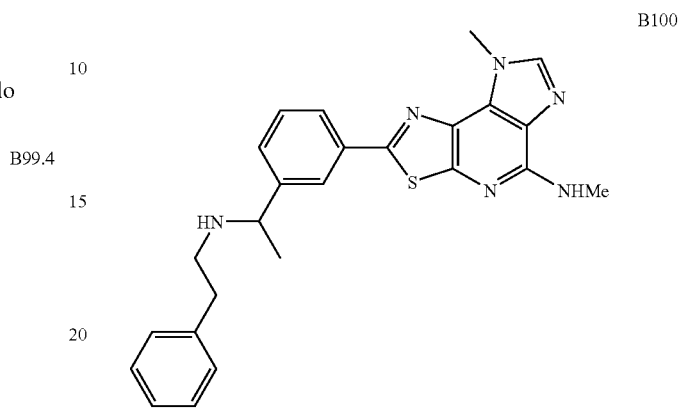

A mixture of B99 (10 mg, 29.64 µmol), phenethylamine (1 mL, 0.06M in THF, 60 µmol) and Ti(Oi-Pr)$_4$ (1 mL, 0.06M in THF, 60 µmol) in a test tube was shaken at 20° C. for 20 hr. NaBH$_4$ (3.79 mg in 1 mL EtOH, 90 µmol) was added and the contents again shacken for 20 h. MeOH/AcOH (1:1, 1 mL) was added, followed by dilution up to 9 mL with MeOH. The reaction was eluted through a Silicycle 1.5 g SCX cartridge. The filtrate was concentrated, then treated with NH$_3$/MeOH solution and concentrated on the SpeedVac. The residue was dissolved in 2 mL DMF, filtered then purified by preparative HPLC to provide 5.3 mg (40%) B100 as a film: MS (ES): m/z 443 [M+H]$^+$ (HPLC 96%).

Examples B101–B122

Examples B101–B122 described in Table B4 were prepared in a similar manner to that used for Example B100 by reacting B99 with the appropriate amine substituted for phenethylamine.

TABLE B4

| Ex. Number | Structure | Name | Retention Time (min) | Observed Mass |
|---|---|---|---|---|
| B101 | 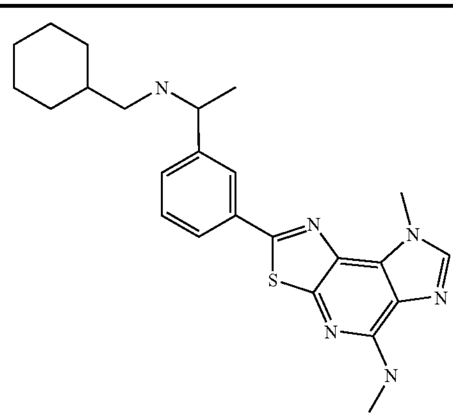 | 8H-imidazo[4,5-d]thiazolo[5,4-b]pyridin-5-amine, 2-[3-[1-[(cyclohexylmethyl)amino]-ethyl]phenyl]-N,8-dimethyl- | 1.94 | 435.36 |

TABLE B4-continued

| Ex. Number | Name | Retention Time (min) | Observed Mass |
|---|---|---|---|
| B102 | 8H-imidazo[4,5-d]thiazolo[5,4-b]pyridin-5-amine, N,8-dimethyl-2-[3-[1-[[(tetrahydro-2-furanyl)methyl]amino]-ethyl]phenyl]- | 1.54 | 423.24 |
| B103 | 8H-imidazo[4,5-d]thiazolo[5,4-b]pyridin-5-amine, N,8-dimethyl-2-[3-[1-[[1-(phenylmethyl)-4-piperidinyl]amino]ethyl]phenyl] | 1.91 | 512.37 |
| B104 | 8H-imidazo[4,5-d]thiazolo[5,4-b]pyridin-5-amine, N,8-dimethyl-2-[3-[1-[[2-(1-piperidinyl)ethyl]amino]-ethyl]phenyl]- | 1.65 | 450.37 |
| B105 | 8H-imidazo[4,5-d]thiazolo[5,4-b]pyridin-5-amine, N,8-dimethyl-2-[3-[1-[(phenylmethyl)amino]-ethyl]phenyl]- | 1.92 | 429.32 |

TABLE B4-continued

| Ex. Number | Structure | Name | Retention Time (min) | Observed Mass |
|---|---|---|---|---|
| B106 | 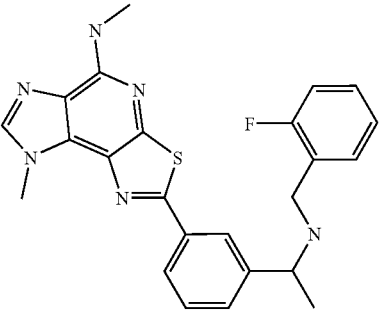 | 8H-imidazo[4,5-d]thiazolo[5,4-b]pyridin-5-amine, 2-[3-[1-[[(2-fluorophenyl)methyl]amino]-ethyl]phenyl]-N,8-dimethyl- | 1.99 | 447.28 |
| B107 | 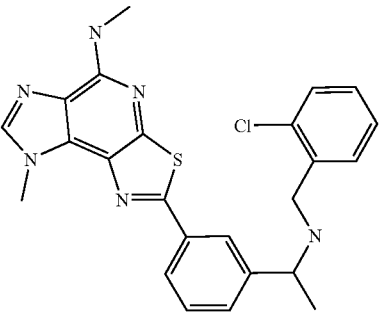 | 8H-imidazo[4,5-d]thiazolo[5,4-b]pyridin-5-amine, 2-[3-[1-[[(2-chlorophenyl)methyl]amino]-ethyl]phenyl]-N,8-dimethyl- | 2.18 | 463.27 |
| B108 | 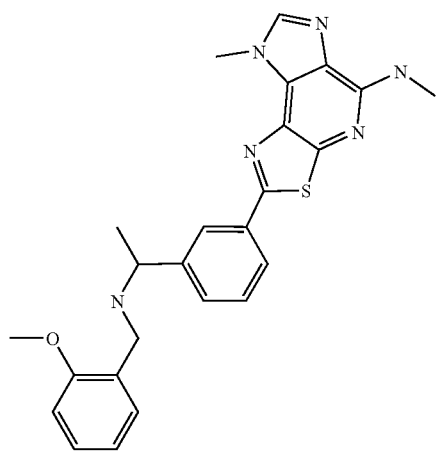 | 8H-imidazo[4,5-d]thiazolo[5,4-b]pyridin-5-amine, 2-[3-[1-[[(2-methoxyphenyl)methyl]-amino]ethyl]phenyl]-N,8-dimethyl- | 1.81 | 459.33 |
| B109 | 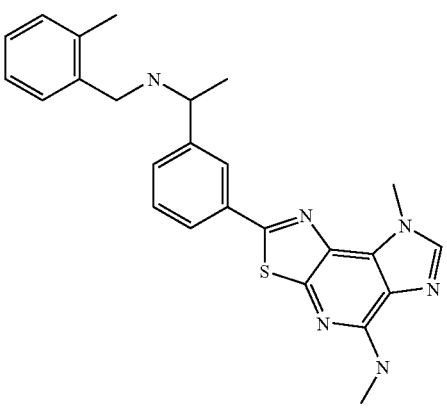 | 8H-imidazo[4,5-d]thiazolo[5,4-b]pyridin-5-amine, N,8-dimethyl-2-[3-[1-[[(2-methylphenyl)-methyl]amino]ethyl]phenyl]- | 2.09 | 443.34 |

TABLE B4-continued

| Ex. Number | Structure | Name | Retention Time (min) | Observed Mass |
|---|---|---|---|---|
| B110 | 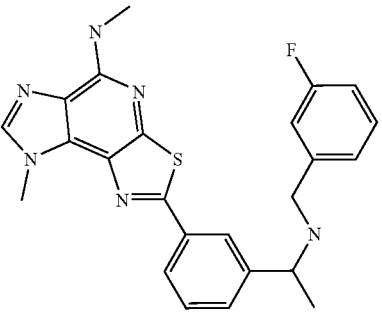 | 8H-imidazo[4,5-d]thiazolo[5,4-b]pyridin-5-amine, 2-[3-[1-[[(3-fluorophenyl)methyl]-amino]ethyl]phenyl]-N,8-dimethyl- | 2.03 | 447.31 |
| B111 | 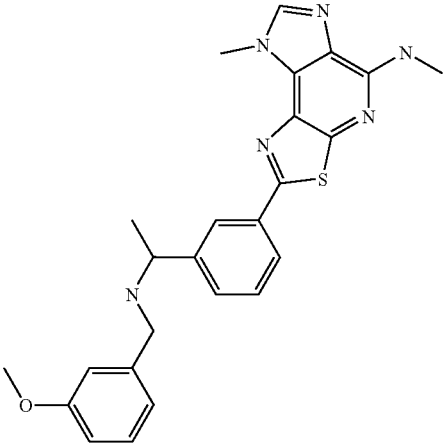 | 8H-imidazo[4,5-d]thiazolo[5,4-b]pyridin-5-amine, 2-[3-[1-[[(3-methoxyphenyl)methyl]-amino]ethyl]phenyl]-N,8-dimethyl- | 1.92 | 459.33 |
| B112 | 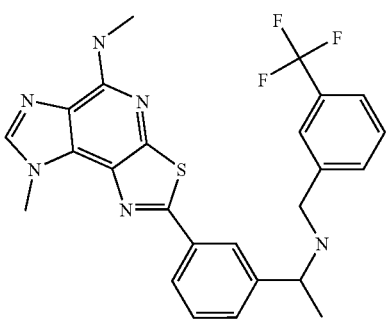 | 8H-imidazo[4,5-d]thiazolo[5,4-b]pyridin-5-amine, N,8-dimethyl-2-(trifluoromethyl)phenyl]methyl]amino]ethyl]phenyl]- | 2.23 | 497.29 |
| B113 | 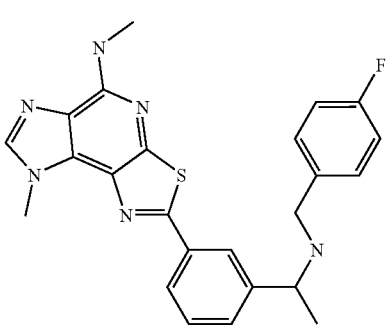 | 8H-imidazo[4,5-d]thiazolo[5,4-b]pyridin-5-amine, 2-[3-[1-[[(4-fluorophenyl)methyl]amino]-ethyl]phenyl]-N,8-dimethyl- | 1.97 | 447.31 |

TABLE B4-continued

| Ex. Number | Structure | Name | Retention Time (min) | Observed Mass |
|---|---|---|---|---|
| B114 | 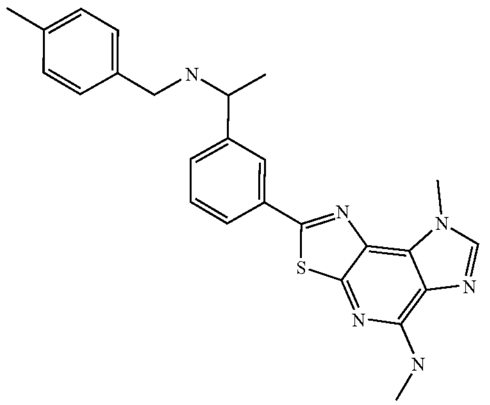 | 8H-imidazo[4,5-d]thiazolo[5,4-b]pyridin-5-amine, N,8-dimethyl-2-[3-[1-[[(4-methylphenyl)-methyl]amino]ethyl]phenyl]- | 2.02 | 443.33 |
| B115 | 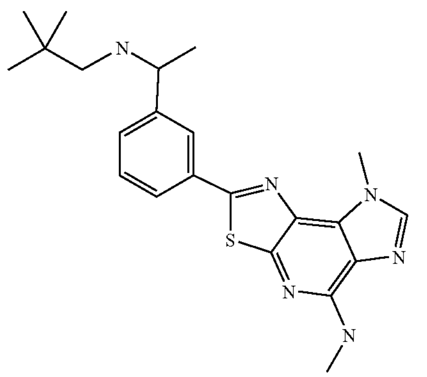 | 8H-imidazo[4,5-d]thiazolo[5,4-b]pyridin-5-amine, 2-[3-[1-[(2,2-dimethylpropyl)amino]ethyl]-phenyl]-N,8-dimethyl- | 1.90 | 409.36 |
| B116 | 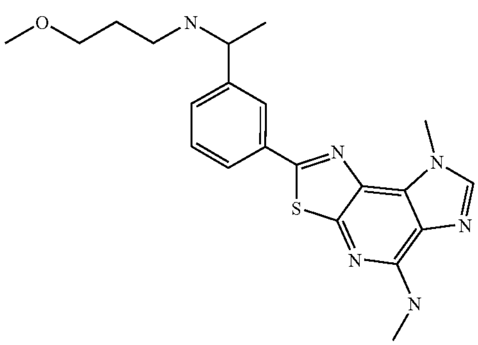 | 8H-imidazo[4,5-d]thiazolo[5,4-b]pyridin-5-amine, 2-[3-[1-[(3-methoxypropyl)amino]ethyl]-phenyl]-N,8-dimethyl- | 1.43 | 411.33 |
| B117 | 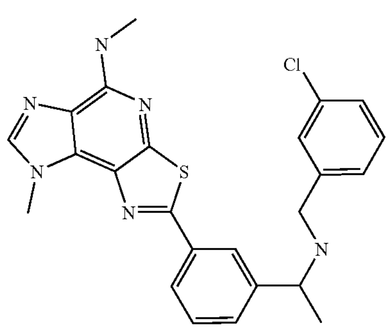 | 8H-imidazo[4,5-d]thiazolo[5,4-b]pyridin-5-amine, 2-[3-[1-[[(3-chlorophenyl)methyl]amino]-ethyl]phenyl]-N,8-dimethyl- | 2.20 | 463.28 |

TABLE B4-continued

| Ex. Number | Structure | Name | Retention Time (min) | Observed Mass |
|---|---|---|---|---|
| B118 | 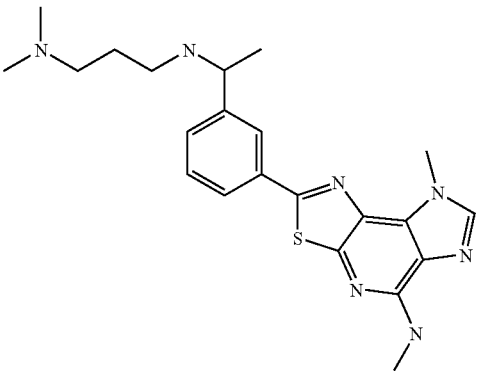 | 1,3-propanediamine, N,N-dimethyl-N'-[1-[3-[8-methyl-5-(methylamino)-8H-imidazo[4,5-d]thiazolo[5,4-b]pyridin-2-yl]phenyl]ethyl]- | 2.13 | 424.36 |
| B119 | 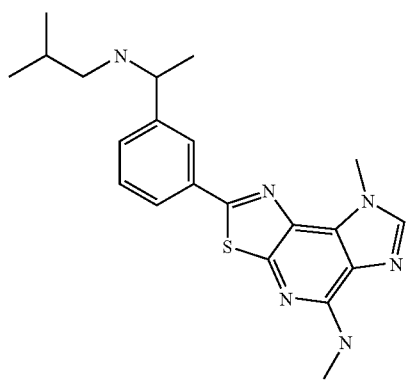 | 8H-imidazo[4,5-d]thiazolo[5,4-b]pyridin-5-amine, N,8-dimethyl-2-[3-[1-[(2-methylpropyl)-amino]ethyl]phenyl]- | 1.63 | 395.34 |
| B120 | 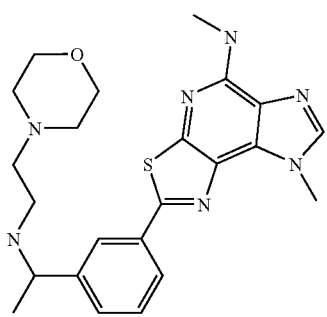 | 8H-imidazo[4,5-d]thiazolo[5,4-b]pyridin-5-amine, N,8-dimethyl-2-[3-[1-[[2-(4-morpholinyl)ethyl]amino]-ethyl]phenyl]- | 1.44 | 452.33 |
| B121 | 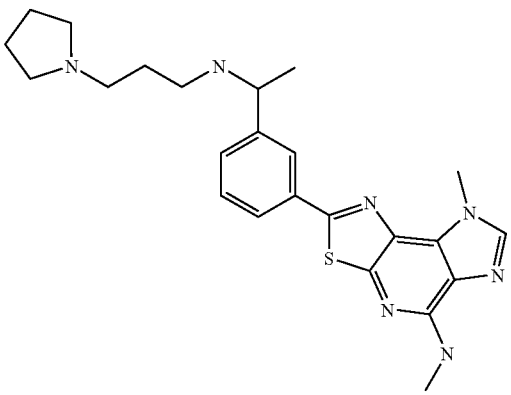 | 8H-imidazo[4,5-d]thiazolo[5,4-b]pyridin-5-amine, N,8-dimethyl-2-[3-[1-[[3-(1-pyrrolidinyl)propyl]amino]-ethyl]phenyl]- | 2.16 | 450.37 |

TABLE B4-continued

| Ex. Number | Structure | Name | Retention Time (min) | Observed Mass |
|---|---|---|---|---|
| B122 | 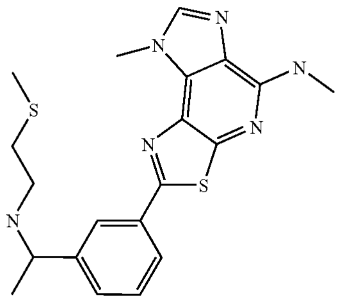 | 8H-imidazo[4,5-d]thiazolo[5,4-b]pyridin-5-amine, N,8-dimethyl-2-[3-[1-[[2-(methylthio)ethyl]amino]ethyl]phenyl]- | 1.66 | 413.29 |

HPLC Conditions: Column: Phenomenex Primesphere C18-HC 4.6 × 30 mm; Solvent A: 10% CH3CN/water 0.05% NH4OAc, Solvent B: 90% CH3CN/water, 0.05%.

Examples B123–B135

Examples B123–B135 described in Table B5 were prepared in a similar manner to that used for Example B99 by reacting B99.3 with the appropriate boronic acid as described in step B99.4 followed by reaction with an appropriate amine as described in step B99.5. B131 was isolated as a by product during the preparation of B130.

TABLE B5

| Example Number | Structure | Name | Retention Time (min) | Observed mass |
|---|---|---|---|---|
| B123 | 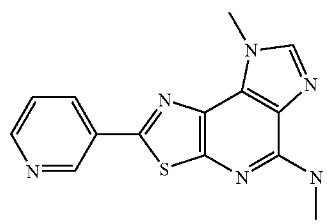 | 8H-imidazo[4,5-d]thiazolo[5,4-b]pyridin-5-amine, N,8-dimethyl-2-(3-pyridinyl)- | 0.98 | 297.00 |
| B124 | 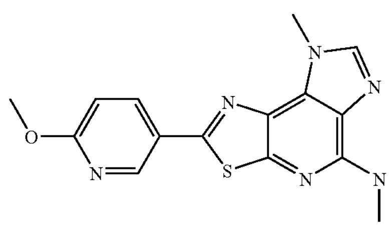 | 8H-imidazo[4,5-d]thiazolo[5,4-b]pyridin-5-amine, 2-(6-methoxy-3-pyridinyl)-N,8-dimethyl- | 1.36 | 327.00 |
| B125 | 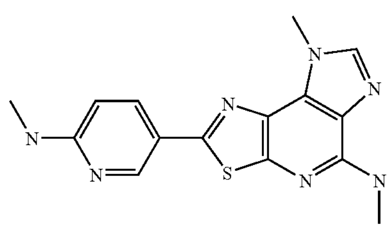 | 8H-imidazo[4,5-d]thiazolo[5,4-b]pyridin-5-amine, N,8-dimethyl-2-[6-(methylamino)-3-pyridinyl]- | 0.95 | 326.00 |
| B126 | 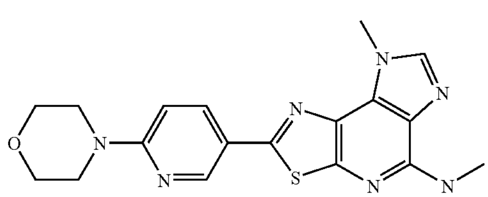 | 8H-imidazo[4,5-d]thiazolo[5,4-b]pyridin-5-amine, N,8-dimethyl-2-[6-(4-morpholinyl)-3-pyridinyl]- | 1.12 | 382.00 |

TABLE B5-continued

| Example Number | Structure | Name | Retention Time (min) | Observed mass |
|---|---|---|---|---|
| B127 | 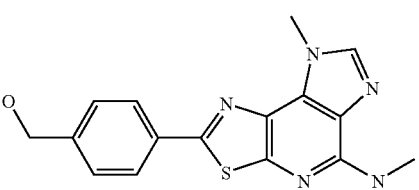 | benzenemethanol, 4-[8-methyl-5-(methylamino)-8H-imidazo[4,5-d]thiazolo[5,4-b]pyridin-2-yl]- | 1.13 | 326.00 |
| B128 | 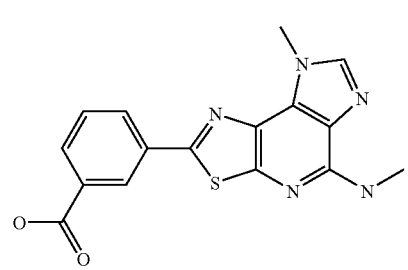 | benzoic acid, 3-[8-methyl-5-(methylamino)-8H-imidazo[4,5-d]thiazolo[5,4-b]pyridin-2-yl]- | 1.25 | 340.00 |
| B129 | 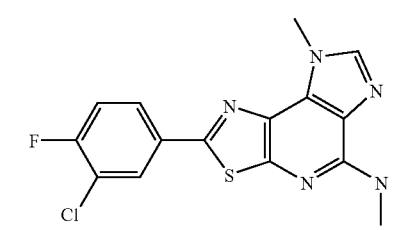 | 8H-imidazo[4,5-d]thiazolo[5,4-b]pyridin-5-amine, 2-(3-chloro-4-fluorophenyl)-N,8-dimethyl- | 1.77 | 348.00 |
| B130 | 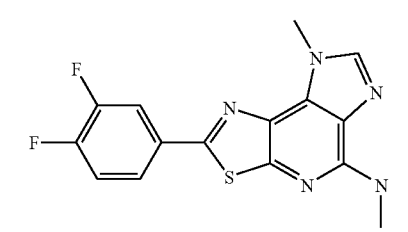 | 8H-imidazo[4,5-d]thiazolo[5,4-b]pyridin-5-amine, 2-(3,4-difluorophenyl)-N,8-dimethyl- | 1.67 | 332.00 |
| B131 | 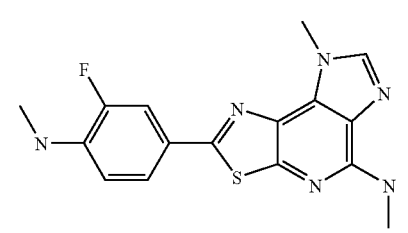 | 8H-imidazo[4,5-d]thiazolo[5,4-b]pyridin-5-amine, 2-[3-fluoro-4-(methylamino)phenyl]-N,8-dimethyl- | 2.46 | 343.00 |

TABLE B5-continued

| Example Number | Structure | Name | Retention Time (min) | Observed mass |
|---|---|---|---|---|
| B132 | 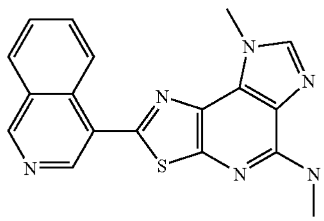 | 8H-imidazo[4,5-d]thiazolo[5,4-b]pyridin-5-amine, 2-(4-isoquinolinyl)-N,8-dimethyl- | 1.18 | 347.00 |
| B133 | 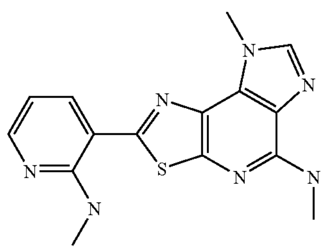 | 8H-imidazo[4,5-d]thiazolo[5,4-b]pyridin-5-amine, N,8-dimethyl-2-[2-(methylamino)-3-pyridinyl]- | 1.03 | 326.00 |
| B134 | 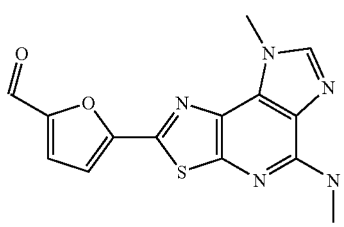 | 2-furancarboxaldehyde, 5-[8-methyl-5-(methylamino)-8H-imidazo[4,5-d]thiazolo[5,4-b]pyridin-2-yl]- | 1.23 | 314.00 |
| B135 | 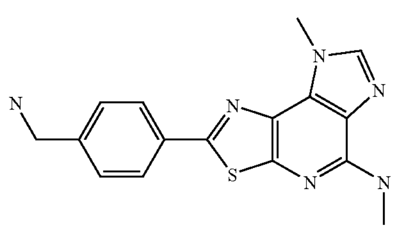 | 8H-imidazo[4,5-d]thiazolo[5,4-b]pyridin-5-amine, 2-[4-(aminomethyl)phenyl]-N,8-dimethyl- | 0.96 | 325.00 |

HPLC conditions: Column: Phenomenex Primesphere C18-HC 4.6 × 30 mm; Solvent A: 10% CH3CN/water 0.05% TFA, Solvent B: 90% CH3CN/water, 0.05% TFA.

Example B136

N,N-diethyl-3-[8-methyl-5-(methylamino)-8H-imidazo[4,5-d]thiazolo[5,4-b]pyridin-2-yl]benzamide

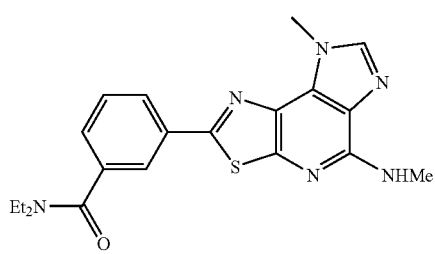

B136

A mixture of B128 (80 mg; 0.25 mmol), EDAC (45 mg, 0.50 mmol), HOBt (64 mg, 0.50 mmol), Et₃N (50 μL), Et₂NH (48 μL, 0.50 mmol) and NMP (4 mL) were stirred at room temperature overnight. The reaction was then purified by preparative HPLC to provide 14 mg B136 as a colourless solid: MS (ES): m/z 395 [M+H]⁺ (HPLC 95%).

Examples B137–B171

Examples B137–B171 described in Table B6 were prepared in a similar manner to that used for Example B136 by reacting B128 with the appropriate amine.

TABLE B6

| Ex. Number | Structure | Name | Retention Time (min) | Observed Mass |
|---|---|---|---|---|
| B137 | 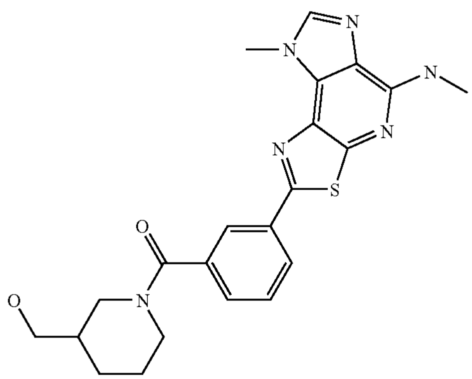 | 3-piperidinemethanol, 1-[8 3-[8-methyl-5-(methylamino)-8H-imidazo[4,5-d]thiazolo[5,4-b]pyridin-2-yl]benzoyl]- | 1.21 | 437.04 |
| B138 | 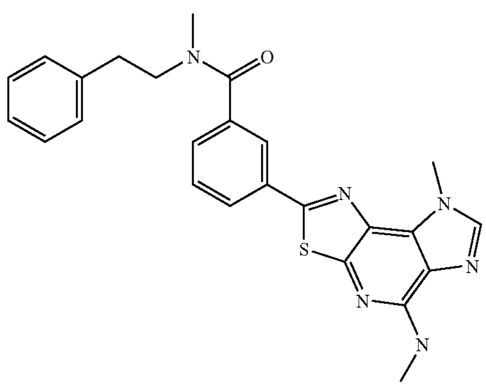 | benzamide, N-methyl-3-[8-methyl-5-(methylamino)-8H-imidazo[4,5-d]thiazolo[5,4-b]pyridin-2-yl]-N-(2-phenylethyl)- | 1.55 | 457.07 |
| B139 | 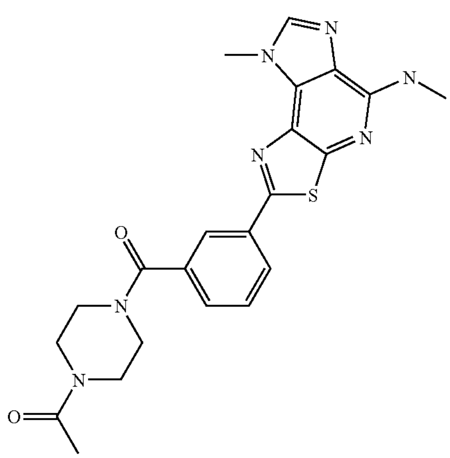 | piperazine, 1-acetyl-4-[3-[8-methyl-5-(methylamino)-8H-imidazo[4,5-d]thiazolo[5,4-b]pyridin-2-yl]benzoyl]- | 1.13 | 450.03 |

TABLE B6-continued

| Ex. Number | Structure | Name | Retention Time (min) | Observed Mass |
|---|---|---|---|---|
| B140 | 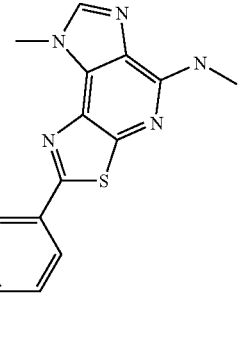 | piperidine, 1-[3-[8-methyl-5-(methylamino)-8H-imidazo[4,5-d]thiazolo[5,4-b]pyridin-2-yl]benzoyl]- | 1.42 | 407.03 |
| B141 | 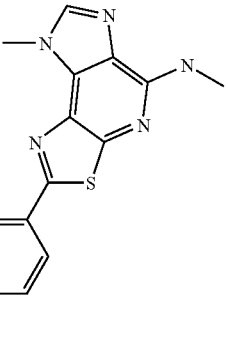 | thiomorpholine, 4-[3-[8-methyl-5-(methylamino)-8H-imidazo[4,5-d]thiazolo[5,4-b]pyridin-2-yl]benzoyl]- | 1.39 | 425.01 |
| B142 | 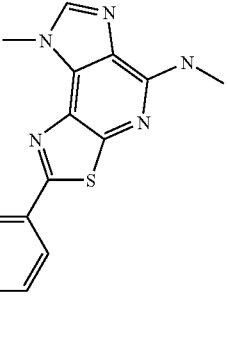 | piperazine, 1-methyl-4-[3-[8-methyl-5-(methylamino)-8H-imidazo[4,5-d]rhiazolo[5,4-b]pyridin-2-yl]benzoyl]- | 1.01 | 422.06 |
| B143 | 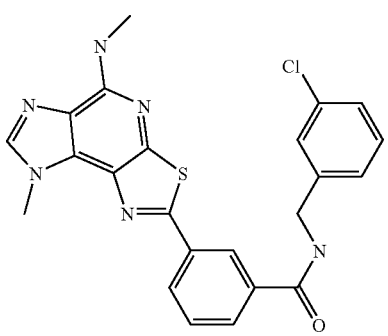 | benzamide, N-[(3-chlorophenyl)methyl]-3-[8-methyl-5-(methylamino)-8H-imidazo[4,5-d]thiazolo[5,4-b]pyridin-2-yl]- | 1.64 | 463.02 |

TABLE B6-continued

| Ex. Number | Structure | Name | Retention Time (min) | Observed Mass |
|---|---|---|---|---|
| B144 | 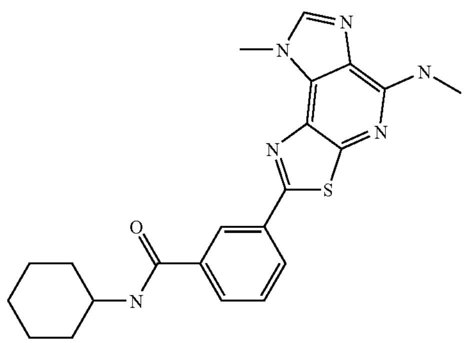 | benzamide, N-cyclohexyl-3-[8-methyl-5-(methylamino)-8H-imidazo[4,5-d]thiazolo[5,4-b]pyridin-2-yl]- | 1.56 | 421.05 |
| B145 | 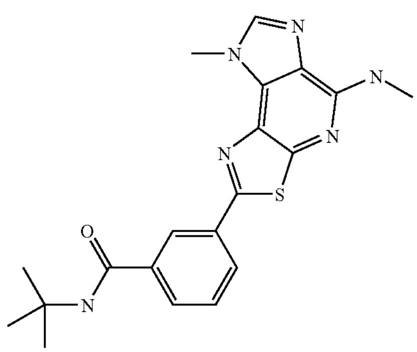 | benzamide, N-(1,1-dimethylethyl)-3-[8-methyl-5-(methylamino)-8H-imidazo[4,5-d]thiazolo[5,4-b]pyridin-2-yl]- | 1.48 | 395.05 |
| B146 | 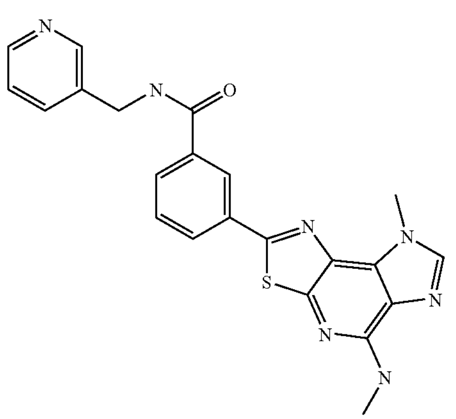 | benzamide, 3-[8-methyl-5-(methylamino)-8H-imidazo[4,5-d]thiazolo[5,4-b]pyridin-2-yl]-N-(3-pyridinylmethyl)- | 1.06 | 430.00 |
| B147 | 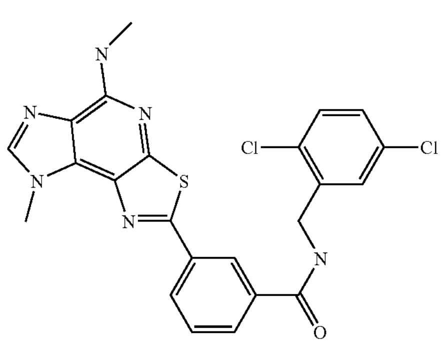 | benzamide, N-[(2,5-dichlorophenyl)methyl]-3-[8-methyl-5-(methylamino)-8H-imidazo[4,5-d]thiazolo[5,4-b]pyridin-2-yl]- | 1.73 | 496.93 |

TABLE B6-continued

| Ex. Number | Structure | Name | Retention Time (min) | Observed Mass |
|---|---|---|---|---|
| B148 | 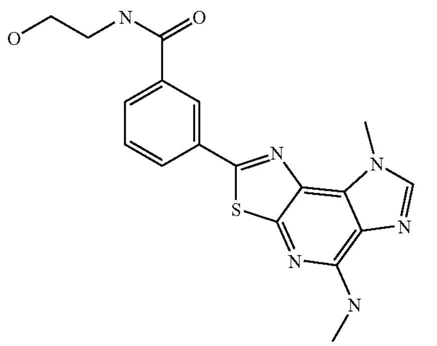 | benzamide, N-(2-hydroxyethyl)-3-[8-methyl-5-(methylamino)-8H-imidazo[4,5-d]thiazolo[5,4-b]pyridin-2-yl]- | 1.08 | 383.00 |
| B149 | 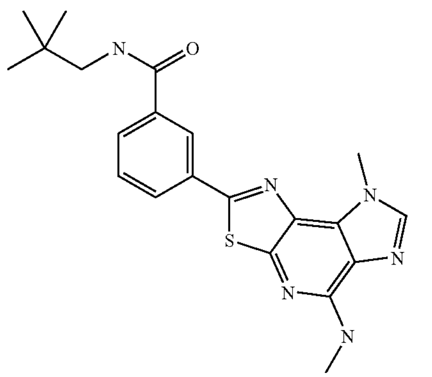 | benzamide, N-(2,2-dimethylpropyl)-3-[8-methyl-5-(methylamino)-8H-imidazo[4,5-d]thiazolo[5,4-b]pyridin-2-yl]- | 1.53 | 409.03 |
| B150 | 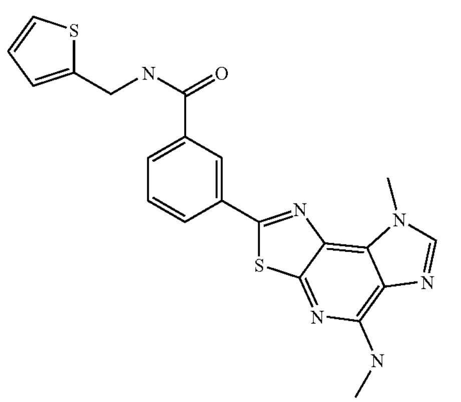 | benzamide, 3-[8-methyl-5-(methylamino)-8H-imidazo[4,5-d]thiazolo[5,4-b]pyridin-2-yl]-N-(2-thienylmethyl)- | 1.47 | 434.94 |
| B151 | 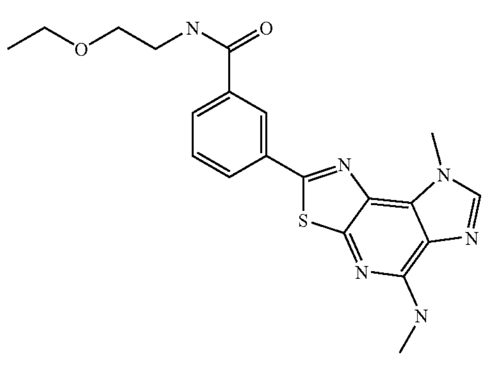 | benzamide, N-(2-ethoxyethyl)-3-[8-methyl-5-(methylamino)-8H-imidazo[4,5-d]thiazolo[5,4-b]pyridin-2-yl]- | 1.28 | 410.99 |

TABLE B6-continued

| Ex. Number | Structure | Name | Retention Time (min) | Observed Mass |
|---|---|---|---|---|
| B152 | 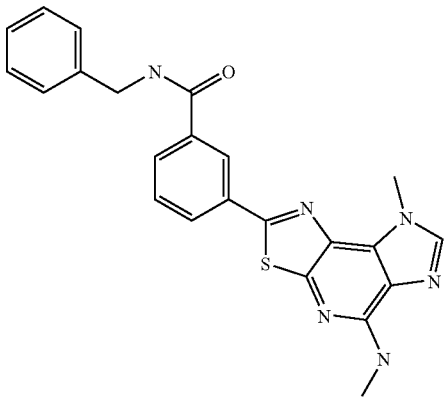 | benzamide, 3-[8-methyl-5-(methylamino)-8H-imidazo[4,5-d]thiazolo[5,4-b]pyridin-2-yl]-N-(phenylmethyl)- | 1.52 | 429.02 |
| B153 | 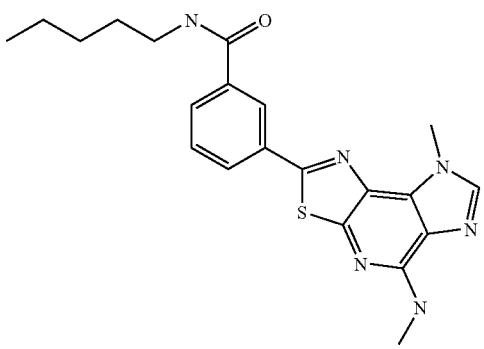 | benzamide, 3-[8-methyl-5-(methylamino)-8H-imidazo[4,5-d]thiazolo[5,4-b]pyridin-2-yl]-N-pentyl- | 1.58 | 409.04 |
| B154 | 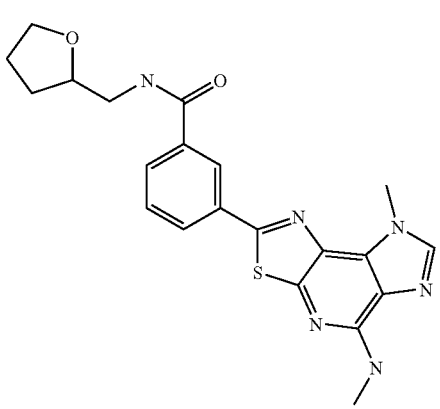 | benzamide, 3-[8-methyl-5-(methylamino)-8H-imidazo[4,5-d]thiazolo[5,4-b]pyridin-2-yl]-N-[(tetrahydro-2-furanyl)methyl]- | 1.26 | 423.03 |
| B155 | 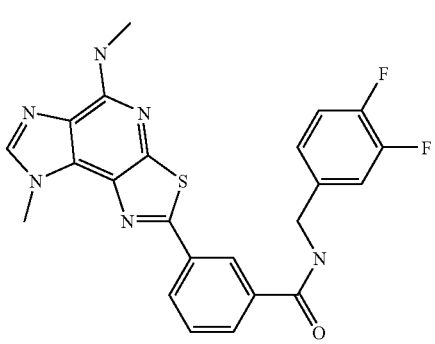 | benzamide, N-[(3,4-difluorophenyl)methyl]-3-[8-methyl-5-(methylamino)-8H-imidazo[4,5-d]thiazolo[5,4-b]pyridin-2-yl]- | 1.59 | 465.01 |

TABLE B6-continued

| Ex. Number | Structure | Name | Retention Time (min) | Observed Mass |
|---|---|---|---|---|
| B156 | 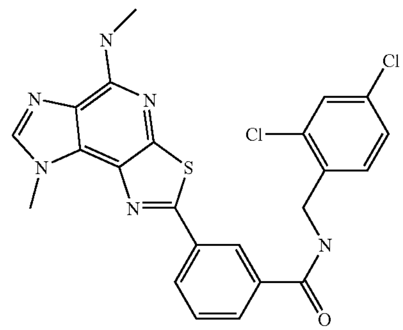 | benzamide, N-[(2,4-dichlorophenyl)methyl]-3-[8-methyl-5-(methylamino)-8H-imidazo[4,5-d]thiazolo[5,4-b]pyridin-2-yl]- | 1.76 | 497.00 |
| B157 | 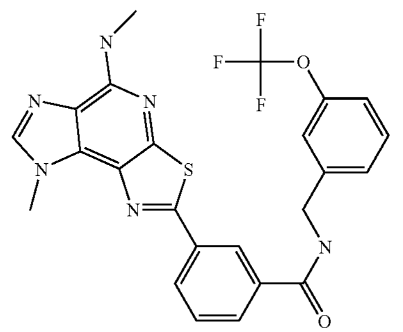 | benzamide, 3-[8-methyl-5-(methylamino)-8H-imidazo[4,5-d]thiazolo[5,4-b]pyridin-2-yl]-N-[[3-(trifluoromethoxy)phenyl]methyl]- | 1.73 | 512.98 |
| B158 | 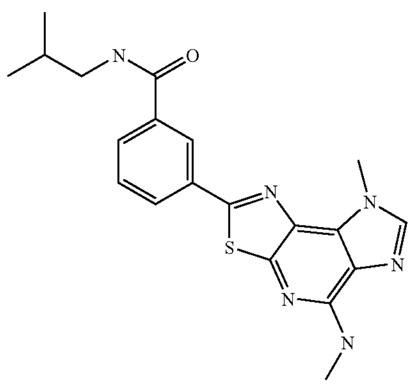 | benzamide, 3-[8-methyl-5-(methylamino)-8H-imidazo[4,5-d]thiazolo[5,4-b]pyridin-2-yl]-N-(2-methylpropyl)- | 1.44 | 395.06 |
| B159 | 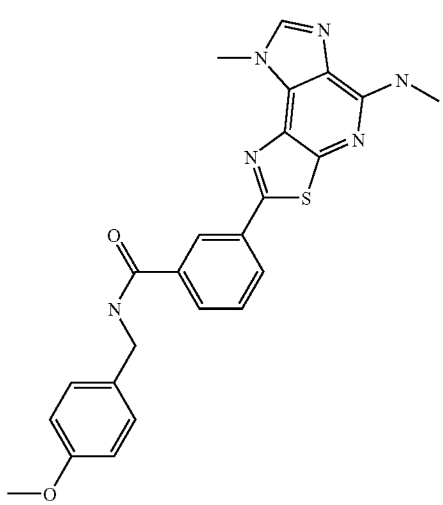 | benzamide, N-[(4-methoxyphenyl)methyl]-3-[8-methyl-5-(methylamino)-8H-imidazo[4,5-d]thiazolo[5,4-b]pyridin-2-yl]- | 1.50 | 458.99 |

TABLE B6-continued

| Ex. Number | Structure | Name | Retention Time (min) | Observed Mass |
|---|---|---|---|---|
| B160 | 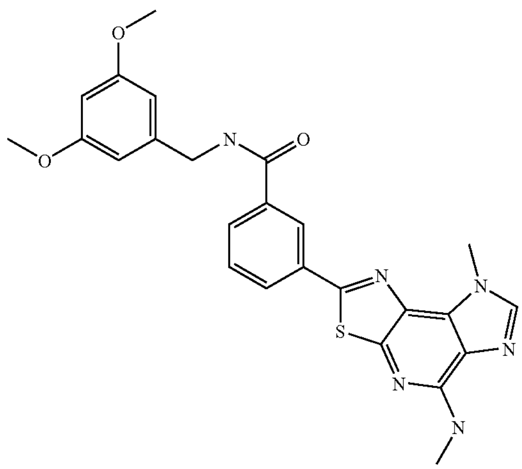 | benzamide, N-[(3,5-dimethoxyphenyl)methyl]-3-[8-methyl-5-(methylamino)-8H-imidazo[4,5-d]thiazolo[5,4-b]pyridin-2-yl]- | 1.53 | 489.00 |
| B161 | 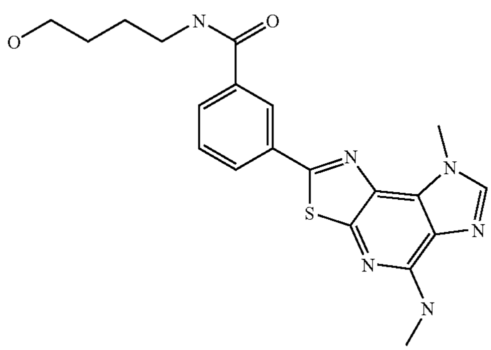 | benzamide, N-(4-hydroxybutyl)-3-[8-methyl-5-(methylamino)-8H-imidazo[4,5-d]thiazolo[5,4-b]pyridin-2-yl]- | 1.13 | 411.04 |
| B162 | 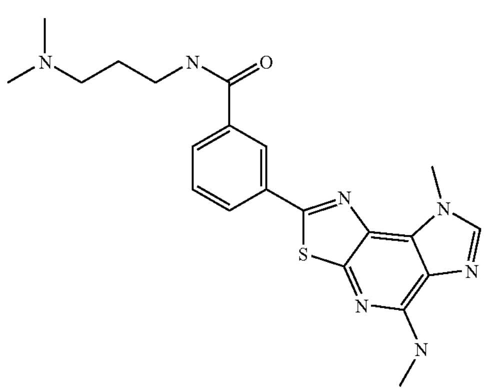 | benzamide, N-[3-(dimethylamino)propyl]-3-[8-methyl-5-(methylamino)-8H-imidazo[4,5-d]thiazolo[5,4-b]pyridin-2-yl]- | 1.06 | 424.05 |

TABLE B6-continued

| Ex. Number | Structure | Name | Retention Time (min) | Observed Mass |
|---|---|---|---|---|
| B163 | 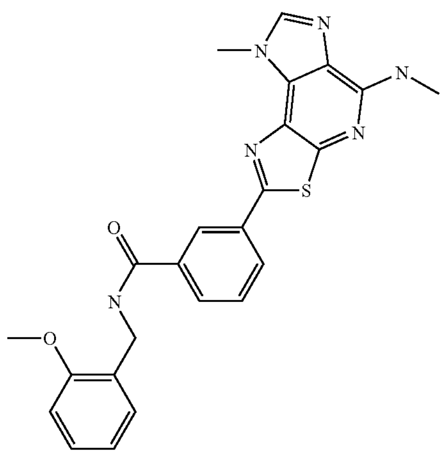 | benzamide, N-[(2-methoxyphenyl)methyl]-3-[8-methyl-5-(methylamino)-8H-imidazo[4,5-d]thiazolo[5,4-b]pyridin-2-yl]- | 1.55 | 458.99 |
| B164 | 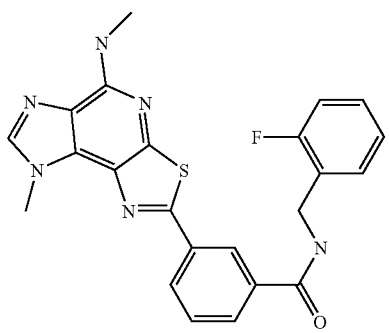 | benzamide, N-[(2-fluorophenyl)methyl]-3-[8-methyl-5-(methylamino)-8H-imidazo[4,5-d]thiazolo[5,4-b]pyridin-2-yl]- | 1.54 | 446.97 |
| B165 | 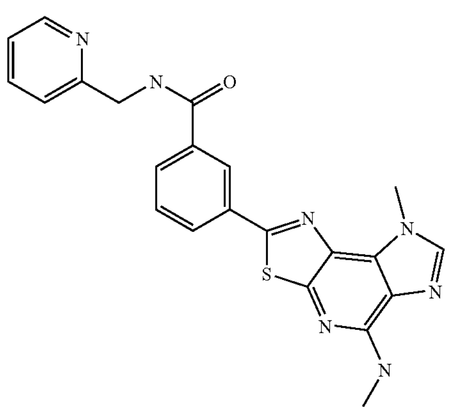 | benzamide, 3-[8-methyl-5-(methylamino)-8H-imidazo[4,5-d]thiazolo[5,4-b]pyridin-2-yl]-N-(2-pyridinylmethyl)- | 1.08 | 430.00 |

TABLE B6-continued

| Ex. Number | Structure | Name | Retention Time (min) | Observed Mass |
|---|---|---|---|---|
| B166 | 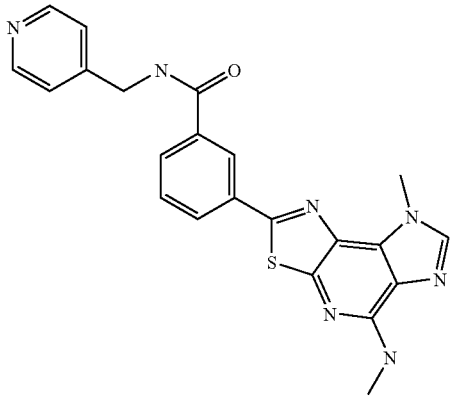 | benzamide, 3-[8-methyl-5-(methylamino)-8H-imidazo[4,5-d]thiazolo[5,4-b]pyridin-2-yl]-N-(4-pyridinylmethyl)- | 1.08 | 430.00 |
| B167 | 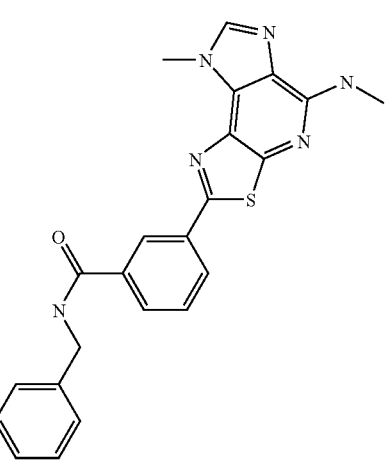 | benzamide, N-[(3-methoxyphenyl)methyl]-3-[8-methyl-5-(methylamino)-8H-imidazo[4,5-d]thiazolo[5,4-b]pyridin-2-yl]- | 1.51 | 459.02 |
| B168 | 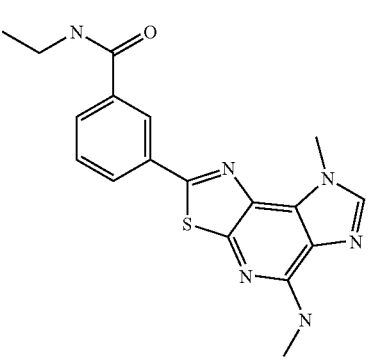 | benzamide, N-ethyl-3-[8-methyl-5-(methylamino)-8H-imidazo[4,5-d]thiazolo[5,4-b]pyridin-2-yl]- | 1.23 | 366.98 |
| B169 | 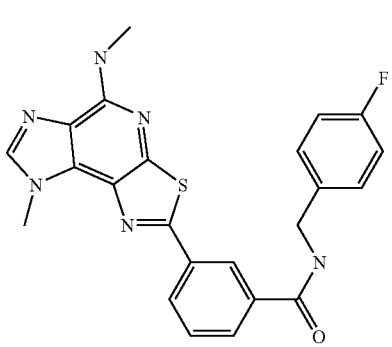 | benzamide, N-[(4-fluorophenyl)methyl]-3-[8-methyl-5-(methylamino)-8H-imidazo[4,5-d]thiazolo[5,4-b]pyridin-2-yl]- | 1.54 | 447.00 |

TABLE B6-continued

| Ex. Number | Structure | Name | Retention Time (min) | Observed Mass |
|---|---|---|---|---|
| B170 | 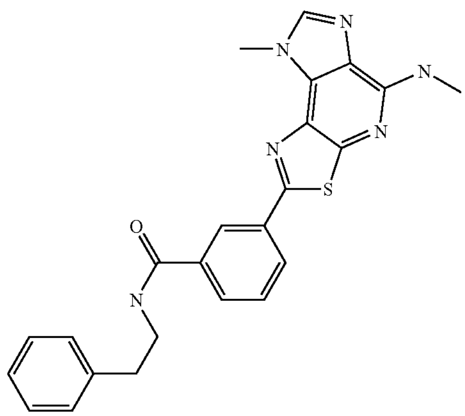 | benzamide, 3-[8-methyl-5-(methylamino)-8H-imidazo[4,5-d]thiazolo[5,4-b]pyridin-2-yl]-N-(2-phenylethyl)- | 1.55 | 443.00 |
| B171 | 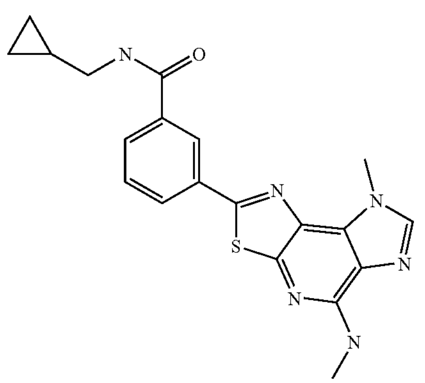 | benzamide, N-(cyclopropylmethyl)-3-[8-methyl-5-(methylamino)-8H-imidazo[4,5-d]thiazolo[5,4-b]pyridin-2-yl]- | 1.37 | 339.01 |

HPLC conditions: Column: Phenomenex Primesphere C18-HC 4.6 × 30 mm; Solvent A: 10% CH3CN/water 0.05% TFA, Solvent B: 90% CH3CN/water, 0.05% TFA.

Example B172

8-methyl-5-(methylamino)-8H-imidazo[4,5-d]thiazolo[5,4-b]pyridine-2-carboxylic acid

B172.1

8-methyl-5-chloro-8H-imidazo[4,5-d]thiazolo[5,4-b]pyridine-2-carboxylic acid methyl ester

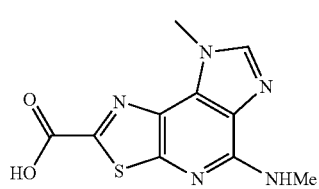

B172

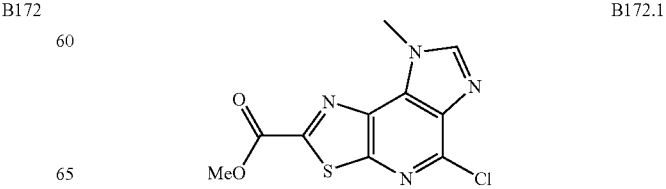

B172.1

A mixture of B99.3 (4.00 g; 13.18 mmol), PdCl$_2$(PPh$_3$)$_2$ (277 mg, 0.395 mmol), Et$_3$N (2.75 mL, 19.7 mmol) in CH$_3$CN (60 mL) and MeOH (60 mL) was stirred under an atmosphere of CO (100 psi) in a bomb at 60° C. After 24 h, the reaction was cooled to rt and depressurized. The solution was concentrated to dryness and triturated with hot EtOAc. Upon cooling, the solid was collected by filtration to afford 3.38 g (91%) of B172.1 as a yellow solid: MS (ES): m/z 283 [$^{35}$Cl M+H]$^+$ (HPLC 95%).

B172.2

8-methyl-5-chloro-8H-imidazo[4,5-d]thiazolo[5,4-b]pyridine-2-carboxylic acid

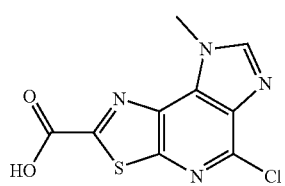

B172.2

To a stirring solution of B171.1 (3.38 g; 12.0 mmol) in THF (700 mL) was slowly added NaOH (1N, 40 mL). After 40 min, the reaction was concentrated to dryness, 25 mL cold H$_2$O was added, acidified with 40 mL 1N HCl and the resulting solid collected by filtration. After drying under high vacuum, 1.717 g (53%) of B172.2 was obtained as a colourless solid: MS (ES): m/z 269 [$^{35}$Cl M+H]$^+$ (HPLC>99%).

B172.3

8-methyl-5-(methylamino)-8H-imidazo[4,5-d]thiazolo[5,4-b]pyridine-2-carboxylic acid Starting with B172.2 (1.71 g) and dividing into 150 mg lots, to each lot was added MeNH$_2$ (33 wt % in EtOH, 1.8 mL) and the suspension heated for 20 min at 150° C. in Personal Chemistry microwave reactor. Once cooled to rt, the solid was collected by filtration. The combined crude solids were dissolved in a solution of 50 mmol NH$_4$OAc in H$_2$O (50 mL), purified on C18 column eluted with 50 mmol NH$_4$OAc in H$_2$O solution and gradient with MeOH. Fractions containing product were combined and concentrated. The resulting solid was dissolved in H$_2$O then lyophilized to provide 605 mg (36%) of B172 as a colourless solid: MS (ES): m/z 264 [M+H]$^+$ (HPLC 95%).

Example B173

N,N-diethyl-8-methyl-5-(methylamino)-8H-imidazo[4,5-d]thiazolo[5,4-b]pyridine-2-carboxamide

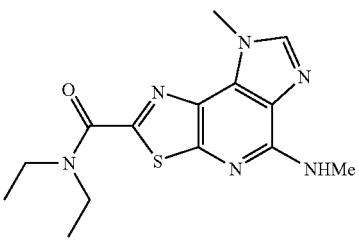

B173

To a stirring solution of B172 (32.4 mg, 0.123 mmol) in NMP (0.50 mL) was added Et$_2$NH (0.043 mL, 0.246 mmol) followed by PyBop (64.1 mg, 0.123 mmol). After 30 min, to the reaction was added AcOH (1 mL), DMF (1 mL). This solution was applied directly onto a preparative HPLC to provide 14 mg (36%) of B173 as a pale yellow solid: MS (ES): m/z 318 [M+H]$^+$ (HPLC 99%).

Examples B174–B217

Examples B174–B217 described in Table B7 were prepared in a similar manner to that used for Example B173 by reacting B172 with the appropriate amine.

TABLE B7

| Ex. No. | Structure | Name | Retention Time (min) | Observed Mass |
|---|---|---|---|---|
| B174 | 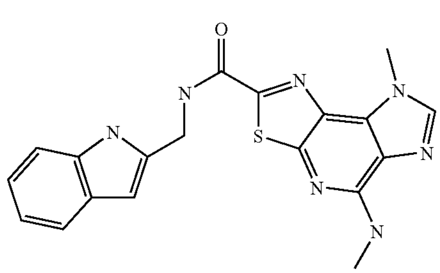 | 8H-imidazo[4,5-d]thiazolo[5,4-b]pyridine-2-carboxamide, N-(1H-benzimidazol-2-ylmethyl)-8-methyl-5-(methylamino)- | 1.27 | 393.24 |

TABLE B7-continued

| Ex. No. | Structure | Name | Retention Time (min) | Observed Mass |
|---|---|---|---|---|
| B175 | 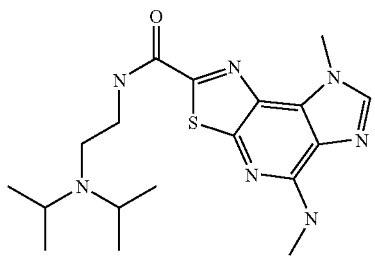 | 8H-imidazo[4,5-d]thiazolo[5,4-b]pyridine-2-carboxamide, N-[2-[bis(1-methylethyl)amino]ethyl]-8-methyl-5-(methylamino)- | 1.39 | 390.33 |
| B176 | 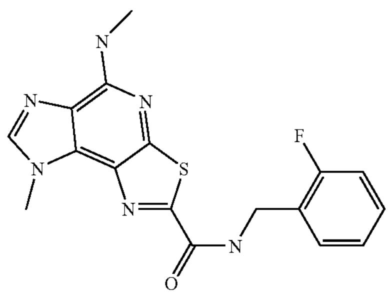 | 8H-imidazo[4,5-d]thiazolo[5,4-b]pyridine-2-carboxamide, N-[(2-fluorophenyl)methyl]-8-methyl-5-(methylamino)- | 1.54 | 371.21 |
| B177 | 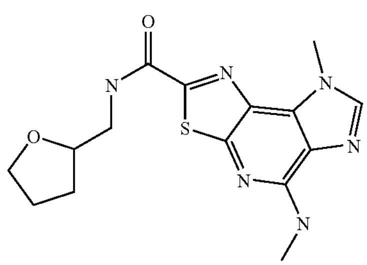 | 8H-imidazo[4,5-d]thiazolo[5,4-b]pyridine-2-carboxamide, 8-methyl-5-(methylamino)-N-[(tetrahydro-2-furanyl)methyl]- | 1.23 | 347.24 |
| B178 | 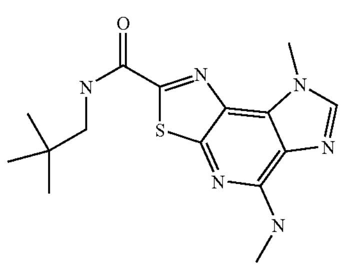 | 8H-imidazo[4,5-d]thiazolo[5,4-b]pyridine-2-carboxamide, N-(2,2-dimethylpropyl)-8-methyl-5-(methylamino)- | 1.56 | 333.29 |
| B179 | 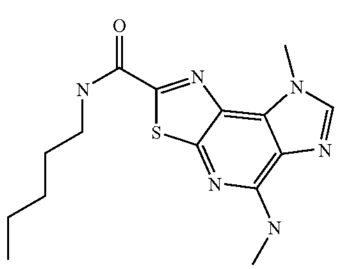 | 8H-imidazo[4,5-d]thiazolo[5,4-b]pyridine-2-carboxamide, 8-methyl-5-(methylamino)-N-pentyl- | 1.60 | 333.28 |

TABLE B7-continued

| Ex. No. | Structure | Name | Retention Time (min) | Observed Mass |
|---|---|---|---|---|
| B180 | 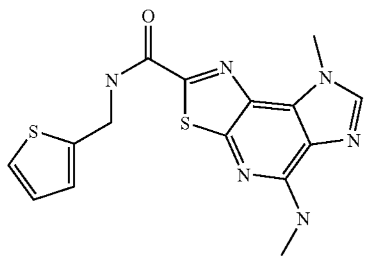 | 8H-imidazo[4,5-d]thiazolo[5,4-b]pyridine-2-carboxamide, 8-methyl-5-(methylamino)-N-(2-thienylmethyl)- | 1.47 | 359.19 |
| B181 | 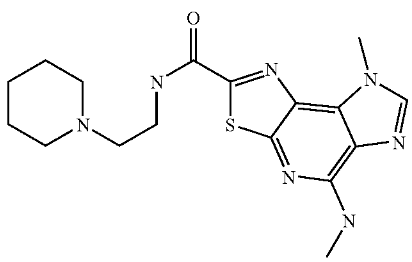 | 8H-imidazo[4,5-d]thiazolo[5,4-b]pyridine-2-carboxamide, 8-methyl-5-(methylamino)-N-[2-(1-piperidinyl)ethyl]- | 1.32 | 374.27 |
| B182 | 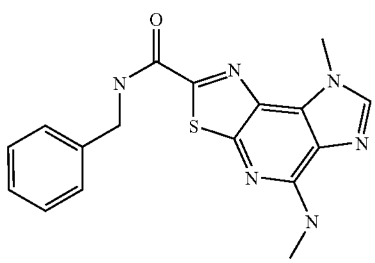 | 8H-imidazo[4,5-d]thiazolo[5,4-b]pyridine-2-carboxamide, 8-methyl-5-(methylamino)-N-(phenylmethyl)- | 1.52 | 353.23 |
| B183 | 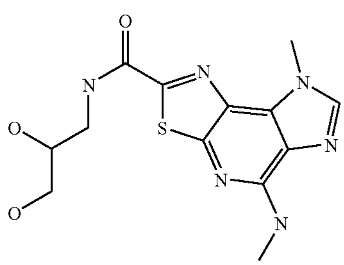 | 8H-imidazo[4,5-d]thiazolo[5,4-b]pyridine-2-carboxamide, N-(2,3-dihydroxypropyl)-8-methyl-5-(methylamino)- | 0.99 | 337.19 |
| B184 | 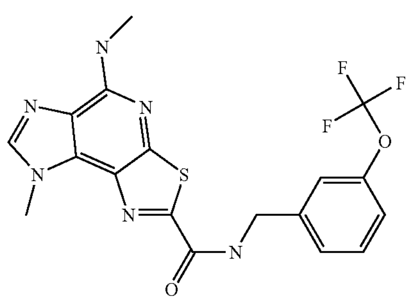 | 8H-imidazo[4,5-d]thiazolo[5,4-b]pyridine-2-carboxamide, 8-methyl-5-(methylamino)-N-[[3-(trifluoromethoxy)phenyl]methyl]- | 1.76 | 437.21 |

TABLE B7-continued

| Ex. No. | Structure | Name | Retention Time (min) | Observed Mass |
|---|---|---|---|---|
| B185 | 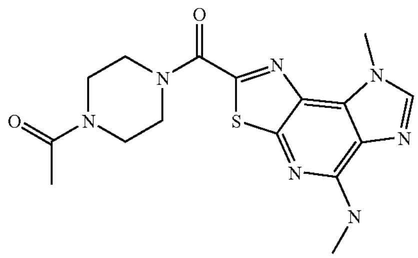 | piperazine, 1-acetyl-4-[[8-methyl-5-(methylamino)-8H-imidazo[4,5-d]thiazolo[5,4-b]pyridin-2-yl]carbonyl]- | 1.11 | 374.25 |
| B186 | 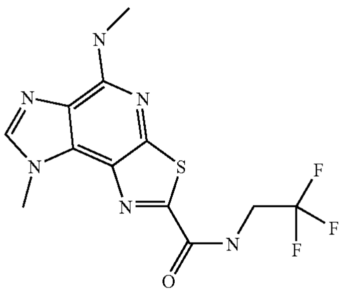 | 8H-imidazo[4,5-d]thiazolo[5,4-b]pyridine-2-carboxamide, 8-methyl-5-(methylamino)-N-(2,2,2-trifluoroethyl)- | 1.40 | 345.17 |
| B187 | 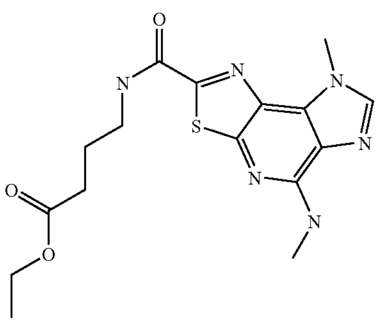 | butanoic acid, 4-[[[8-methyl-5-(methylamino)-8H-imidazo[4,5-d]thiazolo[5,4-b]pyridin-2-yl]carbonyl]amino]-, ethyl ester | 1.35 | 377.25 |
| B188 | 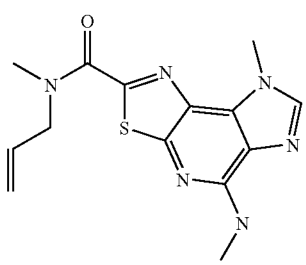 | 8H-imidazo[4,5-d]thiazolo[5,4-b]pyridine-2-carboxamide, N,8-dimethyl-5-(methylamino)-N-2-propenyl- | 1.36 | 317.27 |
| B189 | 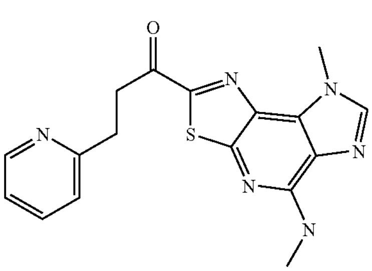 | 8H-imidazo[4,5-d]thiazolo[5,4-b]pyridine-2-carboxamide, 8-methyl-5-(methylamino)-N-(2-pyridinylmethyl)- | 1.44 | 353.95 |

TABLE B7-continued

| Ex. No. | Structure | Name | Retention Time (min) | Observed Mass |
|---|---|---|---|---|
| B190 | 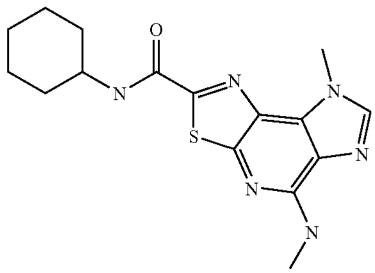 | 8H-imidazo[4,5-d]thiazolo[5,4-b]pyridine-2-carboxamide, N-cyclohexyl-8-methyl-5-(methylamino)- | 0.90 | 345.08 |
| B191 | 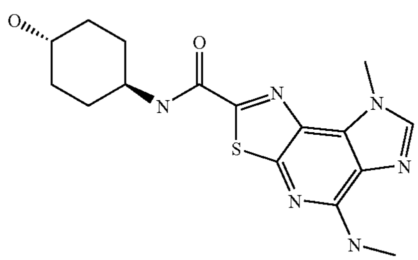 | 8H-imidazo[4,5-d]thiazolo[5,4-b]pyridine-2-carboxamide, N-(trans-4-hydroxycyclohexyl)-8-methyl-5-(methylamino)- | 1.14 | 361.26 |
| B192 | 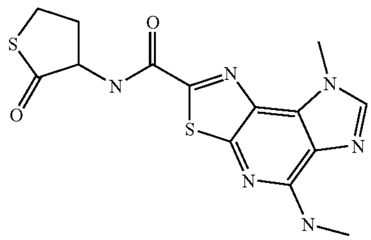 | 8H-imidazo[4,5-d]thiazolo[5,4-b]pyridine-2-carboxamide, 8-methyl-5-(methylamino)-N-(tetrahydro-2-oxo-3-thienyl)- | 1.30 | 363.17 |
| B193 | 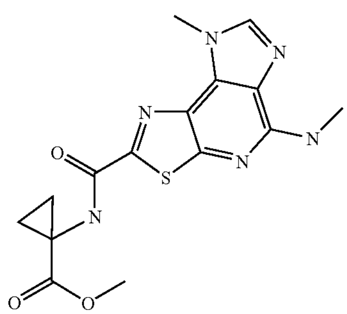 | cyclopropanecarboxylic acid, 1-[[[8-methyl-5-(methylamino)-8H-imidazo[4,5-d]thiazolo[5,4-b]pyridin-2-yl]carbonyl]amino]-, methyl ester | 1.25 | 361.22 |
| B194 | 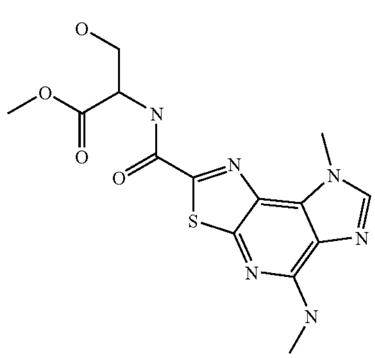 | serine, N-[[8-methyl-5-(methylamino)-8H-imidazo[4,5-d]thiazolo[5,4-b]pyridin-2-yl]carbonyl]-, methyl ester | 1.15 | 365.21 |

TABLE B7-continued

| Ex. No. | Structure | Name | Retention Time (min) | Observed Mass |
|---|---|---|---|---|
| B195 | 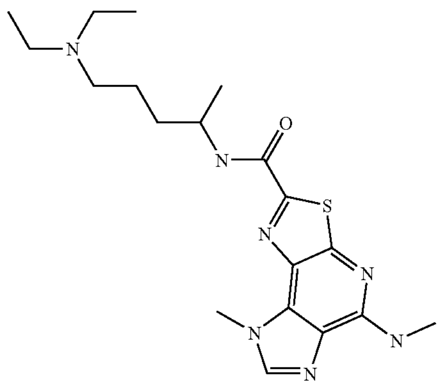 | 8H-imidazo[4,5-d]thiazolo[5,4-b]pyridine-2-carboxamide, N-[4-(diethylamino)-1-methylbutyl]-8-methyl-5-(methylamino)- | 1.34 | 404.33 |
| B196 | 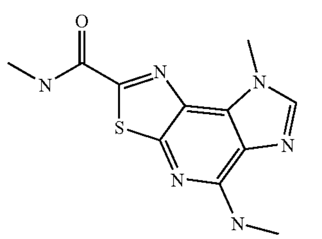 | 8H-imidazo[4,5-d]thiazolo[5,4-b]pyridine-2-carboxamide, N,8-dimethyl-5-(methylamino)- | 1.12 | 277.23 |
| B197 | 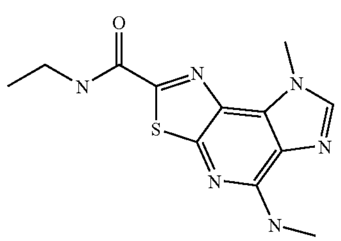 | 8H-imidazo[4,5-d]thiazolo[5,4-b]pyridine-2-carboxamide, N-ethyl-8-methyl-5-(methylamino)- | 1.21 | 291.25 |
| B198 | 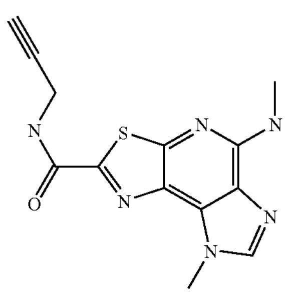 | 8H-imidazo[4,5-d]thiazolo[5,4-b]pyridine-2-carboxamide, 8-methyl-5-(methylamino)-N-2-propynyl- | 1.25 | 301.22 |
| B199 | 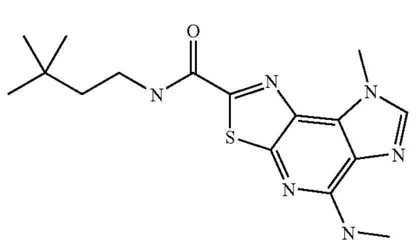 | 8H-imidazo[4,5-d]thiazolo[5,4-b]pyridine-2-carboxamide, N-(3,3-dimethylbutyl)-8-methyl-5-(methylamino)- | 1.69 | 347.25 |

TABLE B7-continued

| Ex. No. | Structure | Name | Retention Time (min) | Observed Mass |
|---|---|---|---|---|
| B200 | 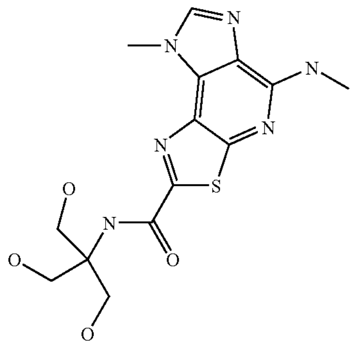 | 8H-imidazo[4,5-d]thiazolo[5,4-b]pyridine-2-carboxamide, N-[2-hydroxy-1,1-bis(hydroxymethyl)ethyl]-8-methyl-5-(methylamino)- | 1.04 | 365.21 |
| B201 | 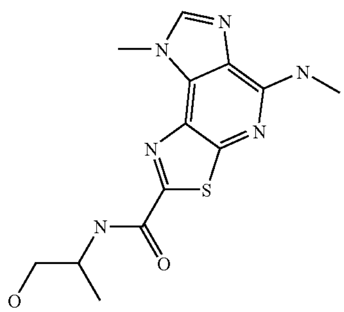 | 8H-imidazo[4,5-d]thiazolo[5,4-b]pyridine-2-carboxamide, N-(2-hydroxy-1-methylethyl)-8-methyl-5-(methylamino)- | 1.09 | 321.24 |
| B202 | 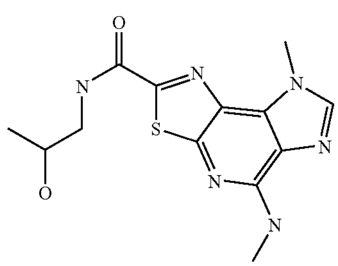 | 8H-imidazo[4,5-d]thiazolo[5,4-b]pyridine-2-carboxamide, N-(2-hydroxypropyl)-8-methyl-5-(methylamino)- | 1.08 | 321.24 |
| B203 | 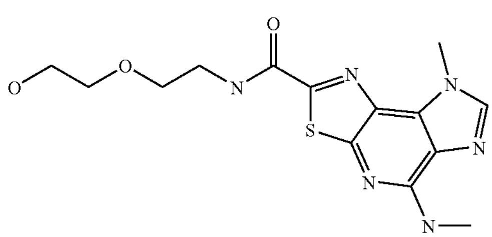 | 8H-imidazo[4,5-d]thiazolo[5,4-b]pyridine-2-carboxamide, N-[2-(2-hydroxyethoxy)ethyl]-8-methyl-5-(methylamino)- | 1.07 | 351.21 |
| B204 | 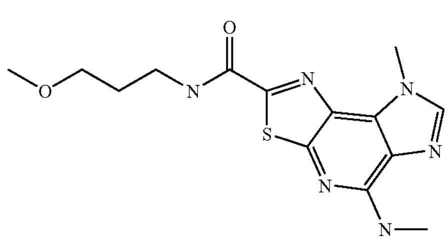 | 8H-imidazo[4,5-d]thiazolo[5,4-b]pyridine-2-carboxamide, N-(3-methoxypropyl)-8-methyl-5-(methylamino)- | 1.23 | 335.24 |

TABLE B7-continued

| Ex. No. | Structure | Name | Retention Time (min) | Observed Mass |
|---|---|---|---|---|
| B205 | 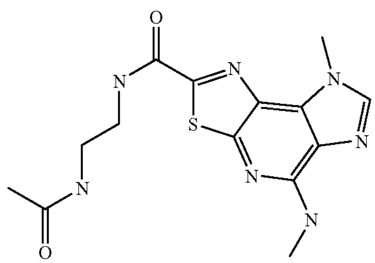 | 8H-imidazo[4,5-d]thiazolo[5,4-b]pyridine-2-carboxamide, N-[2-(acetylamino)ethyl]-8-methyl-5-(methylamino)- | 1.05 | 348.20 |
| B206 | 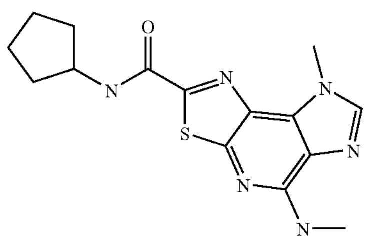 | 8H-imidazo[4,5-d]thiazolo[5,4-b]pyridine-2-carboxamide, N-cyclopentyl-8-methyl-5-(methylamino)- | 1.48 | 331.23 |
| B207 | 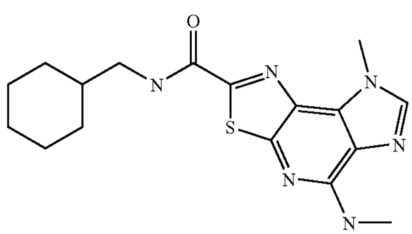 | 8H-imidazo[4,5-d]thiazolo[5,4-b]pyridine-2-carboxamide, N-(cyclohexylmethyl)-8-methyl-5-(methylamino)- | 1.72 | 359.26 |
| B208 | 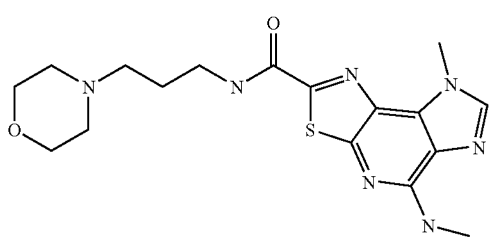 | 8H-imidazo[4,5-d]thiazolo[5,4-b]pyridine-2-carboxamide, 8-methyl-5-(methylamimo)-N-[3-(4-morpholinyl)propyl]- | 1.16 | 390.27 |
| B209 | 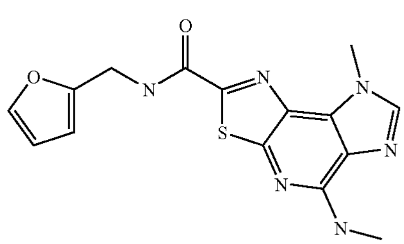 | 8H-imidazo[4,5-d]thiazolo[5,4-b]pyridine-2-carboxamide, N-(2-furanylmethyl)-8-methyl-5-(methylamino)- | 1.38 | 343.21 |
| B210 | 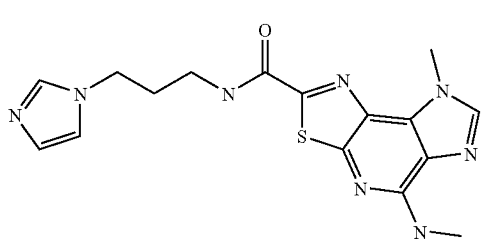 | 8H-imidazo[4,5-d]thiazolo[5,4-b]pyridine-2-carboxamide, N-[3-(1H-imidazol-1-yl)propyl]-8-methyl-5-(methylamino)- | 1.16 | 371.24 |

TABLE B7-continued

| Ex. No. | Structure | Name | Retention Time (min) | Observed Mass |
|---|---|---|---|---|
| B211 | 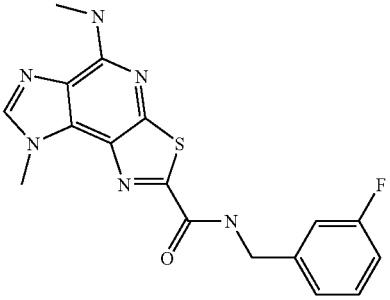 | 8H-imidazo[4,5-d]thiazolo[5,4-b]pyridine-2-carboxamide, N-[(3-fluorophenyl)methyl]-8-methyl-5-(methylamino)- | 1.55 | 371.22 |
| B212 | 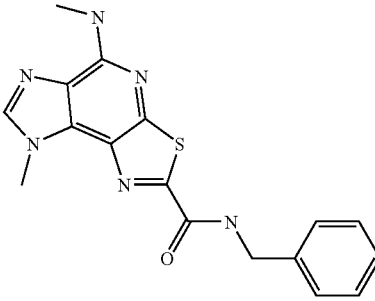 | 8H-imidazo[4,5-d]thiazolo[5,4-b]pyridine-2-carboxamide, N-[(4-fluorophenyl)methyl]-8-methyl-5-(methylamino)- | 1.55 | 371.23 |
| B213 | 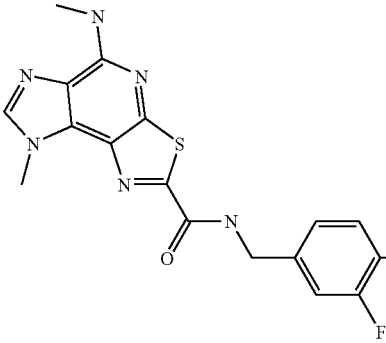 | 8H-imidazo[4,5-d]thiazolo[5,4-b]pyridine-2-carboxamide, N-[(3,4-difluorophenyl)methyl]-8-methyl-5-(methylamino)- | 1.61 | 389.21 |
| B214 | 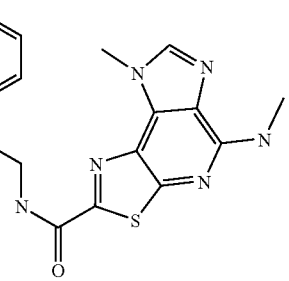 | 8H-imidazo[4,5-d]thiazolo[5,4-b]pyridine-2-carboxamide, N-[2-(3-fluorophenyl)ethyl]-8-methyl-5-(methylamino)- | 1.60 | 385.20 |

TABLE B7-continued

| Ex. No. | Structure | Name | Retention Time (min) | Observed Mass |
|---|---|---|---|---|
| B215 | 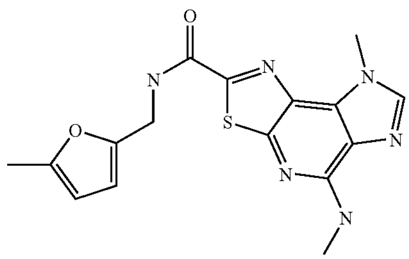 | 8H-imidazo[4,5-d]thiazolo[5,4-b]pyridine-2-carboxamide, 8-methyl-5-(methylamino)-N-[(5-methyl-2-furanyl)methyl]- | 1.49 | 357.23 |
| B216 | 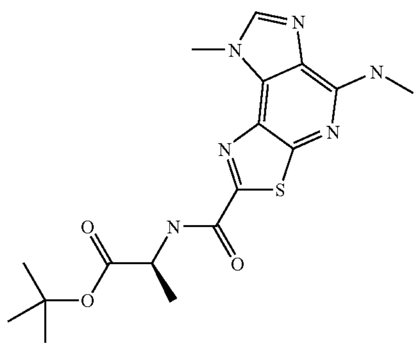 | L-alanine, N-[[8-methyl-5-(methylamino)-8H-imidazo[4,5-d]thiazolo[5,4-b]pyridin-2-yl]carbonyl]-, 1,1-dimethylethyl ester | 1.65 | 391.26 |
| B217 | 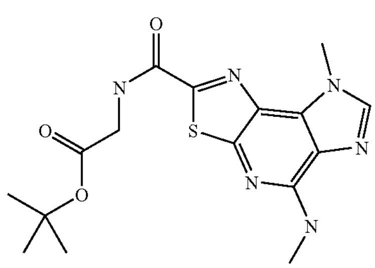 | glycine, N-[[8-methyl-5-(methylamino)-8H-imidazo[4,5-d]thiazolo[5,4-b]pyridin-2-yl]carbonyl]-, 1,1-dimethylethyl ester | 1.52 | 377.23 |

HPLC conditions: Column: Phenomenex Primesphere C18-HC 4.6 × 30 mm; Solvent A: 10% CH3CN/water 0.05% NH4OAc, Solvent B: 90% CH3CN/water, 0.05%

Example B218

N-[8-methyl-5-(methylamino)-8H-imidazo[4,5-d]thiazolo[5,4-b]pyridin-2-yl]benzamide

B218

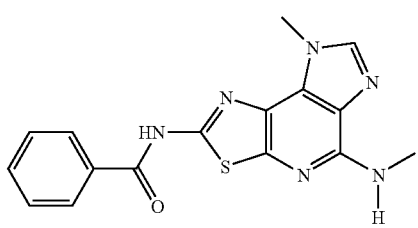

A mixture of B51.6 (20 mg; 0.05 mmol) and benzoyl chloride (0.006 ml; 0.05 mmol) in 0.5 ml of pyridine was stirred at rt for 2 hr. An additional amount of benzoyl chloride (0.012 ml; 0.1 mmol) was added and the reaction mixture was stirred 18 hrs. After one more addition of benzoyl chloride (0.012 ml; 0.1 mmol) and 2 hr of stirring, the volatiles were removed in vacuo and the residue was partitioned between EtOAc (30 ml) and water (30 ml). The organic layer was dried (MgSO$_4$) and concentrated to a green solid. After the solid was dissolved in 1 ml of TFA, the solution was allowed to stand 2 hr at rt. After removing the TFA in vacuo, the residue was co-evaporated from heptane and purified by preparative HPLC. The pure fraction was concentrated to afford 13 mg (66%) of B218 as an off white solid. (M+H)$^+$=339.26 (HPLC>99%).

Example B219

8-Methyl-2-(pyrazol-1-yl)-N-methyl-8H-imidazo[4,5-d]thiazolo[5,4-b]pyridin-5-amine

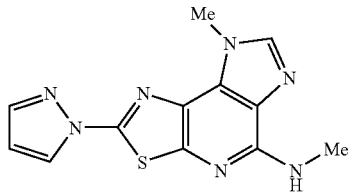

B219

B219.1

8-Methyl-2-hydrazino-N-methyl-8H-imidazo[4,5-d]thiazolo[5,4-b]pyridin-5-amine

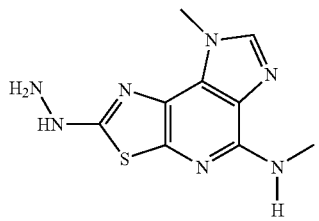

B219.1

A mixture of B5 (120 mg, 0.4 mmol), hydrazine hydrate (0.4 ml) and ethanol (0.4 ml) was heated to 120° C. in a pressure tube for 2 hrs. After allowing the reaction mixture to cool to rt, ethanol (~2.5 ml) was added and the resulting suspension was filtered. The filter cake was rinsed with ethanol, followed by hexane:ethyl ether, 4:1 and dried under vacuum to afford 76 mg (77%) of B219.1 as a tan crystalline solid. $(M+H)^+=250.28$ (HPLC>97%).

B219.2

8-Methyl-2-(pyrazol-1-yl)-N-methyl-8H-imidazo[4,5-d]thiazolo[5,4-b]pyridin-5-amine A mixture of B219.1 (74 mg; 0.3 mmol), 1,1,3,3-tetramethoxypropane (0.08 ml; 0.33 mmol), 2N HCl (0.15 ml) and ethanol (3 ml) was heated to reflux for 2 hrs. After cooling to rt, the reaction mixture was filtered. The filter cake was rinsed with ethanol, followed by hexane and dried under vacuum to afford 50 mg (59%) of B219 as a tan crystalline solid. $(M+H)^+=286.37$ (HPLC>97%).

Example B220

8-Methyl-N-methyl-2-amino-8H-imidazo[4,5-d]thiazolo[5,4-b]pyridin-5-amine

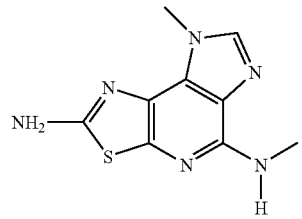

B220

A mixture of B7 (50 mg; 0.2 mmol), Raney Ni® slurry (~0.25 ml) and ethanol (1 ml) was heated to reflux for 30 minutes. After cooling, the reaction mixture was filtered through Celite® and the filtrate was concentrated to a yellow solid. The crude product was purified by preparatory HPLC to provide 23 mg (46%) of B220 as a lavender powder. $(M+H)^+=235.14$ (HPLC>97%).

B221.1

8-Methyl-2-cyclopropyl-5-chloro-8H-imidazo[4,5-d]thiazolo[5,4-b]pyridine

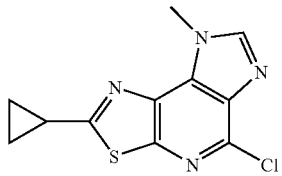

B221.1

A mixture of B99.3 (61 mg; 0.2 mmol), cyclopropylboronic acid (18 mg, 0.2 mmol), Pd(OAc)$_2$ (3 mg; 0.013 mmol), tricyclohexylphosphine (8 mg; 0.027 mmol), K$_3$PO$_4$ (64 mg; 0.3 mmol) and 1 drop of water in 2 ml of toluene was stirred vigorously at 100° C. for 1 hr. At this time, an additional aliquot of cyclopropylboronic acid (18 mg, 0.2 mmol), Pd(OAc)$_2$ (3 mg; 0.013 mmol), tricyclohexylphosphine (8 mg; 0.027 mmol) were added and stirring was continued for an additional hr. After cooling, the reaction mixture was partitioned between water (20 ml) and CHCl$_3$ (40 ml). The organic layer was dried (MgSO$_4$), concentrated and chromatographed on a 2.5×15 cm SiO$_2$ column using a gradient of CHCl$_3$ to 4% MeOH/CHCl$_3$. The purest fractions were concentrated to afford 53 mg (99%) of B221.1 as a yellow solid. $(M+H)^+=265.13$ (267.11; 25%) (HPLC>83%).

B221.2

8-Methyl-2-cyclopropyl-N-methyl-8H-imidazo[4,5-d]thiazolo[5,4-b]pyridin-5-amine

A solution of B221.1 (47 mg; 0.17 mmol) and 8M methylamine (0.5 ml; 4 mmol) in 1.5 ml of n-butanol was heated to 180° C. for 3.5 hr in a microwave apparatus. After removing the volatiles in vacuo, the residue was dissolved in MeOH:1N HCl, 9:1 and subjected to purification by preparative HPLC. The pure fraction was concentrated to afford 35 mg (79%) of B221 as a white solid. $(M+H)^+=260.23$ (HPLC>99%).

Example B222

8-Methyl-2-(4-fluorophenyl)-N-methyl-8H-imidazo[4,5-d]thiazolo[5,4-b]pyridin-5-amine

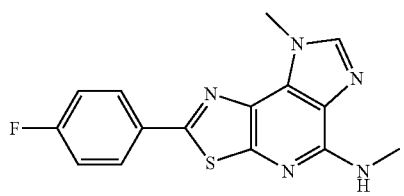

B222

B222.1

8-Methyl-2-(aminocarbonylmethylthio)-5-chloro-8H-imidazo[4,5-d]thiazolo[5,4-b]pyridine

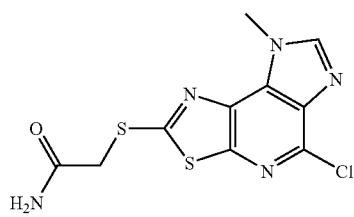

B222.1

A solution of A1.4 (1.00 g, 4.61 mmol), EtOCS$_2$K (1.5 g, 8.96 mmol) in DMF (10 mL) was heated to 145° C. for 5 h. The reaction was cooled to 0° C. and 2-chloroacetamide (850 mg, 9.09 mmol) was added and allowed to warm to rt after. After 45 min, the reaction was concentrated to dryness and the residue triturated with H$_2$O (100 mL), the solid collected and dried under vacuum to provide 1.319 g (91%) B222.1 as a tan solid: MS (ES): m/z 315 [$^{35}$Cl M+H]$^+$ (HPLC 95%).

B222.2

8-Methyl-2-(4-fluorophenyl)-5-chloro-8H-imidazo[4,5-d]thiazolo[5,4-b]pyridine

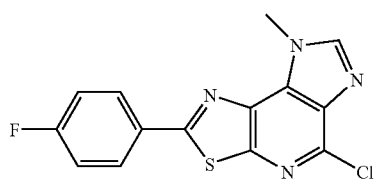

B222.2

To a flask charged with B222.1 (156.2 mg, 0.4978 mmol), 4-fluorophenyl boronic acid (170.1 mg, 1.214 mmol), copper (I) thiophenecarboxylate (CuTC, 153.0 mg, 0.8023 mmol), Pd$_2$(dba)$_3$ (26.0 mg, 0.0284 mmol) and trifurylphosphine (28.0 mg, 0.1206 mmol) was added DME (5.0 mL) and heated to 60° C. with stirring under Ar. After heating overnight, the reaction was cooled to rt, the reaction was diluted with CHCl$_3$, washed with 1-% NH$_4$OH (3×) and brine, dried (MgSO$_4$), filtered, concentrated and purified by flash chromatography (2%→50% CH$_3$CN:DCM) to afford 61.1 mg (39%) B222.2 as a pale yellow solid: MS (ES): m/z 319 [$^{35}$Cl M+H]$^+$ (HPLC 99%).

B222.3

8-Methyl-2-(4-fluorophenyl)-N-methyl-8H-imidazo[4,5-d]thiazolo[5,4-b]pyridin-5-amine A solution of B222.2 (26.5 mg, 0.0831 mmol) and MeNH$_2$ (33 wt % in EtOH, 0.60 mL) was heated in a Personal Chemistry microwave at 150° C. for 60 min. The resulting solid was collected by filtration, washed with EtOH to provide 13.6 mg (52%) B222 as a pale yellow solid: MS (ES): m/z 314 [M+H]+(HPLC 99%).

Examples B223–B228

Examples B223–B228 described in Table B8 were prepared in a similar manner to that used for Example B222 substituting the appropriate boronic acid and amine.

TABLE B8

| Ex. No. | Structure | Name | Retention Time (min) | Observed Mass |
|---|---|---|---|---|
| B223 | 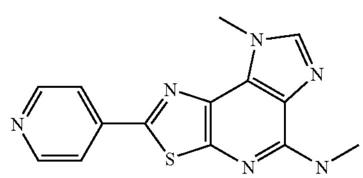 | 8H-imidazo[4,5-d]thiazolo[5,4-b]pyridin-5-amine, N,8-dimethyl-2-(4-pyridinyl)- | 1.01 | 297.00 |
| B224 | 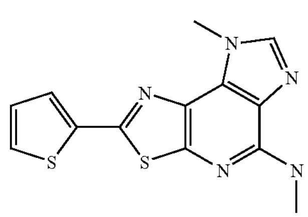 | 8H-imidazo[4,5-d]thiazolo[5,4-b]pyridin-5-amine, N,8-dimethyl-2-(2-thienyl)- | 1.45 | 302.00 |

TABLE B8-continued

| Ex. No. | Structure | Name | Retention Time (min) | Observed Mass |
|---|---|---|---|---|
| B225 | 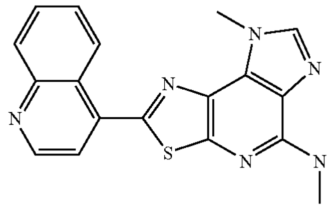 | 8H-imidazo[4,5-d]thiazolo[5,4-b]pyridin-5-amine, N,8-dimethyl-2-(4-quinolinyl)- | 1.16 | 347.00 |
| B226 | 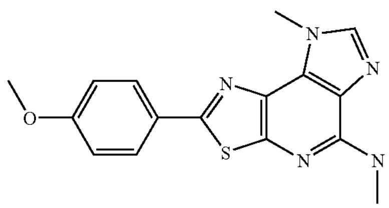 | 8H-imidazo[4,5-d]thiazolo[5,4-b]pyridin-5-amine, 2-(4-methoxyphenyl)-N,8-dimethyl- | 1.45 | 326.00 |
| B227 | 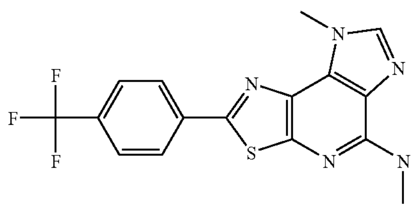 | 8H-imidazo[4,5-d]thiazolo[5,4-b]pyridin-5-amine, N,8-dimethyl-2-[4-(trifluoromethyl)phenyl]- | 1.82 | 364.00 |
| B228 | 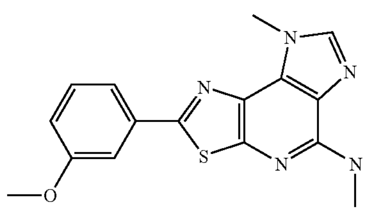 | 8H-imidazo[4,5-d]thiazolo[5,4-b]pyridin-5-amine, 2-(3-methoxyphenyl)-N,8-dimethyl- | 1.51 | 326.00 |

HPLC conditions: Column: Phenomenex Primesphere C18-HC 4.6 × 30 mm; Solvent A: 10% CH3CN/water 0.05% TFA, Solvent B: 90% CH3CN/water, 0.05 TFA.

Example B229

N-[1-[2-Fluoro-5-[8-methyl-5-(methylamino)-8H-imidazo[4,5-d]thiazolo[5,4-b]pyridin-2-yl]phenyl]ethyl]acetamide

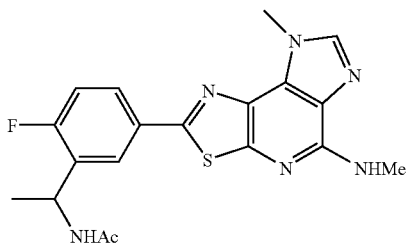

B229

A stirred solution of B29.2 (203 mg, 0.800 mmol), N-(1-(2-fluoro-5-(tributylstannyl)phenyl)ethyl)acetamide (310 mg, 0.901 mmol) and PdCl$_2$(PPh$_3$)$_2$ (22 mg, 0.0313 mmol) in xylene (8 mL) was heated to 120° C. overnight. The reaction was cooled to rt, concentrated to dryness then purified by flash chromatography (3–10% MeOH:EtOAc) to afford a solid, that after trituration with Et$_2$O, provided 83 mg (26%) of B229 as an olive green solid: m/z 399 [M+H]$^+$ (HPLC 99%).

Chiral Separation of B229

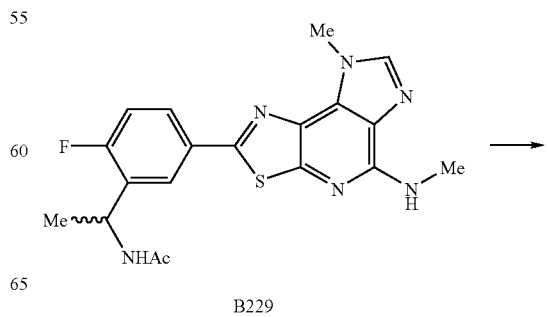

B229

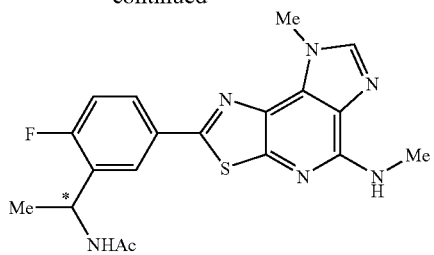

B229a and B229b

B229 (50 mg) was dissolved in approximately 20 mL of a solution of MeOH/EtOH/Heptane (7.5/7.5/85) and purified in two portions using a Chiralpak AS® 500 mm×20 mm 10 micron HPLC column (mobile phase: MeOH/EtOH/Heptane/DEA (7.5/7.5/85/0.1). Flow rate 14–16 ml/min. Evaporation of the mobile phase provided the separated enantiomers.

B229a Fast Eluting Enantiomer: 19.5 mg pale yellow powder (+) by CD detection (254 nM)>99% ee by Chiral HPLC: ret. time=10.61 minChiralpak AS® (250×4.6 mm 10 micron) MeOH/EtOH/Heptane/DEA-7.5/7.5/85/0.1

HPLC retention time 2.55 min. Column: Chromolith SpeedROD 4.6×50 mm (4 min grad) Solvent A: 10% MeOH-90% $H_2O$ 0.2% phosphoric acid Solvent B: 90% MeOH-10% $H_2O$-0.2% phosphoric acid. MS (ES): m/z 399.38 $[M+H]^+$ B229b Slow Eluting Enantiomer: 21.5 mg yellow powder (−) by CD detection (254 nM)>99% ee by Chiral HPLC: ret. time=15.34 min ®Chiralpak AS (250×4.6 mm 10 micron) MeOH/EtOH/Heptane/DEA-7.5/7.5/85/0.1

HPLC retention time 2.55 min. Column: Chromolith SpeedROD® 4.6×50 mm (4 min grad) Solvent A: 10% MeOH-90% $H_2O$ 0.2% phosphoric acid Solvent B: 90% MeOH-10% $H_2O$-0.2% phosphoric acid. MS (ES): m/z 399.38 $[M+H]^+$ Examples B230–B233

Examples B230–B233 described in Table B9 were prepared in a similar manner to that used for Example B229 substituting the appropriate boronic acid or tin reagent.

TABLE B9

| Ex. No. | Structure | Name | Retention Time (min) | Mass spectra |
|---|---|---|---|---|
| B230 | 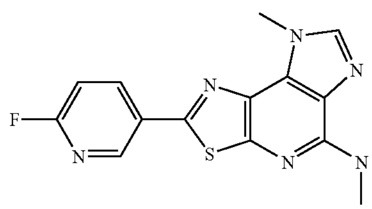 | 8H-imidazo[4,5-d]thiazolo[5,4-b]pyridin-5-amine, 2-(6-fluoro-3-pyridinyl)-N,8-dimethyl- | 1.32 | 315.00 |
| B231 | 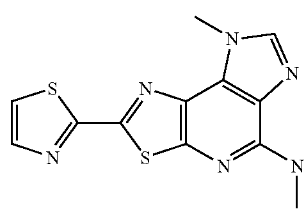 | 8H-imidazo[4,5-d]thiazolo[5,4-b]pyridin-5-amine, N,8-dimethyl-2-(2-thiazolyl)- | 1.29 | 303.00 |
| B232 | 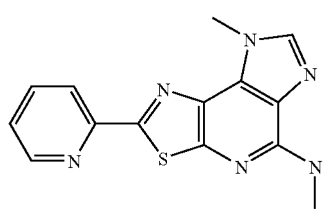 | 8H-imidazo[4,5-d]thiazolo[5,4-b]pyridin-5-amine, N,8-dimethyl-2-(2-pyridinyl)- | 1.20 | 297.00 |
| B233 | 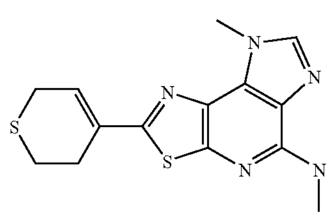 | 8H-imidazo[4,5-d]thiazolo[5,4-b]pyridin-5-amine, 2-(3,6-dihydro-2H-thiopyran-4-yl)-N,8-dimethyl- | 1.38 | 318.00 |

HPLC conditions: Column: Phenomenex Primesphere C18-HC 4.6 × 30 mm; SolventA: 10% CH3CN/water 0.05% TFA, Solvent B: 90% CH3CN/water, 0.05% TFA.

Example B234

8-Methyl-N-methyl-8H-imidazo[4,5-d]thiazolo[5,4-b]pyridin-5-amine

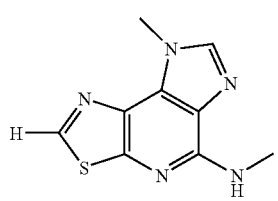

B234

To a solution of B2.1 (393 mg, 1.45 mmol) in EtOH (30 mL) was added Ra—Ni (5 g, 50% in H$_2$O) and the reaction heated to reflux overnight. The reaction was subsequently cooled to rt, filtered through Celite with EtOH wash, then purified by flash chromatography (97:3 DCM:MeOH) to provide 174 mg (53%) B234 as a pale yellow solid: MS (ES): m/z 225 [M+H]$^+$ (HPLC 99%).

Example B235

8-Methyl-N-methyl-2-(4-methoxyphenyl)-8H-imidazo[4,5-d]thiazolo[5,4-b]pyridin-5-amine

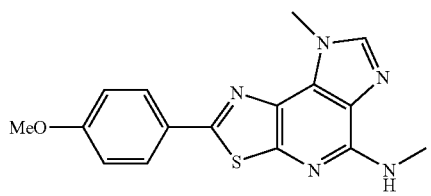

B235

B235.1

8-Methyl-N-methyl-8H-imidazo[4,5-d]thiazolo[5,4-b]pyridin-5-acetamide

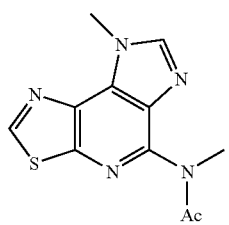

B235.1

A solution of B234 (863 mg, 3.936 mmol) in Ac$_2$O (10 mL) and AcOH (10 mL) was heated to 125° C. with stirring. After 7 h, the reaction was cooled to rt and concentrated. The residue was purified by flash chromatography to afford 412 mg (40%) B235.1 as a tan solid: MS (ES): m/z 262 [M+H]$^+$ (HPLC 95%).

B235.2

8-Methyl-N-methyl-2-(4-methoxyphenyl)-8H-imidazo[4,5-d]thiazolo[5,4-b]pyridin-5-acetamide

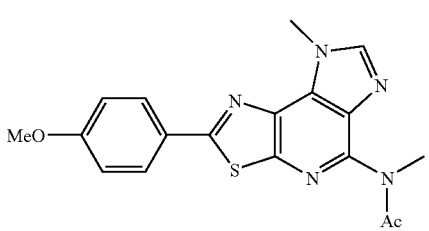

B235.2

To a stirred solution of B235.1 (99.0 mg, 0.379 mmol), 4-iodoanisole (154.1 mg, 0.658 mmol), PdCl$_2$(PPh$_3$)$_2$ (10.3 mg, 0.0147 mmol), CuI (6.0 mg, 0.315 mmol) in DMSO (4 mL) under Ar was added TBAF (0.40 mL, 1 M in THF, 0.40 mmol) then heated to 65° C. overnight. The reaction was cooled to RT, treated with 1 mL AcOH, filtered then purified by preparative HPLC to afford 16.9 mg (12%) B235.2 as a brown solid: MS (ES): m/z 368 [M+H]$^+$ (HPLC 98%).

B235.2

8-Methyl-N-methyl-2-(4-methoxyphenyl)-8H-imidazo[4,5-d]thiazolo[5,4-b]pyridin-5-amine A solution of B235.2 (7.9 mg, 0.0215 mmol), NaOH (0.50 mL, 2M in H$_2$O) in NMP (1 mL) was heated in the microwave at 120° C. for 10 min. The reaction was partitioned between CHCl$_3$ and H$_2$O, the organic phase was separated and dried (MgSO$_4$). Concentration and purification by preparative HPLC provided 3 mg B235: MS (ES): m/z 326 [M+H]$^+$ (HPLC 99%).

Example B236

8-Methyl-2-(4-fluorophenyl)-8H-imidazo[4,5-d]thiazolo[5,4-b]pyridin-5-amine

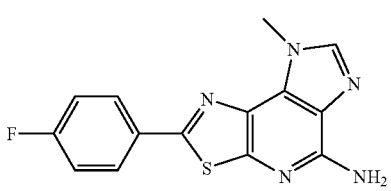

B236

B236.1

8-Methyl-2-(4-fluorophenyl)-N-(4-methoxyphenyl-methyl)-8H-imidazo[4,5-d]thiazolo[5,4-b]pyridin-5-amine

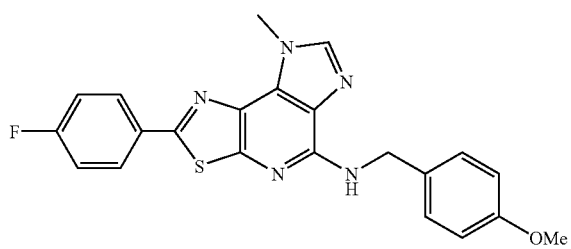

B236.1

A suspension of B222.2 (86.0 mg, 0.2698 mmol) and 4-methyloxybenzylamine (0.53 mL, 4.057 mmol) in EtOH (1 mL) was heated to 100° C. in a sealed tube with stirring overnight. HPLC analysis showed only partial conversion, consequently, an additional amount of The reaction 4-methyloxybenzylamine (0.75 mL) was added, and the reaction heated to 150° C. for 1 h in a Personal Chemistry microwave. The reaction was concentrated then purified by flash chromatography (9:1 Hex:EtOAc→100% EtOAc) to provide 80.0 mg (71%) B236.1 as a yellow solid: MS (ES): m/z 420 [M+H]+ (HPLC 99%).

B235.2

8-Methyl-2-(4-fluorophenyl)-8H-imidazo[4,5-d]thiazolo[5,4-b]pyridin-5-amine

To a stirred solution of B236.1 (58.9 mg, 0.1404 mmol), anisole (0.26 mL, 2.39 mmol) in TFA (0.70 mL) was added MeSO3H (0.14 mL, 1.58 mmol). After 2.5 h, the reaction was partially concentrated, Et2O was added and the solid collected by filtration. The solid was recrystalized from hot CHCl3 and hexane to afford 53.3 mg (92%) of B236 trifluoroacetate salt as a yellow solid: MS (ES): m/z 300 [M+H]+ (HPLC 97%).

Example B237

8-Methyl-N-methyl-2-ethoxy-8H-imidazo[4,5-d]thiazolo[5,4-b]pyridin-5-amine

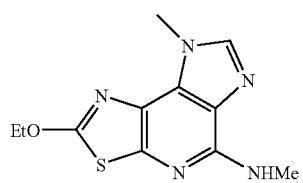

B237

A suspension of B29.1 (100 mg, 0.425 mmol) and EtBr (0.12 mL) and K2CO3 (320 mg) in acetone (10 mL) was heated to 80° C. with stirring overnight. The reaction was cooled to room temperature, the solid removed by filtration and washed with CHCl3, the filtrate concentrated to dryness. The residue was dissolved in DMF and purified directly by preparative HPLC to afford 40 mg (36%) B237 as a tan solid: MS (ES): m/z 264 [M+H]+ (HPLC 99%).

Example B238

N,8-dimethyl-2-[2-(4-morpholinyl)ethoxy]-8H-imidazo[4,5-d]thiazolo[5,4-b]pyridin-5-amine

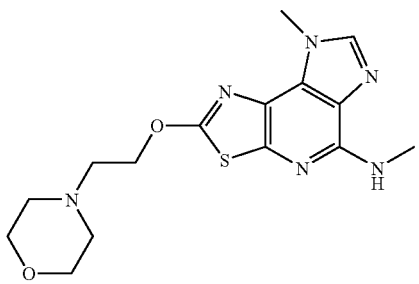

B238

A solution of B29.2 (0.020 g, 0.08 mmol), 2-morpholinoethanol (0.104 g, 0.80 mmol), and sodium hydride (60%, 0.032 g, 0.8 mmol) in dioxane was heated to 85° C. for 3 h. The solution was evaporated, the residue dissolved in MeOH and water, purified by prep HPLC, and concentrated to afford B238 as a white solid (2.0 TFA, 0.035 g) HPLC retention time 0.667 min. Column: Chromolith SpeedROD 4.6×50 mm (4 min grad. 0% B–100% B) Solvent A: 10% MeOH-90% H2O 0.2% phosphoric acid Solvent B: 90% MeOH-10% H2O-0.2% phosphoric acid. MS (ES): m/z 349.45 [M+H]+

B239

N,8-Dimethyl-2-[pentyloxy]-8H-imidazo[4,5-d]thiazolo[5,4-b]pyridin-5-amine

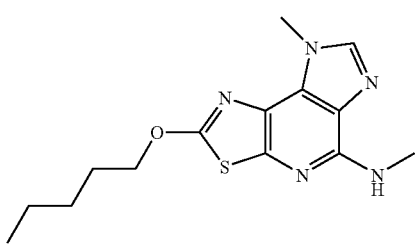

B239

A solution of B5 (0.030 g, 0.11 mmol), 1-pentanol (1 mL), and sodium hydride (60%, 0.010 g, 0.25 mmol) was stirred at r.t for 10 min, then heated in a sealed tube at 117° C. for 1 h. Water was added and the solution was extracted with EtOAc. The extracts were dried over MgSO4 and evaporated to afford B239 as a brown solid (0.033 g) HPLC retention time 3.06 min. Column: Chromolith SpeedROD 4.6×50 mm (4 min grad. 0% B–100% B) Solvent A: 10% MeOH-90% H2O 0.2% phosphoric acid Solvent B: 90% MeOH-10% H2O-0.2% phosphoric acid. MS (ES): m/z 306.2 [M+H]+

Examples B240–B257

Examples B230–B257 described in Table B10 were prepared in a similar manner to that used for Example B239 substituting the appropriate alcohol.

TABLE B10

| Ex. No. | Structure | Name | HPLC r.t (min). | MS (MH+) |
|---|---|---|---|---|
| B240 | 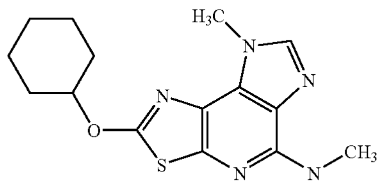 | 8H-imidazo[4,5-d]thiazolo[5,4-b]pyridin-5-amine, 2-(cyclohexyloxy)-N,8-dimethyl- | 2.94 | 318.2 |
| B241 | 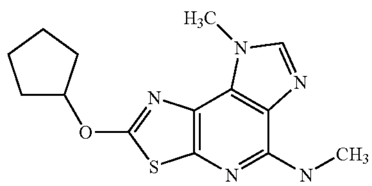 | 8H-imidazo[4,5-d]thiazolo[5,4-b]pyridin-5-amine, 2-(cyclopentyloxy)-N,8-dimethyl- | 2.72 | 304.3 |
| B242 | 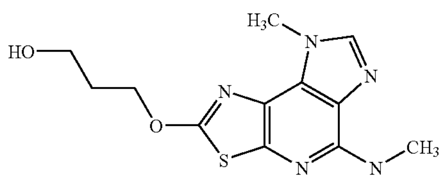 | 1-propanol, 3-[[8-methyl-5-(methylamino)-8H-imidazo[4,5-d]thiazolo[5,4-b]pyridin-2-yl]oxy]- | 1.56 | 294.3 |
| B243 | 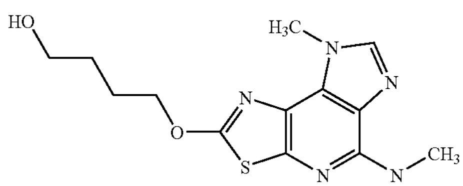 | 1-butanol, 4-[[8-methyl-5-(methylamino)-8H-imidazo[4,5-d]thiazolo[5,4-b]pyridin-2-yl]oxy]- | 1.77 | 308.3 |
| B244 | 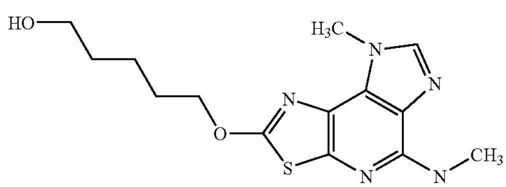 | 1-pentanol, 5-[[8-methyl-5-(methylamino)-8H-imidazo[4,5-d]thiazolo[5,4-b]pyridin-2-yl]oxy]- | 2.03 | 322.3 |
| B245 | 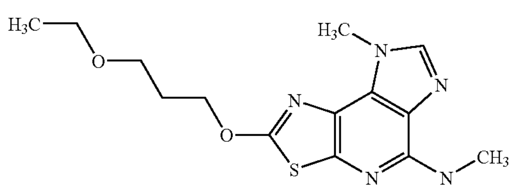 | 8H-imidazo[4,5-d]thiazolo[5,4-b]pyridin-5-amine, 2-(3-ethoxypropoxy)-N,8-dimethyl- | 2.35 | 322.2 |
| B246 | 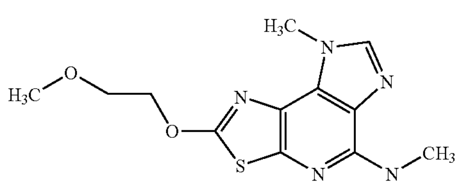 | 8H-imidazo[4,5-d]thiazolo[5,4-b]pyridin-5-amine, 2-(2-methoxyethoxy)-N,8-dimethyl- | 1.74 | 294.2 |
| B247 | 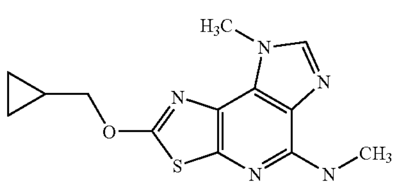 | 8H-imidazo[4,5-d]thiazolo[5,4-b]pyridin-5-amine, 2-(cyclopropylmethoxy)-N,8-dimethyl- | 2.44 | 290.2 |

TABLE B10-continued

| Ex. No. | Structure | Name | HPLC r.t (min). | MS (MH+) |
|---|---|---|---|---|
| B248 | 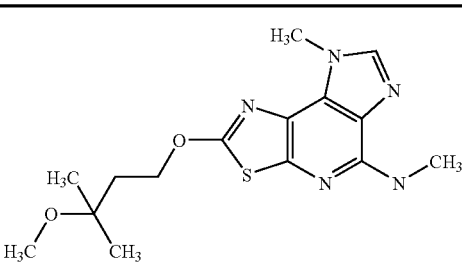 | 8H-imidazo[4,5-d]thiazolo[5,4-b]pyridin-5-amine, 2-(3-methoxy-3-methylbutoxy)-N,8-dimethyl- | 2.48 | 336.5 |
| B249 | 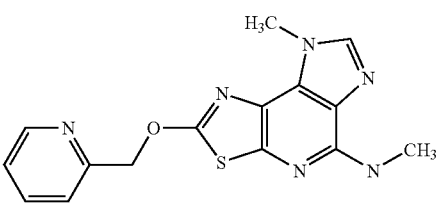 | 8H-imidazo[4,5-d]thiazolo[5,4-b]pyridin-5-amine, N,8-dimethyl-2-(2-pyridinylmethoxy)- | 1.28 | 327.4 |
| B250 | 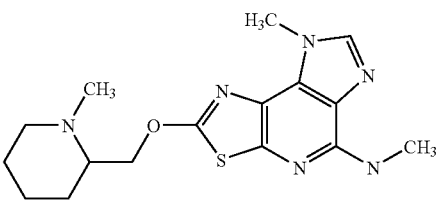 | 8H-imidazo[4,5-d]thiazolo[5,4-b]pyridin-5-amine, N,8-dimethyl-2-[(1-methyl-2-piperidinyl)methoxy]- | 1.35 | 347.2 |
| B251 | 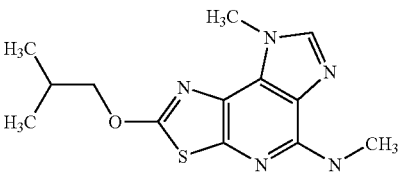 | 8H-imidazo[4,5-d]thiazolo[5,4-b]pyridin-5-amine, N,8-dimethyl-2-(2-methylpropoxy)- | 2.76 | 292.2 |
| B252 | 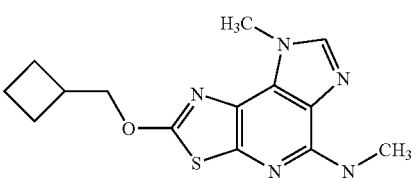 | 8H-imidazo[4,5-d]thiazolo[5,4-b]pyridin-5-amine, 2-(cyclobutylmethoxy)-N,8-dimethyl- | 2.88 | 304.2 |
| B253 | 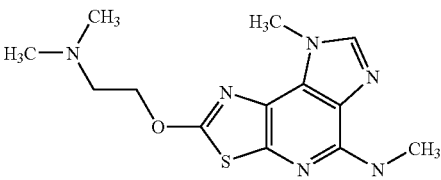 | 8H-imidazo[4,5-d]thiazolo[5,4-b]pyridin-5-amine, 2-[2-(dimethylamino)ethoxy]-N,8-dimethyl- | 0.96 | 307.2 |
| B254 | 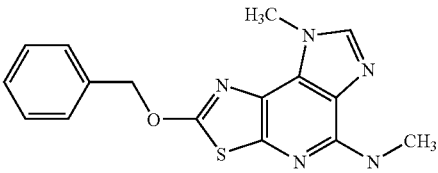 | 8H-imidazo[4,5-d]thiazolo[5,4-b]pyridin-5-amine, N,8-dimethyl-2-(phenylmethoxy)- | 2.78 | 326.5 |

TABLE B10-continued

| Ex. No. | Structure | Name | HPLC r.t (min). | MS (MH+) |
|---|---|---|---|---|
| B255 | 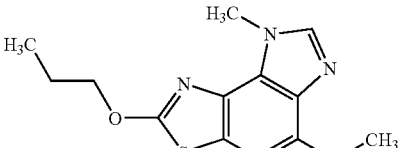 | 8H-imidazo[4,5-d]thiazolo[5,4-b]pyridin-5-amine, N,8-dimethyl-2-propoxy- | 2.35 | 278.5 |
| B256 | 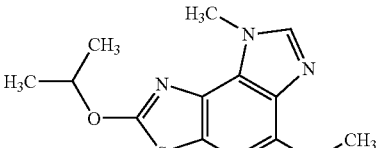 | 8H-imidazo[4,5-d]thiazolo[5,4-b]pyridin-5-amine, N,8-dimethyl-2-(1-methylethoxy)- | 2.20 | 278.5 |
| B257 | 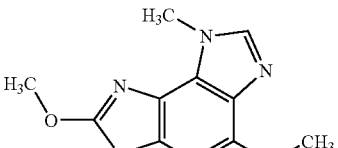 | 8H-imidazo[4,5-d]thiazolo[5,4-b]pyridin-5-amine, 2-methoxy-N,8-dimethyl- | 1.58 | 250.4 |

HPLC conditions: Column: Chromolith SpeedROD 4.6 × 50 mm (4 min grad. 0% B–100% B) Solvent A: 10% MeOH-90% H₂O 0.2% phosphoric acid Solvent B: 90% MeOH-10% H₂O-0.2% phosphoric acid.

Example B258

N-Ethyl-2-(4-fluorophenyl)-8-methyl-8H-imidazo[4,5-d]thiazolo[5,4-b]pyridin-5-amine

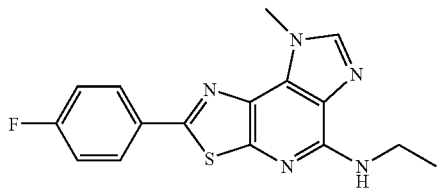

B258

A suspension of B222.2 (10 mg) and EtNH₂ (0.30 mL) in THF (0.30 mL) and NMP (0.30 mL) was heated at 150° C. for 60 min in the Personal Chemistry® microwave. AcOH (0.50 mL) was then added, filtered then purified by preparative HPLC to afford 0.8 mg (8%) B258 as a colourless film: MS (ES): m/z 328 [M+H]⁺ (HPLC 76%).

Examples B259–B270

Examples B259–B270 described in Table B11 were prepared in a similar manner to that used for Example B258 substituting the appropriate amine.

TABLE B11

| Ex. No. | Structure | Name | HPLC r.t (min). | MS (MH+) |
|---|---|---|---|---|
| B259 | 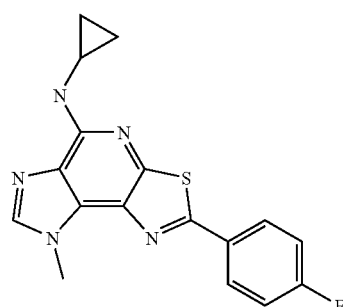 | 8H-imidazo[4,5-d]thiazolo[5,4-b]pyridin-5-amine, N-cyclopropyl-2-(4-fluorophenyl)-8-methyl- | 1.92 | 340.25 |

TABLE B11-continued

| Ex. No. | Structure | Name | HPLC r.t (min). | MS (MH+) |
|---|---|---|---|---|
| B260 | 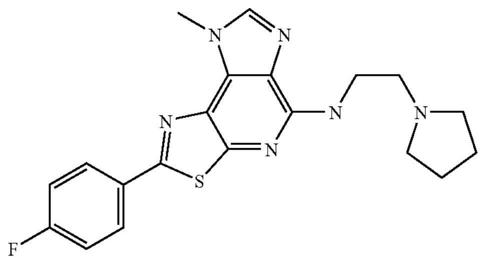 | 8H-imidazo[4,5-d]thiazolo[5,4-b]pyridin-5-amine, 2-(4-fluorophenyl)-8-methyl-N-[2-(1-pyrrolidinyl)ethyl]- | 2.05 | 397.30 |
| B261 | 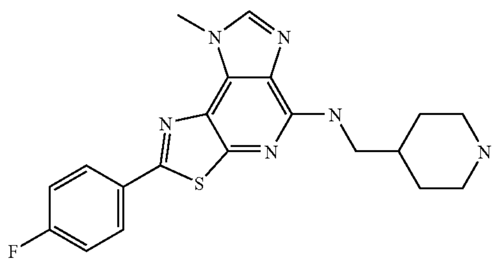 | 8H-imidazo[4,5-d]thiazolo[5,4-b]pyridin-5-amine, 2-(4-fluorophenyl)-8-methyl-N-(4-piperidinylmethyl)- | 1.92 | 397.27 |
| B262 | 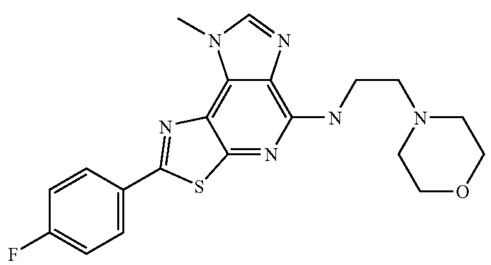 | 8H-imidazo[4,5-d]thiazolo[5,4-b]pyridin-5-amine, 2-(4-fluorophenyl)-8-methyl-N-[2-(4-morpholinyl)ethyl]- | 1.88 | 413.29 |
| B263 | 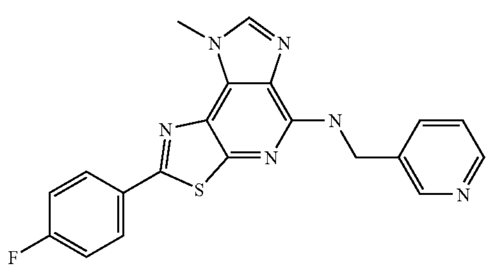 | 8H-imidazo[4,5-d]thiazolo[5,4-b]pyridin-5-amine, 2-(4-fluorophenyl)-8-methyl-N-(3-pyridinylmethyl)- | 1.94 | 391.23 |
| B264 | 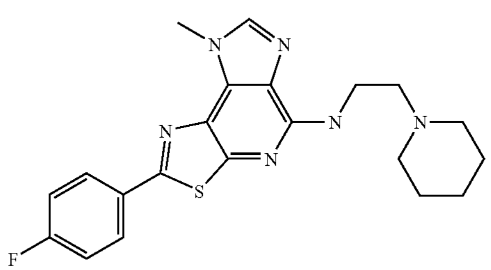 | 8H-imidazo[4,5-d]thiazolo[5,4-b]pyridin-5-amine, 2-(4-fluorophenyl)-8-methyl-N-[2-(1-piperidinyl)ethyl]- | 2.02 | 411.32 |

TABLE B11-continued

| Ex. No. | Structure | Name | HPLC r.t (min). | MS (MH+) |
|---|---|---|---|---|
| B265 | 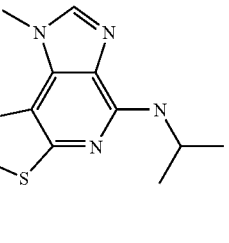 | 8H-imidazo[4,5-d]thiazolo[5,4-b]pyridin-5-amine, 2-(4-fluorophenyl)-8-methyl-N-(1-methylethyl)- | 2.18 | 342.23 |
| B266 | 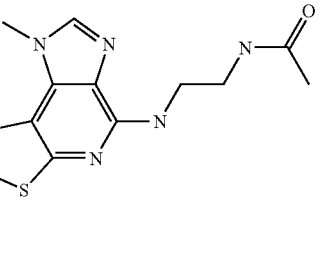 | acetamide, N-[2-[[2-(4-fluorophenyl)-8-methyl-8H-imidazo[4,5-d]thiazolo[5,4-b]pyridin-5-yl]amino]ethyl]- | 1.60 | 385.27 |
| B267 | 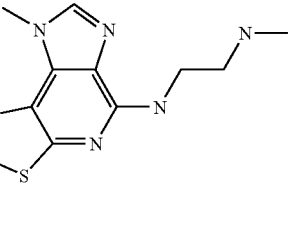 | 1,2-ethanediamine, N-[2-(4-fluorophenyl)-8-methyl-8H-imidazo[4,5-d]thiazolo[5,4-b]pyridin-5-yl]-N'-methyl- | 1.93 | 357.22 |
| B268 | 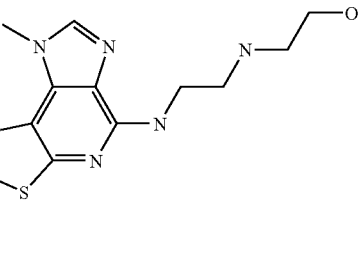 | ethanol, 2-[[2-[[2-(4-fluorophenyl)-8-methyl-8H-imidazo[4,5-d]thiazolo[5,4-b]pyridin-5-yl]amino]ethyl]amino]- | 1.66 | 387.26 |
| B269 | 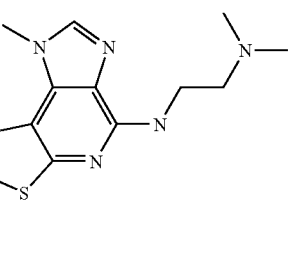 | 1,2-ethanediamine, N'-[2-(4-fluorophenyl)-8-methyl-8H-imidazo[4,5-d]thiazolo[5,4-b]pyridin-5-yl]-N,N-dimethyl- | 2.03 | 371.25 |

TABLE B11-continued

| Ex. No. | Structure | Name | HPLC r.t (min). | MS (MH+) |
|---|---|---|---|---|
| B270 | 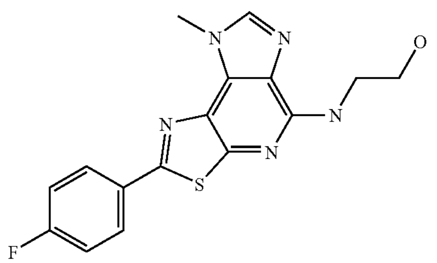 | ethanol, 2-[[2-(4-fluorophenyl)-8-methyl-8H-imidazo[4,5-d]thiazolo[5,4-b]pyridin-5-yl]amino]- | 1.64 | 344.22 |

HPLC conditions: Column: Phenomenex Primesphere C18-HC 4.6 × 30 mm; Solvent A: 10% CH3CN/water 0.05% NH4OAc, Solvent B: 90% CH3CN/water, 0.05% NH$_4$OAc.

Example B271

N-methyl-N'-[8-methyl-5-(methylamino)-8H-imidazo[4,5-d]thiazolo[5,4-b]pyridin-2-yl]urea

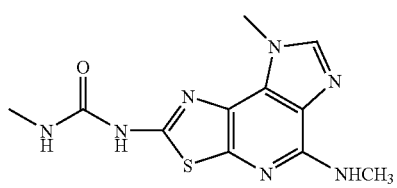

B271

B271.1

N,8-dimethyl-N-[(4-methoxyphenyl)methyl]-2-[(bis-phenyloxcarbonyl)amino]-8H-imidazo[4,5-d]thiazolo[5,4-b]pyridin-5-amine

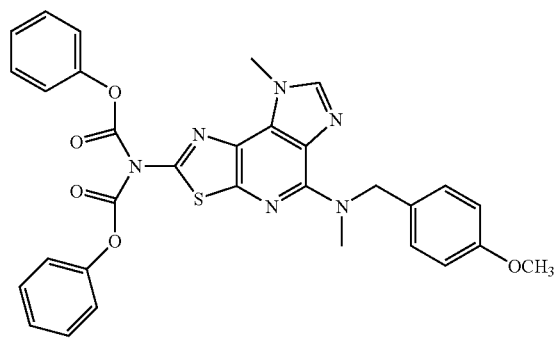

B271.1

A mixture of B11.6 (90 mg; 0.25 mmol), phenylchloroformate (0.07 ml; 0.55 mmol) and pyridine (0.05 ml; 0.65 mmol) in 0.5 ml of dichloromethane was stirred 3 hrs at rt. After partitioning the reaction mixture between EtOAc (30 ml) and water (30 ml), the organic layer was washed with brine (30 ml), dried (MgSO$_4$) and concentrated to afford 145 mg (98%) of B217.1 as a green oil. (M+H)$^+$=595.11 (HPLC>90%).

B271.2

N-methyl-N'-[8-methyl-5-(methylamino)-8H-imidazo[4,5-d]thiazolo[5,4-b]pyridin-2-yl]urea A solution of 2M methylamine in THF (0.5 ml; 1 mmol) was added to a solution of B271.1 (25 mg; 0.042 mmol) in 1 ml of THF at rt. After standing 18 hr at rt, the volatiles were removed in vacuo and the residue was treated with 0.5 ml of TFA. After standing 1.5 hr at rt, the TFA was removed in vacuo and the residue was co-evaporated from heptane (2×2 ml). The solid residue was triturated with ethyl ether: MeOH, 9:1. After filtering, the filter cake was washed with ethyl ether and hexane. Drying afforded 12 mg (98%) of B271 as a dark green powder. (M+H)$^+$=292.14 (HPLC>99%).

Example B272

2-(4-Fluorophenyl)-N-methyl-8H-imidazo[4,5-d]thiazolo[5,4-b]pyridin-5-amine

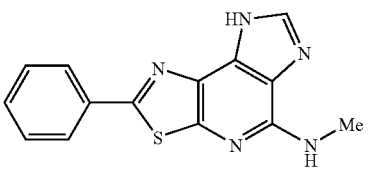

B272

B272.1

N-allyl-3,5-dinitropyridin-4-amine

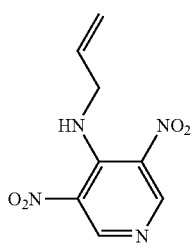

B272.1

A solution of 3,5-dinitropyridin-4-ol (5 g, 27 mmol) and DIPEA (5 mL) in POCl$_3$ (75 mL) was heated to reflux for 4 h. Upon cooling, the solution was concentrated in vacuo and the residue dissolved in THF (100 mL) and cooled to −78°

C. Allylamine (2.3 mL, 29.7 mmol) was added dropwise and the reaction was warmed to r.t. and stirred for 16 h. DIPEA (5 mL) was added dropwise and the reaction stirred overnight at r.t. The solution was partitioned between EtOAc and sat. aq. NaHCO$_3$ and the aq. layer extracted with EtOAc. The combined organics were washed with brine, dried over MgSO$_4$, and concentrated in to afford B272.1 as a dark oil (5.87 g, 97%). HPLC retention time 1.99 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 225.4 [M+H]$^+$

B272.2

N$^4$-allyl-2,6-dichloropyridine-3,4,5-triamine

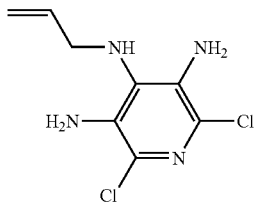

To a solution of B272.1 (5.87 g, 26.2 mmol) in HCl (10 mL), cooled in an ice/brine bath (temp ~−10 to −15° C.) was added SnCl$_2$ (39.8 g, 209.6 mmol) in several portions, keeping the internal tremperature between −8° C. and 0° C. The reaction was stitrred at 0° C. for 1.5 h, then gradually warmed to r.t. over 2 h. The solution was cooled to 0° C. and carefully basified with 3 N NaOH resulting in the formation of a precipitate which was collected by filtration and air-dried. The initial solid was slurried in warm MeOH and re-filtered. The filtrate was evaporated to give B272.2 as a reddish brown solid (1.98 g, 32%). HPLC retention time 1.70 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 233.4, 235.4 [M+H]$^+$

B272.3

1-allyl-4,6-dichloro-1H-imidazo[4,5-c]pyridin-7-amine

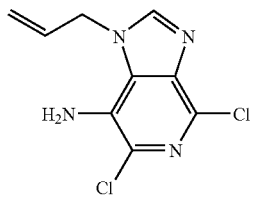

A solution of B272.2 (1.98 g, 8.53 mmol) and trimethylorthoformate (0.957 mL, 8.74 mmol) in acetonitrile was heated to reflux for 4.5 h. An additional portion of trimethylorthoformate (0.050 mL) was added and reflux continued for 5 h. The solution was concentrated in vacuo to afford B272.3 (2.2 g) as a light brown solid. HPLC retention time 1.62 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 243.4, 245.4 [M+H]$^+$

B272.4

N-(1-allyl-4,6-dichloro-1H-imidazo[4,5-c]pyridin-7-yl)-4-fluorobenzamide

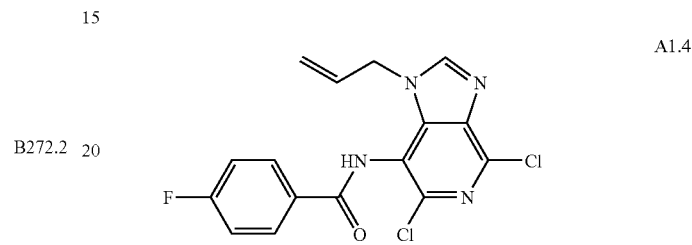

To a solution of B272.3 (1.5 g, 6.17 mmol) in DMA (5 mL) at r.t. was added 4-flourobenzoyl chloride (0.888 mL, 7.4 mmol) dropwise. The reaction was stirred at r.t. overnight, then quenched by addition of water (−3–5 mL). The resulting precipitate was collected by filtration and air-dried to afford B272.4 as an off-white solid (1.908 g, 85% AP). The material was used for further reaction without additional purification. HPLC retention time 2.19 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 365.2, 367.2 [M+H]$^+$

B272.5

N-(1-allyl-6-chloro-4-(methylamino)-1H-imidazo[4,5-c]pyridin-7-yl)-4-fluorobenzamide

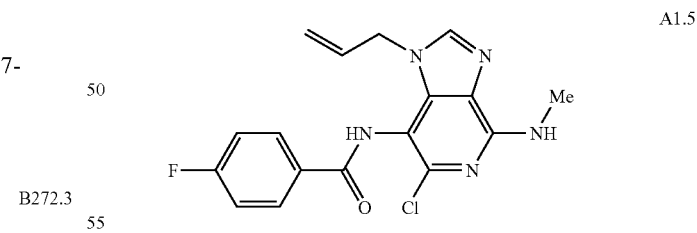

To a solution of B272.4 (0.60 g, 0.164 mmol) in 8M MeNH$_2$/EtOH (2 mL) was heated in a sealed tube in a microwave reactor (Personal Chemistry Smith Synthesizer) for 0.5 h at 150° C. The solution was evaporated and the resulting solid recrystallized from minimal cold EtOH to afford B272.5 as a white solid (0.286 mg, 51%) HPLC retention time 2.01 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 360.4, 362.4 [M+H]$^+$

B272.6

2-(4-fluorophenyl)-N-methyl-8-(2-propenyl)-8H-imidazo[4,5-d]thiazolo[5,4-b]pyridin-5-amine

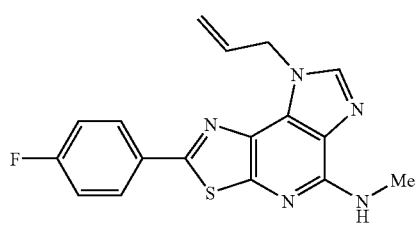

A solution of B272.5 (0.280 g, 0.778 mmol) and Lawesson's Reagent (0.387 g, 0.932 mmol) in toluene (50 mL) was heated to reflux for 2.5 h. The solution was cooled to r.t. and the resulting precipitate collected by filtration. The solid was slurried in hot chloroform and collected by filtration to provide B272.6 (0.191 g, 96% AP). The filtrate was concentrated and purified by prep HPLC to afford additional B272.6 (1.00 TFA salt, 0.0495 g, 14%) as an off-white solid. HPLC retention time 3.40 min. Column: Chromolith SpeedROD 4.6×50 mm (4 min grad. 0% B–100% B) Solvent A: 10% MeOH-90% $H_2O$ 0.2% phosphoric acid Solvent B: 90% MeOH-10% $H_2O$-0.2% phosphoric acid. MS (ES): m/z 340.4 $[M+H]^+$

B272.7

2-(4-Fluorophenyl)-N-methyl-8H-imidazo[4,5-d]thiazolo[5,4-b]pyridin-5-amine

To an oven dried flask under argon was added B272.6 (0.040 g, 0.118 mmol), Pd(PPh$_3$)$_4$ (0.0137 g, 0.012 mmol), AcOH (1 mL), and DCM (4 mL) followed by phenylsilane (29 µL, 0.236 mmol). The reaction was stirred at r.t. overnight, leading to the formation of a precipitate which was collected by filtration and recrystallized from acetonitrile to give B272 (0.0242 g) as a light tan solid. HPLC retention time 2.68 min. Column: Chromolith SpeedROD 4.6×50 mm (4 min grad. 0% B–100% B) Solvent A: 10% MeOH-90% $H_2O$ 0.2% phosphoric acid Solvent B: 90% MeOH-10% $H_2O$-0.2% phosphoric acid. MS (ES): m/z 300.4 $[M+H]^+$

Example B273

N-[1-[2-fluoro-5-[5-[(2-hydroxyethyl)amino]-8-methyl-8H-imidazo[4,5-d]thiazolo[5,4-b]pyridin-2-yl]phenyl]ethyl]acetamide

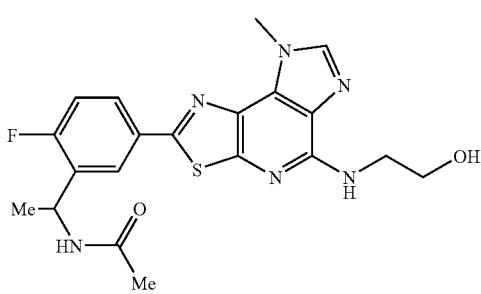

B273.1

N-[1-[2-fluoro-5-chloro-8-methyl-8H-imidazo[4,5-d]thiazolo[5,4-b]pyridin-2-yl]phenyl]ethyl]acetamide

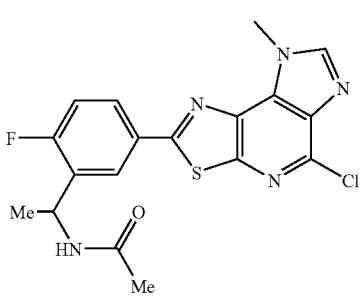

A solution of B99.3 (0.230 g, 0.758 mmol), N-(1-(2-fluoro-5-(trimethylstannyl)phenyl)ethyl)acetamide (0.287 g, 0.834 mmol) and PdCl$_2$(Ph$_3$P)$_2$ (0.0266 g, 0.038 mmol) in dry xylenes (8 mL) was heated to reflux for 4 h. Upon cooling, the solid that formed was collected by filtration and dried in vacuo to give B273.1 (86% AP) HPLC retention time 2.96 min. Column: Chromolith SpeedROD 4.6×50 mm (4 min grad. 0% B–100% B) Solvent A: 10% MeOH-90% $H_2O$ 0.2% phosphoric acid Solvent B: 90% MeOH-10% $H_2O$-0.2% phosphoric acid. MS (ES): m/z 404.3, 406.3 $[M+H]^+$

B273.2

N-[1-[2-fluoro-5-[5-[(2-hydroxyethyl)amino]-8-methyl-8H-imidazo[4,5-d]thiazolo[5,4-b]gyridin-2-yl]phenyl]ethyl]acetamide A solution of B273.1 (0.020 g, 0.0495 mmol) and ethanolamine (0.30 mL) in NMP (0.30 mL) and THF (0.30 mL) was heated in a sealed tube in a microwave reactor (Personal Chemistry Smith Synthesizer) for 0.5 h at 150° C. The solution was partially evaporated under a stream of nitrogen and the residue purified by prep HPLC to afford B273 (1.0 TFA, 0.010 g) HPLC retention time 2.52 min. Column: Chromolith SpeedROD 4.6×50 mm (4 min grad. 0% B–100% B) Solvent A: 10% MeOH-90% $H_2O$ 0.2% phosphoric acid Solvent B: 90% MeOH-10% $H_2O$-0.2% phosphoric acid. MS (ES): m/z 429.3 $[M+H]^+$

Examples B274–B288

Examples B274–B288 described in Table B12 were prepared in a similar manner to that used for Example B273 substituting the appropriate amine.

TABLE B12

| Ex. | Structure | Name | HPLC r.t (min). | MS (MH+) |
|---|---|---|---|---|
| B274 | 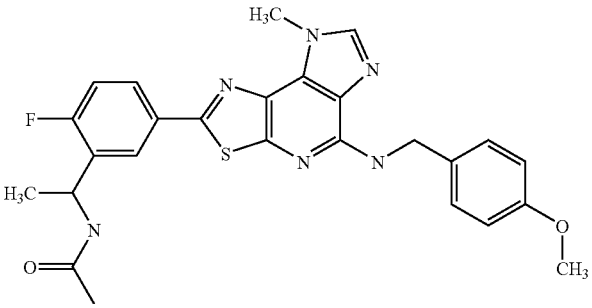 | acetamide, N-[1-[2-fluoro-5-[5-[[(4-methoxyphenyl)methyl]amino]-8-methyl-8H-imidazo[4,5-d]thiazolo[5,4-b]pyridin-2-yl]phenyl]ethyl]- | 3.46 | 505.3 |
| B275 | 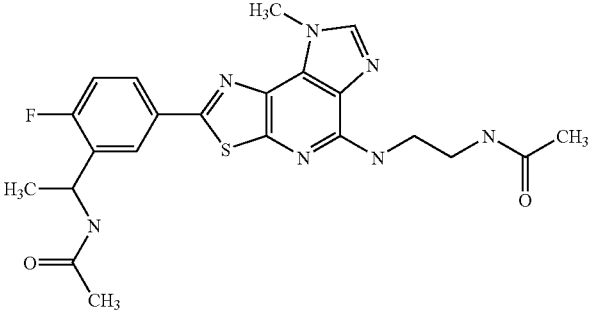 | acetamide, N-[1-[5-[5-[[2-(acetylamino)ethyl]amino]-8-methyl-8H-imidazo[4,5-d]thiazolo[5,4-b]pyridin-2-yl]-2-fluorophenyl]ethyl]- | 2.60 | 470.3 |
| B276 | 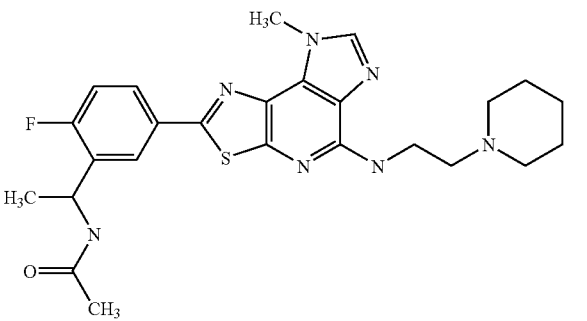 | acetamide, N-[1-[2-fluoro-5-[8-methyl-5-[[2-(1-piperidinyl)ethyl]amino]-8H-imidazo[4,5-d]thiazolo[5,4-b]pyridin-2-yl]phenyl]ethyl]- | 2.37 | 496.4 |
| B277 | 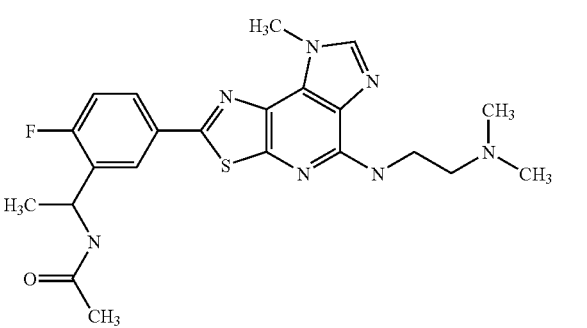 | acetamide, N-[1-[5-[5-[[2-(dimethylamino)ethyl]amino]-8-methyl-8H-imidazo[4,5-d]thiazolo[5,4-b]pyridin-2-yl]-2-fluorophenyl]ethyl]- | 2.23 | 456.3 |

TABLE B12-continued

| Ex. | Structure | Name | HPLC r.t (min). | MS (MH+) |
|---|---|---|---|---|
| B278 | 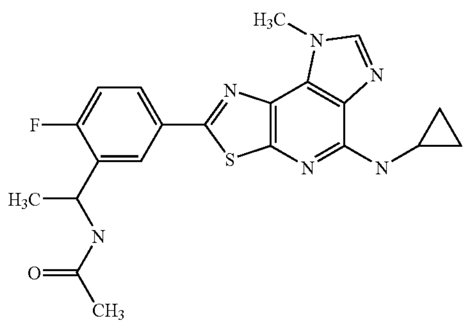 | acetamide, N-[1-[5-[5-(cyclopropylamino)-8-methyl-8H-imidazo[4,5-d]thiazolo[5,4-b]pyridin-2-yl]-2-fluorophenyl]ethyl]- | 2.62 | 425.3 |
| B279 | 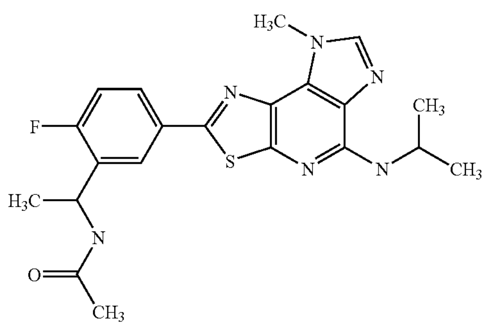 | acetamide, N-[1-[2-fluoro-5-[8-methyl-5-[(1-methylethyl)amino]-8H-imidazo[4,5-d]thiazolo[5,4-b]pyridin-2-yl]phenyl]ethyl - | 3.06 | 427.3 |
| B280 | 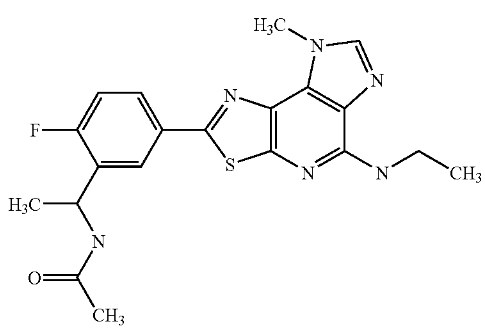 | acetamide, N-[1-[5-[5-(ethylamino)-8-methyl-8H-imidazo[4,5-d]thiazolo[5,4-b]pyridin-2-yl]-2-fluorophenyl]ethyl]- | 2.81 | 413.3 |
| B281 | 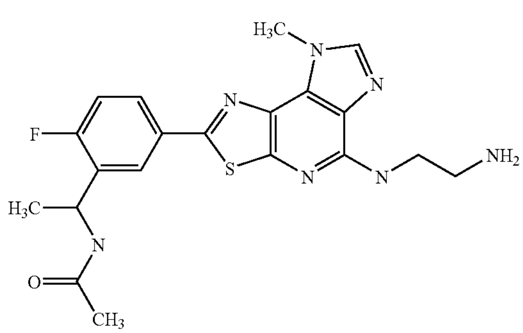 | acetamide, N-[1-[5-[5-[(2-aminoethyl)amino]-8-methyl-8H-imidazo[4,5-d]thiazolo[5,4-b]pyridin-2-yl]-2-fluorophenyl]ethyl]- | 2.20 | 428.3 |
| B282 | 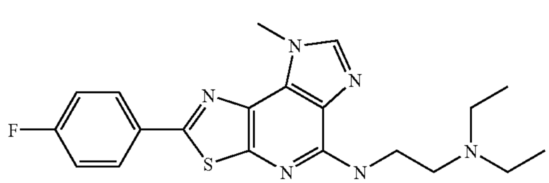 | acetamide, N-[1-[5-[5-[(2-diethylaminoethyl)amino]-8-methyl-8H-imidazo[4,5-d]thiazolo[5,4-b]pyridin-2-yl]-2-fluorophenyl]ethyl]- | 2.73 | 399.3 |

TABLE B12-continued

| Ex. | Structure | Name | HPLC r.t (min). | MS (MH+) |
|---|---|---|---|---|
| B283 | 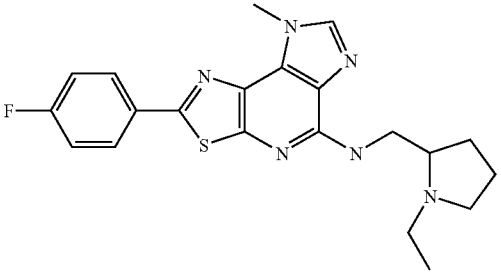 | acetamide, N-[1-[5-[5-[(1-ethylpyrrolidin-2-yl)methylamino]-8-methyl-8H-imidazo[4,5-d]thiazolo[5,4-b]pyridin-2-yl]-2-fluorophenyl]ethyl]- | 2.71 | 411.2 |
| B284 | 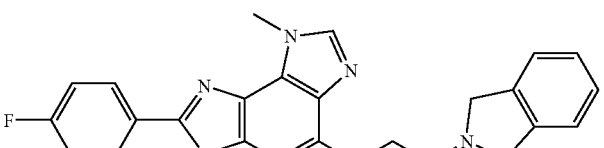 | acetamide, N-[1-[5-[5-[(2-(2-azaindan-2-yl)ethyl)amino]-8-methyl-8H-imidazo[4,5-d]thiazolo[5,4-b]pyridin-2-yl]-2-fluorophenyl]ethyl]- | 2.86 | 445.3 |
| B285 | 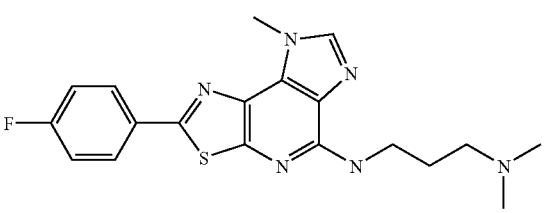 | acetamide, N-[1-[5-[5-[(3-dimethylaminopropyl)amino]-8-methyl-8H-imidazo[4,5-d]thiazolo[5,4-b]pyridin-2-yl]-2-fluorophenyl]ethyl]- | 2.61 | 385.3 |
| B286 | 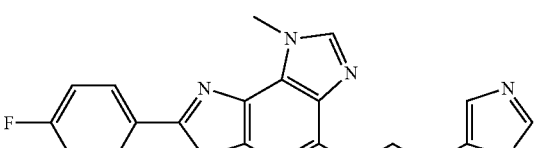 | acetamide, N-[1-[5-[5-[(2-imidazol-4-ylethyl)amino]-8-methyl-8H-imidazo[4,5-d]thiazolo[5,4-b]pyridin-2-yl]-2-fluorophenyl]ethyl]- | 2.71 | 394.2 |
| B287 | 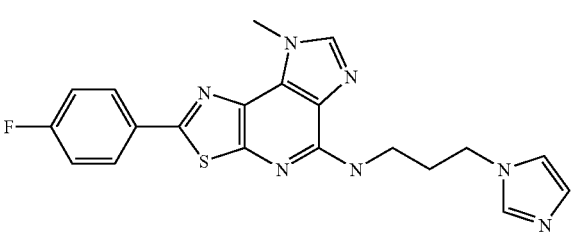 | acetamide, N-[1-[5-[5-[(3-imidazol-1-ylpropyl)amino]-8-methyl-8H-imidazo[4,5-d]thiazolo[5,4-b]pyridin-2-yl]-2-fluorophenyl]ethyl]- | 2.67 | 408.2 |
| B288 | 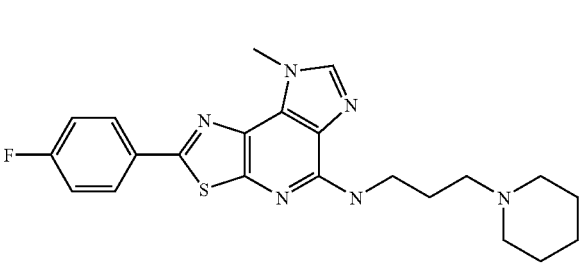 | acetamide, N-[1-[5-[5-[(3-piperidin-1-ylpropyl)amino]-8-methyl-8H-imidazo[4,5-d]thiazolo[5,4-b]pyridin-2-yl]-2-fluorophenyl]ethyl]- | 2.71 | 425.3 |

HPLC conditions: Column: Chromolith SpeedROD ® 4.6 × 50 mm (4 mm grad. 0% B–100% B) Solvent A: 10% MeOH-90% H$_2$O 0.2% phosphoric acid Solvent B: 90% MeOH-10% H$_2$O-0.2% phosphoric acid.

Example B289

2-(3-(2-carboxyethenyl)phenyl)-N-(2-aminoethyl)-8-methyl-8H-imidazo[4,5-d]thiazolo[5,4-b]pyridin-5-amine

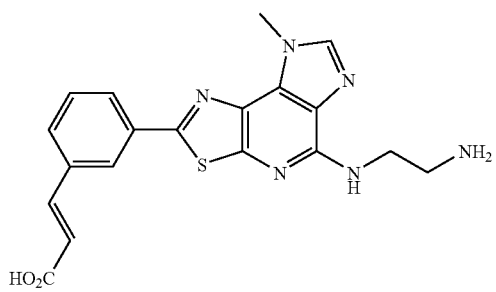

B289

B289.1

5-Chloro-2-(3-(2-carboxyethenyl)phenyl)-N-(2-aminoethyl)-8-methyl-8H-imidazo[4,5-d]thiazolo[5,4-b]pyridine

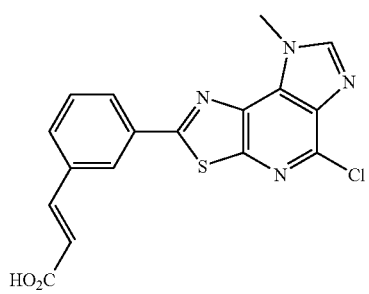

B289.1

A solution of B99.3 (0.5 g, 1.65 mmol), (E)-3-(3-boronophenyl)acrylic acid is (0.473 g, 2.475 mmol), Pd(Ph$_3$P)$_4$ (0.095 g, 0.0825 mmol), and 2M aq. K$_2$CO$_3$ (1.65 mL) in DME (10 mL) and EtOH (4 mL) was heated to 87° C. for 8 h. Upon cooling, the product was filtered and washed with EtOH, then the product was recrystallized from THF to afford B289.1 (0.275 g) as a light yellow solid. HPLC retention time 3.30 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 371.06, 373.06 [M+H]$^+$

B289.2

2-(3-(2-carboxyethenyl)phenyl)-N-(2-aminoethyl)-8-methyl-8H-imidazo[4,5-d]thiazolo[5,4-b]pyridin-5-amine A solution of B289.1 (0.030 g, 0.081 mmol) and 1,2-ethylenediamine (0.30 mL) in n-butanol (0.60 mL) was heated in a sealed tube in a microwave reactor (Personal Chemistry Smith Synthesizer) for 0.5 h at 150° C. The solution was partially evaporated under a stream of nitrogen and the residue purified by prep HPLC to afford B289 (2 TFA, 0.0163 g) HPLC retention time 2.59 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 395.34 [M+H]$^+$

Example B290

3-[8-methyl-5-[[2-(1-piperidinyl)ethyl]amino]-8H-imidazo[4,5-d]thiazolo[5,4-b]pyridin-2-yl]benzeneacetonitrile

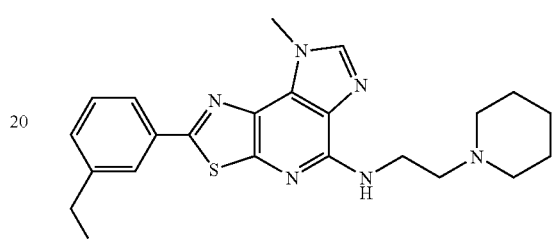

B290

B290.1

3-[8-methyl-5-chloro-8H-imidazo[4,5-d]thiazolo[5,4-b]pyridin-2-yl]benzeneacetonitrile

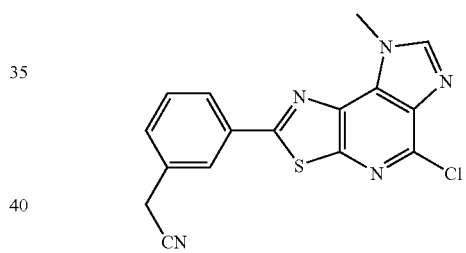

B290.1

A solution of B99.3 (0.25 g, 0.825 mmol), 3-(cyanomethyl)phenylboronic acid (0.199 g, 1.24 mmol), Pd(Ph$_3$P)$_4$ (0.0476 g, 0.04 mmol), and 2M aq. K$_2$CO$_3$ (1.25 mL) in DME (10 mL) and EtOH (4 mL) was heated to 87° C. for 8 h. Upon cooling, the product was filtered and washed with EtOH, then the product was recrystallized from THF to afford B290.1 (0.305 g) as a light yellow solid. HPLC retention time 2.95 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 340.09, 342.12 [M+H]$^+$

B290

3-[8-methyl-5-[[2-(1-piperidinyl)ethyl]amino]-8H-imidazo[4,5-d]thiazolo[5,4-b]pyridin-2-yl]benzeneacetonitrile A solution of B290.1 (0.30 g, 0.089 mmol) and 2-(piperidin-1-yl)ethanamine (0.30 mL) in NMP (0.30 mL) and THF (0.30 mL) was heated in a sealed tube in a microwave reactor (Personal Chemistry Smith Synthesizer) for 0.83 h at 150° C. The solution was partially evaporated under a stream of nitrogen and the residue purified by prep HPLC to afford B290 (2 TFA, 0.023 g) HPLC retention time 2.46 min. Column: Chromolith SpeedROD 4.6×50 mm (4 min grad. 0% B–100% B) Solvent A: 10% MeOH-90% H$_2$O 0.2% phosphoric acid Solvent B: 90% MeOH-10% H$_2$O-0.2% phosphoric acid. MS (ES): m/z 432.36 [M+H]$^+$ Examples B291–B299

Examples B291–B299 described in Table B13 were prepared in a similar manner to that used for Example B289 and B290 substituting the appropriate amine.

TABLE B13

| Example | Structure | Name | HPLC r.t (min.) | MS (MH+) |
|---|---|---|---|---|
| B291 | 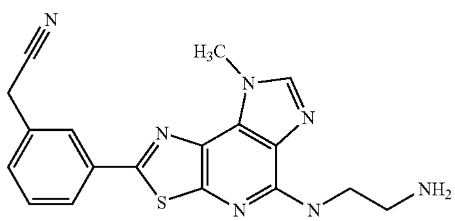 | benzeneacetonitrile, 3-[5-[(2-aminoethyl)amino]-8-methyl-8H-imidazo[4,5-d]thiazolo[5,4-b]pyridin-2-yl]- | 2.25 | 364.23 |
| B292 | 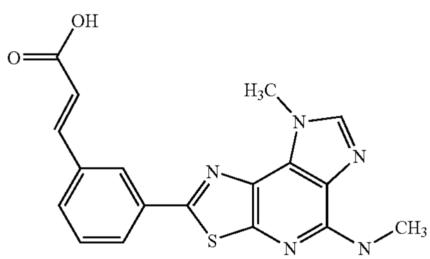 | 2-propenoic acid, 3-[3-[8-methyl-5-(methylamino)-8H-imidazo[4,5-d]thiazolo[5,4-b]pyridin-2-yl]phenyl]-, (2E)- | 2.8 | 366.2 |
| B293 | 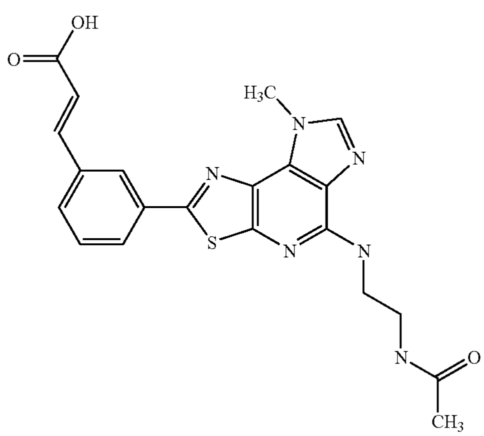 | 2-propenoic acid, 3-[3-[5-[[2-(acetylamino)ethyl]amino]-8-methyl-8H-imidazo[4,5-d]thiazolo[5,4-b]pyridin-2-yl]phenyl]-, (2E)- | 2.79 | 437.3 |
| B294 | 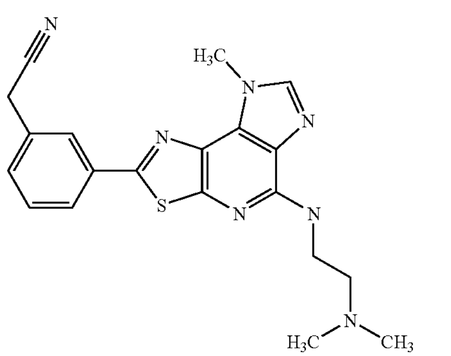 | benzeneacetonitrile, 3-[5-[[2-(dimethylamino)ethyl]amino]-8-methyl-8H-imidazo[4,5-d]thiazolo[5,4-b]pyridin-2-yl]- | 2.27 | 392.32 |

TABLE B13-continued

| Example | Name | HPLC r.t (min.) | MS (MH+) |
|---|---|---|---|
| B295 | benzeneacetonitrile, 3-[5-[(2-hydroxyethyl)amino]-8-methyl-8H-imidazo[4,5-d]thiazolo[5,4-b]pyridin-2-yl]- | 2.34 | 365.23 |
| B296 | benzeneacetonitrile, 3-[8-methyl-5-(methylamino)-8H-imidazo[4,5-d]thiazolo[5,4-b]pyridin-2-yl]- | 2.39 | 335.25 |
| B297 | benzeneacetonitrile, 3-[5-[[(4-methoxyphenyl)methyl]amino]-8-methyl-8H-imidazo[4,5-d]thiazolo[5,4-b]pyridin-2-yl]- | 3.34 | 441.33 |
| B298 | benzeneacetonitrile, 3-[8-methyl-5-[[2-(1-piperidinyl)ethyl]amino]-8H-imidazo[4,5-d]thiazolo[5,4-b]pyridin-2-yl]- | 2.46 | 432.36 |

TABLE B13-continued

| Example | Structure | Name | HPLC r.t (min.) | MS (MH+) |
|---|---|---|---|---|
| B299 | 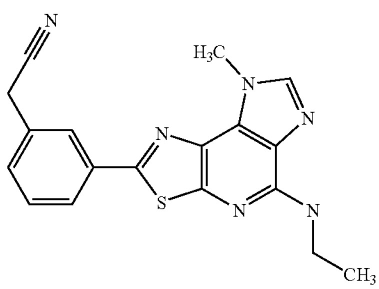 | benzeneacetonitrile, 3-[5-(ethylamino)-8-methyl-8H-imidazo[4,5-d]thiazolo[5,4-b]pyridin-2-yl]- | 2.63 | 349.25 |

HPLC conditions: Column: Chromolith SpeedROD 4.6 × 50 mm (4 min grad. 0% B–100% B) Solvent A: 10% MeOH-90% H$_2$O 0.2% phosphoric acid Solvent B: 90% MeOH-10% H$_2$O-0.2% phosphoric acid.

Example B300

2-Fluoro-5-[8-methyl-5-(methylamino)-8H-imidazo[4,5-d]thiazolo[5,4-b]pyridin-2-yl]benzonitrile

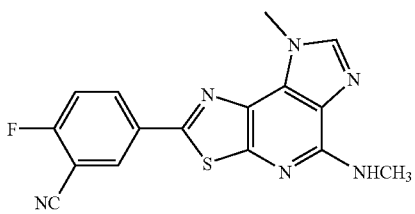

B300

Example B300 was prepared in a similar manner to example B229 using 3-cyano-4-fluorophenylboronic acid. HPLC Ret. Time 1.56 min (Phenomenex S5® 2 min gradient) 10% MeOH, 90% H$_2$O, 0.1% TFA to 90% MeOH, 10% H$_2$O, 0.1% TFA. Observed Mass=338.00; $^1$H NMR d$_6$DMSO δ 8.56–8.54, m, 1H, 8.40–8.36, m 1H, 8.19, s, 1H, 7.24–7.76, m, 1H, 7.41, br s, 1H, 4.23 s, 3H, 3.03, s, 3H.

Example B301

2-(3-Amino-1,2-benzisoxazol-5-yl)-N,8-dimethyl-8H-imidazo[4,5-d]thiazolo[5,4-b]pyridin-5-amine

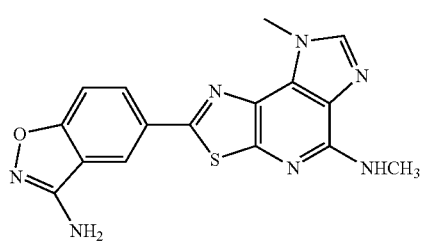

B301

Example B310 was prepared from B300 by reaction with acetoneoxime according to the method described by Lam, et. al. J. Med Chem 2003, 46, 4405–4418. Retention time=11.44 min, 97% purity, Observed mass=352 (M+1).

Example B302

N,8-dimethyl-2-[3-[1-(methylamino)ethyl]phenyl]-8H-imidazo[4,5-d]thiazolo[5,4-b]pyridin-5-amine

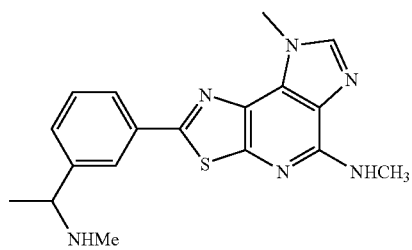

B302

B302 was prepared in a similar manner to that used for Example B100 by reacting B99 with the appropriate amine. Retention time 1.08 min, observed mass 353. Column: Phenomenex Primesphere C18-HC 4.6×30 mm; Solvent A: 10% CH3CN/water 0.05% TFA, Solvent B: 90% CH3CN/water, 0.05% TFA

Examples B303–B309

Examples B303–B309 described in Table B14 were prepared in a similar manner to that used for Example B99 by reacting B29.2 with the appropriate boronic acid as described in step B99.4.

TABLE B14

| Example Number | Name | Retention Time (min) | Observed mass |
|---|---|---|---|
| B303 | benzenepropanoic acid, 4-[8-methyl-5-(methylamino)-8H-imidazo[4,5-d]thiazolo[5,4-b]pyridin-2-yl]- | 1.31 | 367.99 |
| B304 | 8H-imidazo[4,5-d]thiazolo[5,4-b]pyridin-5-amine, 2-(3,5-difluorophenyl)-N,8-dimethyl- | 1.77 | 331.97 |
| B305 | 8H-imidazo[4,5-d]thiazolo[5,4-b]pyridin-5-amine, 2-(1H-indol-5-yl)-N,8-dimethyl- | 1.45 | 338.03 |
| B306 | 8H-imidazo[4,5-d]thiazolo[5,4-b]pyridin-5-amine, N,8-dimethyl-2-[3-(methylthio)phenyl]- | 171. | 342.01 |
| B307 | benzonitrile, 3-[8-methyl-5-(methylamino)-8H-imidazo[4,5-d]thiazolo[5,4-b]pyridin-2-yl]- | 1.50 | 321.03 |

TABLE B14-continued

| Example Number | Structure | Name | Retention Time (min) | Observed mass |
|---|---|---|---|---|
| B308 | 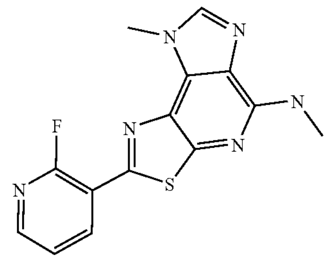 | 8H-imidazo[4,5-d]thiazolo[5,4-b]pyridin-5-amine, 2-(2-fluoro-3-pyridinyl)-N,8-dimethyl- | 1.30 | 315.01 |
| B309 | 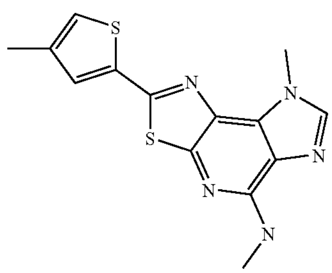 | 8H-imidazo[4,5-d]thiazolo[5,4-b]pyridin-5-amine, N,8-dimethyl-2-(4-methyl-2-thienyl)- | 1.62 | 315.97 |

HPLC conditions: Column: Phenomenex Primesphere C18-HC 4.6 × 30 mm; Solvent A: 10% CH3CN/water 0.05% TFA, Solvent B: 90% CH3CN/water, 0.05% TFA.

Example B310

2-[3-(aminomethyl)phenyl]-N,8-dimethyl-8H-imidazo[4,5-d]thiazolo[5,4-b]pyridin-5-amine

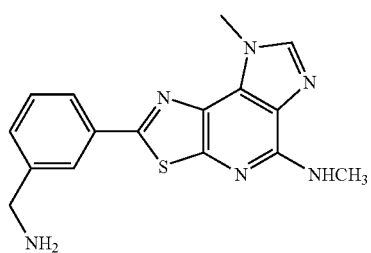

B310

B307 (320 mg, 1.0 mmol) was dissolved in 100 mL of anhydrous THF at room temperature. Lithium aluminum hydride (1.0 mL of a 1M solution in THF, 1.0 mmol) was added slowly. The reaction mixture was stirred overnight at room temperature. The reaction was quenched by the sequential addition of 1 mL of water, followed by 1 mL of 15% aqueous sodium hydroxide, followed by the addition of 3 mL of water with stirring. The supernatant was separated and concentrated in vacuo to provide 215 mg of crude B310. The product was dissolved in methanol, filtered and the filtrate concentrated to provide 175 mg of B310 as a yellow solid. M+H=325.24 HPLC retention time=1.51 min (Column: Xterra® 4.6×30 mm; 4 min gradient; Solvent A: 10% CH3CN/water 0.05% TFA, Solvent B: 90% CH3CN/water, 0.05% TFA. $^1$H NMR CD$_3$OD δ 8.06, s, 2H, 7.99 d, 1H, 7.43, s 2H, 4.28 s, 3H, 3.76, s, 2H, 3.12, s, 3H.

B311

N-[[3-[8-methyl-5-(methylamino)-8H-imidazo[4,5-d]thiazolo[5,4-b]pyridin-2-yl]phenyl]methyl]acetamide

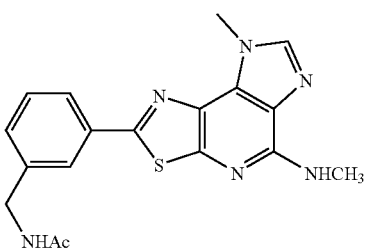

B311

B310 (20 mg, 0.06 mmol) was dissolved in 3 mL of anhydrous THF, acetic anhydride (10 mg, 0.1 mmol) and 0.5 mL of pyridine were added and the reaction mixture stirred at room temperature overnight. The reaction mixture was concentrated in vacuo, and the residue purified by reverse phase HPLC to yield 14 mg of B311. Retention time 1.21 min, observed mass 367.31 Column: Phenomenex Primesphere C18-HC 4.6×30 mm; Solvent A: 10% CH3CN/water 0.05% TFA, Solvent B: 90% CH3CN/water, 0.05% TFA. $^1$H NMR CD$_3$OD δ 8.11, s, 1H, 7.84–7.80, m, 2H, 7.43–7.40, m 2H, 4.42 s, 2H, 4.21 s, 3H, 3.13, s, 3H, 2.04, s, 3H.

B312

N-[[3-[8-methl-5-(methylamino)-8H-imidazo[4,5-d]thiazolo[5,4-b]pyridin-2-yl]phenyl]methyl]methanesulfonamide

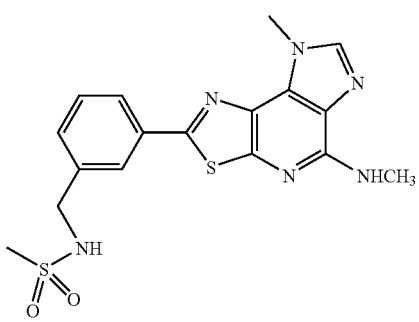

B312

B310 (20 mg, 0.06 mmol) was dissolved in 3 mL of anhydrous THF, methansulfonyl chloride (10 mg, 0.08 mmol) and 0.5 mL of pyridine were added and the reaction mixture stirred at room temperature overnight. The reaction mixture was concentrated in vacuo, and the residue purified by reverse phase HPLC to yield 16 mg of B312. Retention time 1.24 min, observed mass 403.27 Column: Phenomenex S5 4.6×30 mm; Solvent A: 10% CH3CN/water 0.05% TFA, Solvent B: 90% CH3CN/water, 0.05% TFA. $^1$H NMR CD$_3$OD δ 8.19, s, 1H, 8.00, s, 1H, 7.84–7.80, m, 2H, 7.50, m 2H, 4.35 s, 2H, 4.25 s, 3H, 3.16, s, 3H, 2.99, s, 3H.

Example B313

2-[3-(1-aminoethyl)phenyl]-N,8-dimethyl-8H-imidazo[4,5-d]thiazolo[5,4-b]pyridin-5-amine

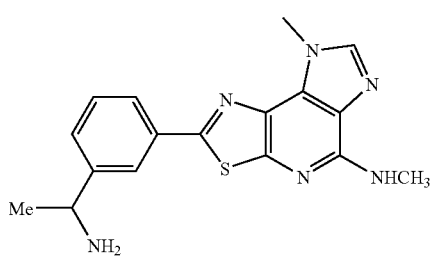

B313

B307 (320 mg, 1.0 mmol) was dissolved in 100 mL of anhydrous THF at room temperature. Methylmagnesium bromide (1 mL of a 3M solution in THF) was added and the reaction mixture was stirred overnight at room temperature. Lithium aluminum hydride (1 mL of a 1 M solution in THF) was added during which time an exotherm was noted. The reaction mixture was allowed to stir for an additional 3 h at room temperature. The reaction mixture was quenched by the sequential addition of 2 mL of water, followed by 2 mL of 15% aqueous sodium hydroxide, followed by the addition of 6 mL of water with stirring. The supernate was decanted. The aqueous layer was treated with an additional 25 mL of THF and the supernate removed. The combined organic layers were evaporated in vacuo and the residue purified by reverse phase preparatory HPLC, to provide 88 mg of B313. Retention time 1.13 min, observed mass 339.26 Column: Phenomenex S5 4.6×30 mm; Solvent A: 10% CH3CN/water 0.05% TFA, Solvent B: 90% CH3CN/water, 0.05% TFA. $^1$H NMR CD$_3$OD δ 8.20–8.16, m, 3H, 7.65–7.58, m, 2H, 4.68–4.58, m, 1H, 4.36 s, 3H, 3.19, s, 3H, 1.70, d, (J=6.9 Hz) 3H.

Example B314

N-[1-[3-[8-methyl-5-(methylamino)-8H-imidazo[4,5-d]thiazolo[5,4-b]pyridin-2-yl]phenyl]ethyl]acetamide

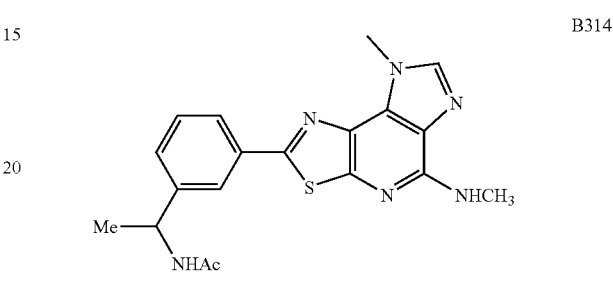

B314

B313 (20 mg, 0.06 mmol) was dissolved in 3 mL of anhydrous THF, acetic anhydride (10 mg, 0.1 mmol) and 0.5 mL of pyridine were added and the reaction mixture stirred at room temperature overnight. The reaction mixture was concentrated in vacuo, and the residue purified by reverse phase HPLC to yield 15 mg of B314. Retention time 1.30 min, observed mass 381.33 Column: Phenomenex S5 4.6×30 mm; Solvent A: 10% CH3CN/water 0.05% TFA, Solvent B: 90% CH3CN/water, 0.05% TFA. $^1$H NMR CD$_3$OD δ 8.18, s, 1H, 7.95, s, 1H, 7.90–7.84, m, 1H, 7.51, m 2H, 5.15–5.05, m, 1H, 4.26 s, 3H, 4.26 s, 3H, 3.17, s, 3H, 2.05, s, 3H, 1.53, d, (J=7.0 Hz) 3H.

Example B315

N-[1-[3-[8-methyl-5-(methylamino)-8H-imidazo[4,5-d]thiazolo[5,4-b]pyridin-2-yl]phenyl]ethyl]methanesulfonamide

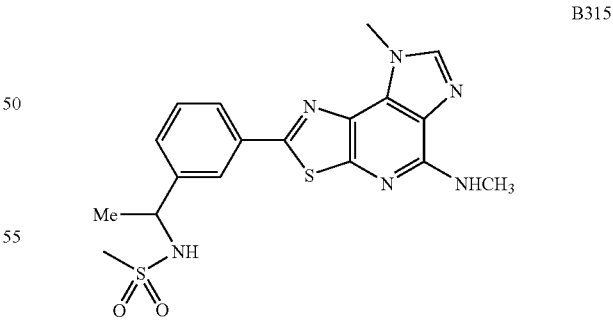

B315

B313 (20 mg, 0.06 mmol) was dissolved in 3 mL of anhydrous THF, methansulfonyl chloride (10 mg, 0.08 mmol) and 0.5 mL of pyridine were added and the reaction mixture stirred at room temperature overnight. The reaction mixture was concentrated in vacuo, and the residue purified by reverse phase HPLC to yield 15 mg of B315. Retention time 1.78 min, observed mass 531.15 (M+H+TFA) Column: Phenomenex S5 4.6×30 mm; Solvent A: 10% CH3CN/water 0.05% TFA, Solvent B: 90% CH3CN/water, 0.05% TFA. ¹H NMR CD₃OD δ 8.19, s, 1H, 8.03, s, 1H, 7.92, s, 1H, 7.85–7.75, m 1H, 7.45–7.43, m, 2H, 5.18–5.10, m (q), 1H, 4.15 s, 3H, 3.30 s, 3H, 3.08, s, 3H, 1.56, d, (J=7.1 Hz), 3H.

Example B316

N-[1-methyl-1-[3-[8-methyl-5-(methylamino)-8H-imidazo[4,5-d]thiazolo[5,4-b]pyridin-2-yl]phenyl]ethyl]amine

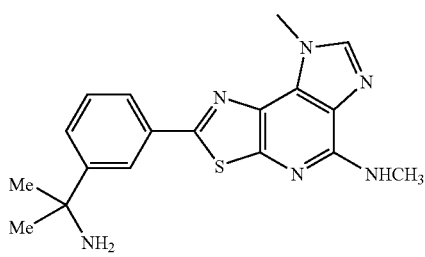

Cerium chloride (738 g, 3.0 mmol) was dissolved in 25 mL of THF and cooled to −78° C. Methyl lithium (2 mL of a 1.6 M solution in ether) was added dropwise and the mixture stirred for 1 h. A suspension of B307 (320 mg, 0.1 mmol) was added and the reaction mixture was allowed to warm to room temperature and stirred overnight. The reaction mixture was quenched by the addition of 1 mL of water and 50% NH4OH solution. The reaction mixture was filtered and the filtrate concentrated in vacuo. The residue was purified by preparatory HPLC to provide 139 mg of B316 as a yellow-brown solid. Retention time 1.15 min, observed mass 353.28 (M+H) Column: Phenomenex S5 4.6×30 mm; Solvent A: 10% CH3CN/water 0.05% TFA, Solvent B: 90% CH3CN/water, 0.05% TFA.

Example B317

N-[1-methyl-1-[3-[8-methyl-5-(methylamino)-8H-imidazo[4,5-d]thiazolo[5,4-b]pyridin-2-yl]phenyl]ethyl]acetamide

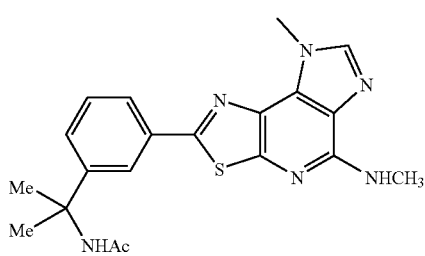

B316 (35 mg, 0.1 mmol) was dissolved in 5 mL of anhydrous THF, acetic anhydride (11 mg, 0.1 mmol) and 0.5 mL of pyridine were added and the reaction mixture stirred at room temperature overnight. The reaction mixture was quenched with 1N HCl, and concentrated in vacuo, and the residue purified by reverse phase HPLC to yield 11 mg of B317. Retention time 1.35 min, observed mass 395.39 Column: YMC ODS-A 4.6×33 mm; Solvent A: 10% CH3CN/water 0.05% TFA, Solvent B: 90% CH3CN/water, 0.05% TFA. ¹H NMR CD₃OD δ 8.05, s, 1H, 7.95, s, 1H, 7.72, d, 1H, 7.58, d 1H, 7.43, t, 1H, 4.15 s, 3H, 3.05, s, 3H, 2.06, s, 3H, 1.73, s, 6H.

Example B318

N-[1,1-dimethyl-1-[3-[8-methyl-5-(methylamino)-8H-imidazo[4,5-d]thiazolo[5,4-b]pyridin-2-yl]4-fluorophenyl]ethyl]amine

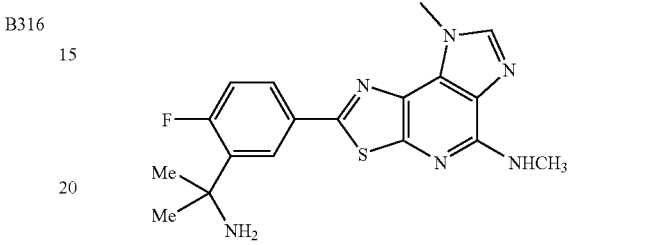

Cerium chloride (738 g, 3.0 mmol) was dissolved in 25 mL of THF and cooled to −78° C. Methyl lithium (2 mL of a 1.6 M solution in ether) was added dropwise and the mixture stirred for 1 h. A suspension of B300 (338 mg, 0.1 mmol) was added and the reaction mixture was allowed to warm to room temperature and stirred overnight. An additional 2 mL of methyl lithium (1.6M solution in ether) was added and the reaction mixture stirred for 2 d. HPLC analysis showed approximately 50% conversion to B318. Lithium aluminum hydride (2 mL of a 1 M solution in THF) was added and the reaction stirred for an additional 1 h. The reaction was quenched by the sequential addition of 2 mL of water, followed by 2 mL of 15% aqueous sodium hydroxide, followed by the addition of 6 mL of water with stirring. The supernate was decanted and concentrated in vacuo. The residue was purified by preparatory HPLC to provide 163 mg of a yellow-brown solid. Purification of this solid by reverse phase HPLC yielded 30 mg of B318. Retention time 1.18 min, observed mass 371.28 (M+H) Column: Phenomenex S5 4.6×30 mm; Solvent A: 10% CH3CN/water 0.05% TFA, Solvent B: 90% CH3CN/water, 0.05% TFA.

Example B319

N-[1-[2-fluoro-5-[8-methyl-5-(methylamino)-8H-imidazo[4,5-d]thiazolo[5,4-b]pyridin-2-yl]phenyl]-1-methylethyl]-acetamide,

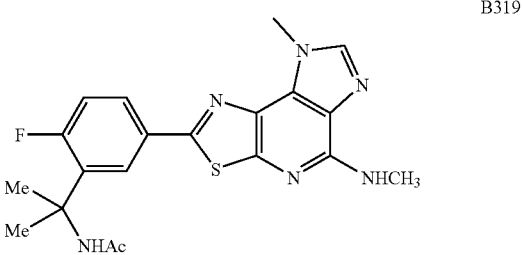

B318 (37 mg, 0.1 mmol) was dissolved in 5 mL of anhydrous THF, acetic anhydride (11 mg, 0.1 mmol) and 0.5 mL of pyridine were added and the reaction mixture stirred at room temperature overnight. The reaction mixture was quenched with 1N HCl, and concentrated in vacuo, and the residue purified by reverse phase HPLC to yield 10 mg of B317. Retention time 1.41 min, observed mass 413.36 Column: YMC ODS-A 4.6×33 mm; Solvent A: 10% CH3CN/water 0.05% TFA, Solvent B: 90% CH3CN/water, 0.05% TFA. $^1$H NMR CD$_3$OD δ 8.13, s, 1H, 8.05–8.00, m, 1H, 7.94–7.86, m, 1H, 7.25–7.15, m 1H, 4.24 s, 3H, 3.15, s, 3H, 2.02, s, 3H, 1.80, s, 6H.

Examples B320–B333

Examples B320–B333 described in Table B15 were prepared in a similar manner to that used for Example B99 by reacting B29.2 with the appropriate boronic acid as described in step B99.4.

TABLE B15

| Example Number | Structure | Name | Retention Time (min) | Observed mass |
|---|---|---|---|---|
| B320 | 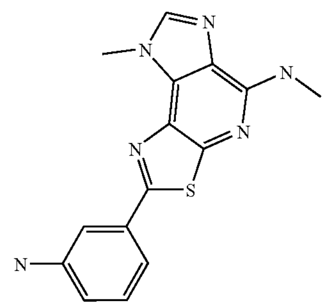 | 8H-imidazo[4,5-d]thiazolo[5,4-b]pyridin-5-amine, 2-(3-aminophenyl)-N,8-dimethyl- | 1.04 | 311.05 |
| B321 | 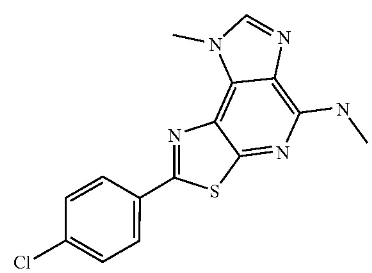 | 8H-imidazo[4,5-d]thiazolo[5,4-b]pyridin-5-amine, 2-(4-chlorophenyl)-N,8-dimethyl- | 1.78 | 329.99 |
| B322 | 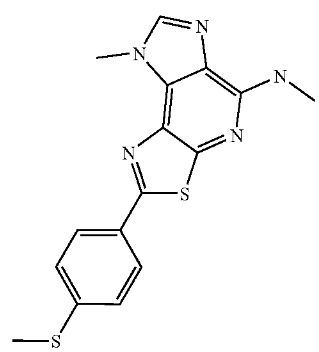 | 8H-imidazol[4,5-d]thiazolo[5,4-b]pyridin-5-amine, N,8-dimethyl-2-[4-(methylthio)phenyl]- | 1.70 | 341.98 |
| B323 | 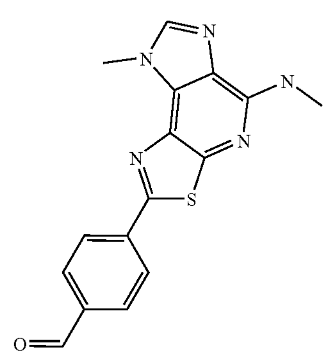 | benzaldehyde, 4-[8-methyl-5-(methylamino)-8H-imidazo[4,5-d]thiazolo[5,4-b]pyridin-2-yl]- | 1.45 | 324.03 |

TABLE B15-continued

| Example Number | Structure | Name | Retention Time (min) | Observed mass |
|---|---|---|---|---|
| B324 | 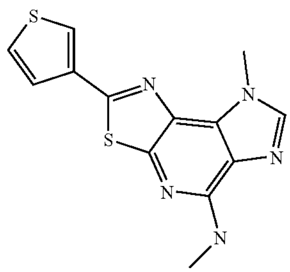 | 8H-imidazo[4,5-d]thiazolo [5,4-b]pyridin-5-amine, N,8-dimethyl-2-(3-thienyl)- | 1.41 | 301.96 |
| B325 | 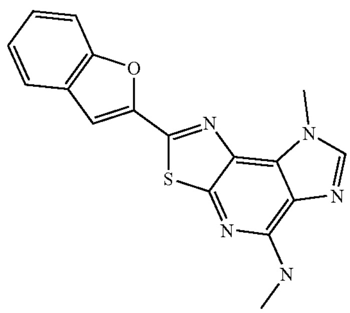 | 8H-imidazo[4,5-d]thiazolo[5,4-b]pyridin-5-amine, 2-(2-benzofuranyl)-N,8-dimethyl- | 1.79 | 336.00 |
| B326 | 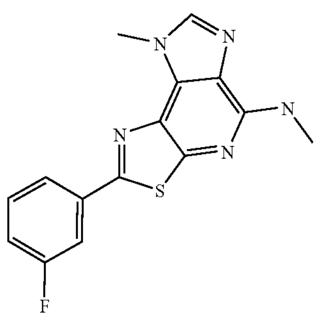 | 8H-imidazo[4,5-d]thiazolo[5,4-b]pyridin-5-amine, 2-(3-fluorophenyl)-N,8-dimethyl- | 1.60 | 313.99 |
| B327 | 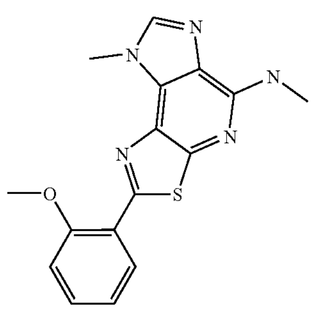 | 8H-imidazo[4,5-d]thiazolo[5,4-b]pyridin-5-amine, 2-(2-methoxyphenyl)-N,8-dimethyl- | 1.51 | 326.02 |
| B328 | 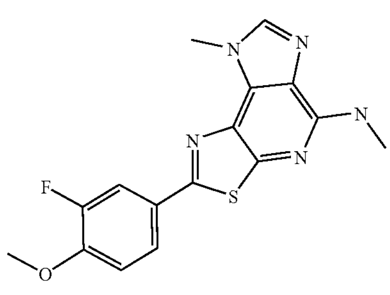 | 8H-imidazo[4,5-d]thiazolo[5,4-b]pyridin-5-amine, 2-(3-fluoro-4-methoxyphenyl)-N,8-dimethyl- | 1.58 | 344.00 |

TABLE B15-continued

| Example Number | Structure | Name | Retention Time (min) | Observed mass |
|---|---|---|---|---|
| B329 | 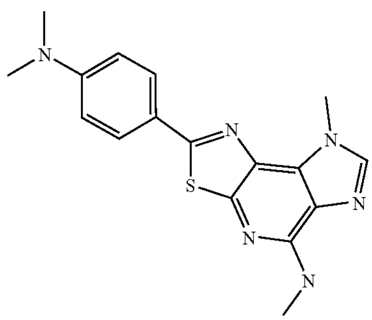 | 8H-imidazo[4,5-d]thiazolo[5,4-b]pyridin-5-amine, 2-[4-(dimethylamino)phenyl]-N,8-dimethyl- | 1.50 | 339.07 |
| B330 | 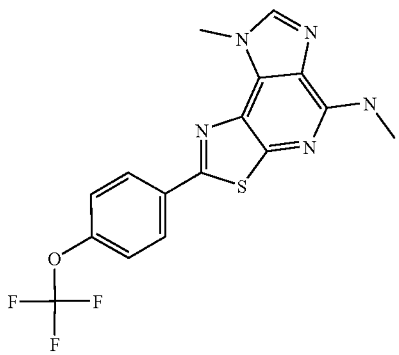 | 8H-imidazo[4,5-d]thiazolo[5,4-b]pyridin-5-amine, N,8-dimethyl-2-[4-(trifluoromethoxy)phenyl]- | 1.85 | 379.96 |
| B331 | 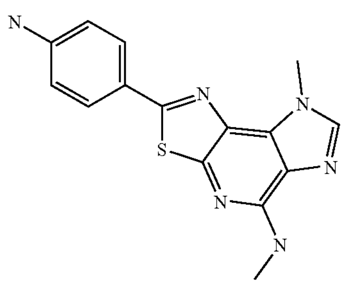 | 8H-imidazo[4,5-d]thiazolo[5,4-b]pyridin-5-amine, 2-(4-aminophenyl)-N,8-dimethyl- | 1.09 | 311.05 |
| B332 | 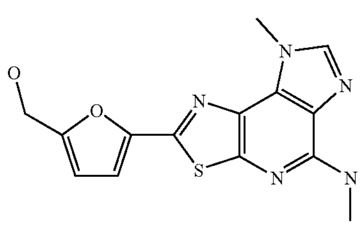 | 2-furanmethanol, 5-[8-methyl-5-(methylamino)-8H-imidazo[4,5-d]thiazolo[5,4-b]pyridin-2-yl]- | 1.08 | 316 |
| B333 | 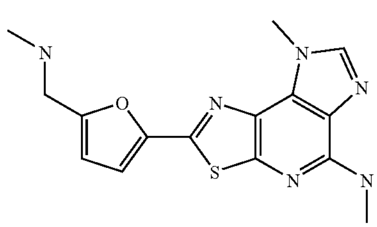 | 8H-imidazo[4,5-d]thiazolo[5,4-b]pyridin-5-amine, N,8-dimethyl-2-[5-[(methylamino)methyl]-2-furanyl]- | 0.98 | 329 |

Example B334

N,8-dimethyl-8H-imidazo[4,5-d]thiazolo[5,4-b]pyridin-5-amine, 2-[3-(aminomethyl)-4-fluorophenyl

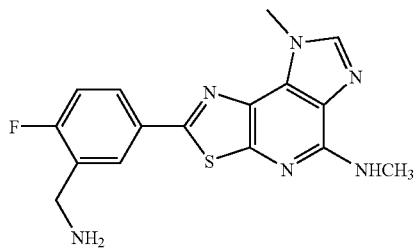

Example B334 was prepared in the same manner as B310 using B300 as the starting material. Retention time 1.05 min, observed mass 343.22 (M+H) Column: Phenomenex S5 4.6×30 mm; Solvent A: 10% CH3CN/water 0.05% TFA, Solvent B: 90% CH3CN/water, 0.05% TFA.

Example B335

N-[[2-fluoro-5-[8-methyl-5-(methylamino)-8H-imidazo[4,5-d]thiazolo[5,4-b]pyridin-2-yl]phenyl]methyl]acetamide

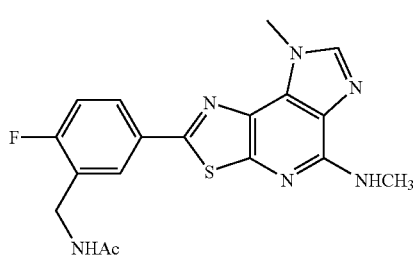

Example B335 was prepared in the same manner as B311 using B334 as the starting material. Retention time 1.29 min, observed mass 381.33 (M+H) Column: Phenomenex S5 4.6×30 mm; Solvent A: 10% CH3CN/water 0.05% TFA, Solvent B: 90% CH3CN/water, 0.05% TFA.

Example B336

N-[[2-fluoro-5-[8-methyl-5-(methylamino)-8H-imidazo[4,5-d]thiazolo[5,4-b]pyridin-2-yl]phenyl]methyl]methanesulfonamide

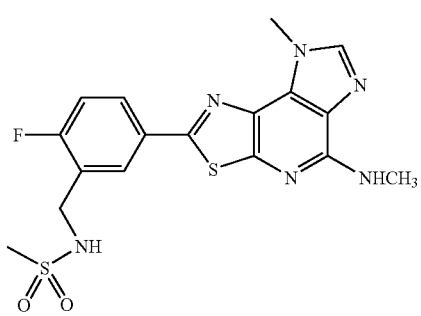

Example B336 was prepared in the same manner as B312 using B334 as the starting material. Retention time 1.29 min, observed mass 381.33 (M+H+TFA) Column: Phenomenex S5 4.6×30 mm; Solvent A: 10% CH3CN/water 0.05% TFA, Solvent B: 90% CH3CN/water, 0.05% TFA.

Example B337 alpha-methyl-3-[8-methyl-5-(methylamino)-8H-imidazo[4,5-d]thiazolo[5,4-b]pyridin-2-yl]benzenemethanol

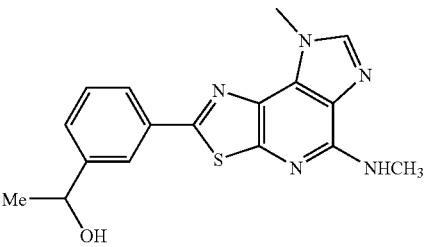

Example B337 was isolated as a byproduct of the preparation of the compounds in Table B4, by reduction of the B99 with sodium borohydride. HPLC retention time 2.49 min. Column: Chromolith SpeedROD 4.6×50 mm (4 min grad) Solvent A: 10% MeOH-90% H2O 0.2% phosphoric acid Solvent B: 90% MeOH-10% $H_2O$-0.2% phosphoric acid. LCMS (M+H) 340.4

Examples B338–B340

Examples B338–B340 described in Table B16 were prepared in a similar manner to that used for Example B273 substituting the appropriate amine and chlorointermediate B222.2 or B1.1.

TABLE B16

| Ex. No. | Structure | Name | Retention Time (min) | Observed mass |
|---|---|---|---|---|
| B338 | 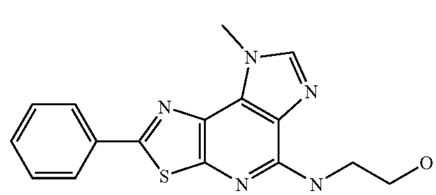 | ethanol, 2-[(8-methyl-2-phenyl-8H-imidazo[4,5-d]thiazolo[5,4-b]pyridin-5-yl)amino]- | 1.55 | 326.24 |

TABLE B16-continued

| Ex. No. | Structure | Name | Retention Time (min) | Observed mass |
|---|---|---|---|---|
| B339 | 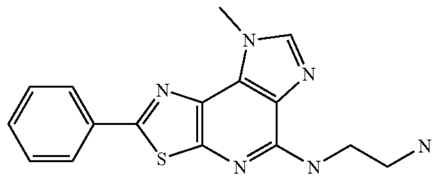 | 1,2-ethanediamine, N-(8-methyl-2-phenyl-8H-imidazo[4,5-d]thiazolo[5,4-b]pyridin-5-yl)- | 1.50 | 325.24 |
| B340 | 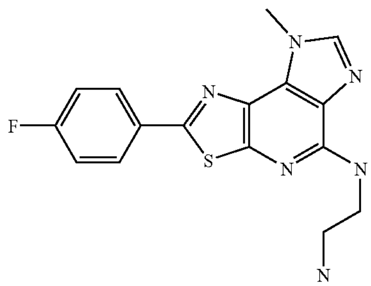 | 1,2-ethanediamine, N-[2-(4-fluorophenyl)-8-methyl-8H-imidazo[4,5-d]thiazolo[5,4-b]pyridin-5-yl]- | 1.36 | 343 |

Utility

The compounds and compositions of this invention are useful in treating conditions that are characterized by the activity of IKK, release of NF-κB, and/or enhanced levels of TNF-α. The term "treating" or "treatment" denotes prevention, partial alleviation, or cure of the disease or disorder or its symptoms or consequences. Inhibition or suppression of IKK, NF-κB and/or TNF-α may occur locally, for example, within certain tissues of the subject, or more extensively throughout the subject being treated for such a disease. Inhibition or suppression of IKK, NF-κB and/or TNF-α may occur by one or more mechanisms, e.g., by inhibiting or suppressing any step of the pathway(s). The term "NF-κB-associated condition" refers to diseases that are characterized by release of NF-κB from the cytoplasm (e.g., upon phosphorylation of IκB). The term "TNF-α-associated condition" is a condition characterized by enhanced levels of TNF-α. In the instant specification, the term "NF-κB-associated condition" will include a TNF-α-associated condition but is not limited thereto as NF-κB is involved in the activity and upregulation of other pro-inflammatory proteins and genes. The term "inflammatory or immune disease" is used herein to encompass IKK-associated conditions, NF-κB-associated conditions, and TNF-α-associated conditions, e.g., any condition, disease, or disorder that is associated with activity of IKK, NF-κB and/or enhanced levels of TNF-α.

The inventive compounds and compositions are useful for treating a variety of diseases including, but not limited to, treatment of transplant rejections (e.g., kidney, liver, heart, lung, pancreas, bone marrow, cornea, small bowel, skin allografts, skin homografts and heterografts, etc.) or tolerance to organ transplantion; rheumatoid arthritis, psoriatic arthritis, multiple sclerosis, inflammatory bowel disease (such as Crohn's disease and ulcerative colitis); antiviral and autoimmune diseases including herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, and autoimmune polyglandular disease (also known as autoimmune polyglandular syndrome); Alzheimer's, Parkinson's, and Creutzfeldt-Jacob diseases; septic shock; prevention of reperfusion injury; inflammatory diseases such as osteoarthritis, acute pancreatitis, and chronic pancreatitis; inflammatory disorders of the central nervous system, including HIV encephalitis, cerebral malaria, and meningitis, atherosclerosis, and ataxia telangiectasis; inflammatory states of the cardiac system including heart failure, respiratory allergies including asthma, hayfever, and allergic rhinitis; fungal infections such as mycosis fungoides; and psoriasis, glomerulonephritis, serum sickness, lupus (systematic lupus erythematosis), urticaria, scleroderma, contact dermatitis, dermatomyositis, alopecia, atopic eczemas, and ichthyosis. The term "inflammatory or immune disease" as used herein includes all of the above-referenced diseases and disorders.

The inventive compounds are also effective in treating oncological diseases, in treating cancer and tumors, such as solid tumors, lymphomas and leukemia, and in particular, breast cancer, prostate cancer, and Hodgkin's lymphoma.

Additionally this invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid or liquid tumors which are associated with IKK, especially those tumors which are significantly dependent on IKK for their growth and spread, including for example, hematopoietic tumors, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of the skin, including melanoma;

hematopoietic tumors including those of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

hematopoietic tumors including those of plasma cell lineage such as multiple myeloma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of IKK kinase activity, such as melanomas, and multiple myeloma. By the administration of a composition (or a combination) of the compounds of this invention, development of tumors in a mammalian host is reduced.

The invention also provides a pharmaceutical composition comprising a compound of formula I in combination with pharmaceutically acceptable carrier and an anti-cancer or cytotoxic agent. In a preferred embodiment said anti-cancer or cytotoxic agent is selected from the group consisting of linomide; inhibitors of integrin $\alpha v \beta 3$ function; angiostatin; razoxin; tamoxifen; toremifen; raloxifene; droloxifene; iodoxyfene; megestrol acetate; anastrozole; letrazole; borazole; exemestane; flutamide; nilutamide; bicalutamide; cyproterone acetate; gosereline acetate; luprolide; finasteride; metalloproteinase inhibitors; inhibitors of urokinase plasminogen activator receptor function; growth factor antibodies; growth factor receptor antibodies such as Avastin® and Erbitux®; tyrosine kinase inhibitors; serine/threonine kinase inhibitors); methotrexate; 5-fluorouracil; purine; adenosine analogues; cytosine arabinoside; doxorubicin; daunomycin; epirubicin; idarubicin; mitomycin-C; dactinomycin; mithramycin); cisplatin; carboplatin; nitrogen mustard; melphalan; chlorambucil; busulphan; cyclophosphamide; ifosfamide nitrosoureas; thiotephan; vincristine; Taxol®; Taxotere®; epothilone analogs; discodermolide analogs; eleutherobin analogs; etoposide; teniposide; amsacrine; topotecan; and flavopyridols.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

1: antiangiogenic agents such as inhibitors of VEGF or related kinases (such as FLT, or KDR), linomide, antibodies which block angiogenesis, inhibitors of integrin $\alpha v \beta 3$ function, angiostatin, razoxin;

2: cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutaminde, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® and Erbitux®, tyrosine kinase inhibitors and serine/threonine kinase inhibitors);

3: antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like Taxol®, Taxotere® and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols).

The present invention thus provides methods for treating such conditions, comprising administering to a subject in need thereof an effective amount of at least one compound of formula I or a salt thereof. Other therapeutic agents such as those described herein may be employed in combination with compounds of formula I. In the methods of the present invention, such other therapeutic agent(s) may be administered prior to, simultaneously with, or following administration of the inventive compound(s).

The present invention also provides pharmaceutical compositions capable of treating IKK, NF-κB and/or TNF-α associated conditions, as described above. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Subjects for treatment include animals, most preferably mammalian species such as humans, and domestic animals such as dogs, cats, horses, and the like, subject to IKK, NF-κB and/or TNF-α associated conditions.

The inventive compounds and compositions may be employed alone or in combination with each other and/or other suitable therapeutic agents useful in treating IKK, NF-κB and/or TNF-α associated conditions. Exemplary of such other therapeutic agents include corticosteroids, rolipram, calphostin, CSAIDs, 4-substituted imidazo [1,2-A] quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof; and other cancer drugs and treatments, including radiation treatments and daunorubicin.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells ($1.4 \times 10^6$/mL, $2.5 \times 10^5$ cells/well) in 180 μL RPMI-1640 was added 10 μL of the test compound in 10% DMSO. Typically, test compound concentrations of 0.1–100 μM were used in the assay. After one hour at 37° C., 10 μL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

We claim:
1. A compound of formula (I),

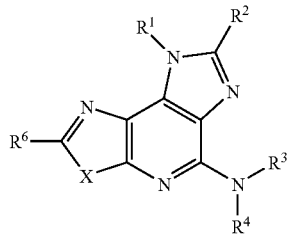

(I)

enantiomers, diastereomers, salts, and solvates thereof wherein

X is selected from O or S;

$R^1$ is selected from hydrogen, $C_{1-3}$ alkyl, $C_{2-3}$ alkenyl, and $C_{2-3}$ alkynyl;

$R^2$ is hydrogen, halo, cyano,
(b) alkyl, alkenyl, alkynyl, haloalkyl, alkoxy, cycloalkoxy, heterocyclooxy, aryloxy, heteroaryloxy, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1a}$, $Z^{2a}$ and $Z^{3a}$; or
(c) $-OR^{10a}$, $-SR^{10a}$, or $-SO_2R^{10a}$;

$R^3$ and $R^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) $-OR^{11}$, $-NR^{12}R^{13}$, $-N(R^{12})C(O)R^{14}$, $-N(R^{12})C(O)OR^{14}$, $-N(R^{12})SO_2R^{14}$, $-N(R^{12})C(O)NR^{12a}R^{13}$ or $-N(R^{12})SO_2NR^{12a}R^{13}$ or $-C(O)OR^{14}$, $-C(O)R^{11}$, $-C(O)NR^{12}R^{13}$, $-SO_2R^{14}$, $-SO_2NR^{12}R^{13}$;
(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^6$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) $-OR^{7a}$, $-SR^{7a}$, $-NR^{8a}R^{9a}$, $-N(R^{8a})SO_2R^{10}$, $-N(R^{8a})SO_2NR^{8b}R^{9b}$, $-N(R^{8a})SO_2R^{10}$, $-N(R^{8a})C(O)R^{7a}$, $-N(R^{8a})N(R^{8a})C(O)R^{7a}$, $-N(R^{8a})C(O)NR^{8b}R^{9b}$, $-N(R^{8a})C(O)OR^{7a}$, $-SO_2R^{10}$, $-SO_2NR^{8b}R^{9b}$, $-C(O)R^{7a}$, $-C(O)OR^{7a}$, $-OC(O)R^{7a}$, $-C(O)NR^{8a}R^{9a}$, or $-OC(O)NR^{8a}R^{9a}$;

$R^{7a}$ and $R^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$; or $R^{10}$, $R^{10a}$, at each occurance, are independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1a-1e}$, $Z^{2a-2e}$, and $Z^{3a-3e}$ are optional substituents at each occurrence independently selected from $-W^1-V^1$; $-W^2-V^2$; $-W^3-V^3$; $-W^4-V^4$; $-W^5-V^5$;

where $W^{1-5}$ are independently
(1) a bond
(2) alkyl, (hydroxy)alkyl, (alkoxy)alkyl, alkenyl, alkynyl, haloalkyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) $-U^1-O-Y^5$,
(4) $-U^1-S-Y^5$,
(5) $-U^1-C(O)_t-H$, $-U^1-C(O)_t-Y^5$ where t is 1 or 2,
(6) $-U^1-SO_3-H$, or $-U^1-S(O)_tY^5$,
(7) $-U^1$-halo,
(8) $-U^1$-cyano,
(9) $-U^1$-nitro,
(10) $-U^1-NY^2Y^3$,

(11) —U$^1$—N(Y$^4$)—C(O)—Y$^1$,
(12) —U$^1$—N(Y$^4$)—C(S)—Y$^1$,
(13) —U$^1$—N(Y$^4$)—C(O)—NY$^2$Y$^3$,
(14) —U$^1$—N(Y$^4$)—C(S)—NY$^2$Y$^3$,
(15) —U$^1$—N(Y$^4$)—C(O)O—Y$^5$,
(16) —U$^1$—N(Y$^4$)—S(O)$_2$—Y$^1$,
(17) —U$^1$—N(Y$^4$)—S(O)$_2$—NY$^2$Y$^3$,
(18) —U$^1$—C(O)—NY$^2$Y$^3$,
(19) —U$^1$—OC(O)—NY$^2$Y$^3$
(20) —U$^1$—S(O)$_2$—N(Y$^4$)—Y$^1$,
(21) —U$^1$—N(Y$^4$)—C(=NV$^{1a}$)—NY$^2$Y$^3$,
(22) —U$^1$—N(Y$^4$)—C(=NV$^{1a}$)—Y$^1$,
(23) —U$^1$—C(=NV$^{1a}$)—NY$^2$Y$^3$;
(24) oxo;
(25) —U$^1$—Y$^5$;

V$^{1a}$ is independently hydrogen, alkyl, —CN, —C(O)Y$^1$, —S(O)$_2$Y$^5$, S(O)$_2$NY$^2$Y$^3$;

Y$^1$, Y$^2$, Y$^3$, Y$^4$ and Y$^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl, any of which may be optionally independently substituted as valence allows with one or more Z$^4$, Z$^5$ and Z$^6$; or
(2) Y$^2$ and Y$^3$ may together be alkylene or alkenylene, completing a 3- to 8-membered saturated or unsaturated ring together with the atoms to which they are attached, or
(4) Y$^2$ and Y$^3$ together with the nitrogen atom to which they are attached may combine to form a group —N=CY$^6$Y$^7$ where Y$^6$ and Y$^7$ are each independently H or alkyl; and Z$^4$, Z$^5$, and Z$^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —U$^1$—O—Y$^{5a}$,
(4) —U$^1$—S-Y$^{5a}$,
(5) —U$^1$—C(O)$_t$—H, or —U$^1$—C(O)$_t$—Y$^{5a}$ where t is 1 or 2,
(6) —U$^1$—SO$_3$—H, or —U$^1$—S(O)$_t$Y$^{5a}$,
(7) —U$^1$-halo,
(8) —U$^1$-cyano,
(9) —U$^1$-nitro,
(10) —U$^1$NY$^{2a}$Y$^{3a}$,
(11) —U$^1$—N(Y$^{4a}$)—C(O)—Y$^{1a}$,
(12) —U$^1$—N(Y$^{4a}$)—C(S)—Y$^{1a}$,
(13) —U$^1$—N(Y$^{4a}$)—C(O)—NY$^{2a}$Y$^{3a}$,
(14) —U$^1$—N(Y$^{4a}$)—C(S)—NY$^{2a}$Y$^{3a}$,
(15) —U$^1$—N(Y$^{4a}$)—C(O)O—Y$^{5a}$,
(16) —U$^1$—N(Y$^{4a}$)—S(O)$_2$—Y$^{1a}$,
(17) —U$^1$—N(Y$^{4a}$)—S(O)$_2$—NY$^{2a}$Y$^{3a}$,
(18) —U$^1$—C(O)—NY$^{2a}$Y$^{3a}$,
(19) —U$^1$—OC(O)—NY$^{2a}$Y$^{3a}$
(20) —U$^1$—S(O)$_2$—N(Y$^{4a}$)—Y$^{1a}$,
(21) —U$^1$—N(Y$^{4a}$)—C(=NV$^{1a}$)—NY$^{2a}$Y$^{3a}$,
(22) —U$^1$—N(Y$^{4a}$)—C(=NV$^{1a}$)—Y$^{1a}$,
(23) —U$^1$—C(=NV$^{1a}$)—NY$^{2a}$Y$^{3a}$,
(24) oxo;
(25) —U$^1$—Y$^{5a}$;

Y$^{1a}$, Y$^{2a}$, Y$^{3a}$, Y$^{4a}$, and Y$^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;

U$^1$ is independently
(1) a single bond,
(2) alkylene,
(3) alkenylene, or
(4) alkynylene.

2. A compound of claim 1 wherein
R$^3$ and R$^4$ are independently
(a) hydrogen,
(b) alkyl, haloalkyl, (hydroxy)alkyl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1b}$, Z$^{2b}$ and Z$^{3b}$;
(c) —NR$^{12}$R$^{13}$; or
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$.

3. A compound of claim 2 wherein
R$^6$ is
(a) hydrogen, alkyl, alkenyl, alkynyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1d}$, Z$^{2d}$ and Z$^{3d}$; or
(b) —OR$^{7a}$, —SR$^{7a}$, —NR$^{8a}$R$^{9a}$, —N(R$^{8a}$)SO$_2$R$^{10}$, —N(R$^{8a}$)SO$_2$NR$^{8b}$R$^{9b}$, —N(R$^{8a}$)SO$_2$R$^{10}$, —N(R$^{8a}$)C(O)R$^{7a}$, —N(R$^{8a}$)N(R$^{8a}$)C(O)R$^{7a}$, —N(R$^{8a}$)C(O)NR$^{8b}$R$^{9b}$, —N(R$^{8a}$)C(O)OR$^{7a}$, —SO$_2$R$^{10}$, —SO$_2$NR$^{8b}$R$^{9b}$, —C(O)R$^{7a}$, —C(O)OR$^{7a}$, —OC(O)R$^{7a}$, —C(O)NR$^{8a}$R$^{9a}$, or —OC(O)NR$^{8a}$R$^{9a}$.

4. A compound of claim 3 wherein
R$^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$.

5. A compound of claim 4 wherein
R$^3$ and
R$^4$ are independently hydrogen, alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more Z$^{1b}$, Z$^{2b}$ and Z$^{3b}$; —NR$^{12}$R$^{13}$; or
alternatively, R$^3$ and R$^4$ together with the nitrogen atom to which they are attached combine to form a 3 to 6 membered heterocyclic ring selected from piperidinyl, morpholinyl, pyrrolidinyl, piperazinyl, and azetidinyl; optionally independently substituted as valence allows with one or more Z$^{1b}$, Z$^{2b}$ and Z$^{3b}$;
R$^6$ is
(a) hydrogen, alkyl, aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more Z$^{1d}$, Z$^{2d}$ and Z$^{3d}$; or
(b) —OR$^{7a}$, —SR$^{7a}$, —NR$^{8a}$R$^{9a}$, —N(R$^{8a}$)SO$_2$R$^{10}$, —N(R$^{8a}$)SO$_2$R$^{10}$, —N(R$^{8a}$)C(O)R$^{7a}$, —N(R$^{8a}$)N $(R^{8a})C(O)R^{7a}$, —$N(R^{8a})C(O)NR^{8b}R^{9b}$, —$SO_2R^{10}$, —$C(O)R^{7a}$, or —$C(O)NR^{8a}R^{9a}$.

6. A compound of claim 5 wherein
$R^1$ is hydrogen, methyl, ethyl, propyl, i-propyl, prop-2-enyl, prop-1-enyl; and
$R^2$ is hydrogen, methyl, trifluoromethyl, and phenyl.

7. A compound of claim 1 wherein
$R^1$ is selected from hydrogen and $C_{1-3}$ alkyl;
$R^6$ is
  (a) hydrogen, hydroxy, halo, or cyano,
  (b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
  (c) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})C(O)NR^{8b}R^{9b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$;
$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;
where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where $V^{1-5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—$C(O)_t$—H, —$U^1$—$C(O)_t$—$Y^5$ where t is 1 or 2,
  (6) —$U^1$—$SO_3$—H, or —$U^1$—$S(O)_tY^5$,
  (7) —$U^1$-halo,
  (8) —$U^1$-cyano,
  (9) —$U^1$-nitro,
  (10) —$U^1$—$NY^2Y^3$,
  (12) —$U^1$—$N(Y^4)$—C(S)—$Y^1$,
  (13) —$U^1$—$N(Y^4)$—C(O)—$NY^2Y^3$,
  (14) —$U^1$—$N(Y^4)$—C(S)—$NY^2Y^3$,
  (15) —$U^1$—$N(Y^4)$—C(O)O—$Y^5$,
  (16) —$U^1$—$N(Y^4)$—$S(O)_2$—$Y^1$,
  (17) —$U^1$—$N(Y^4)$—$S(O)_2$—$NY^2Y^3$,
  (18) —$U^1$—C(O)—$NY^2Y^3$,
  (19) —$U^1$—OC(O)—$NY^2Y^3$
  (20) —$U^1$—$S(O)_2$—$N(Y^4)$—$Y^1$,
  (21) —$U^1$—$N(Y^4)$—$C(=NV^{1a})$—$NY^2Y^3$,
  (22) —$U^1$—$N(Y^4)$—$C(=NV^{1a})$—$Y^1$,
  (23) —$U^1$—$C(=NV^{1a})$—$NY^2Y^3$,
  (24) oxo;
  (25) —$U^1$—$Y^5$;
$V^{1a}$ is independently hydrogen, alkyl, —CN, —$C(O)Y^1$, —$S(O)_2Y^5$, $S(O)_2NY^2Y^3$;
$Y^1$, $Y^2$, $Y^3$, $Y^4$ and $Y^5$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl; or
  (2) $Y^2$ and $Y^3$ may together be alkylene or alkenylene, completing a 3- to 8-membered saturated or unsaturated ring together with the atoms to which they are attached, or
  (4) $Y^2$ and $Y^3$ together with the nitrogen atom to which they are attached may combine to form a group —$N=CY^6Y^7$ where $Y^6$ and $Y^7$ are each independently H or alkyl.

8. A compound of claim 7 wherein
$R^3$ and $R^4$ are independently
  (a) hydrogen,
  (b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}$, $Z^{2b}$ and $Z^{3b}$;
  (c) —$NR^{12}R^{13}$; or
  (d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$.

9. A compound of claim 8 wherein
$R^6$ is
  (a) alkyl, alkenyl, alkynyl, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
  (b) —$OR^{7a}$, —$SR^{7a}$, —$NR^{8a}R^{9a}$, —$N(R^{8a})SO_2R^{10}$, —$N(R^{8a})SO_2NR^{8b}R^{9b}$, —$N(R^{8a})SO_2R^{10}$, —$N(R^{8a})C(O)R^{7a}$, —$N(R^{8a})C(O)NR^{8b}R^{8b}$, —$N(R^{8a})C(O)OR^{7a}$, —$SO_2R^{10}$, —$SO_2NR^{8b}R^{9b}$, —$C(O)R^{7a}$, —$C(O)OR^{7a}$, —$OC(O)R^{7a}$, —$C(O)NR^{8a}R^{9a}$, or —$OC(O)NR^{8a}R^{9a}$.

10. A compound of claim 9 wherein
$R^{7a}$ is independently selected from
  (a) hydrogen, or
  (b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$.

11. A compound of claim 10 wherein
$Z^{1b}$, $Z^{2b}$ and $Z^{3b}$ are optional substituents independently selected from alkyl, heteroaryl, —OH, —O—$Y^5$, —$U^1$—$NY^2Y^3$, —$C(O)_tH$, —$C(O)_tY^5$;
$Z^{1c}$ is
  (a) —OH, —$OY^5$ or
  (b) aryl optionally substituted with —OH or —$OY^5$;
$Z^{1d}$, $Z^{2d}$ and $Z^{3d}$ are optional substituents independently selected from
  (a) cyano, halo, —OH, —$OY^5$, —$U^1$—$NY^2Y^3$, —$C(O)_tH$, —$C(O)_tY$, —$S(O)_tY^5$;
  (b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$-heteroaryl.

12. A compound of claim 11 wherein
$R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;

alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1b}$, $Z^{2b}$ and $Z^{3b}$;

$R^6$ is
- (a) alkynyl optionally substituted with $Z^{1d}$ where $Z^{1d}$ is aryl which may be further optionally independently substituted with one or more cyano, halo, —OH, —OY, —U$^1$—NY$^2$Y$^3$, —C(O)$_t$H, —C(O)$_t$Y, or, —S(O)$_t$Y;
- (b) aryl optionally independently substituted as valence allows with one or more $Z^{1d}$, $Z^{2d}$ and $Z^{3d}$; or
- (c) —OR$^{7a}$, —SR$^{7a}$, —SO$_2$R$^{10}$, —SO$_2$NR$^{8b}$R$^{9b}$, —OC(O)R$^{7a}$, or —OC(O)NR$^{8a}$R$^{9a}$;

$Z^{1b}$, $Z^{2b}$ and $Z^{3b}$ are optional substituents independently selected from —OH, —OY, —U$^1$—NY$^2$Y$^3$, —C(O)$_t$H, —C(O)$_t$Y, —U$^1$—N(Y$^4$)—C(O)—Y$^1$, or —U$^1$—N(Y$^4$)—C(O)O—Y$^5$,
where
$U^1$ is a bond or alkylene;

$Z^{1c}$ is
- (a) —OY where Y is aryl, or
- (b) aryl optionally substituted with —OH or —OY where Y is alkyl;

$Z^{1d}$, $Z^{2d}$ and $Z^{3d}$ are optional substituents independently selected from
- (a) cyano, halo, —OH, —OY, —C(O)$_t$H, —C(O)$_t$Y, —S(O)$_t$Y, or
- (b) alkyl or alkoxy optionally substituted with one or more cyano, halo, —OH, —OY, —U$^1$—NY$^2$Y$^3$, —C(O)$_t$H, —C(O)$_t$Y, —S(O)$_t$Y, —U$^1$—N(Y$^4$)—C(O)—Y$^1$, —U$^1$—N(Y$^4$)—C(O)—Y$^1$, or —U$^1$—N(Y$^4$)—S(O)$_2$—Y$^1$,
where
$U^1$ is a bond or alkylene.

13. A compound of claim 12 wherein
$R^1$ is alkyl; and
$R^2$ is hydrogen.

14. A compound of claim 1, wherein the compound is selected from

8-Methyl-5-methylamino-2-phenyl-8H-imidazo[4,5-d]oxazolo[5,4-b]pyridine;
8-Methyl-5-methylamino-2-[4-fluorophenyl]-8H-imidazo[4,5-d]oxazolo[5,4-b]pyridine;
8-Methyl-5-methylamino-2-[3-bromophenyl]-8H-imidazo[4,5-d]oxazolo[5,4-b]pyridine;
8-Methyl-5-methylamino-2-[4-trifluoromethoxyphenyl] 8H-imidazo[4,5-d]oxazolo[5,4-b]pyridine;
8-Methyl-5-methylamino-2-[4-chlorophenyl]-8H-imidazo[4,5-d]oxazolo[5,4-b]pyridine;
8-Methyl-5-methylamino-2-[4-methylphenyl]-8H-imidazo[4,5-d]oxazolo[5,4-b]pyridine;
8-Methyl-5-methylamino-2-[4-(dimethylamino)phenyl]-8H-imidazo[4,5-d]oxazolo[5,4-b]pyridine;
8-Methyl-5-methylamino-2-[4-methoxyphenyl]-8H-imidazo[4,5-d]oxazolo[5,4-b]pyridine;
8-Methyl-5-[4-hydroxypiperidin-1-yl]-2-phenyl-8H-imidazo[4,5-d]oxazolo[5,4-b]pyridine;
8-Methyl-5-[morpholin-1-yl]-2-phenyl-8H-imidazo[4,5-d]oxazolo[5,4-b]pyridine;
8-Methyl-5-[(tetrazol-5-ylmethyl)methylamino]-2-phenyl-8H-imidazo[4,5-d]oxazolo[5,4-b]pyridine;
8-Methyl-5-[2-hydroxyethylamino]-2-phenyl-8H-imidazo[4,5-d]oxazolo[5,4-b]pyridine;
8-Methyl-5-[3-dimethylamino)propylamino]-2-phenyl-8H-imidazo[4,5-d]oxazolo[5,4-b]pyridine;
8-Methyl-5-[N'N'-dimethylhydrazino]-2-phenyl-8H-imidazo[4,5-d]oxazolo[5,4-b]pyridine;
8-Methyl-5-methylamino-2-[3-(tetrazol-5-yl)phenyl]-8H-imidazo[4,5-d]oxazolo[5,4-b]pyridine;
8-Methyl-5-methylamino-2-[3-cyanophenyl]-8H-imidazo[4,5-d]oxazolo[5,4-b]pyridine;
8-Methyl-5-methylamino-2-[4-(methoxycarbonyl)phenyl]-8H-imidazo[4,5-d]oxazolo[5,4-b]pyridine;
8-Methyl-5-methylamino-2-[4-(methylaminocarbonyl)phenyl]-8H-imidazo[4,5-d]oxazolo[5,4-b]pyridine;
8-Methyl-5-methylamino-2-[4-(carboxy)phenyl]-8H-imidazo[4,5-d]oxazolo[5,4-b]pyridine;
8-Methyl-5-methylamino-2-[3-[2-(tetrazol)-5yl](E)-ethenyl]phenyl]-8H-imidazo[4,5-d]oxazolo[5,4-b]pyridine;
8-Methyl-5-methylamino-2-[3-[2-(tetrazol-5-yl)ethyl]phenyl]-8H-imidazo[4,5-d]oxazolo[5,4-b]pyridine;
8-methyl-5-dimethylamino-2-[3-[2-(tetrazol-5-yl)ethyl]phenyl]-8H-imidazo[4,5-d]oxazolo[5,4-b]pyridine;
8-Methyl-5-methylamino-2-[3-(2-cyano-(E)-ethenyl)phenyl]-8H-imidazo[4,5-d]oxazolo[5,4-b]pyridine;
8-Methyl-5-methylamino-2-[3-(2-carboxyethyl)phenyl]-8H-imidazo[4,5-d]oxazolo[5,4-b]pyridine;
8-Methyl-5-methylamino-2-[3-(2-ethoxycarbonyl-(E)-prop-2-enyl)phenyl]-8H-imidazo[4,5-d]oxazolo[5,4-b]pyridine;
8-Methyl-5-methylamino-2-[3-(2-carboxy-(E)-prop-2-enyl)phenyl]-8H-imidazo[4,5-d]oxazolo[5,4-b]pyridine;
4-Methyl-7-[3-aminopropylamino]-2-phenyl-4H-imidazo[4,5-d]oxazolo[4,5-b]pyridine;
4-Methyl-7-[3-methylaminopropylamino]-2-phenyl-4H-imidazo[4,5-d]oxazolo[4,5-b]pyridine;
8-Methyl-5-methylamino-2-(2-methylethyl)-8H-imidazo[4,5-d]oxazolo[5,4-b]pyridine;
8-Methyl-5-dimethylamino-2-(2-methylethyl)-8H-imidazo[4,5-d]oxazolo[5,4-b]pyridine;
8-Methyl-5-methylamino-2-(2,2-dimethylpropyl)-8H-imidazo[4,5-d]oxazolo[5,4-b]pyridine;
8-Methyl-5-methylamino-2-(cyclopentylmethyl)-8H-imidazo[4,5-d]oxazolo[5,4-b]pyridine;
8-Methyl-5-methylamino-2-(2-furyl)-8H-imidazo[4,5-d]oxazolo[5,4-b]pyridine;
8-Methyl-5-methylamino-2-(2,4-dimethylphenyl)-8H-imidazo[4,5-d]oxazolo[5,4-b]pyridine;
8-Methyl-5-methylamino-2-(3,4-dimethylphenyl)-8H-imidazo[4,5-d]oxazolo[5,4-b]pyridine;
8-Methyl-5-methylamino-2-(3-methylphenyl)-8H-imidazo[4,5-d]oxazolo[5,4-b]pyridine;
8-Methyl-5-methylamino-2-(3-trifluoromethyl-4-methylphenyl)-8H-imidazo[4,5-d]oxazolo[5,4-b]pyridine;
8-Methyl-5-methylamino-2-(3-trifluoromethylphenyl)-8H-imidazo[4,5-d]oxazolo[5,4-b]pyridine;
8-Methyl-5-methylamino-2-(3-methoxyphenyl)-8H-imidazo[4,5-d]oxazolo[5,4-b]pyridine;
8-Methyl-5-methylamino-2-(2-methylbutyl)-8H-imidazo[4,5-d]oxazolo[5,4-b]pyridine;
8-Methyl-5-methylamino-2-(3,5-dimethylphenyl)-8H-imidazo[4,5-d]oxazolo[5,4-b]pyridine;
8-Methyl-5-methylamino-2-(3-phenyloxyphenyl)-8H-imidazo[4,5-d]oxazolo[5,4-b]pyridine;
8-Methyl-5-methylamino-2-(3-methyl-4-fluorophenyl)-8H-imidazo[4,5-d]oxazolo[5,4-b]pyridine;
8-Methyl-5-ethylamino-2-(3-methyl-4-fluorophenyl)-8H-imidazo[4,5-d]oxazolo[5,4-b]pyridine;

8-Methyl-5-methylamino-2-(2-trifluoromethylpyridin-5-yl)-8H-imidazo[4,5-d]oxazolo[5,4-b]pyridine;
8-Methyl-5-methylamino-2-(3,5-dimethoxyphenyl)-8H-imidazo[4,5-d]oxazolo[5,4-b]pyridine;
8-Methyl-5-methylamino-2-(trans-2-phenylcyclopropyl)-8H-imidazo[4,5-d]oxazolo[5,4-b]pyridine;
8-Methyl-5-methylamino-2-(2,3-dimethylphenyl)-8H-imidazo[4,5-d]oxazolo[5,4-b]pyridine;
8-Methyl-5-methylamino-2-(2,2-dimethylethyl)-8H-imidazo[4,5-d]oxazolo[5,4-b]pyridine;
8-Methyl-5-methylamino-2-ethyl-8H-imidazo[4,5-d]oxazolo[5,4-b]pyridine;
8-Methyl-5-methylamino-2-propyl-8H-imidazo[4,5-d]oxazolo[5,4-b]pyridine;
8-Methyl-5-(Phenylmethylamino)-2-phenyl-8H-imidazo[4,5-d]oxazolo[5,4-b]pyridine;
8-Methyl-5-methylamino-2-(pyridine-2-yl)-8H-imidazo[4,5-d]oxazolo[5,4-b]pyridine;
8-Methyl-5-methylamino-2-(pyridine-3-yl)-8H-imidazo[4,5-d]oxazolo[5,4-b]pyridine;
8-Methyl-5-methylamino-2-(pyridine-4-yl)-8H-imidazo[4,5-d]oxazolo[5,4-b]pyridine;
8-Methyl-5-(2-methylethylamino)-2-phenyl-8H-imidazo[4,5-d]oxazolo[5,4-b]pyridine;
8-Methyl-5-methylamino-2-methyl-8H-imidazo[4,5-d]oxazolo[5,4-b]pyridine;
8-Methyl-5-(2-aminoethylamino)-2-phenyl-8H-imidazo[4,5-d]oxazolo[5,4-b]pyridine;
8-Methyl-5-[3-dimethylaminopropylamino]-2-phenyl-8H-imidazo[4,5-d]oxazolo[5,4-b]pyridine;
8-Methyl-5-[ethylamino]-2-phenyl-8H-imidazo[4,5-d]oxazolo[5,4-b]pyridine;
8-Methyl-5-[(2-hydroxypropyl)amino]-2-phenyl-8H-imidazo[4,5-d]oxazolo[5,4-b]pyridine;
8-Methyl-5-[cyclopentylamino]-2-phenyl-8H-imidazo[4,5-d]oxazolo[5,4-b]pyridine;
8-Methyl-5-[2-dimethylaminoethylamino]-2-phenyl-8H-imidazo[4,5-d]oxazolo[5,4-b]pyridine;
8-Methyl-5-[((tetrahydrofuran-2-yl)methyl)amino]-2-phenyl-8H-imidazo[4,5-d]oxazolo[5,4-b]pyridine;
8-Methyl-5-[2-(acetylamino)ethylamino]-2-phenyl-8H-1-idazo[4,5-d]oxazolo[5,4-b]pyridine;
8-Methyl-5-[(5-hydroxy-3-oxypentyl)amino]-2-phenyl-8H-imidazo[4,5-d]oxazolo[5,4-b]pyridine;
8-Methyl-5-[2-(1-pyrrolidinyl)ethylamino]-2-phenyl-8H-imidazo[4,5-d]oxazolo[5,4-b]pyridine;
8-Methyl-5-[2-(pyridin-2-yl))ethylamino]-2-phenyl-8H-imidazo[4,5-d]oxazolo[5,4-b]pyridine;
8-Methyl-5-[3-(imidazol-1-yl)propylamino]-2-phenyl-8H-imidazo[4,5-d]oxazolo[5,4-b]pyridine;
8-Methyl-5-[2-(morpholin-4-yl)ethylamino]-2-phenyl-8H-imidazo[4,5-d]oxazolo[5,4-b]pyridine;
8-Methyl-5-[3-(morphylin-4-yl)propylamino]-2-phenyl-8H-imidazo[4,5-d]oxazolo[5,4-b]pyridine;
8-Methyl-5-[3-(1-methyl-4-piperazinyl)propylamino]-2-phenyl-8H-imidazo[4,5-d]oxazolo[5,4-b]pyridine;
8-Methyl-5-methylamino-2-(3-aminomethyl)phenyl-8H-imidazo[4,5-d]oxazolo[5,4-b]pyridine;
8-Methyl-5-methylamino-2-[(3-acetylaminomethyl)phenyl]-8H-imidazo[4,5-d]oxazolo[5,4-b]pyridine;
8-Methyl-5-methylamino-2-[3-(phenylcarbonylaminomethyl)phenyl]-8H-imidazo[4,5-d]oxazolo[5,4-b]pyridine;
8-Methyl-5-methylamino-2-[3-(ethylcarbonylaminomethyl)phenyl]-8H-imidazo[4,5-d]oxazolo[5,4-b]pyridine;
8-Methyl-5-methylamino-2-[3-(pyrazin-2-ylcarbonylaminomethyl)phenyl]-8H-imidazo[4,5-d]oxazolo[5,4-b]pyridine;
8-Methyl-5-methylamino-2-[3-(1-cyanocyclopropylcarbonylaminomethyl)phenyl]-8H-imidazo[4,5-d]oxazolo[5,4-b]pyridine;
8-Methyl-5-methylamino-2-[3-(1-phenylcyclopropylcarbonylaminomethyl)phenyl]-8H-imidazo[4,5-d]oxazolo[5,4-b]pyridine;
8-Methyl-5-methylamino-2-[3-((trans-2-phenylcyclopropyl)carbonylaminomethyl)phenyl]-8H-imidazo[4,5-d]oxazolo[5,4-b]pyridine;
8-Methyl-5-methylamino-2-[3-(cyclobutylcarbonylaminomethyl)phenyl]-8H-imidazo[4,5-d]oxazolo[5,4-b]pyridine;
8-Methyl-5-methylamino-2-[3-(cyclopentylcarbonylaminomethyl)phenyl]-8H-imidazo[4,5-d]oxazolo[5,4-b]pyridine;
8-Methyl-5-methylamino-2-[3-(1-phenylcyclopentylcarbonylaminomethyl)phenyl]-8H-imidazo[4,5-d]oxazolo[5,4-b]pyridine;
8-Methyl-5-methylamino-2-[3-(cyclopentylmethylcarbonylaminomethyl)phenyl]-8H-imidazo[4,5-d]oxazolo[5,4-b]pyridine;
8-Methyl-5-methylamino-2-[3-(cyclohexylcarbonylaminomethyl)phenyl]-8H-imidazo[4,5-d]oxazolo[5,4-b]pyridine;
8-Methyl-5-methylamino-2-[3-(cyclohexylmethylcarbonylaminomethyl)phenyl-8H-imidazo[4,5-d]oxazolo[5,4-b]pyridine;
8-Methyl-5-methylamino-2-[3-((2-fluorophenyl)carbonylaminomethyl)phenyl]-8H-imidazo[4,5-d]oxazolo[5,4-b]pyridine;
5-Methyl-8-methylamino-2-[3-((2,5-difluorophenyl)carbonylaminomethyl)phenyl]-8H-imidazo[4,5-d]oxazolo[5,4-b]pyridine;
8-Methyl-5-methylamino-2-[3-((2,6-difluorophenyl)carbonylaminomethyl)phenyl]-8H-imidazo[4,5-d]oxazolo[5,4-b]pyridine;
8-Methyl-5-methylamino-2-[3-((2-chlorophenyl)carbonylaminomethyl)phenyl]-8H-imidazo[4,5-d]oxazolo[5,4-b]pyridine;
8-Methyl-5-methylamino-2-[3-((2-methoxyphenyl)carbonylaminomethyl)phenyl]-8H-imidazo[4,5-d]oxazolo[5,4-b]pyridine;
8-Methyl-5-methylamino-2-[3-((2-trifluoromethylphenyl)carbonylaminomethyl)phenyl]-8H-imidazo[4,5-d]oxazolo[5,4-b]pyridine;
8-Methyl-5-methylamino-2-[3-((3-fluorophenyl)carbonylaminomethyl)phenyl]-8H-imidazo[4,5-d]oxazolo[5,4-b]pyridine;
8-Methyl-5-methylamino-2-[3-((3-dimethylaminophenyl)carbonylaminomethyl)phenyl]-8H-imidazo[4,5-d]oxazolo[5,4-b]pyridine;
8-Methyl-5-methylamino-2-[3-((3-methoxyphenyl)aminophenyl)carbonylaminomethyl)phenyl]-8H-imidazo[4,5-d]oxazolo[5,4-b]pyridine;
8-Methyl-5-methylamino-2-[3-((3-methylphenyl)aminophenyl)carbonylaminomethyl)phenyl]-8H-imidazo[4,5-d]oxazolo[5,4-b]pyridine;
8-Methyl-5-methylamino-2-[3-(4-(dimethylamino)phenylcarbonylaminomethyl)phenyl]-8H-imidazo[4,5-d]oxazolo[5,4-b]pyridine;
8-Methyl-5-methylamino-2-[3-((2-methylethyl)carbonylaminomethyl)phenyl]-8H-imidazo[4,5-d]oxazolo[5,4-b]pyridine;

8-Methyl-5-methylamino-2-[3-((2-methylpropyl)carbonylaminomethyl)phenyl]-8H-imidazo[4,5-d]oxazolo[5,4-b]pyridine;
8-Methyl-5-methylamino-2-[3-((2,2-dimethylpropyl)carbonylaminomethyl)phenyl]-8H-imidazo[4,5-d]oxazolo[5,4-b]pyridine;
8-Methyl-5-methylamino-2-[3-((2-methylpropyl)carbonylaminomethyl)phenyl]-8H-imidazo[4,5-d]oxazolo[5,4-b]pyridine;
8-Methyl-5-methylamino-2-[3-((2-phenyloxyethyl)carbonylaminomethyl)phenyl]-8H-imidazo[4,5-d]oxazolo[5,4-b]pyridine;
8-Methyl-5-methylamino-2-[3-(phenylethylcarbonylaminomethyl)phenyl]-8H-imidazo[4,5-d]oxazolo[5,4-b]pyridine;
8-Methyl-5-methylamino-2-[3-(propylcarbonylaminomethyl)phenyl]-8H-imidazo[4,5-d]oxazolo[5,4-b]pyridine;
8-Methyl-5-methylamino-2-[3-((2-furyl)carbonylaminomethyl)phenyl]-8H-imidazo[4,5-d]oxazolo[5,4-b]pyridine;
8-Methyl-5-methylamino-2-(3-(cycloheptylcarbonylaminomethyl)phenyl]-8H-imidazo[4,5-d]oxazolo[5,4-b]pyridine;
8-Methyl-5-methylamino-2-[3-((2,2-dimethylethyl)carbonylaminomethl)phenyl]-8H-imidazo[4,5-d]oxazolo[5,4-b]pyridine;
8-Methyl-5-methylamino-2-[3-((difluoromethyl)carbonylaminomethyl)phenyl]-8H-imidazo[4,5-d]oxazolo[5,4-b]pyridine;
8-Methyl-5-methylamino-2-[3-((difluoromethyl)carbonylaminomethyl)phenyl]-8H-imidazo[4,5-d]oxazolo[5,4-b]pyridine;
8-Methyl-5-methylamino-2-[3-((2-(trifluoromethyl)phenyl)carbonylaminomethyl)phenyl]-8H-imidazo[4,5-d]oxazolo[5,4-b]pyridine;
8-Methyl-5-methylamino-2-[3-(3-(trans-phenylethenyl)carbonylaminomethyl)phenyl]-8H-imidazo[4,5-d]oxazolo[5,4-b]pyridine;
8-Methyl-5-methylamino-2-[3-(3-(3-phenylpropyl)carbonylaminomethyl)phenyl]-8H-imidazo[4,5-d]oxazolo[5,4-b]pyridine;
8-Methyl-5-methylamino-2-[3-(butylcarbonylaminomethyl)phenyl]-8H-imidazo[4,5-d]oxazolo[5,4-b]pyridine;
8-Methyl-5-methylamino-2-[3-(pentylcarbonylaminomethyl)phenyl]-8H-imidazo[4,5-d]oxazolo[5,4-b]pyridine;
8-Methyl-5-methylamino-2-[3-(thiophen-2-ylmethylcarbonylaminomethyl)phenyl]-8H-imidazo[4,5-d]oxazolo[5,4-b]pyridine;
8-Methyl-5-methylamino-2-[3-(thiophen-3-ylcarbonylaminomethyl)phenyl]-8H-imidazo[4,5-d]oxazolo[5,4-b]pyridine;
8-Methyl-5-methylamino-2-[3-(indol-3-ylmethylcarbonylaminomethyl)phenyl]-8H-imidazo[4,5-d]oxazolo[5,4-b]pyridine;
8-Methyl-5-methylamino-2-[3-(furan-2-ylcarbonylaminomethyl)phenyl]-8H-imidazo[4,5-d]oxazolo[5,4-b]pyridine;
8-Methyl-5-methylamino-2-[3-(pyridin-2-ylcarbonylaminomethyl)phenyl]-8H-imidazo[4,5-d]oxazolo[5,4-b]pyridine;
8-Methyl-5-methylamino-2-[3-(pyridin-3-ylcarbonylaminomethyl)phenyl]-8H-imidazo[4,5-d]oxazolo[5,4-b]pyridine;
8-Methyl-5-methylamino-2-[3-(pyridin-4-ylcarbonylaminomethyl)phenyl]-8H-imidazo[4,5-d]oxazolo[5,4-b]pyridine;
8-Methyl-5-methylamino-2-[3-(2-piperidin-1-ylethylcarbonylaminomethyl)phenyl]-8H-imidazo[4,5-d]oxazolo[5,4-b]pyridine;
8-Methyl-5-methylamino-2-[3-(4-nitrophenylcarbonylaminomethyl)phenyl]-8H-imidazo[4,5-d]oxazolo[5,4-b]pyridine;
8-Methyl-5-methylamino-2-[3-(acyloxyethylcarbonylaminomethyl)phenyl]-8H-imidazo[4,5-d]oxazolo[5,4-b]pyridine;
8-Methyl-5-methylamino-2-[3-(imidazol-2-ylmethylcarbonylaminomethyl)phenyl]-8H-imidazo[4,5-d]oxazolo[5,4-b]pyridine;
8-Methyl-5-methylamino-2-[3-(pyridin-3-ylmethylcarbonylaminomethyl)phenyl]-8H-imidazo[4,5-d]oxazolo[5,4-b]pyridine;
8-Methyl-5-methylamino-2-[3-((1-methyl-1-phenylethyl)carbonylaminomethyl)phenyl]-8H-imidazo[4,5-d]oxazolo[5,4-b]pyridine;
8-Methyl-5-methylamino-2-[3-(3-methylcarboxyphenylcarbonylaminomethyl)phenyl]-8H-imidazo[4,5-d]oxazolo[5,4-b]pyridine;
8-Methyl-5-methylamino-2-[3-(cyclopropylethylcarbonylaminomethyl)phenyl]-8H-imidazo[4,5-d]oxazolo[5,4-b]pyridine;
8-Methyl-5-methylamino-2-[3-(methoxymethylcarbonylaminomethyl)phenyl]-8H-imidazo[4,5-d]oxazolo[5,4-b]pyridine;
8-Methyl-5-methylamino-2-[3-(thiadiazol-4-ylcarbonylaminomethyl)phenyl]-8H-imidazo[4,5-d]oxazolo[5,4-b]pyridine;
8-Methyl-5-methylamino-2-[3-(2-(pyridine-3-yl)thiazol-4-yl)carbonylaminomethyl)phenyl]-8H-imidazo[4,5-d]oxazolo[5,4-b]pyridine;
8-Methyl-5-methylamino-2-[3-(4-dimethyaminophenylmethylcarbonylaminomethyl)phenyl]-8H-imidazo[4,5-d]oxazolo[5,4-b]pyridine;
8-Methyl-5-methylamino-2-[3-(2,2,2-trifluoroethylcarbonylaminomethyl)phenyl]-8H-imidazo[4,5-d]oxazolo[5,4-b]pyridine;
8-Methyl-5-methylamino-2-[3-((1-ethyl-3-methylpyrazol-5-yl)carbonylaminomethyl)phenyl]-8H-imidazo[4,5-d]oxazolo[5,4-b]pyridine;
8-Methyl-5-methylamino-2-[3-((4-bromo-1-ethyl-3-methylpyrazol-5-yl)carbonylaminomethyl)phenyl]-8H-imidazo[4,5-d]oxazolo[5,4-b]pyridine
8-Methyl-5-methylamino-2-[3-(2-methylsulfonylphenylcarbonylaminomethyl)phenyl]-8H-imidazo[4,5-d]oxazolo[5,4-b]pyridine;
8-Methyl-5-methylamino-2-[3-(dihydrobenzoxazol-7-ylcarbonylaminomethyl)phenyl]-8H-imidazo[4,5-d]oxazolo[5,4-b]pyridine;
8-Methyl-5-methylamino-2-[3-((5-methylisoxazol-4-yl)carbonylaminomethyl)phenyl]-8H-imidazo[4,5-d]oxazolo[5,4-b]pyridine;
8-Methyl-5-methylamino-2-[3-(cycloheptylmethylcarbonylaminomethyl)phenyl]-8H-imidazo[4,5-d]oxazolo[5,4-b]pyridine;
8-Methyl-5-methylamino-2-[3-(dimethylaminomethylcarbonylaminomethyl)phenyl]-8H-imidazo[4,5-d]oxazolo[5,4-b]pyridine;
8-Methyl-5-methylamino-2-[3-((3-methylphenyl)carbonylaminomethyl)phenyl]-8H-imidazo[4,5-d]oxazolo[5,4-b]pyridine;

8-Methyl-5-methylamino-2-[3-(aminomethylcarbonylaminomethyl)phenyl]-8H-imidazo[4,5-d]oxazolo[5,4-b]pyridine;
8-Methyl-5-methylamino-2-[3-(S-aminoethylcarbonylaminomethyl)phenyl]-8H-imidazo[4,5-d]oxazolo[5,4-b]pyridine;
8-Methyl-5-methylamino-2-[3-((R-2-amino-3-methylpropyl)carbonylaminomethyl)phenyl]-8H-imidazo[4,5-d]oxazolo[5,4-b]pyridine;
8-Methyl-5-methylamino-2-[3-((R-2-amino-4-methylbutyl)carbonylaminomethyl)phenyl]-8H-imidazo[4,5-d]oxazolo[5,4-b]pyridine;
8-Methyl-5-methylamino-2-[3-(R-aminophenylmethylcarbonylaminomethyl)phenyl]-8H-imidazo[4,5-d]oxazolo[5,4-b]pyridine;
8-Methyl-5-methylamino-2-[3-(R-amino-2-(phenyl)ethylcarbonylaminomethyl)phenyl]-8H-imidazo[4,5-d]oxazolo[5,4-b]pyridine;
8-Methyl-5-methylamino-2-[3-(R-aminoethylcarbonylaminomethyl)phenyl]-8H-imidazo[4,5-d]oxazolo[5,4-b]pyridine;
8-Methyl-5-methylamino-2-(3-(R-2-(aminocarbonyl)-1-amino ethylcarbonylaminomethyl)phenyl]-8H-imidazo[4,5-d]oxazolo[5,4-b]pyridine;
8-Methyl-5-methylamino-2-[3-(S-1-amino-2-imidazol-4-yl-ethylcarbonylaminomethyl)phenyl]-8H-imidazo[4,5-d]oxazolo[5,4-b]pyridine;
8-Methyl-5-methylamino-2-[3-(R-1-amino-R-2-methylbutylcarbonylaminomethyl)phenyl]-8H-imidazo[4,5-d]oxazolo[5,4-b]pyridine;
8-Methyl-5-methylamino-2-[3-(R-1-amino-4-aminobutylcarbonylaminomethyl)phenyl]-8H-imidazo[4,5-d]oxazolo[5,4-b]pyridine;
8-Methyl-5-methylamino-2-[3-(S-1-amino-4-guanidinylbutylylcarbonylaminomethyl)phenyl]-8H-imidazo[4,5-d]oxazolo[5,4-b]pyridine;
8-Methyl-5-methylamino-2-[3-(R-1-amino-S-2-hydroxypropylcarbonylaminomethyl)phenyl]-8H-imidazo[4,5-d]oxazolo[5,4-b]pyridine;
8-Methyl-5-methylamino-2-[3-(R-1-amino-2-carboxyethylcarbonylaminomethyl)phenyl]-8H-imidazo[4,5-d]oxazolo[5,4-b]pyridine;
8-Methyl-5-methylamino-2-[benzothiazol-6-ylcarboxyphenylcarbonylaminomethyl)phenyl]-8H-imidazo[4,5-d]oxazolo[5,4-b]pyridine;
8-Methyl-5-methylamino-2-[isoxazol-5-ylcarboxyphenylcarbonylaminomethyl)phenyl]-8H-imidazo[4,5-d]oxazolo[5,4-b]pyridine;
8-Methyl-5-methylamino-2-[1-methylpyrrol-2-ylcarboxyphenylcarbonylaminomethyl)phenyl]-8H-imidazo[4,5-d]oxazolo[5,4-b]pyridine;
8-Methyl-5-methylamino-2-[1-methylpyrrol-2-ylcarboxyphenylcarbonylaminomethyl)phenyl]-8H-imidazo[4,5-d]oxazolo[5,4-b]pyridine;
8-Methyl-5-methylamino-2-[3-(phenyloxycarbonylaminomethyl)phenyl]-8H-imidazo[4,5-d]oxazolo[5,4-b]pyridine;
8-Methyl-5-methylamino-2-[3-(ethyloxycarbonylaminomethyl)phenyl]-8H-imidazo[4,5-d]oxazolo[5,4-b]pyridine;
8-Methyl-5-methylamino-2-[3-(2-methoxyethyloxycarbonylaminomethyl)phenyl]-8H-imidazo[4,5-d]oxazolo[5,4-b]pyridine;
8-Methyl-5-methylamino-2-[3-(2-propynyloxycarbonylaminomethyl)phenyl]-8H-imidazo[4,5-d]oxazolo[5,4-b]pyridine;
8-Methyl-5-methylamino-2-[3-(4-fluorophenyloxycarbonylaminomethyl)phenyl]-8H-imidazo[4,5-d]oxazolo[5,4-b]pyridine;
8-Methyl-5-methylamino-2-[3-(4-methoxyphenyloxycarbonylaminomethyl)phenyl]-8H-imidazo[4,5-d]oxazolo[5,4-b]pyridine;
8-Methyl-5-methylamino-2-[3-(2-napthyloxycarbonylaminomethyl)phenyl]-8H-imidazo[4,5-d]oxazolo[5,4-b]pyridine;
8-Methyl-5-methylamino-2-[3-(isopropyloxycarbonylaminomethyl)phenyl]-8H-imidazo[4,5-d]oxazolo[5,4-b]pyridine;
8-Methyl-5-methylamino-2-[3-(3-butynyloxycarbonylaminomethyl)phenyl]-8H-imidazo[4,5-d]oxazolo[5,4-b]pyridine;
8-Methyl-5-methylamino-2-[3-(2-nitrophenylsulfonyloaminomethyl)phenyl]-8H-imidazo[4,5-d]oxazolo[5,4-b]pyridine;
8-Methyl-5-methylamino-2-[3-(propylsulfonyloaminomethyl)phenyl]-8H-imidazo[4,5-d]oxazolo[5,4-b]pyridine;
8-Methyl-5-methylamino-2-[3-(2-nitrophenylsulfonyloaminomethyl)phenyl]-8H-imidazo[4,5-d]oxazolo[5,4-b]pyridine;
8-Methyl-5-methylamino-2-[3-((2-acetamido-4-methylthiazol-5-yl)sulfonyloaminomethyl)phenyl]-8H-imidazo[4,5-d]oxazolo[5,4-b]pyridine;
8-Methyl-5-methylamino-2-[3-(4-fluorophenylsulfonyloaminomethyl)phenyl]-8H-imidazo[4,5-d]oxazolo[5,4-b]pyridine;
8-Methyl-5-methylamino-2-[3-(2-trifluoromethoxyphenylsulfonyloaminomethyl)phenyl]-8H-imidazo[4,5-d]oxazolo[5,4-b]pyridine;
8-Methyl-5-methylamino-2-[3-(3,5-dimethylisoxazol-4-ylsulfonyloaminomethyl)phenyl]-8H-imidazo[4,5-d]oxazolo [5,4-b]pyridine;
8-Methyl-5-methylamino-2-[3-(2,5-difluorophenylsulfonyloaminomethyl)phenyl]-8H-imidazo[4,5-d]oxazolo[5,4-b]pyridine;
8-Methyl-5-methylamino-2-[3-(4-acetylphenylsulfonyloaminomethyl)phenyl]-8H-imidazo[4,5-d]oxazolo[5,4-b]pyridine;
8-Methyl-5-methylamino-2-[3-(5-methylisoxazol-4-ylsulfonyloaminomethyl)phenyl]-8H-imidazo[4,5-d]oxazolo[5,4-b]pyridine;
8-Methyl-5-methylamino-2-[3-(thiophen-3-ylsulfonyloaminomethyl)phenyl]-8H-imidazo[4,5-d]oxazolo[5,4-b]pyridine;
2-[3-(1-amino-1-methylethyl)phenyl]-N,8-dimethyl-8H-imidazo[4,5-d]oxazolo[5,4-b]pyridine;
2-[3-(1-acetamido-1-methylethyl)phenyl]-N,8-dimethyl-8H-imidazo[4,5-d]oxazolo[5,4-b]pyridine;
2-[3-(1-amino-1-methylethyl)phenyl]-N,8-dimethyl-8H-imidazo[4,5-d]oxazolo[5,4-b]pyridine;
N-[1-[5-[8-methyl-5-(methylamino)-8H-imidazo[4,5-d]oxazolo[5,4-b]pyridin-2-yl]phenyl]ethyl]acetamide;
N-[1-[5-[8-methyl-5-(methylamino)-8H-imidazo[4,5-d]oxazolo[5,4-b]pyridin-2-yl]phenyl]ethyl]N-methylurea;
N,8-dimethyl-2-phenyl-8H-imidazo[4,5-d]thiazolo[5,4-b]pyridin-5-amine;
N,8-dimethyl-2-(methylthio)-8H-imidazo[4,5-d]thiazolo[5,4-b]pyridin-5-amine;
N-(3-methoxypropyl)-8-methyl-2-(methylthio)-8H-imidazo[4,5-d]thiazolo[5,4-b]pyridin-5-amine;
N,8-dimethyl-2-[(1-methylethyl)thio]-8H-imidazo[4,5-d]thiazolo[5,4-b]pyridin-5-amine;

N,8-dimethyl-2-(methylsulfonyl)-8H-imidazo[4,5-d]thiazolo[5,4-b]pyridin-5-amine;
N,8-dimethyl-2-(1-piperidinyl)-8H-imidazo[4,5-d]thiazolo[5,4-b]pyridin-5-amine;
2-(hexahydro-1H-azepin-1-yl)-N,8-dimethyl-8H-imidazo[4,5-d]thiazolo[5,4-b]pyridin-5-amine;
3-piperidinemethanol,1-[8-methyl-5-(methylamino)-8H-imidazo[4,5-d]thiazolo[5,4-b]pyridin-2-yl]-;
8H-imidazo[4,5-d]thiazolo[5,4-b]pyridine-2,5-diamine, $N^2,N^5,8$-trimethyl-$N^2$-(2-phenylethyl)-;
8H-imidazo[4,5-d]thiazolo[5,4-b]pyridine-2,5-diamine, $N^2$-(cyclopropylmethyl)-$N^5$,8-dimethyl-$N^2$-propyl-;
8H-imidazo[4,5-d]thiazolo[5,4-b]pyridin-5-amine, N,8-dimethyl-2-(4-morpholinyl)-;
piperazine,1-acetyl-4-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, N,8-dimethyl-2-(4-thiomorpholinyl)-;
8H-imidazo[4,5-d]thiazolo[5,4-b]pyridine-2,5-diamine, $N^2$-butyl-$N^2,N^5$,8-trimethyl-;
8H-imidazo[4,5-d]thiazolo[5,4-b]pyridine-2,5-diamine, $N^2$-[2-(1H-indol-3-yl)ethyl]-$N^5$,8-dimethyl-;
8H-imidazo[4,5-d]thiazolo[5,4-b]pyridine-2,5-diamine, $N^2$-cyclohexyl-$N^5$,8-dimethyl-;
8H-imidazo[4,5-d]thiazolo[5,4-b]pyridine-2,5-diamine, $N^2$-(2,2-dimethylpropyl)-$N^5$,8-dimethyl-;
8H-imidazo[4,5-d]thiazolo[5,4-b]pyridine-2,5-diamine, $N^2$-cyclopentyl-$N^5$,8-dimethyl-;
8H-imidazo[4,5-d]thiazolo[5,4-b]pyridine-2,5-diamine, $N^5$,8-dimethyl-$N^2$-(phenylmethyl)-;
8H-imidazo[4,5-d]thiazolo[5,4-b]pyridine-2,5-diamine, $N^5$,8-dimethyl-$N^2$-pentyl-;
8H-imidazo[4,5-d]thiazolo[5,4-b]pyridine-2,5-diamine, $N^2$-(3-methoxypropyl)-$N^5$,8-dimethyl-;
8H-imidazo[4,5-d]thiazolo[5,4-b]pyridine-2,5-diamine, $N^5$,8-dimethyl-$N^2$-(2-methylpropyl)-;
8H-imidazo[4,5-d]thiazolo[5,4-b]pyridine-2,5-diamine, $N^2$-[(4-methoxyphenyl)methyl]-$N^5$,8-dimethyl-;
8H-imidazo[4,5-d]thiazolo[5,4-b]pyridine-2,5-diamine, $N^2$-butyl-$N^5$,8-dimethyl-;
8H-imidazo[4,5-d]thiazolo[5,4-b]pyridine-2,5-diamine, $N^2$-[(2-methoxyphenyl)methyl]-$N^5$,8-dimethyl-;
8H-imidazo[4,5-d]thiazolo[5,4-b]pyridine-2,5-diamine, $N^2$-[(3-methoxyphenyl)methyl]-$N^5$,8-dimethyl-;
8H-imidazo[4,5-d]thiazolo[5,4-b]pyridine-2,5-diamine, $N^2$-ethyl-$N^5$,8-dimethyl-;
8H-imidazo[4,5-d]thiazolo[5,4-b]pyridine-2,5-diamine, $N^2$-[(4-fluorophenyl)methyl]-$N^5$,8-dimethyl-;
$N^2$-(2-ethoxyethyl)-$N^5$,8-dimethyl-8H-imidazo[4,5-d]thiazolo[5,4-b]pyridine-2,5-diamine;
3-piperidinecarboxamide, 1-[8-methyl-5-(methylamino)-8H-imidazo[4,5-d]thiazolo[5,4-b]pyridin-2-yl]-;
8H-imidazo[4,5-d]thiazolo[5,4-b]pyridine-2,5-diamine, $N^2$-(2-furanylmethyl)-$N^5$,8-dimethyl-;
8H-imidazo[4,5-d]thiazolo[5,4-b]pyridine-2,5-diamine, $N^5$,8-dimethyl-$N^2$-(3-pyridinylmethyl)-;
1-butanol, 4-[[8-methyl-5-(methylamino)-8H-imidazo[4,5-d]thiazolo[5,4-b]pyridin-2-yl]amino]-;
1-pentanol, 2-[[8-methyl-5-(methylamino)-8H-imidazo[4,5-d]thiazolo[5,4-b]pyridin-2-yl]amino]-;
1-propanol, 2-[[8-methyl-5-(methylamino)-8H-imidazo[4,5-d]thiazolo[5,4-b]pyridin-2-yl]amino]-;
ethanol, 2-[2-[[8-methyl-5-(methylamino)-8H-imidazo[4,5-d]thiazolo[5,4-b]pyridin-2-yl]amino]ethoxy]-;
ethanol, 2-[[8-methyl-5-(methylamino)-8H-imidazo[4,5-d]thiazolo[5,4-b]pyridin-2-yl]amino]-;
8H-imidazo[4,5-d]thiazolo[5,4-b]pyridin-5-amine, 2-(2,6-dimethyl-4-morpholinyl)-N,8-dimethyl-;
1H-1,4-diazepine, 1-acetylhexahydro-4-[8-methyl-5-(methylamino)-8H-imidazo[4,5-d]thiazolo[5,4-b]pyridin-2-yl]-;
ethanol, 2-[ethyl[8-methyl-5-(methylamino)-8H-imidazo[4,5-d]thiazolo[5,4-b]pyridin-2-yl]amino]-;
8H-imidazo[4,5-d]thiazolo[5,4-b]pyridin-5-amine, 2-(2,5-dihydro-1H-pyrrol-1-yl)-N,8-dimethyl-;
8H-imidazo[4,5-d]thiazolo[5,4-b]pyridin-5-amine, 2-(3,6-dihydro-1(2H)-pyridinyl)-N,8-dimethyl-;
8H-imidazo[4,5-d]thiazolo[5,4-b]pyridine-2,5-diamine, $N^2,N^5,8$-trimethyl-$N^{2-2}$-propenyl-;
8H-imidazo[4,5-d]thiazolo[5,4-b]pyridine-2,5-diamine, $N^5$,8-dimethyl-$N^2,N^2$-di-2-propenyl-;
8H-imidazo[4,5-d]thiazolo[5,4-b]pyridine-2,5-diamine, $N^2$-ethyl-$N^5$,8-dimethyl-$N^2$-(2-methyl-2-propenyl)-;
ethanol, 2-[methyl[8-methyl-5-(methylamino)-8H-imidazo[4,5-d]thiazolo[5,4-b]pyridin-2-yl]amino]-;
8H-imidazo[4,5-d]thiazolo[5,4-b]pyridine-2,5-diamine, $N^2$-butyl-$N^2$-ethyl-$N^5$,8-dimethyl-;
ethanol, 2,2'-[[8-methyl-5-(methylamino)-8H-imidazo[4,5-d]thiazolo[5,4-b]pyridin-2-yl]imino]bis-;
8H-imidazo[4,5-d]thiazolo[5,4-b]pyridine-2,5-diamine, $N^5$,8-dimethyl-$N^2,N^2$-bis(1-methylethyl)-;
4-piperidinol, 1-[8-methyl-5-(methylamino)-8H-imidazo[4,5-d]thiazolo[5,4-b]pyridin-2-yl]-;
2-fluoro-N-[8-methyl-5-(methylamino)-8H-imidazo[4,5-d]thiazolo[5,4-b]pyridin-2-yl]-benzamide;
benzamide, 2-chloro-N-[8-methyl-5-(methylamino)-8H-imidazo[4,5-d]thiazolo[5,4-b]pyridin-2-yl]-;
benzamide, 2-methoxy-N-[8-methyl-5-(methylamino)-8H-imidazo[4,5-d]thiazolo[5,4-b]pyridin-2-yl]-;
benzamide, N-[8-methyl-5-(methylamino)-8H-imidazo[4,5-d]thiazolo[5,4-b]pyridin-2-yl]-2-(trifluoromethyl)-;
benzamide, 3-methyl-N-[8-methyl-5-(methylamino)-8H-imidazo[4,5-d]thiazolo[5,4-b]pyridin-2-yl]-;
benzamide, 4-fluoro-N-[8-methyl-5-(methylamino)-8H-imidazo[4,5-d]thiazolo[5,4-b]pyridin-2-yl]-;
benzamide, 4-methyl-N-[8-methyl-5-(methylamino)-8H-imidazo[4,5-d]thiazolo[5,4-b]pyridin-2-yl]-;
propanamide, 2,2-dimethyl-N-[8-methyl-5-(methylamino)-8H-imidazo[4,5-d]thiazolo[5,4-b]pyridin-2-yl]-;
propanamide, 2-methyl-N-[8-methyl-5-(methylamino)-8H-imidazo[4,5-d]thiazolo[5,4-b]pyridin-2-yl]-;
acetamide, N-[8-methyl-5-(methylamino)-8H-imidazo[4,5-d]thiazolo[5,4-b]pyridin-2-yl];
benzeneacetamide, N-[8-methyl-5-(methylamino)-8H-imidazo[4,5-d]thiazolo[5,4-b]pyridin-2-yl]-;
butanamide, 3,3-dimethyl-N-[8-methyl-5-(methylamino)-8H-imidazo[4,5-d]thiazolo[5,4-b]pyridin-2-yl]-;
butanamide, 3-methyl-N-[8-methyl-5-(methylamino)-8H-imidazo[4,5-d]thiazolo[5,4-b]pyridin-2-yl]-;
propanamide, N-[8-methyl-5-(methylamino)-8H-imidazo[4,5-d]thiazolo[5,4-b]pyridin-2-yl]-;
benzenepropanamide, N-[8-methyl-5-(methylamino)-8H-imidazo[4,5-d]thiazolo[5,4-b]pyridin-2-yl]-;
butanamide, N-[8-methyl-5-(methylamino)-8H-imidazo[4,5-d]thiazolo[5,4-b]pyridin-2-yl]-;
pentanamide, N-[8-methyl-5-(methylamino)-8H-imidazo[4,5-d]thiazolo[5,4-b]pyridin-2-yl]-;
hexanamide, N-[8-methyl-5-(methylamino)-8H-imidazo[4,5-d]thiazolo[5,4-b]pyridin-2-yl]-;

cyclopropanecarboxamide, N-[8-methyl-5-(methylamino)-8H-imidazo[4,5-d]thiazolo[5,4-b]pyridin-2-yl]-;
cyclobutanecarboxamide, N-[8-methyl-5-(methylamino)-8H-imidazo[4,5-d]thiazolo[5,4-b]pyridin-2-yl]-;
cyclopentanecarboxamide, N-[8-methyl-5-(methylamino)-8H-imidazo[4,5-d]thiazolo[5,4-b]pyridin-2-yl]-;
cyclohexanecarboxamide, N-[8-methyl-5-(methylamino)-8H-imidazo[4,5-d]thiazolo[5,4-b]pyridin-2-yl]-;
benzamide, 4-cyano-N-[8-methyl-5-(methylamino)-8H-imidazo[4,5-d]thiazolo[5,4-b]pyridin-2-yl]-;
2-furancarboxamide, N-[8-methyl-5-(methylamino)-8H-imidazo[4,5-d]thiazolo[5,4-b]pyridin-2-yl]-;
2-thiophenecarboxamide, N-[8-methyl-5-(methylamino)-8H-imidazo[4,5-d]thiazolo[5,4-b]pyridin-2-yl]-;
2-thiopheneacetamide, N-[8-methyl-5-(methylamino)-8H-imidazo[4,5-d]thiazolo[5,4-b]pyridin-2-yl]-;
benzamide, 3,5-dichloro-N-[8-methyl-5-(methylamino)-8H-imidazo[4,5-d]thiazolo[5,4-b]pyridin-2-yl]-;
acetamide, N-[8-methyl-5-(methylamino)-8H-imidazo[4,5-d]thiazolo[5,4-b]pyridin-2-yl]-2-(phenylmethoxy)-;
benzamide, 3-cyano-N-[8-methyl-5-(methylamino)-8H-imidazo[4,5-d]thiazolo[5,4-b]pyridin-2-yl]-;
1,3-benzodioxole-5-carboxamide, N-[8-methyl-5-(methylamino)-8H-imidazo[4,5-d]thiazolo[5,4-b]pyridin-2-yl]-;
benzo[b]thiophene-2-carboxamide, N-[8-methyl-5-(methylamino)-8H-imidazo[4,5-d]thiazolo[5,4-b]pyridin-2-yl]-;
benzamide, N-[8-methyl-5-(methylamino)-8H-imidazo[4,5-d]thiazolo[5,4-b]pyridin-2-yl]-4-(trifluoromethoxy)-;
benzamide, 4-fluoro-N-[8-methyl-5-(methylamino)-8H-imidazo[4,5-d]thiazolo[5,4-b]pyridin-2-yl]-2-(trifluoromethyl)-;
benzamide, 2,4,6-trifluoro-N-[8-methyl-5-(methylamino)-8H-imidazo[4,5-d]thiazolo[5,4-b]pyridin-2-yl]-;
tricyclo[3.3.1.1$^{3,7}$]decane-1-carboxamide, N-[8-methyl-5-(methylamino)-8H-imidazo[4,5-d]thiazolo[5,4-b]pyridin-2-yl]-benzamide,
N-[8-methyl-5-(methylamino)-8H-imidazo[4,5-d]thiazolo[5,4-b]pyridin-2-yl]-2,5-bis(trifluoromethyl)-benzamide, 2,3,4-trifluoro-N-[8-methyl-5-(methylamino)-8H-imidazo[4,5-d]thiazolo[5,4-b]pyridin-2-yl]-;
3-furancarboxamide, 2,5-dimethyl-N-[8-methyl-5-(methylamino)-8H-imidazo[4,5-d]thiazolo[5,4-b]pyridin-2-yl]-;
3-pyridinecarboxamide, N-[8-methyl-5-(methylamino)-8H-imidazo[4,5-d]thiazolo[5,4-b]pyridin-2-yl]-;
4-pyridinecarboxamide, N-[8-methyl-5-(methylamino)-8H-imidazo[4,5-d]thiazolo[5,4-b]pyridin-2-yl]-;
3-pyridinecarboxamide, 2-(ethylthio)-N-[8-methyl-5-(methylamino)-8H-imidazo[4,5-d]thiazolo[5,4-b]pyridin-2-yl]-;
benzamide, 4-(dimethylamino)-N-[8-methyl-5-(methylamino)-8H-imidazo[4,5-d]thiazolo[5,4-b]pyridin-2-yl]-;
1H-pyrrole-2-carboxamide, 1-methyl-N-[8-methyl-5-(methylamino)-8H-imidazo[4,5-d]thiazolo[5,4-b]pyridin-2-yl]-;
5-pyrimidinecarboxamide, 2-chloro-N-[8-methyl-5-(methylamino)-8H-imidazo[4,5-d]thiazolo[5,4-b]pyridin-2-yl]-4-(trifluoromethyl)-;
propanamide, 2-(acetyloxy)-2-methyl-N-[8-methyl-5-(methylamino)-8H-imidazo[4,5-d]thiazolo[5,4-b]pyridin-2-yl]-;
benzeneacetamide, alpha-(acetyloxy)-N-[8-methyl-5-(methylamino)-8H-imidazo[4,5-d]thiazolo[5,4-b]pyridin-2-yl]-;
acetamide, 2-(acetyloxy)-N-[8-methyl-5-(methylamino)-8H-imidazo[4,5-d]thiazolo[5,4-b]pyridin-2-yl]-;
propanamide, 2-(acetyloxy)-N-[8-methyl-5-(methylamino)-8H-imidazo[4,5-d]thiazolo[5,4-b]pyridin-2-yl]-, (2S)-benzamide,
benzamide, 3-(acetyloxy)-2-methyl-N-[8-methyl-5-(methylamino)-8H-imidazo[4,5-d]thiazolo[5,4-b]pyridin-2-yl]-;
propanoic acid, 3-[[8-methyl-5-(methylamino)-8H-imidazo[4,5-d]thiazolo[5,4-b]pyridin-2-yl]amino]-3-oxo-;
propanoic acid, 3-[[8-methyl-5-(methylamino)-8H-imidazo[4,5-d]thiazolo[5,4-b]pyridin-2-yl]amino]-3-oxo-, ethyl ester;
butanoic acid, 4-[[8-methyl-5-(methylamino)-8H-imidazo[4,5-d]thiazolo[5,4-b]pyridin-2-yl]amino]-4-oxo-;
butanoic acid, 4-[[8-methyl-5-(methylamino)-8H-imidazo[4,5-d]thiazolo[5,4-b]pyridin-2-yl]amino]-4-oxo-, methyl ester;
pentanoic acid, 5-[[8-methyl-5-(methylamino)-8H-imidazo[4,5-d]thiazolo[5,4-b]pyridin-2-yl]amino]-5-oxo-;
pentanoic acid, 5-[[8-methyl-5-(methylamino)-8H-imidazo[4,5-d]thiazolo[5,4-b]pyridin-2-yl]amino]-5-oxo-, methyl ester;
benzoic acid, 4-[[[8-methyl-5-(methylamino)-8H-imidazo[4,5-d]thiazolo[5,4-b]pyridin-2-yl]amino]carbonyl]-;
benzoic acid, 4-[[[8-methyl-5-(methylamino)-8H-imidazo[4,5-d]thiazolo[5,4-b]pyridin-2-yl]amino]carbonyl]-, methyl ester;
1-[4-[8-methyl-5-(methylamino)-8H-imidazo[4,5-d]thiazolo[5,4-b]pyridin-2-yl]phenyl]-ethanone;
N,8-dimethyl-2-[3-[1-[(2-phenylethyl)amino]ethyl]phenyl]-8H-imidazo[4,5-d]thiazolo[5,4-b]pyridin-5-amine;
8H-imidazo[4,5-d]thiazolo[5,4-b]pyridin-5-amine, 2-[3-[1-[(cyclohexylmethyl)amino]ethyl]phenyl]-N,8-dimethyl-;
8H-imidazo[4,5-d]thiazolo[5,4-b]pyridin-5-amine, N,8-dimethyl-2-[3-[1-[[(tetrahydro-2-furanyl)methyl]amino]ethyl]phenyl]-;
8H-imidazo[4,5-d]thiazolo[5,4-b]pyridin-5-amine, N,8-dimethyl-2-[3-[1-[[1-(phenylmethyl)-4-piperidinyl]amino]ethyl]phenyl]-;
8H-imidazo[4,5-d]thiazolo[5,4-b]pyridin-5-amine, N,8-dimethyl-2-[3-[1-[[2-(1-piperidinyl)ethyl]amino]ethyl]phenyl]-;
8H-imidazo[4,5-d]thiazolo[5,4-b]pyridin-5-amine, N,8-dimethyl-2-[3-[1-[(phenylmethyl)amino]ethyl]phenyl]-;
8H-imidazo[4,5-d]thiazolo[5,4-b]pyridin-5-amine, 2-[3-[1-[[(2-fluorophenyl)methyl]amino]ethyl]phenyl]-N,8-dimethyl-;
8H-imidazo[4,5-d]thiazolo[5,4-b]pyridin-5-amine, 2-[3-[1-[[(2-chlorophenyl)methyl]amino]ethyl]phenyl]-N,8-dimethyl-;
8H-imidazo[4,5-d]thiazolo[5,4-b]pyridin-5-amine, 2-[3-[1-[[(2-methoxyphenyl)methyl]amino]ethyl]phenyl]-N,8-dimethyl-;
8H-imidazo[4,5-d]thiazolo[5,4-b]pyridin-5-amine, N,8-dimethyl-2-[3-[1-[[(2-methylphenyl)methyl]amino]ethyl]phenyl]-;

8H-imidazo[4,5-d]thiazolo[5,4-b]pyridin-5-amine, 2-[3-[1-[[(3-fluorophenyl)methyl]amino]ethyl]phenyl]-N,8-dimethyl-;
8H-imidazo[4,5-d]thiazolo[5,4-b]pyridin-5-amine, 2-[3-[1-[[(3-methoxyphenyl)methyl]amino]ethyl]phenyl]-N,8-dimethyl-;
8H-imidazo[4,5-d]thiazolo[5,4-b]pyridin-5-amine, N,8-dimethyl-2-[3-[1-[[[3-(trifluoromethyl)phenyl]methyl]amino]ethyl]phenyl]-;
8H-imidazo[4,5-d]thiazolo[5,4-b]pyridin-5-amine, 2-[3-[1-[[(4-fluorophenyl)methyl]amino]ethyl]phenyl]-N,8-dimethyl-;
8H-imidazo[4,5-d]thiazolo[5,4-b]pyridin-5-amine, N,8-dimethyl-2-[3-[1-[[(4-methylphenyl)methyl]amino]ethyl]phenyl]-;
8H-imidazo[4,5-d]thiazolo[5,4-b]pyridin-5-amine, 2-[3-[1-[(2,2-dimethylpropyl)amino]ethyl]phenyl]-N,8-dimethyl-;
8H-imidazo[4,5-d]thiazolo[5,4-b]pyridin-5-amine, 2-[3-[1-[(3-methoxypropyl)amino]ethyl]phenyl]-N,8-dimethyl-;
8H-imidazo[4,5-d]thiazolo[5,4-b]pyridin-5-amine, 2-[3-[1-[[(3-chlorophenyl)methyl]amino]ethyl]phenyl]-N,8-dimethyl-;
1,3-propanediamine, N,N-dimethyl-N'-[1-[3-[8-methyl-5-(methylamino)-8H-imidazo[4,5-d]thiazolo[5,4-b]pyridin-2-yl]phenyl]ethyl]-;
8H-imidazo[4,5-d]thiazolo[5,4-b]pyridin-5-amine, N,8-dimethyl-2-[3-[1-[(2-methylpropyl)amino]ethyl]phenyl]-;
8H-imidazo[4,5-d]thiazolo[5,4-b]pyridin-5-amine, N,8-dimethyl-2-[3-[1-[[2-(4-morpholinyl)ethyl]amino]ethyl]phenyl]-;
8H-imidazo[4,5-d]thiazolo[5,4-b]pyridin-5-amine, N,8-dimethyl-2-[3-[1-[[3-(1-pyrrolidinyl)propyl]amino]ethyl]phenyl]-;
8H-imidazo[4,5-d]thiazolo[5,4-b]pyridin-5-amine, N,8-dimethyl-2-[3-[1-[[2-(methylthio)ethyl]amino]ethyl]phenyl]-;
8H-imidazo[4,5-d]thiazolo[5,4-b]pyridin-5-amine, N,8-dimethyl-2-(3-pyridinyl)-;
8H-imidazo[4,5-d]thiazolo[5,4-b]pyridin-5-amine, 2-(6-methoxy-3-pyridinyl)-N,8-dimethyl-;
8H-imidazo[4,5-d]thiazolo[5,4-b]pyridin-5-amine, N,8-dimethyl-2-[6-(methylamino)-3-pyridinyl]-;
8H-imidazo[4,5-d]thiazolo[5,4-b]pyridin-5-amine, N,8-dimethyl-2-[6-(4-morpholinyl)-3-pyridinyl]-;
benzenemethanol, 4-[8-methyl-5-(methylamino)-8H-imidazo[4,5-d]thiazolo[5,4-b]pyridin-2-yl]-;
benzoic acid, 3-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, 2-(3-chloro-4-fluorophenyl)-N,8-dimethyl-;
8H-imidazo[4,5-d]thiazolo[5,4-b]pyridin-5-amine, 2-(3,4-difluorophenyl)-N,8-dimethyl-;
8H-imidazo[4,5-d]thiazolo[5,4-b]pyridin-5-amine, 2-[3-fluoro-4-(methylamino)phenyl]-N,8-dimethyl-;
8H-imidazo[4,5-d]thiazolo[5,4-b]pyridin-5-amine, 2-(4-isoquinolinyl)-N,8-dimethyl-;
8H-imidazo[4,5-d]thiazolo[5,4-b]pyridin-5-amine, N,8-dimethyl-2-[2-(methylamino)-3-pyridinyl]-;
2-furancarboxaldehyde, 5-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, 2-[4-(aminomethyl)phenyl]-N,8-dimethyl-;
N,N-diethyl-3-[8-methyl-5-(methylamino)-8H-imidazo[4,5-d]thiazolo[5,4-b]pyridin-2-yl]benzamide;
3-piperidinemethanol, 1-[3-[8-methyl-5-(methylamino)-8H-imidazo[4,5-d]thiazolo[5,4-b]pyridin-2-yl]benzoyl]-;
benzamide, N-methyl-3-[8-methyl-5-(methylamino)-8H-imidazo[4,5-d]thiazolo[5,4-b]pyridin-2-yl]-N-(2-phenylethyl)-;
piperazine, 1-acetyl-4-[3-[8-methyl-5-(methylamino)-8H-imidazo[4,5-d]thiazolo[5,4-b]pyridin-2-yl]benzoyl]-;
piperidine, 1-[3-[8-methyl-5-(methylamino)-8H-imidazo[4,5-d]thiazolo[5,4-b]pyridin-2-yl]benzoyl]-;
thiomorpholine, 4-[3-[8-methyl-5-(methylamino)-8H-imidazo[4,5-d]thiazolo[5,4-b]pyridin-2-yl]benzoyl]-;
piperazine, 1-methyl-4-[3-[8-methyl-5-(methylamino)-8H-imidazo[4,5-d]thiazolo[5,4-b]pyridin-2-yl]benzoyl]-;
benzamide, N-[(3-chlorophenyl)methyl]-3-[8-methyl-5-(methylamino)-8H-imidazo[4,5-d]thiazolo[5,4-b]pyridin-2-yl]-;
benzamide, N-cyclohexyl-3-[8-methyl-5-(methylamino)-8H-imidazo[4,5-d]thiazoio[5,4-b]pyridin-2-yl]-;
benzamide, N-(1,1-dimethylethyl)-3-[8-methyl-5-(methylamino)-8H-imidazo[4,5-d]thiazolo[5,4-b]pyridin-2-yl]-;
benzamide, 3-[8-methyl-5-(methylamino)-8H-imidazo[4,5-d]thiazolo[5,4-b]pyridin-2-yl]-N-(3-pyridinylmethyl)-;
benzamide, N-[(2,5-dichlorophenyl)methyl]-3-[8-methyl-5-(methylamino)-8H-imidazo[4,5-d]thiazolo[5,4-b]pyridin-2-yl]-;
benzamide, N-(2-hydroxyethyl)-3-[8-methyl-5-(methylamino)-8H-imidazo[4,5-d]thiazolo[5,4-b]pyridin-2-yl]-;
benzamide, N-(2,2-dimethylpropyl)-3-[8-methyl-5-(methylamino)-8H-imidazo[4,5-d]thiazolo[5,4-b]pyridin-2-yl]-;
benzamide, 3-[8-methyl-5-(methylamino)-8H-imidazo[4,5-d]thiazolo[5,4-b]pyridin-2-yl]-N-(2-thienylmethyl)-;
benzamide, N-(2-ethoxyethyl)-3-[8-methyl-5-(methylamino)-8H-imidazo[4,5-d]thiazolo[5,4-b]pyridin-2-yl]-;
benzamide, 3-[8-methyl-5-(methylamino)-8H-imidazo[4,5-d]thiazolo[5,4-b]pyridin-2-yl]-N-(phenylmethyl)-;
benzamide, 3-[8-methyl-5-(methylamino)-8H-imidazo[4,5-d]thiazolo[5,4-b]pyridin-2-yl]-N-pentyl-;
benzamide, 3-[8-methyl-5-(methylamino)-8H-imidazo[4,5-d]thiazolo[5,4-b]pyridin-2-yl]-N-[(tetrahydro-2-furanyl)methyl]-;
benzamide, N-[(3,4-difluorophenyl)methyl]-3-[8-methyl-5-(methylamino)-8H-imidazo[4,5-d]thiazolo[5,4-b]pyridin-2-yl]-;
benzamide, N-[(2,4-dichlorophenyl)methyl]-3-[8-methyl-5-(methylamino)-8H-imidazo[4,5-d]thiazolo[5,4-b]pyridin-2-yl]-;
benzamide, 3-[8-methyl-5-(methylamino)-8H-imidazo[4,5-d]thiazolo[5,4-b]pyridin-2-yl]-N-[[3-(trifluoromethoxy)phenyl]methyl]-;
benzamide, 3-[8-methyl-5-(methylamino)-8H-imidazo[4,5-d]thiazolo[5,4-b]pyridin-2-yl]-N-(2-methylpropyl)-;
benzamide, N-[(4-methoxyphenyl)methyl]-3-[8-methyl-5-(methylamino)-8H-imidazo[4,5-d]thiazolo[5,4-b]pyridin-2-yl]-;
benzamide, N-[(3,5-dimethoxyphenyl)methyl]-3-[8-methyl-5-(methylamino)-8H-imidazo[4,5-d]thiazolo[5,4-b]pyridin-2-yl]-;

benzamide, N-(4-hydroxybutyl)-3-[8-methyl-5-(methylamino)-8H-imidazo[4,5-d]thiazolo[5,4-b]pyridin-2-yl]-;
benzamide, N-[3-(dimethylamino)propyl]-3-[8-methyl-5-(methylamino)-8H-imidazo[4,5-d]thiazolo[5,4-b]pyridin-2-yl]-;
benzamide, N-[(2-methoxyphenyl)methyl]-3-[8-methyl-5-(methylamino)-8H-imidazo[4,5-d]thiazolo[5,4-b]pyridin-2-yl]-;
benzamide, N-[(2-fluorophenyl)methyl]-3-[8-methyl-5-(methylamino)-8H-imidazo[4,5-d]thiazolo[5,4-b]pyridin-2-yl]-;
benzamide, 3-[8-methyl-5-(methylamino)-8H-imidazo[4,5-d]thiazolo[5,4-b]pyridin-2-yl]-N-(2-pyridinylmethyl)-;
benzamide, 3-[8-methyl-5-(methylamino)-8H-imidazo[4,5-d]thiazolo[5,4-b]pyridin-2-yl]-N-(4-pyridinylmethyl)-;
benzamide, N-[(3-methoxyphenyl)methyl]-3-[8-methyl-5-(methylamino)-8H-imidazo[4,5-d]thiazolo[5,4-b]pyridin-2-yl]-;
benzamide, N-ethyl-3-[8-methyl-5-(methylamino)-8H-imidazo[4,5-d]thiazolo[5,4-b]pyridin-2-yl]-;
benzamide, N-[(4-fluorophenyl)methyl]-3-[8-methyl-5-(methylamino)-8H-imidazo[4,5-d]thiazolo[5,4-b]pyridin-2-yl]-;
benzamide, 3-[8-methyl-5-(methylamino)-8H-imidazo[4,5-d]thiazolo[5,4-b]pyridin-2-yl]-N-(2-phenylethyl)-;
benzamide, N-(cyclopropylmethyl)-3-[8-methyl-5-(methylamino)-8H-imidazo[4,5-d]thiazolo[5,4-b]pyridin-2-yl]-;
8-methyl-5-(methylamino)-8H-imidazo[4,5-d]thiazolo[5,4-b]pyridine-2-carboxylic acid;
N,N-diethyl-8-methyl-5-(methylamino)-8H-imidazo[4,5-d]thiazolo[5,4-b]pyridine-2-carboxamide;
8H-imidazo[4,5-d]thiazolo[5,4-b]pyridine-2-carboxamide, N-(1H-benzimidazol-2-ylmethyl)-8-methyl-5-(methylamino)-;
8H-imidazo[4,5-d]thiazolo[5,4-b]pyridine-2-carboxamide, N-[2-[bis(1-methylethyl)amino]ethyl]-8-methyl-5-(methylamino)-;
8H-imidazo[4,5-d]thiazolo[5,4-b]pyridine-2-carboxamide, N-[(2-fluorophenyl)methyl]-8-methyl-5-(methylamino)-;
8H-imidazo[4,5-d]thiazolo[5,4-b]pyridine-2-carboxamide, 8-methyl-5-(methylamino)-N-[(tetrahydro-2-furanyl)methyl]-;
8H-imidazo[4,5-d]thiazolo[5,4-b]pyridine-2-carboxamide, N-(2,2-dimethylpropyl)-8-methyl-5-(methylamino)-;
8H-imidazo[4,5-d]thiazolo[5,4-b]pyridine-2-carboxamide, 8-methyl-5-(methylamino)-N-pentyl-;
8H-imidazo[4,5-d]thiazolo[5,4-b]pyridine-2-carboxamide, 8-methyl-5-(methylamino)-N-(2-thienylmethyl)-;
8H-imidazo[4,5-d]thiazolo[5,4-b]pyridine-2-carboxamide, 8-methyl-5-(methylamino)-N-[2-(1-piperidinyl)ethyl]-;
8H-imidazo[4,5-d]thiazolo[5,4-b]pyridine-2-carboxamide, 8-methyl-5-(methylamino)-N-(phenylmethyl)-;
8H-imidazo[4,5-d]thiazolo[5,4-b]pyridine-2-carboxamide, N-(2,3-dihydroxypropyl)-8-methyl-5-(methylamino)-;
8H-imidazo[4,5-d]thiazolo[5,4-b]pyridine-2-carboxamide, 8-methyl-5-(methylamino)-N-[[3-(trifluoromethoxy)phenyl]methyl]-;
piperazine, 1-acetyl-4-[[8-methyl-5-(methylamino)-8H-imidazo[4,5-d]thiazolo[5,4-b]pyridin-2-yl]carbonyl]-;
8H-imidazo[4,5-d]thiazolo[5,4-b]pyridine-2-carboxamide, 8-methyl-5-(methylamino)-N-(2,2,2-trifluoroethyl)-;
butanoic acid, 4-[[[8-methyl-5-(methylamino)-8H-imidazo[4,5-d]thiazolo[5,4-b]pyridin-2-yl]carbonyl]amino]-, ethyl ester;
8H-imidazo[4,5-d]thiazolo[5,4-b]pyridine-2-carboxamide, N,8-dimethyl-5-(methylamino)-N-2-propenyl-;
8H-imidazo[4,5-d]thiazolo[5,4-b]pyridine-2-carboxamide, 8-methyl-5-(methylamino)-N-(2-pyridinylmethyl)-;
8H-imidazo[4,5-d]thiazolo[5,4-b]pyridine-2-carboxamide, N-cyclohexyl-8-methyl-5-(methylamino)-;
8H-imidazo[4,5-d]thiazolo[5,4-b]pyridine-2-carboxamide, N-(trans-4-hydroxycyclohexyl)-8-methyl-5-(methylamino)-;
8H-imidazo[4,5-d]thiazolo[5,4-b]pyridine-2-carboxamide, 8-methyl-5-(methylamino)-N-(tetrahydro-2-oxo-3-thienyl)-;
cyclopropanecarboxylic acid, 1-[[[8-methyl-5-(methylamino)-8H-imidazo[4,5-d]thiazolo[5,4-b]pyridin-2-yl]carbonyl]amino]-, methyl ester;
serine, N-[[8-methyl-5-(methylamino)-8H-imidazo[4,5-d]thiazolo[5,4-b]pyridin-2-yl]carbonyl]-, methyl ester;
8H-imidazo[4,5-d]thiazolo[5,4-b]pyridine-2-carboxamide, N-[4-(diethylamino)-1-methylbutyl]-8-methyl-5-(methylamino)-;
8H-imidazo[4,5-d]thiazolo[5,4-b]pyridine-2-carboxamide, N,8-dimethyl-5-(methylamino)-;
8H-imidazo[4,5-d]thiazolo[5,4-b]pyridine-2-carboxamide, N-ethyl-8-methyl-5-(methylamino)-;
8H-imidazo[4,5-d]thiazolo[5,4-b]pyridine-2-carboxamide, 8-methyl-5-(methylamino)-N-2-propynyl-;
8H-imidazo[4,5-d]thiazolo[5,4-b]pyridine-2-carboxamide, N-(3,3-dimethylbutyl)-8-methyl-5-(methylamino)-;
8H-imidazo[4,5-d]thiazolo[5,4-b]pyridine-2-carboxamide, N-[2-hydroxy-1,1-bis(hydroxymethyl)ethyl]-8-methyl-5-(methylamino)-;
8H-imidazo[4,5-d]thiazolo[5,4-b]pyridine-2-carboxamide, N-(2-hydroxy-1-methylethyl)-8-methyl-5-(methylamino)-;
8H-imidazo[4,5-d]thiazolo[5,4-b]pyridine-2-carboxamide, N-(2-hydroxypropyl)-8-methyl-5-(methylamino)-;
8H-imidazo[4,5-d]thiazolo[5,4-b]pyridine-2-carboxamide, N-[2-(2-hydroxyethoxy)ethyl]-8-methyl-5-(methylamino)-;
8H-imidazo[4,5-d]thiazolo[5,4-b]pyridine-2-carboxamide, N-(3-methoxypropyl)-8-methyl-5-(methylamino)-;
8H-imidazo[4,5-d]thiazolo[5,4-b]pyridine-2-carboxamide, N-[2-(acetylamino)ethyl]-8-methyl-5-(methylamino)-;
8H-imidazo[4,5-d]thiazolo[5,4-b]pyridine-2-carboxamide, N-cyclopentyl-8-methyl-5-(methylamino)-;
8H-imidazo[4,5-d]thiazolo[5,4-b]pyridine-2-carboxamide, N-(cyclohexylmethyl)-8-methyl-5-(methylamino)-;
8H-imidazo[4,5-d]thiazolo[5,4-b]pyridine-2-carboxamide, 8-methyl-5-(methylamino)-N-[3-(4-morpholinyl)propyl]-;
8H-imidazo[4,5-d]thiazolo[5,4-b]pyridine-2-carboxamide, N-(2-furanylmethyl)-8-methyl-5-(methylamino)-;
8H-imidazo[4,5-d]thiazolo[5,4-b]pyridine-2-carboxamide, N-[3-(1H-imidazol-1-yl)propyl]-8-methyl-5-(methylamino)-;

8H-imidazo[4,5-d]thiazolo[5,4-b]pyridine-2-carboxamide, N-[(3-fluorophenyl)methyl]-8-methyl-5-(methylamino)-;

8H-imidazo[4,5-d]thiazolo[5,4-b]pyridine-2-carboxamide, N-[(4-fluorophenyl)methyl]-8-methyl-5-(methylamino)-;

8H-imidazo[4,5-d]thiazolo[5,4-b]pyridine-2-carboxamide, N-[(3,4-difluorophenyl)methyl]-8-methyl-5-(methylamino)-;

8H-imidazo[4,5-d]thiazolo[5,4-b]pyridine-2-carboxamide, N-[2-(3-fluorophenyl)ethyl]-8-methyl-5-(methylamino)-;

8H-imidazo[4,5-d]thiazolo[5,4-b]pyridine-2-carboxamide, 8-methyl-5-(methylamino)-N-[(5-methyl-2-furanyl)methyl]-;

L-alanine, N-[[8-methyl-5-(methylamino)-8H-imidazo[4,5-d]thiazolo[5,4-b]pyridin-2-yl]carbonyl]-, 1,1-dimethylethyl ester;

glycine, N-[[8-methyl-5-(methylamino)-8H-imidazo[4,5-d]thiazolo[5,4-b]pyridin-2-yl]carbonyl]-, 1,1-dimethylethyl ester;

N-[8-methyl-5-(methylamino)-8H-imidazo[4,5-d]thiazolo[5,4-b]pyridin-2-yl]benzamide;

8-Methyl-2-(pyrazol-1-yl)-N-methyl-8H-imidazo[4,5-d]thiazolo[5,4-b]pyridin-5-amine;

8-Methyl-N-methyl-2-amino-8H-imidazo[4,5-d]thiazolo[5,4-b]pyridin-5-amine;

8-Methyl-2-(4-fluorophenyl)-N-methyl-8H-imidazo[4,5-d]thiazolo[5,4-b]pyridin-5-amine;

8H-imidazo[4,5-d]thiazolo[5,4-b]pyridin-5-amine, N,8-dimethyl-2-(4-pyridinyl)-;

8H-imidazo[4,5-d]thiazolo[5,4-b]pyridin-5-amine, N,8-dimethyl-2-(2-thienyl)-;

8H-imidazo[4,5-d]thiazolo[5,4-b]pyridin-5-amine, N,8-dimethyl-2-(4-quinolinyl)-;

8H-imidazo[4,5-d]thiazolo[5,4-b]pyridin-5-amine, 2-(4-methoxyphenyl)-N,8-dimethyl-;

8H-imidazo[4,5-d]thiazolo[5,4-b]pyridin-5-amine, N,8-dimethyl-2-[4-(trifluoromethyl)phenyl]-;

8H-imidazo[4,5-d]thiazolo[5,4-b]pyridin-5-amine, 2-(3-methoxyphenyl)-N,8-dimethyl-;

N-[1-[2-Fluoro-5-[8-methyl-5-(methylamino)-8H-imidazo[4,5-d]thiazolo[5,4-b]pyridin-2-yl]phenyl]ethyl]acetamide;

8H-imidazo[4,5-d]thiazolo[5,4-b]pyridin-5-amine, 2-(6-fluoro-3-pyridinyl)-N,8-dimethyl-;

8H-imidazo[4,5-d]thiazolo[5,4-b]pyridin-5-amine, N,8-dimethyl-2-(2-thiazolyl)-;

8H-imidazo[4,5-d]thiazolo[5,4-b]pyridin-5-amine, N,8-dimethyl-2-(2-pyridinyl)-;

8H-imidazo[4,5-d]thiazolo[5,4-b]pyridin-5-amine, 2-(3,6-dihydro-2H-thiopyran-4-yl)-N,8-dimethyl-;

8-Methyl-N-methyl-8H-imidazo[4,5-d]thiazolo[5,4-b]pyridin-5-amine;

8-Methyl-N-methyl-2-(4-methoxyphenyl)-8H-imidazo[4,5-d]thiazolo[5,4-b]pyridin-5-amine;

8-Methyl-2-(4-fluorophenyl)-8H-imidazo[4,5-d]thiazolo[5,4-b]pyridin-5-amine;

8-Methyl-N-methyl-2-ethoxy-8H-imidazo[4,5-d]thiazolo[5,4-b]pyridin-5-amine;

N,8-dimethyl-2-[2-(4-morpholinyl)ethoxy]-8H-imidazo[4,5-d]thiazolo[5,4-b]pyridin-5-amine;

N,8-Dimethyl-2-[pentyloxy]-8H-imidazo[4,5-d]thiazolo[5,4-b]pyridin-5-amine;

8H-imidazo[4,5-d]thiazolo[5,4-b]pyridin-5-amine, 2-(cyclohexyloxy)-N,8-dimethyl-;

8H-imidazo[4,5-d]thiazolo[5,4-b]pyridin-5-amine, 2-(cyclopentyloxy)-N,8-dimethyl-;

1-propanol, 3-[[8-methyl-5-(methylamino)-8H-imidazo[4,5-d]thiazolo[5,4-b]pyridin-2-yl]oxy]-;

1-butanol, 4-[[8-methyl-5-(methylamino)-8H-imidazo[4,5-d]thiazolo[5,4-b]pyridin-2-yl]oxy]-;

1-pentanol, 5-[[8-methyl-5-(methylamino)-8H-imidazo[4,5-d]thiazolo[5,4-b]pyridin-2-yl]oxy]-;

8H-imidazo[4,5-d]thiazolo[5,4-b]pyridin-5-amine, 2-(cyclopropylmethoxy)-N,8-dimethyl-;

8H-imidazo[4,5-d]thiazolo[5,4-b]pyridin-5-amine, 2-(2-methoxyethoxy)-N,8-dimethyl-;

8H-imidazo[4,5-d]thiazolo[5,4-b]pyridin-5-amine, 2-(3-methoxy-3-methylbutoxy)-N,8-dimethyl-;

8H-imidazo[4,5-d]thiazolo[5,4-b]pyridin-5-amine, N,8-dimethyl-2-(2-pyridinylmethoxy)-;

8H-imidazo[4,5-d]thiazolo[5,4-b]pyridin-5-amine, N,8-dimethyl-2-[(1-methyl-2-piperidinyl)methoxy]-;

8H-imidazo[4,5-d]thiazolo[5,4-b]pyridin-5-amine, N,8-dimethyl-2-(2-methylpropoxy)-;

8H-imidazo[4,5-d]thiazolo[5,4-b]pyridin-5-amine, 2-(cyclobutylmethoxy)-N,8-dimethyl-;

8H-imidazo[4,5-d]thiazolo[5,4-b]pyridin-5-amine, 2-[2-(dimethylamino)ethoxy]-N,8-dimethyl-;

8H-imidazo[4,5-d]thiazolo[5,4-b]pyridin-5-amine, N,8-dimethyl-2-(phenylmethoxy)-;

8H-imidazo[4,5-d]thiazolo[5,4-b]pyridin-5-amine, N,8-dimethyl-2-propoxy-;

8H-imidazo[4,5-d]thiazolo[5,4-b]pyridin-5-amine, N,8-dimethyl-2-(1-methylethoxy)-;

8H-imidazo[4,5-d]thiazolo[5,4-b]pyridin-5-amine, 2-methoxy-N,8-dimethyl-;

N-Ethyl-2-(4-fluorophenyl)-8-methyl-8H-imidazo[4,5-d]thiazolo[5,4-b]pyridin-5-amine;

8H-imidazo[4,5-d]thiazolo[5,4-b]pyridin-5-amine, N-cyclopropyl-2-(4-fluorophenyl)-8-methyl-;

8H-imidazo[4,5-d]thiazolo[5,4-b]pyridin-5-amine, 2-(4-fluorophenyl)-8-methyl-N-[2-(1-pyrrolidinyl)ethyl]-;

8H-imidazo[4,5-d]thiazolo[5,4-b]pyridin-5-amine, 2-(4-fluorophenyl)-8-methyl-N-(4-piperidinylmethyl)-;

8H-imidazo[4,5-d]thiazolo[5,4-b]pyridin-5-amine, 2-(4-fluorophenyl)-8-methyl-N-[2-(4-morpholinyl)ethyl]-;

8H-imidazo[4,5-d]thiazolo[5,4-b]pyridin-5-amine, 2-(4-fluorophenyl)-8-methyl-N-(3-pyridinylmethyl)-;

8H-imidazo[4,5-d]thiazolo[5,4-b]pyridin-5-amine, 2-(4-fluorophenyl)-8-methyl-N-[2-(1-piperidinyl)ethyl]-;

8H-imidazo[4,5-d]thiazolo[5,4-b]pyridin-5-amine, 2-(4-fluorophenyl)-8-methyl-N-(1-methylethyl)-;

acetamide, N-[2-[[2-(4-fluorophenyl)-8-methyl-8H-imidazo[4,5-d]thiazolo[5,4-b]pyridin-5-yl]amino]ethyl]-;

1,2-ethanediamine, N-[2-(4-fluorophenyl)-8-methyl-8H-imidazo[4,5-d]thiazolo[5,4-b]pyridin-5-yl]-N'-methyl-;

ethanol, 2-[[2-[[2-(4-fluorophenyl)-8-methyl-8H-imidazo[4,5-d]thiazolo[5,4-b]pyridin-5-yl]amino]ethyl]amino]-;

1,2-ethanediamine, N'-[2-(4-fluorophenyl)-8-methyl-8H-imidazo[4,5-d]thiazolo[5,4-b]pyridin-5-yl]-N,N-dimethyl-;

ethanol, 2-[[2-(4-fluorophenyl)-8-methyl-8H-imidazo[4,5-d]thiazolo[5,4-b]pyridin-5-yl]amino]-;

N-methyl-N'-[8-methyl-5-(methylamino)-8H-1-imidazo[4,5-d]thiazolo[5,4-b]pyridin-2-yl]urea;

2-(4-Fluorophenyl)-N-methyl-8H-imidazo[4,5-d]thiazolo[5,4-b]pyridin-5-amine;

N-[1-[2-fluoro-5-[5-[(2-hydroxyethyl)amino]-8-methyl-8H-imidazo[4,5-d]thiazolo[5,4-b]pyridin-2-yl]phenyl]ethyl]acetamide;
acetamide, N-[1-[2-fluoro-5-[5-[[(4-methoxyphenyl)methyl]amino]-8-methyl-8H-imidazo[4,5-d]thiazolo[5,4-b]pyridin-2-yl]phenyl]ethyl]-;
acetamide, N-[1-[5-[5-[[2-(acetylamino)ethyl]amino]-8-methyl-8H-imidazo[4,5-d]thiazolo[5,4-b]pyridin-2-yl]-2-fluorophenyl]ethyl]-;
acetamide, N-[1-[2-fluoro-5-[8-methyl-5-[[2-(1-piperidinyl)ethyl]amino]-8H-imidazo[4,5-d]thiazolo[5,4-b]pyridin-2-yl]phenyl]ethyl]-;
acetamide, N-[1-[5-[5-[[2-(dimethylamino)ethyl]amino]-8-methyl-8H-imidazo[4,5-d]thiazolo[5,4-b]pyridin-2-yl]-2-fluorophenyl]ethyl]-;
acetamide, N-[1-[5-[5-(cyclopropylamino)-8-methyl-8H-imidazo[4,5-d]thiazolo[5,4-b]pyridin-2-yl]-2-fluorophenyl]ethyl]-;
acetamide, N-[1-[2-fluoro-5-[8-methyl-5-[(1-methylethyl)amino]-8H-imidazo[4,5-d]thiazolo[5,4-b]pyridin-2-yl]phenyl]ethyl]-;
acetamide, N-[1-[5-[5-(ethylamino)-8-methyl-8H-imidazo[4,5-d]thiazolo[5,4-b]pyridin-2-yl]-2-fluorophenyl]ethyl]-;
acetamide, N-[1-[5-[5-[(2-aminoethyl)amino]-8-methyl-8H-imidazo[4,5-d]thiazolo[5,4-b]pyridin-2-yl]-2-fluorophenyl]ethyl]-;
acetamide, N-[1-[5-[5-[(2-diethylaminoethyl)amino]-8-methyl-8H-imidazo[4,5-d]thiazolo[5,4-b]pyridin-2-yl]-2-fluorophenyl]ethyl]-;
acetamide, N-[1-[5-[5-[(1-ethylpyrrolidin-2-yl)methylamino]-8-methyl-8H-imidazo[4,5-d]thiazolo[5,4-b]pyridin-2-yl]-2-fluorophenyl]ethyl]-;
acetamide, N-[1-[5-[5-[(2-(2-azaindan-2-yl)ethyl)amino]-8-methyl-8H-imidazo[4,5-d]thiazolo[5,4-b]pyridin-2-yl]-2-fluorophenyl]ethyl]-;
acetamide, N-[1-[5-[5-[(3-dimethylaminopropyl)amino]-8-methyl-8H-imidazo[4,5-d]thiazolo[5,4-b]pyridin-2-yl]-2-fluorophenyl]ethyl]-;
acetamide, N-[1-[5-[5-[(3-imidazol-1-ylpropyl)amino]-8-methyl-8H-imidazo[4,5-d]thiazolo[5,4-b]pyridin-2-yl]-2-fluorophenyl]ethyl]-;
acetamide, N-[1-[5-[5-[(3-piperidin-1-ylpropyl)amino]-8-methyl-8H-imidazo[4,5-d]thiazolo[5,4-b]pyridin-2-yl]-2-fluorophenyl]ethyl]-;
2-(3-(2-carboxyethenyl)phenyl)-N-(2-aminoethyl)-8-methyl-8H-imidazo[4,5-d]thiazolo[5,4-b]pyridin-5-amine;
3-[8-methyl-5-[[2-(1-piperidinyl)ethyl]amino]-8H-imidazo[4,5-d]thiazolo[5,4-b]pyridin-2-yl]benzeneacetonitrile;
benzeneacetonitrile, 3-[5-[(2-aminoethyl)amino]-8-methyl-8H-imidazo[4,5-d]thiazolo[5,4-b]pyridin-2-yl]-;
2-propenoic acid, 3-[3-[8-methyl-5-(methylamino)-8H-imidazo[4,5-d]thiazolo[5,4-b]pyridin-2-yl]phenyl]-, (2E)-;
2-propenoic acid, 3-[3-[5-[[2-(acetylamino)ethyl]amino]-8-methyl-8H-imidazo[4,5-d]thiazolo[5,4-b]pyridin-2-yl]phenyl]-, (2E)-;
benzeneacetonitrile, 3-[5-[[2-(dimethylamino)ethyl]amino]-8-methyl-8H-imidazo[4,5-d]thiazolo[5,4-b]pyridin-2-yl]-;
benzeneacetonitrile, 3-[5-[(2-hydroxyethyl)amino]-8-methyl-8H-imidazo[4,5-d]thiazolo[5,4-b]pyridin-2-yl]-;
benzeneacetonitrile, 3-[8-methyl-5-(methylamino)-8H-imidazo[4,5-d]thiazolo[5,4-b]pyridin-2-yl]-;
benzeneacetonitrile, 3-[5-[[(4-methoxyphenyl)methyl]amino]-8-methyl-8H-imidazo[4,5-d]thiazolo[5,4-b]pyridin-2-yl]-;
benzeneacetonitrile, 3-[8-methyl-5-[[2-(1-piperidinyl)ethyl]amino]-8H-imidazo[4,5-d]thiazolo[5,4-b]pyridin-2-yl]-;
benzeneacetonitrile, 3-[5-(ethylamino)-8-methyl-8H-imidazo[4,5-d]thiazolo[5,4-b]pyridin-2-yl]-;
2-Fluoro-5-[8-methyl-5-(methylamino)-8H-imidazo[4,5-d]thiazolo[5,4-b]pyridin-2-yl]benzonitrile;
2-(3-Amino-1,2-benzisoxazol-5-yl)-N,8-dimethyl-8H-imidazo[4,5-d]thiazolo[5,4-b]pyridin-5-amine;
N,8-dimethyl-2-[3-[1-(methylamino)ethyl]phenyl]-8H-imidazo[4,5-d]thiazolo[5,4-b]pyridin-5-amine;
benzenepropanoic acid, 4-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, 2-(3,5-difluorophenyl)-N,8-dimethyl-;
8H-imidazo[4,5-d]thiazolo[5,4-b]pyridin-5-amine, 2-(1H-indol-5-yl)-N,8-dimethyl-;
8H-imidazo[4,5-d]thiazolo[5,4-b]pyridin-5-amine, N,8-dimethyl-2-[3-(methylthio)phenyl]-;
benzonitrile, 3-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, 2-(2-fluoro-3-pyridinyl)-N,8-dimethyl-;
8H-imidazo[4,5-d]thiazolo[5,4-b]pyridin-5-amine, N,8-dimethyl-2-(4-methyl-2-thienyl)-;
2-[3-(aminomethyl)phenyl]-N,8-dimethyl-8H-imidazo[4,5-d]thiazolo[5,4-b]pyridin-5-amine;
N-[[3-[8-methyl-5-(methylamino)-8H-imidazo[4,5-d]thiazolo[5,4-b]pyridin-2-yl]phenyl]methyl]acetamide;
N-[[3-[8-methyl-5-(methylamino)-8H-imidazo[4,5-d]thiazolo[5,4-b]pyridin-2-yl]phenyl]methyl]methanesulfonamide;
2-[3-(1-aminoethyl)phenyl]-N,8-dimethyl-8H-imidazo[4,5-d]thiazolo[5,4-b]pyridin-5-amine;
N-[1-[3-[8-methyl-5-(methylamino)-8H-imidazo[4,5-d]thiazolo[5,4-b]pyridin-2-yl]phenyl]ethyl]acetamide;
N-[1-[3-[8-methyl-5-(methylamino)-8H-imidazo[4,5-d]thiazolo[5,4-b]pyridin-2-yl]phenyl]ethyl]methanesulfonamide;
N-[1-methyl-1-[3-[8-methyl-5-(methylamino)-8H-imidazo[4,5-d]thiazolo[5,4-b]pyridin-2-yl]phenyl]ethyl]amine;
N-[1-methyl-1-[3-[8-methyl-5-(methylamino)-8H-imidazo[4,5-d]thiazolo[5,4-b]pyridin-2-yl]phenyl]ethyl]acetamide;
N-[1,1-dimethyl-1-[3-[8-methyl-5-(methylamino)-8H-imidazo[4,5-d]thiazolo[5,4-b]pyridin-2-yl]4-fluorophenyl]ethyl]amine;
N-[1-[2-fluoro-5-[8-methyl-5-(methylamino)-8H-imidazo[4,5-d]thiazolo[5,4-b]pyridin-2-yl]phenyl]-1-methylethyl]-acetamide;
8H-imidazo[4,5-d]thiazolo[5,4-b]pyridin-5-amine, 2-(3-aminophenyl)-N,8-dimethyl-;
8H-imidazo[4,5-d]thiazolo[5,4-b]pyridin-5-amine, 2-(4-chlorophenyl)-N,8-dimethyl-;
8H-imidazo[4,5-d]thiazolo[5,4-b]pyridin-5-amine, N,8-dimethyl-2-[4-(methylthio)phenyl]-;
benzaldehyde, 4-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, N,8-dimethyl-2-(3-thienyl)-;
8H-imidazo[4,5-d]thiazolo[5,4-b]pyridin-5-amine, 2-(2-benzofuranyl)-N,8-dimethyl-;

8H-imidazo[4,5-d]thiazolo[5,4-b]pyridin-5-amine, 2-(3-fluorophenyl)-N,8-dimethyl-;
8H-imidazo[4,5-d]thiazolo[5,4-b]pyridin-5-amine, 2-(2-methoxyphenyl)-N,8-dimethyl-;
8H-imidazo[4,5-d]thiazolo[5,4-b]pyridin-5-amine, 2-(3-fluoro-4-methoxyphenyl)-N,8-dimethyl-;
8H-imidazo[4,5-d]thiazolo[5,4-b]pyridin-5-amine, 2-[4-(dimethylamino)phenyl]-N,8-dimethyl-;
8H-imidazo[4,5-d]thiazolo[5,4-b]pyridin-5-amine, N,8-dimethyl-2-[4-(trifluoromethoxy)phenyl]-;
8H-imidazo[4,5-d]thiazolo[5,4-b]pyridin-5-amine, 2-(4-aminophenyl)-N,8-dimethyl-;
2-furanmethanol, 5-[8-methyl-5-(methylamino)-8H-imidazo[4,5-d]thiazolo[5,4-b]pyridin-2-yl]-;
8H-imidazo[4,5-d]thiazolo[5,4-b]pyridin-5-amine, N,8-dimethyl-2-[5-[(methylamino)methyl]-2-furanyl]-;
N,8-dimethyl-8H-imidazo[4,5-d]thiazolo[5,4-b]pyridin-5-amine, 2-[3-(aminomethyl)-4-fluorophenyl];
N-[[2-fluoro-5-[8-methyl-5-(methylamino)-8H-imidazo[4,5-d]thiazolo[5,4-b]pyridin-2-yl]phenyl]methyl]acetamide;
N-[[2-fluoro-5-[8-methyl-5-(methylamino)-8H-imidazo[4,5-d]thiazolo[5,4-b]pyridin-2-yl]phenyl]methyl]methanesulfonamide;
alpha-methyl-3-[8-methyl-5-(methylamino)-8H-imidazo[4,5-d]thiazolo[5,4-b]pyridin-2-yl]benzenemethanol;
ethanol, 2-[(8-methyl-2-phenyl-8H-imidazo[4,5-d]thiazolo[5,4-b]pyridin-5-yl)amino]-;
1,2-ethanediamine, N-(8-methyl-2-phenyl-8H-imidazo[4,5-d]thiazolo[5,4-b]pyridin-5-yl)-; and
1,2-ethanediamine, N-[2-(4-fluorophenyl)-8-methyl-8H-imidazo[4,5-d]thiazolo[5,4-b]pyridin-5-yl]-.

15. A pharmaceutical composition comprising (a) at least one compound according to claim 1, or a pharmaceutically acceptable salt or hydrate thereof, and (b) a pharmaceutically-acceptable carrier or diluent.

16. A method of treating disorders wherein the disorder is selected from rheumatoid arthritis, asthma, inflammatory bowel disease, chronic obstructive pulmonary disease, and psoriasis comprising administering to a mammal in need thereof a therapeutically-effective amount of at least on e compound according to claim 1.

17. A pharmaceutical composition comprising (a) at least one compound according to claim 6, or a pharmaceutically acceptable salt or hydrate thereof, and (b) a pharmaceutically-acceptable carrier or diluent.

18. A method of treating disorders wherein the disorder is selected from rheumatoid arthritis, asthma, inflammatory bowel disease, chronic obstructive pulmonary disease, and psoriasis, comprising administering to a mammal in need thereof a therapeutically-effective amount of at least one compound according to claim 6.

19. A pharmaceutical composition comprising (a) at least one compound according to claim 7, or a pharmaceutically acceptable salt or hydrate thereof, and (b) a pharmaceutically-acceptable carrier or diluent.

20. A method of treating disorders wherein the disorder is selected from rheumatoid arthritis, asthma, inflammatory bowel disease, chronic obstructive pulmonary disease, and psoriasis, comprising administering to a mammal in need thereof a therapeutically-effective amount of at least one compound according to claim 7.

* * * * *

UNITED STATES PATENT AND TRADEMARK OFFICE
CERTIFICATE OF CORRECTION

PATENT NO.       : 7,176,214 B2                                           Page 1 of 1
APPLICATION NO.  : 10/848412
DATED            : February 13, 2007
INVENTOR(S)      : William J. Pitts et al.

It is certified that error appears in the above-identified patent and that said Letters Patent is hereby corrected as shown below:

At Column 277, Claim 7, between lines 46 and 47, please insert
-- (11)  $-U^1-N(Y^4)-C(O)-Y^1$ , --.

Signed and Sealed this

Sixteenth Day of October, 2007

JON W. DUDAS
*Director of the United States Patent and Trademark Office*